United States Patent
Wrasidlo et al.

(10) Patent No.: US 7,208,493 B2
(45) Date of Patent: Apr. 24, 2007

(54) VASCULOSTATIC AGENTS AND METHODS OF USE THEREOF

(75) Inventors: Wolfgang Wrasidlo, La Jolla, CA (US); John Doukas, Encinitas, CA (US); Ivor Royston, La Jolla, CA (US); Glenn Noronha, Oceanside, CA (US); John D. Hood, San Diego, CA (US); Elena Dneprovskaia, San Diego, CA (US); Xianchang Gong, San Diego, CA (US); Ute Splittgerber, La Mesa, CA (US); Ningning Zhao, San Diego, CA (US)

(73) Assignee: TargeGen, Inc., San Diego, CA (US)

( * ) Notice: Subject to any disclaimer, the term of this patent is extended or adjusted under 35 U.S.C. 154(b) by 367 days.

(21) Appl. No.: 10/679,209

(22) Filed: Oct. 2, 2003

(65) Prior Publication Data

US 2004/0167198 A1   Aug. 26, 2004

Related U.S. Application Data

(60) Provisional application No. 60/479,295, filed on Jun. 17, 2003, provisional application No. 60/466,983, filed on Apr. 30, 2003, provisional application No. 60/463,818, filed on Apr. 17, 2003, provisional application No. 60/443,752, filed on Jan. 29, 2003, provisional application No. 60/440,234, filed on Jan. 14, 2003, provisional application No. 60/415,981, filed on Oct. 3, 2002.

(51) Int. Cl.
*A61K 31/4985* (2006.01)
*C07D 471/02* (2006.01)

(52) U.S. Cl. ..................... 514/249; 544/256

(58) Field of Classification Search ............... None
See application file for complete search history.

(56) References Cited

U.S. PATENT DOCUMENTS

| | | | |
|---|---|---|---|
| 2,667,486 A * | 1/1954 | Cain ................ 544/260 |
| 5,214,059 A | 5/1993 | Tegeler et al. |
| 5,597,901 A | 1/1997 | Stern |
| 5,776,502 A | 7/1998 | Foulkes et al. |
| 5,830,880 A | 11/1998 | Sedlacek et al. |
| 6,070,126 A | 5/2000 | Kokolus et al. |
| 6,121,434 A | 9/2000 | Peyman |
| 6,136,779 A | 10/2000 | Foulkes et al. |
| 6,194,191 B1 | 2/2001 | Zhnag et al. |
| 6,204,260 B1 | 3/2001 | Bruns, Jr. et al. |
| 6,326,487 B1 | 12/2001 | Peyman et al. |
| 6,348,312 B1 | 2/2002 | Peyman et al. |
| 6,471,968 B1 | 10/2002 | Baker, Jr. et al. |
| 6,489,328 B2 | 12/2002 | Snow et al. |
| 6,506,769 B2 | 1/2003 | Snow et al. |
| 6,635,626 B1 | 10/2003 | Barrish et al. |
| 6,685,938 B1 | 2/2004 | Cheresh et al. |
| 6,689,778 B2 | 2/2004 | Benis et al. |

FOREIGN PATENT DOCUMENTS

| | | |
|---|---|---|
| WO | WO 2004/005283 A1 | 0/2004 |
| WO | WO 02/097116 A2 | 12/2002 |
| WO | WO 2004/032709 A2 | 4/2004 |
| WO | WO 2004/037814 A1 | 5/2004 |

OTHER PUBLICATIONS

S. Taghavi-Moghadam and W. Pfleiderer, "A New, General and Regioselective Method for the Synthesis of 2,6-Disubstituted 4-Aminopteridines", *Elsevier Science Ltd., Pergamon*, 6835-6836, 1997.

Lothar G. Fröhlich et al., "Inhibition of Neuronal Nitric Oxide Synthase by 4-Amino Pteridine Derivatives: Structures-Activity Relationship of Antagonists of (6R)-5,6,7,8-Tetrahydrobiopterin Cofactor", *J. Med. Chem.*, vol. 42, 4108-4121, 1999.

T. Weber, Ph.D., "Molecular Approaches to Study Cellular Roadblocks to Transfection and Transduction (Non-Viral Vectors and AAV-Based Vectors for Gene Therapy)", http://www.mssm.edu/genetherapy/weber.htm, 1-8, Nov. 11, 2002.

N. Kobayashi et al., "Functional coupling of the src-family protein tyrosine kinases p59fyn and p53/56lyn with the interleukin 2 receptor: implications for redundancy and pleiotropsim in cytokine signal transduction", *Proc. Natl. Acad. Sci., USA*, vol. 1:90, No. 9, 4201-4205, Abstract, PMID 8483935, May 1993.

New Mexico Department of Health, INTERLEUKIN-2, http://www.aidsinfonet.org, *Project of the New Mexico Aids Education and Training Center*, Fact Sheet No. 622, Apr. 30, 2002.

(Continued)

*Primary Examiner*—Kamal A. Saeed
(74) *Attorney, Agent, or Firm*—DLA Piper US LLP

(57) ABSTRACT

Compositions and methods and are provided for treating disorders associated with compromised vasculostasis. Invention methods and compositions are useful for treating a variety of disorders including for example, stroke, myocardial infarction, cancer, ischemia/reperfusion injury, autoimmune diseases such as rheumatoid arthritis, eye diseases such as retinopathies or macular degeneration or other vitreoretinal diseases, inflammatory diseases, vascular leakage syndrome, edema, transplant rejection, adult/acute respiratory distress syndrome (ARDS), and the like.

9 Claims, 10 Drawing Sheets

OTHER PUBLICATIONS

N. Tanaka et al., "novel human tyrosine kinase gene inducible in T cells by interleukin 2", *FEBS Lett.*, vol. 7:324, No. 1, 1-5, PMID 9504851, Jun. 1993.

A. Granelli-Piperno, "SRC-related proto-oncongenes and transcription factors in primary human T cells: modulation by cyclosporine A and FK506", *J. Autoimmun.*, vol. 5, Suppl. A, 145-158, PMID 1380242, Apr. 1992.

T. Torigoe et al., "Regulation of SRC-family protein tyrosine kinases by interleukin, IL-2, and IL-3", *Leukemia*, vol. 6, Supplemental 3, 94S—97S, PMID 1602836, 1992.

J.J. O'Shea et al., "Expression of v-src in a murine T-cell hybridoma results in constitutive T-cell receptor phosphorylation and interleukin 2 production", *Proc. Natl. Acad. Sci. USA*, vol. 1;88, No. 5, 1741-1745, PMID 200381, 1991.

J.B. Bolen et al., "Expression and interaction of the Src family of tyrosine protein kinases in T lymphocytes", *Adv. Cancer Res.*, vol. 57., 103-149, PMID 1950702, 1991.

T. Yamamoto et al., "Role of src-like protooncogenes in lymphocotye proliferation", *Princess Takamastu Symp.*, vol. 22, 293-305 Review, PMID 1668889, 1991.

* cited by examiner

N-(2-(1H-indol-2-yl)-phenyl)phthalamic acid 6,7-bis(3-hydroxyphenyl)-pteridine-2,4,-diamine, sulfate salt 6,7-bis(4-hydroxyphenyl)-pteridine-4-ylamine, sulfate salt 6,7-diphenyl-pteridine-2,4-diamine, sulfate salt 6,7-bis(3-hydroxyphenyl)-pteridine-2,4-diamine, sulfate salt 6,7-bis(3-hydroxyphenyl)-pteridine-2,4,-diamine, dihydrochloride salt 2,3-bis(3,4-dihydroxyphenyl)-pyrido(2,3,b)-pyrazine-6-ylamine, dihydrochloride salt Control (untreated) lung above
Lung treated with doxorubicin (3 mg/kg) and compound B (20 mg/kg) below
Tumors are whitish nodules, lung is brownish tissue

VASCULOSTATIC AGENTS AND METHODS OF USE THEREOF

CROSS REFERENCE TO RELATED APPLICATIONS

This application is a provisional-to-utility application and claims the benefit under 35 USC § 119(e) of U.S. application Ser. Nos. 60/479,295 filed Jun. 17, 2003, 60/466,983 filed Apr. 30, 2003, 60/463,818 filed Apr. 17, 2003, 60/443,752 filed Jan. 29, 2003, 60/440,234 filed Jan. 14, 2003 and 60/415,981 filed Oct. 3, 2002. This disclosure each of the prior applications is considered part of and is incorporated by reference in the disclosure of this application.

FIELD OF THE INVENTION

The present invention relates generally to treating disorders associated with vascular functioning, and more specifically to compounds and methods of treating such disorders.

BACKGROUND OF THE INVENTION

The vascular system is a prime mediator of homeostasis, playing key roles in the maintainence of normal physiologic functioning. For example, the vascular endothelium's barrier function serves to regulate the entry of fluid, electrolytes, and proteins into tissues, blood vessel tone contributes to the regulation of tissue perfusion, and the vascular endothelium's low mitotic index contributes to the regulation of tissue growth. The term "vasculostasis" refers to the maintenance of this homeostatic vascular functioning, and "vasculostatic agents" as agents that seek to address conditions in which vasculostasis is compromised by preventing the loss of or restoring or maintaining vasculostasis.

Compromised vasculostasis has serious pathologic consequences. For example, if vascular permeability increases beyond manageable levels, the resulting edema may negatively impact tissue and organ function and ultimately survival. Examples where excessive vascular permeability leads to particularly deleterious effects include pulmonary edema, cerebral edema, and cardiac edema (Ritchie AC: *Boyd's Textbook of Pathology*. London Lea and Febiger, 1990). In general, however, edema in any tissue or organ leads to some loss of normal function, and therefore to the risk of morbidity or even mortality. Similarly, excessive endothelial proliferation may damage tissues (such as the retina in proliferative retinopathies) or fuel unwanted tissue growth (such as with tumor growth).

Many pathologic and disease situations are marked by multiple disregulations in vasculostasis. Angiogenesis, for example, encompasses both enhanced vascular proliferation and permeability, as newly-formed blood vessels do not generally exhibit the same level of vascular barrier function as well-established or mature vessels. Examples of such hyperpermeable vasculature can be found in cancers, vasculoproliferative diseases, retinal diseases, and rheumatoid arthritis. The connection between angiogenesis and hyperpermeability may partly result from the dual action of factors such as vascular endothelial growth factor (VEGF), which induces both endothelial proliferation and vascular permeability. This connection may also reflect the immature nature of angiogenic vessels, in which the intracellular and/or extracellular structures or mechanisms that establish normal vascular barrier function have not yet fully formed. It may also be the case that angiogenesis and vascular permeability are linked by a co-dependence on common cellular mechanisms, for example in the case of cellular junction disassembly which would serve to enhance both paracellular permeability and cellular migration (both being components of the angiogenic process). A comprehensive treatment for many diseases, then, might involve vasculostatic agents that act upon one or more components of vasculostasis disregulation (based, for example, upon their level of action along intracellular signaling cascades). One such example would be a single therapeutic agent that impacts both angiogenesis and vascular permeability.

One way of impacting vasculostasis is by influencing endothelial cell responses to environmental signals (such as hypoxia) or vasoactive agents. For example, the vascular endothelium regulates fluid balance by adjusting both transcellular permeability (movement of fluid and proteins across endothelial cells via a network of vesicles) and paracellular permeability (movement of fluid and proteins between inter-endothelial cell junctions). Edema is most commonly thought to result from a breakdown in the inter-endothelial cell barrier, leading to increased paracellular permeability at the capillary and postcapillary venule level. Mechanistically, paracellular vascular leakage results from a breakdown in inter-cellular junctional integrity, via the dissolution of tight junctions and coupled to changes in cytoskeletal support elements that maintain normal cell-to-cell apposition. Several vasoactive mediators can trigger dissolution of these cellular elements, including histamine, bradykinin, thrombin, nitric oxide, eicosanoids (e.g., thromboxanes and leukotrienes), platelet activating factor (PAF), tumor necrosis factor (TNF), interleukins (e.g., IL-1 and IL-6), hepatocyte growth factor (HGF), and vascular endothelial growth factor (VEGF). Using VEGF as an example, the sequence of events that lead to vascular leakage is generally believed to be as follows: reduced blood flow (e.g., as a result of thrombus formation) leads to tissue hypoxia, which leads to the upregulation of VEGF production, which leads to induction of vascular leakage. This VEGF effect is at the level of the endothelial cell, in other words VEGF binding to specific VEGF receptors expressed on endothelial cells leads to a cascade of intracellular events culminating in the loss of normal intercellular barrier function. Therefore, by affecting these intracellular events, vasulostatic agents could counter the negative effects of environmental signals such as hypoxia or vasoactive mediators such as VEGF, and thereby work to restore vasculostasis.

The cascade of events that leads to the loss of endothelial barrier function is complex and incompletely understood. Data support a role for kinases as at least one aspect of this process. For example, VEGF-mediated edema has been shown to involve intracellular signaling by Src family kinases, protein kinase C, and Akt kinase. Kinases are believed to mediate the phosphorylation of junctional proteins such as beta-catenin and vascular endothelial (VE)-cadherin, leading to the dissolution of adherens junctions and the dissociation of cadherin-catenin complexes from their cytoskeletal anchors. In addition, proteins which regulate the intercellular contractile machinery such as myosin light chain kinase (MLCK) and myosin light chain (MLC) are also activated, resulting in cellular contraction, and therefore an opening of intercellular junctions.

Maintaining or restoring vasculostasis should be beneficial to overall patient outcome in situations such as inflammation, allergic diseases, cancer, cerebral stroke, myocardial infarction, pulmonary and cardiac insufficiency, renal failure, and retinopathies, to name a few. In addition, edema formation is a recognized but unwanted consequence of many therapeutic interventions, such as immunotherapy, cancer chemotherapy and radiation therapy, therefore vasculostatic agents that inhibit vascular permeability could be used in a co-therapy approach to reduce the deleterious side-effects of such therapies. Furthermore, in many cases edema formation causes uneven delivery of therapeutic agents to diseased tissues, therefore vasculostatic agents that inhibit vascular permeability could be used in a co-therapy approach to enhance delivery and efficacy of such therapies. Finally, as edema is a general consequence of tissue hypoxia, it can also be concluded that inhibition of vascular leakage represents a potential approach to the treatment of tissue hypoxia. For example, interruption of blood flow by pathologic conditions (such as thrombus formation) or medical intervention (such as cardioplegia, organ transplantation, and angioplasty) or physical trauma, could be treated both acutely and prophylactically using vasculostatic agents that reduce vascular permeability.

SUMMARY OF THE INVENTION

The present invention is based on the discovery that certain chemical compounds are effective vasculostatic agents. Compounds of the invention are effective for the treatment of such indications as myocardial infarction (MI), stroke, ischemia or reperfusion related tissue injury and cancer, for example. Thus, compositions and methods are provided for treating disorders associated with compromised vasculostasis, examples of which are edema resulting from excess vascular permeability or vascular leakage and angiogenesis associated with retinal diseases and cancer. Some of the compounds described herein are effective kinase inhibitors, including but not limited to tyrosine, serine or threonine kinase inhibitors, for example, Src-family inhibitors.

Such vasculostatic agents, alone or in combination with other agents, are effective in blocking vascular permeability or leakage or angiogenesis. In one embodiment, the invention provides a composition containing a therapeutically effective amount of a compound of the invention in a pharmaceutically acceptable carrier.

In one embodiment, the invention provides a method for treating a disorder associated with compromised vasculostasis in a subject, comprising administering to a subject in need thereof an effective amount of a compound that is a vasculostatic agent. In an illustrative example, the method includes use of at least one of the compounds as set forth in Structures I, II, III, IIIa, IV, V, VI or VII or any combination thereof. In one aspect, the compound is set forth in FIG. 1.

In one embodiment, compounds are provided having the structure (I):

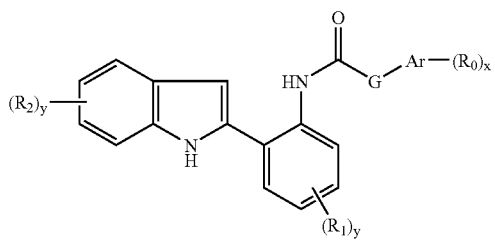

wherein:
each $R_0$ is independently —H, —COOH, —OR', —SO$_3$H, wherein R' is —H or lower alkyl, or when x=2, each $R_0$ is taken together to form a 1,3-dioxolyl ring, or each $R_0$ is independently alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, halogen, amino, amido, nitro, or thioalkyl, $R_1$ and $R_2$ are each independently hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, or substituted arylalkynyl, G is NH, O, S, or $(CR''_2)_p$, wherein R'' is —H, lower alkyl, or acetamido, and wherein p is 0–3, Ar is aryl or heteroaryl, and x and y are each independently 1–4.

In another embodiment, compounds are provided having the structure (II):

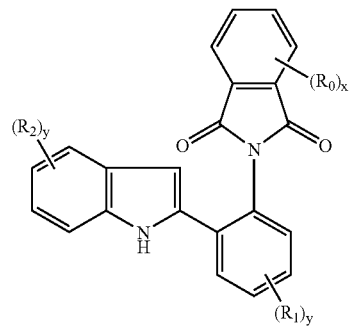

wherein $R_0$, $R_1$, $R_2$, x, and y are as defined above.

In yet another embodiment, compounds are provided having the structure (III):

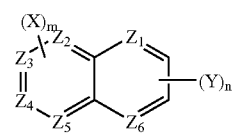

wherein:

$Z_1$–$Z_6$ are each independently C, —C=O, N, or $NR^a$, wherein $R^a$ is —H, alkyl, or substituted alkyl, wherein said substituents are halogen, hydroxy, oxo, or amino, each X is independently halogen, —$OR^b$, —$NR^b_2$, or —$SR^b$, wherein $R^b$ is —H lower alkyl, —(CH$_2$)$_2$NH(CH$_2$CH$_3$), —(CH$_2$)$_3$morpholyn-1-yl, —(CH$_2$)$_3$(N-methylpiperazinyn-1-yl), aryl, heteroaryl, —(NH—NH—$R^c$), —(N=N—NH—$R^c$), wherein $R^c$ is H or lower alkyl, each Y is independently —$OR^d$, —$NR^d_2$, —$SR^d$, or —OPO$_3$H$_2$ wherein $R^d$ is H, lower alkyl, aryl, heteroaryl, —(CH$_2$)$_2$NH(CH$_2$CH$_3$), —(CH$_2$)$_3$morpholyn-1-yl, or —(CH$_2$)$_3$(N-methylpiperazinyn-1-yl); or each Y is independently alkyl, substituted alkyl, aryl, substituted aryl, heteroaryl, substituted heteroaryl, or halogen, wherein said substituents are selected from halogen, —OR$^e$, —NR$^e_2$, —SR$^e$, —P(O)(OH)$_2$, wherein R$^e$ is —H, lower alkyl, aryl, or heteroaryl; or each Y is independently CH$_2$glycinyl, CH$_2$NHethoxy, CH$_2$NHCH$_2$alkyl, CH$_2$NHCH$_2$t-Bu, CH$_2$NHCH$_2$aryl, CH$_2$NHCH$_2$substituted aryl, CH$_2$NHCH$_2$heteroaryl, CH$_2$NHCH$_2$substituted heteroaryl; or when n is 2, each Y is taken together to form a fused aromatic or heteroaromatic ring system; and m and n are each independently 1 to 4, wherein when $Z_1$, $Z_3$, $Z_5$, and $Z_6$ are each N, X is NH$_2$, and m=n=2, Y is not phenyl or 4-hydroxyphenyl, or tautomers thereof.

In still another embodiment, compounds are provided having the structure (IV):

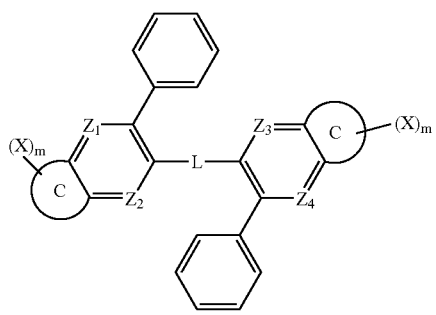

wherein:
L is an arylene, substituted arylene, oxyarylene, thioalkylene, substituted thioalkylene, or substituted oxyarylene linking moiety,
C is 5- or 6-membered aromatic or heteroaromatic ring,
each X is independently H, OR, NR$_2$, or SR, wherein R is H or lower alkyl,
$Z_1$–$Z_4$ are each independently CH or N, and
m is 1 to 4.

In still another embodiment, compounds are provided having the structure (V):

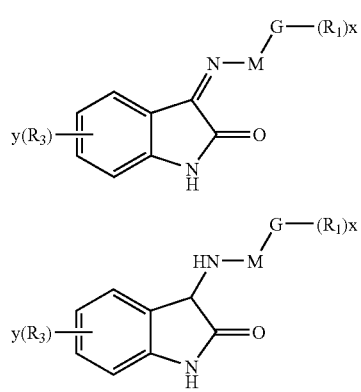

wherein:
$R_1$, x, and y are as defined above,
$R_3$ is —H, —SO$_3$H, or —SO$_2$NMe$_2$,
M is NH, CO, SO$_2$, (CH$_2$)p, wherein p is 0 to 2,
G is aryl or heteroaryl, and
x and y are each independently 0–4.

In a further embodiment, there are provided methods for treating disorders associated with compromised vasculostasis, including administering to a subject in need thereof an effective amount of a compound having the structure (VI):

wherein:
A and B are each independently 5- or 6-membered aromatic rings, wherein at least one of A and B is an aromatic heterocyclic ring having at least one heteroatom in the heterocyclic ring,
each X is independently —H, OR, NR$_2$, or SR, wherein R is H or lower alkyl,
each Y is independently hydrogen, alkyl, substituted alkyl, alkenyl,
substituted alkenyl, alkynyl, substituted alkynyl, cycloalkyl,
substituted cycloalkyl, heterocyclic, substituted heterocyclic, aryl,
substituted aryl, heteroaryl, substituted heteroaryl, alkylaryl, substituted alkylaryl, arylalkyl, substituted arylalkyl, arylalkenyl, substituted arylalkenyl, arylalkynyl, substituted
arylalkynyl, or oxo, with the proviso
that at least one Y is not hydrogen, or
when n is 2, each Y is taken together to form a fused aromatic ring system comprising at least one aromatic ring, and
m and n are each independently 1 to 4, thereby treating the disorder.

In yet another embodiment, invention methods include administering to a subject in need thereof an effective amount of a compound having the structure (VII):

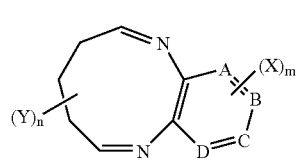

wherein:
A, B, C, and D are each independently C, N, O, or S,
each X is independently OR, NR$_2$, or SR, wherein R is H or lower alkyl,
each Y is independently hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, with the proviso that at least one Y is not hydrogen, and
m and n are each independently 1 to 4, thereby treating the disorder.

In another embodiment, the invention provides a method for treating a disorder associated with compromised vasculostasis, comprising administering to a subject in need thereof an effective amount of a compound having the structure:

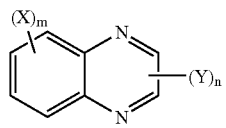

wherein:
  each X is independently H, OR, NR$_2$, or SR, wherein R is H or lower alkyl,
  each Y is independently hydrogen, alkyl, substituted alkyl, alkenyl substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, with the proviso that at least one Y is not hydrogen, or
  when n is 2, each Y is taken together to form a fused aromatic ring system comprising at least one aromatic ring,
  m is 1 to 4, and
  n is 1 or 2, thereby treating the disorder.

In another embodiment, the invention provides a method for treating a disorder associated with compromised vasculostasis, comprising administering to a subject in need thereof an effective amount of a compound having the structure:

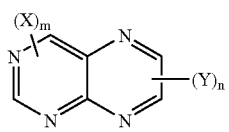

wherein:
  each X is independently H, OR, NR$_2$, or SR, wherein R is H or lower alkyl,
  each Y is independently hydrogen, alkyl, substituted alkyl, alkenyl substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, with the proviso that at least one Y is not hydrogen, or
  when n is 2, each Y is taken together to form a fused aromatic ring system comprising at least one aromatic ring, and
  m and n are each independently 1 or 2.

In another embodiment, the invention provides a method for treating a disorder associated with compromised vasculostasis, comprising administering to a subject in need thereof an effective amount of a compound having the structure:

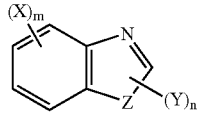

wherein:
  Z is N, O, or S;
  each X is independently H, OR, NR$_2$, or SR, wherein R is H or lower alkyl,
  each Y is independently hydrogen, alkyl, substituted alkyl, alkenyl substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, with the proviso that at least one Y is not hydrogen, or
  when n is 2, each Y is taken together to form a fused aromatic ring system comprising at least one aromatic ring, and
  m is 1 to 4, and
  n is 1 or 2.

In another embodiment, the invention provides a method for treating a disorder associated with compromised vasculostasis comprising administering to a subject in need thereof an effective amount of a compound having structure (VII):

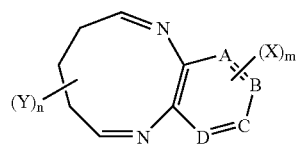

VII wherein:
  A, B, C, and D are each independently C, N, O, or S,
  each X is independently H, OR, NR$_2$, or SR, wherein R is H or lower alkyl,
  each Y is independently hydrogen, alkyl, substituted alkyl,
  alkenyl, substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, with the proviso that at least one Y is not hydrogen, and
  m and n are each independently 1 to 4, thereby treating the disorder.

In one embodiment, the invention provides a method for treating a disorder associated with compromised vasculostasis, comprising administering to a subject in need thereof an effective amount of a compound, wherein the compound is set forth in Structures I, II, III, IIIa, IV, V, or any combination thereof. The disorder is for example, but not limited to, myocardial infarction, stroke, congestive heart failure, an ischemia or reperfusion injury, cancer, arthritis or other arthropathy, retinopathy or vitreoretinal disease, macular degeneration, autoimmune disease, vascular leakage syndrome, inflammatory disease, edema, transplant rejection, burn, or acute or adult respiratory distress syndrome (ARDS).

In still another embodiment, there are provided articles of manufacture including packaging material and a pharmaceutical composition contained within the packaging material, wherein the pharmaceutical composition is capable of treating a disorder associated with compromised vasculostasis, wherein the pharmaceutical composition comprises at least one compound having any one of the structures as set forth above.

In one embodiment, the invention provides a pharmaceutical composition comprising a compound as set forth in Structures I, II, III, IIIa, IV, V, or VII, or any combination thereof, in a pharmaceutically acceptable carrier.

In one embodiment, the invention provides an article of manufacture comprising packaging material and a pharmaceutical composition contained within said packaging material, wherein said packaging material comprises a label which indicates that said pharmaceutical composition can be used for treatment of disorders associated with compromised vasculostasis and wherein said pharmaceutical composition comprises a compound set forth in Structures I, II, III, IIIa, IV, V, VI or VII, or any combination thereof.

In one embodiment, the invention provides an article of manufacture comprising packaging material and a pharmaceutical composition contained within said packaging material, wherein said packaging material comprises a label which indicates that said pharmaceutical composition can be used for treatment of disorders associated with vascular permeability leakage or compromised vasculostasis selected from is myocardial infarction, stroke, congestive heart failure, an ischemia or reperfusion injury, cancer, arthritis or other arthropathy, retinopathy or vitreoretinal disease, macular degeneration, autoimmune disease, vascular leakage syndrome, inflammatory disease, edema, transplant rejection, burns, or acute or adult respiratory distress syndrome (ARDS) and wherein said pharmaceutical composition comprises a compound set forth in Structures I, II, III, IIIa, IV, V, VI or VII, or any combination thereof.

In one embodiment, the invention provides a method of treating a compromised vasculostasis disorder, comprising the administration of a therapeutically effective amount of at least one compound set forth in Structures I, II, III, IIIa, IV, V, VI or VII, or any combination thereof, or pharmaceutically acceptable salts, hydrates, solvates, crystal forms and individual diastereomers thereof, to a subject in need of such treatment.

In one embodiment, the invention provides a method of treating a disorder associated with vasculostasis, comprising the administration of a therapeutically effective amount of at least one compound as set forth in Structures I, II, III, IIIa, IV, V, VI or VII, or any combination thereof, or pharmaceutically acceptable salts, hydrates, solvates, crystal forms and individual diastereomers thereof, in combination with an anti-inflammatory, chemotherapeutic agent, immunomodulatory agent, therapeutic antibody or a protein kinase inhibitor, to a subject in need of such treatment.

In one embodiment, the invention provides a method of treating a subject having or at risk of having myocardial infarction comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having vascular leakage syndrome (VLS) comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having cancer comprising administering to the subject a therapeutically effective amount of a compound as set forth in Structures I, II, III, IIIa, IV, V, or VII, or any combination thereof thereby treating the subject.

In one embodiment, the invention provides a method of treating a subject having or at risk of having stroke comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having ARDS comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having burns comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having arthritis comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having edema comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having vascular leakage syndrome (VLS) comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having retinopathy or vitreoretinal disease comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having ischemic or reperfusion related tissue injury or damage, comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having autoimmune disease, comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having transplant rejection, comprising administering to the subject a therapeutically effective amount of a compound as set forth in Structures I, II, III, IIIa, IV, V, VI or VII, or any combination thereof thereby treating the subject.

In one embodiment, the invention provides a method of treating a subject having or at risk of having inflammatory disease, comprising administering to the subject a therapeutically effective amount of a compound as set forth in Structures I, II, III, IIIa, IV, V, VI or VII, or any combination thereof thereby treating the subject.

In one embodiment, the invention provides a process for making a pharmaceutical composition comprising combining a combination of a compound set forth in Structures I, II, III, IIIa, IV, V, VI or VII, or any combination thereof or its pharmaceutically acceptable salts, hydrates, solvates, crystal forms salts and individual diastereomers thereof and a pharmaceutically acceptable carrier.

In one embodiment, the invention provides a pharmaceutical composition comprising a compound as set forth in Structure I, II, III, IIIa, IV, V, VII, or VIII in a pharmaceutically acceptable carrier.

In one embodiment, the invention provides a method for inhibiting or reducing vascular leakage in a subject, comprising administering to a subject in need thereof an effective amount of IL-2 in combination with a compound of Structure set forth in Structures I, II, III, IIIa, IV, V, VI or VII or any combination thereof, thereby reducing vascular leakage in the subject. In one aspect, the compound may be N-(2-(1H-Indol-2-yl)-phenyl)-phthalamic acid or 6,7-bis-(3-hydroxyphenyl)-pteridine-2,4-diamine.

In one embodiment, the invention provides a pharmaceutical composition comprising IL-2 and at least one compound as set forth in Structures I, II, III, IIIa, IV, V, VI or VII or any combination thereof, in a concentration effective to reduce vascular leakage associated with IL-2 administration.

In one embodiment, the invention provides a method for treating cancer or a tumor in a subject, comprising administering to a subject in need thereof an effective amount of a therapeutic antibody, chemotherapeutic agent or immunotoxic agents, in combination with a compound set forth in Structures I, II, III, IIIa, IV, V, VI or VII or any combination thereof, thereby treating the cancer or tumor in the subject.

In one embodiment, the invention provides a pharmaceutical composition comprising a therapeutic agent and at least one compound as set forth in Structures I, II, III, IIIa, IV, V, VI or VII or any combination thereof, in a concentration effective to treat cancer in a subject. The cancer may be any cancer, including but not limited to an alimentary/gastrointestinal tract cancer, colon cancer, liver cancer, skin cancer, breast cancer, ovarian cancer, prostate cancer, lymphoma, leukemia, kidney cancer, lung cancer, muscle cancer, bone cancer, bladder cancer or brain cancer.

In one embodiment, the invention provides a method for treating a T-cell mediated disorder, comprising the administration of a therapeutically effective amount of at least one compound set forth in Structures I, II, III, IIIa, IV, V, VI or VII, or any combination thereof or pharmaceutically acceptable salts, hydrates, solvates, crystal forms salts and individual diastereomers thereof, to a subject in need of such treatment.

DETAILED DESCRIPTION OF THE INVENTION

Figure 1A:
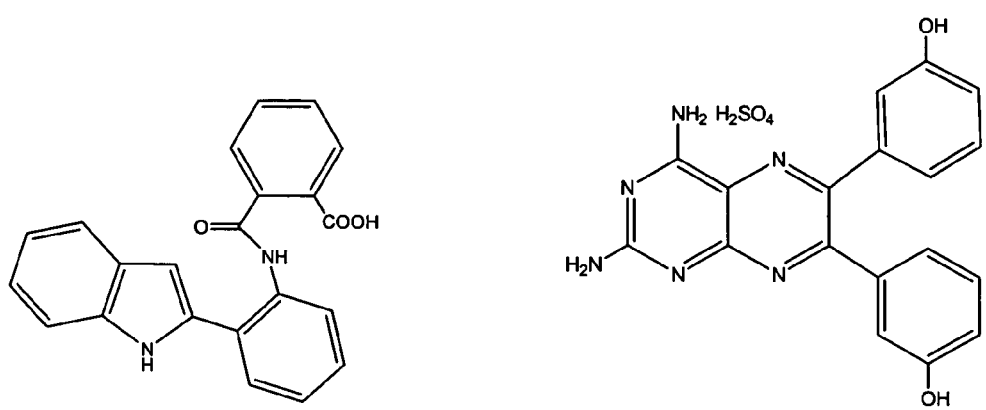
FIGS. 1A–1F shows exemplary compounds of the invention.
Figure 1B:
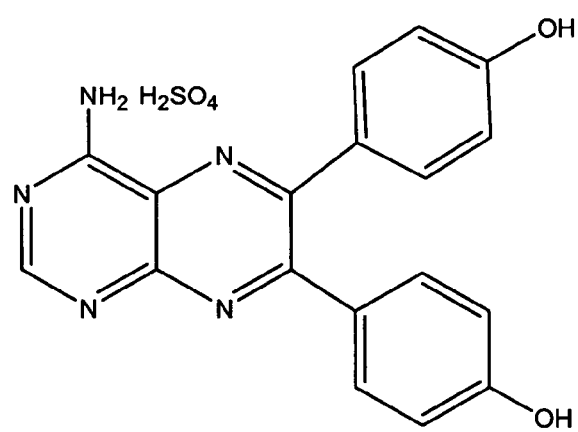
Figure 1C:
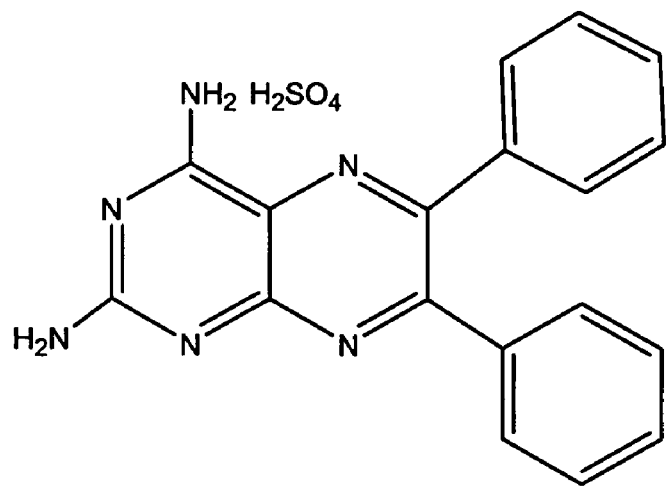
Figure 1D:
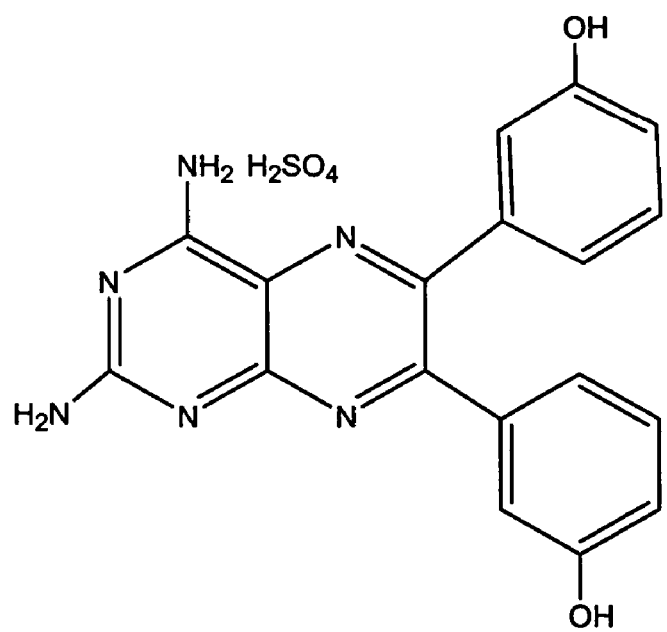
Figure 1E:
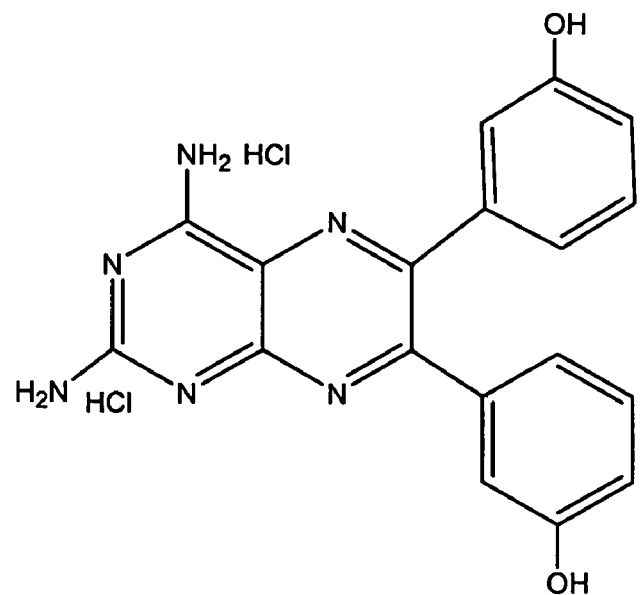
Figure 1F:
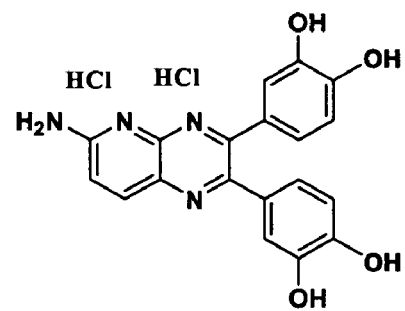

The invention provides compounds which are vasculostatic agents and methods of use thereof. Invention compounds are useful in treating a variety of disorders, including but not limited to myocardial infarction, stroke, cancer, vascular leakage syndrome (VLS), ocular and retinal disease, bone disease, pleural effusion, edema, and ischemia. The term "vasculostasis" is hereby defined as referring to the maintenance of a homeostatic vascular functioning, and "vasculostatic agents" as agents that seek to address conditions in which vasculostasis is compromised by preventing the loss of or restoring or maintaining vasculostasis.

In one embodiment, the present invention provides compounds of structure (I):

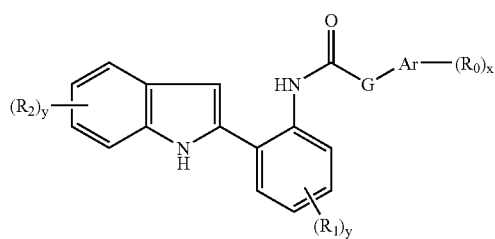

wherein:
each $R_0$ is independently —H, —COOH, —OR', —SO$_3$H, wherein R' is —H or lower alkyl, or when x=2, each $R_0$ is taken together to form a 1,3-dioxolyl ring, or
each $R_0$ is independently alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, halogen, amino, amido, nitro, or thioalkyl,
$R_1$ and $R_2$ are each independently hydrogen, alkyl, substituted alkyl, alkenyl substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, or substituted arylalkynyl,
G is NH, O, S, or $(CR''_2)_p$, wherein R'' is —H, lower alkyl, or acetamido, and wherein p is 0–3,
Ar is aryl or heteroaryl, and
x and y are each independently 0–4.

In one embodiment, $R_0$ is —COOH, x=1, and each $R_1$ and $R_2$ is hydrogen.

Exemplary compounds of structure I include:

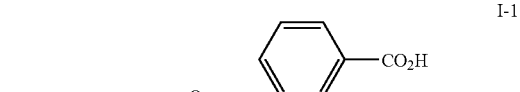

-continued
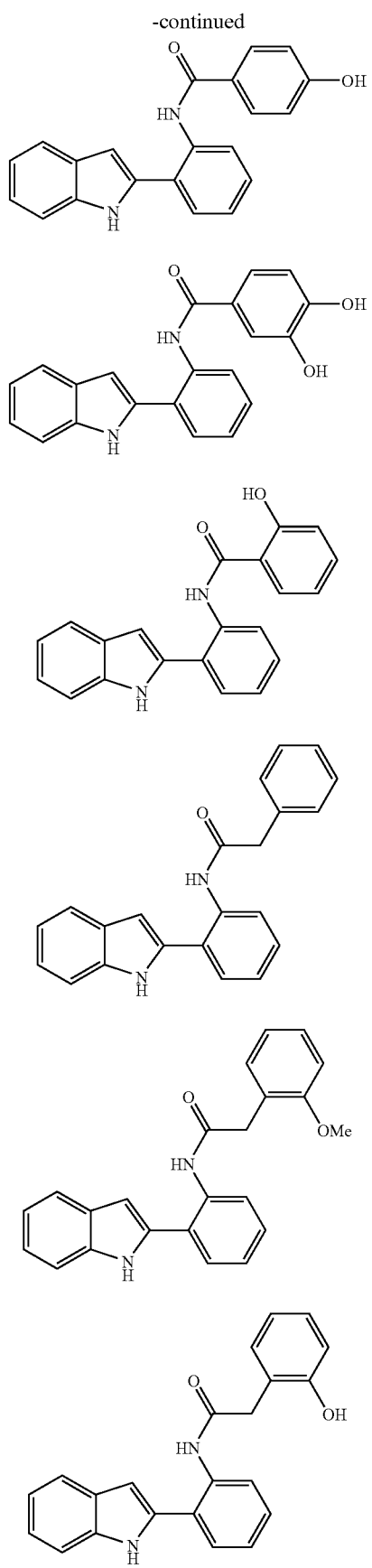
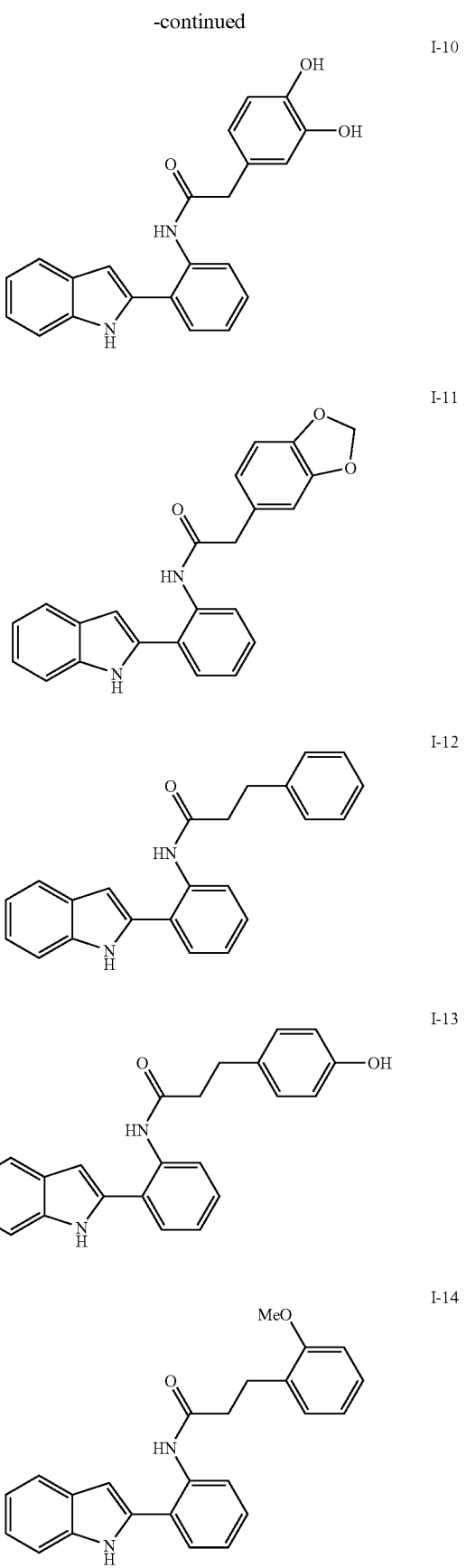

-continued

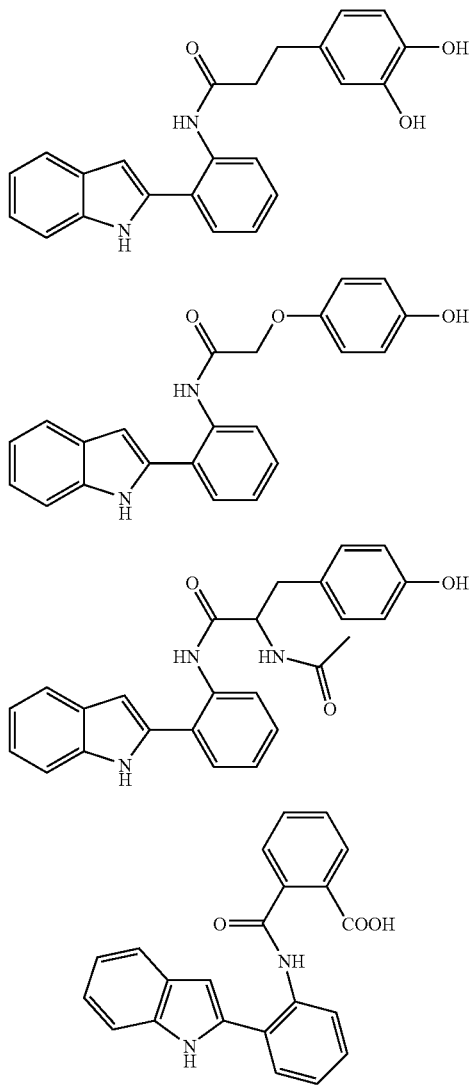

I-15

I-16

I-17

I-18

In another embodiment of the invention, there are provided compounds of structure (II):

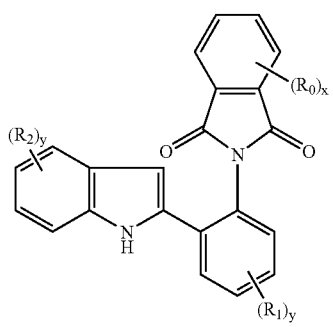

wherein:
  wherein $R_0$, $R_1$, and $R_2$, x, and y are as defined above.

In one embodiment, $R_0$ is —COOH, x=1, and $R_1$ and $R_2$ are each hydrogen.

In yet another embodiment of the invention, there are provided compounds of structure (III):

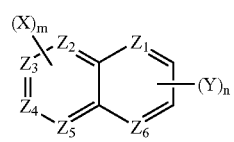

III wherein:
  $Z_1$–$Z_6$ are each independently C, —C=O, N, or $NR^a$, wherein $R^a$ is —H, alkyl, or substituted alkyl, wherein said substituents are halogen, hydroxy, oxo, or amino,
  each X is independently halogen, —$OR^b$, —$NR^b_2$, or —$SR^b$, wherein $R^b$ is —H lower alkyl, —$(CH_2)_2NH(CH_2CH_3)$, —$(CH_2)_3$morpholyn-1-yl, —$(CH_2)_3$(N-methylpiperazinyn-1-yl), aryl, heteroaryl, —(NH—NH—$R^c$), —(N=N—NH—$R^c$), wherein $R^c$ is H or lower alkyl,
  each Y is independently —$OR^d$, —$NR^d_2$, —$SR^d$, or —$OPO_3H_2$ wherein $R^d$ is H, lower alkyl, aryl, heteroaryl, —$(CH_2)_2NH(CH_2CH_3)$, —$(CH_2)_3$morpholyn-1-yl, or —$(CH_2)_3$(N-methylpiperazinyn-1-yl); or
  each Y is independently alkyl, substituted alkyl, aryl, substituted aryl, heteroaryl, substituted heteroaryl, or halogen, wherein said substituents are selected from halogen, —$OR^e$, —$NR^e_2$, —$SR^e$, —$P(O)(OH)_2$, wherein $R^e$ is —H, lower alkyl, aryl, or heteroaryl; or
  each Y is independently $CH_2$glycinyl, $CH_2$NHethoxy, $CH_2$NHCH$_2$alkyl, $CH_2$NHCH$_2$t-Bu, $CH_2$NHCH$_2$aryl, $CH_2$NHCH$_2$substituted aryl, $CH_2$NHCH$_2$heteroaryl, $CH_2$NHCH$_2$substituted heteroaryl; or when n is 2, each Y is taken together to form a fused aromatic or heteroaromatic ring system; and
  m and n are each independently 1 to 4,
  wherein when $Z_1$, $Z_3$, $Z_5$, and $Z_6$ are each N, X is $NH_2$, and m=n=2, Y is not phenyl or 4-hydroxyphenyl, or tautomers thereof.

Exemplary compounds of structure III include pteridines and quinoxalines, such as

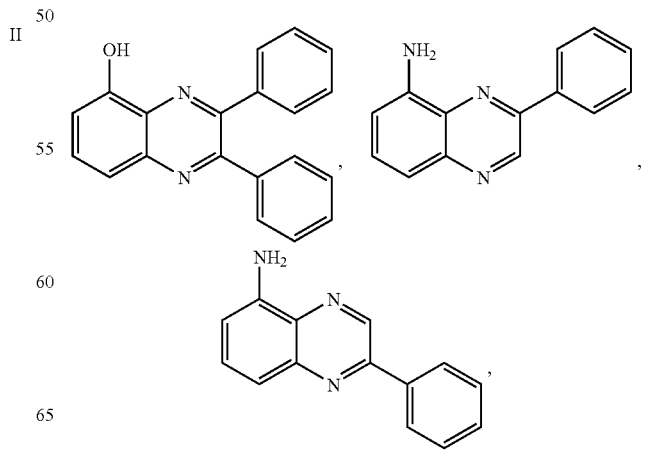

-continued

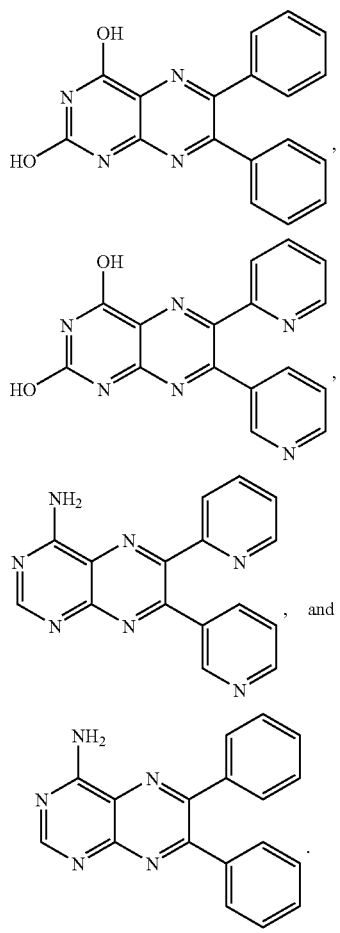

Particularly effective vasculostatic agents of structure (III) include compounds bearing hydroxy-substituted aryl rings. Exemplary compounds according to this embodiment are set forth below:

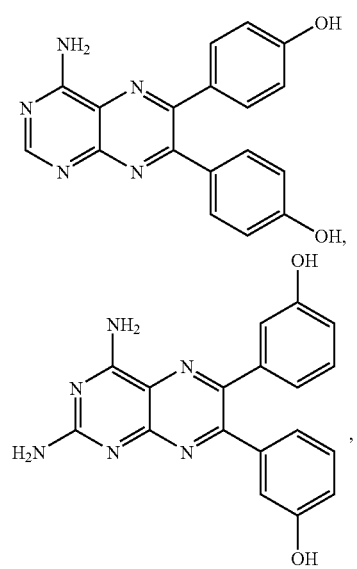

-continued

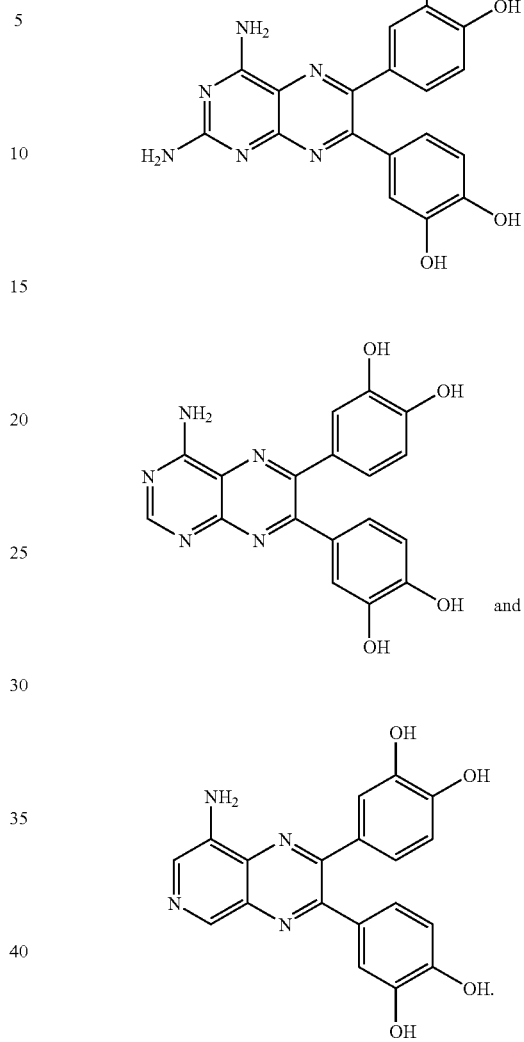

An additional exemplary compound of structure (III) is set forth below:

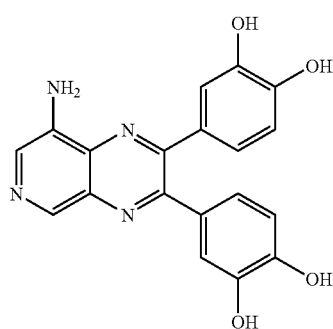

Additional exemplary compounds of structure (III) include pteridines having the structure:

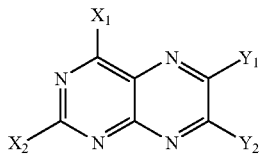

wherein when $X_1=X_2=$—NHR, wherein R is —H, aryl, or substituted aryl, $Y_1$ and $Y_2$ include but are not limited to the following structures III-1 to III-24:

| Structure | $Y_1$ | $Y_2$ |
|---|---|---|
| III-1 | $C_6H_5$ | H |
| III-2 | H | $C_6H_5$ |
| III-3 | $C_6H_5$ | $C_6H_5$ |
| III-4 | 4-$C_6H_4OH$ | H |
| III-5 | H | 4-$C_6H_4OH$ |
| III-6 | 3,4-$C_6H_3(OH)_2$ | H |
| III-7 | H | 3,4-$C_6H_3(OH)_2$ |
| III-8 | 4-$C_6H_4F$ | $C_6H_5$ |
| III-9 | $C_6H_5$ | 4-$C_6H_4F$ |
| III-10 | 4-$C_6H_4Br$ | $C_6H_5$ |
| III-11 | $C_6H_5$ | 4-$C_6H_4Br$ |
| III-12 | 4-$C_6H_4OPh$ | $C_6H_5$ |
| III-13 | $C_6H_5$ | 4-$C_6H_4OPh$ |
| III-14 | 4-$C_6H_4OH$ | $C_6H_5$ |
| III-15 | $C_6H_5$ | 4-$C_6H_4OH$ |
| III-16 | $C_5H_4N$ (pyr) | $C_5H_4N$ (pyr) |
| III-17 | 4-$C_6H_4F$ | 4-$C_6H_4F$ |
| III-18 | 3-$C_6H_4F$ | 3-$C_6H_4F$ |
| III-19 | 4-$C_6H_4OMe$ | 4-$C_6H_4OMe$ |
| III-20 | 3-$C_6H_4OMe$ | 3-$C_6H_4OMe$ |
| III-21 | 4-$C_6H_4OH$ | 4-$C_6H_4OH$ |
| III-22 | 3-$C_6H_4OH$ | 3-$C_6H_4OH$ |
| III-23 | 3,4-$C_6H_3(OH)_2$ | 3,4-$C_6H_3(OH)_2$ |
| III-24 | $Y_1$ and $Y_2$ taken together to form a phenathrolinyl group | |

Further exemplary pteridines have the structure $X_1=X_2=OR$, wherein R is —H, aryl, or substituted aryl, and $Y_1$ and $Y_2$ include but are not limited to the following the structures III-25 to III-48:

| Structure | $Y_1$ | $Y_2$ |
|---|---|---|
| III-25 | $C_6H_5$ | H |
| III-26 | H | $C_6H_5$ |
| III-27 | $C_6H_5$ | $C_6H_5$ |
| III-28 | 4-$C_6H_4OH$ | H |
| III-29 | H | 4-$C_6H_4OH$ |
| III-30 | 3,4-$C_6H_3(OH)_2$ | H |
| III-31 | H | 3,4-$C_6H_3(OH)_2$ |
| III-32 | 4-$C_6H_4F$ | $C_6H_5$ |
| III-33 | $C_6H_5$ | 4-$C_6H_4F$ |
| III-34 | 4-$C_6H_4Br$ | $C_6H_5$ |
| III-35 | $C_6H_5$ | 4-$C_6H_4Br$ |
| III-36 | 4-$C_6H_4OPh$ | $C_6H_5$ |
| III-37 | $C_6H_5$ | 4-$C_6H_4OPh$ |
| III-38 | 4-$C_6H_4OH$ | $C_6H_5$ |
| III-39 | $C_6H_5$ | 4-$C_6H_4OH$ |
| III-40 | $C_5H_4N$ (pyr) | $C_5H_4N$ (pyr) |
| III-41 | 4-$C_6H_4F$ | 4-$C_6H_4F$ |
| III-42 | 3-$C_6H_4F$ | 3-$C_6H_4F$ |
| III-43 | 4-$C_6H_4OMe$ | 4-$C_6H_4OMe$ |
| III-44 | 3-$C_6H_4OMe$ | 3-$C_6H_4OMe$ |
| III-45 | 4-$C_6H_4OH$ | 4-$C_6H_4OH$ |
| III-46 | 3-$C_6H_4OH$ | 3-$C_6H_4OH$ |
| III-47 | 3,4-$C_6H_3(OH)_2$ | 3,4-$C_6H_3(OH)_2$ |
| III-48 | $Y_1$ and $Y_2$ taken together to form a phenathrolinyl group | |

Further exemplary pteridines have the structure $X_1=OR$ and $X_2=NHR$, wherein R is —H, aryl or substituted aryl, and $Y_1$ and $Y_2$ include but are not limited to the following structures

| Structure | $Y_1$ | $Y_2$ |
|---|---|---|
| III-49 | $C_6H_5$ | H |
| III-50 | H | $C_6H_5$ |
| III-51 | $C_6H_5$ | $C_6H_5$ |
| III-52 | 4-$C_6H_4OH$ | H |
| III-53 | H | 4-$C_6H_4OH$ |
| III-54 | 3,4-$C_6H_3(OH)_2$ | H |
| III-55 | H | 3,4-$C_6H_3(OH)_2$ |
| III-56 | 4-$C_6H_4F$ | $C_6H_5$ |
| III-57 | $C_6H_5$ | 4-$C_6H_4F$ |
| III-58 | 4-$C_6H_4Br$ | $C_6H_5$ |
| III-59 | $C_6H_5$ | 4-$C_6H_4Br$ |
| III-60 | 4-$C_6H_4OPh$ | $C_6H_5$ |
| III-61 | $C_6H_5$ | 4-$C_6H_4OPh$ |
| III-62 | 4-$C_6H_4OH$ | $C_6H_5$ |
| III-63 | $C_6H_5$ | 4-$C_6H_4OH$ |
| III-64 | $C_5H_4N$ (pyr) | $C_5H_4N$ (pyr) |
| III-65 | 4-$C_6H_4F$ | 4-$C_6H_4F$ |
| III-66 | 3-$C_6H_4F$ | 3-$C_6H_4F$ |
| III-67 | 4-$C_6H_4OMe$ | 4-$C_6H_4OMe$ |
| III-68 | 3-$C_6H_4OMe$ | 3-$C_6H_4OMe$ |
| III-69 | 4-$C_6H_4OH$ | 4-$C_6H_4OH$ |
| III-70 | 3-$C_6H_4OH$ | 3-$C_6H_4OH$ |
| III-71 | 3,4-$C_6H_3(OH)_2$ | 3,4-$C_6H_3(OH)_2$ |
| III-72 | $Y_1$ and $Y_2$ taken together to form a phenathrolinyl group | |

Further exemplary pteridines have the structure $X_1=NHR$ and $X_2=OR$, wherein R is —H, aryl or substituted aryl, and $Y_1$ and $Y_2$ include but are not limited to the following structures

| Structure | $Y_1$ | $Y_2$ |
|---|---|---|
| III-73 | $C_6H_5$ | H |
| III-74 | H | $C_6H_5$ |
| III-75 | $C_6H_5$ | $C_6H_5$ |
| III-76 | 4-$C_6H_4OH$ | H |
| III-77 | H | 4-$C_6H_4OH$ |
| III-78 | 3,4-$C_6H_3(OH)_2$ | H |
| III-79 | H | 3,4-$C_6H_3(OH)_2$ |
| III-80 | 4-$C_6H_4F$ | $C_6H_5$ |
| III-81 | $C_6H_5$ | 4-$C_6H_4F$ |
| III-82 | 4-$C_6H_4Br$ | $C_6H_5$ |
| III-83 | $C_6H_5$ | 4-$C_6H_4Br$ |
| III-84 | 4-$C_6H_4OPh$ | $C_6H_5$ |
| III-85 | $C_6H_5$ | 4-$C_6H_4OPh$ |
| III-86 | 4-$C_6H_4OH$ | $C_6H_5$ |
| III-87 | $C_6H_5$ | 4-$C_6H_4OH$ |
| III-88 | $C_5H_4N$ (pyr) | $C_5H_4N$ (pyr) |
| III-89 | 4-$C_6H_4F$ | 4-$C_6H_4F$ |
| III-90 | 3-$C_6H_4F$ | 3-$C_6H_4F$ |
| III-91 | 4-$C_6H_4OMe$ | 4-$C_6H_4OMe$ |
| III-92 | 3-$C_6H_4OMe$ | 3-$C_6H_4OMe$ |
| III-93 | 4-$C_6H_4OH$ | 4-$C_6H_4OH$ |
| III-94 | 3-$C_6H_4OH$ | 3-$C_6H_4OH$ |
| III-95 | 3,4-$C_6H_3(OH)_2$ | 3,4-$C_6H_3(OH)_2$ |
| III-96 | $Y_1$ and $Y_2$ taken together to form a phenathrolinyl group | |

Additional exemplary pteridines have the structure

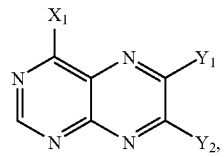

wherein $X_1$=NHR, wherein R is —H, aryl or substituted aryl, and $Y_1$ and $Y_2$ include but are not limited to the following structures:

| Structure | $Y_1$ | $Y_2$ |
| --- | --- | --- |
| III-97 | $C_6H_5$ | H |
| III-98 | H | $C_6H_5$ |
| III-99 | $C_6H_5$ | $C_6H_5$ |
| III-100 | 4-$C_6H_4$OH | H |
| III-101 | H | 4-$C_6H_4$OH |
| III-102 | 3,4-$C_6H_3(OH)_2$ | H |
| III-103 | H | 3,4-$C_6H_3(OH)_2$ |
| III-104 | 4-$C_6H_4$F | $C_6H_5$ |
| III-105 | $C_6H_5$ | 4-$C_6H_4$F |
| III-106 | 4-$C_6H_4$Br | $C_6H_5$ |
| III-107 | $C_6H_5$ | 4-$C_6H_4$Br |
| III-108 | 4-$C_6H_4$OPh | $C_6H_5$ |
| III-109 | $C_6H_5$ | 4-$C_6H_4$OPh |
| III-110 | 4-$C_6H_4$OH | $C_6H_5$ |
| III-111 | $C_6H_5$ | 4-$C_6H_4$OH |
| III-112 | $C_5H_4$N (pyr) | $C_5H_4$N (pyr) |
| III-113 | 4-$C_6H_4$F | 4-$C_6H_4$F |
| III-114 | 3-$C_6H_4$F | 3-$C_6H_4$F |
| III-115 | 4-$C_6H_4$OMe | 4-$C_6H_4$OMe |
| III-116 | 3-$C_6H_4$OMe | 3-$C_6H_4$OMe |
| III-117 | 4-$C_6H_4$OH | 4-$C_6H_4$OH |
| III-118 | 3-$C_6H_4$OH | 3-$C_6H_4$OH |
| III-119 | 3,4-$C_6H_3(OH)_2$ | 3,4-$C_6H_3(OH)_2$ |
| III-120 | $Y_1$ and $Y_2$ taken together to form a phenathrolinyl group. | |

Still further exemplary pteridines have the structure:

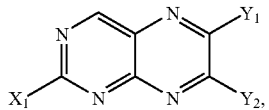

wherein $X_1$=NHR, wherein R is —H, aryl or substituted aryl, and $Y_1$ and $Y_2$ include but are not limited to the following structures:

| Structure | $Y_1$ | $Y_2$ |
| --- | --- | --- |
| III-121 | $C_6H_5$ | H |
| III-122 | H | $C_6H_5$ |
| III-123 | $C_6H_5$ | $C_6H_5$ |
| III-124 | 4-$C_6H_4$OH | H |
| III-125 | H | 4-$C_6H_4$OH |
| III-126 | 3,4-$C_6H_3(OH)_2$ | H |
| III-127 | H | 3,4-$C_6H_3(OH)_2$ |
| III-128 | 4-$C_6H_4$F | $C_6H_5$ |
| III-129 | $C_6H_5$ | 4-$C_6H_4$F |
| III-130 | 4-$C_6H_4$Br | $C_6H_5$ |
| III-131 | $C_6H_5$ | 4-$C_6H_4$Br |
| III-132 | 4-$C_6H_4$OPh | $C_6H_5$ |

| Structure | $Y_1$ | $Y_2$ |
| --- | --- | --- |
| III-133 | $C_6H_5$ | 4-$C_6H_4$OPh |
| III-134 | 4-$C_6H_4$OH | $C_6H_5$ |
| III-135 | $C_6H_5$ | 4-$C_6H_4$OH |
| III-136 | $C_5H_4$N (pyr) | $C_5H_4$N (pyr) |
| III-137 | 4-$C_6H_4$F | 4-$C_6H_4$F |
| III-138 | 3-$C_6H_4$F | 3-$C_6H_4$F |
| III-139 | 4-$C_6H_4$OMe | 4-$C_6H_4$OMe |
| III-140 | 3-$C_6H_4$OMe | 3-$C_6H_4$OMe |
| III-141 | 4-$C_6H_4$OH | 4-$C_6H_4$OH |
| III-142 | 3-$C_6H_4$OH | 3-$C_6H_4$OH |
| III-143 | 3,4-$C_6H_3(OH)_2$ | 3,4-$C_6H_3(OH)_2$ |
| III-144 | $Y_1$ and Y2 taken together to form a phenathrolinyl group. | |

Additional exemplary pteridines have the structure

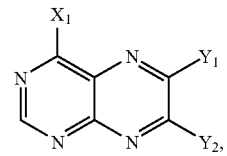

wherein $X_1$=OR, wherein R is —H, aryl or substituted aryl, and $Y_1$ and $Y_2$ include but are not limited to the following structures:

| Structure | $Y_1$ | $Y_2$ |
| --- | --- | --- |
| III-145 | $C_6H_5$ | H |
| III-146 | H | $C_6H_5$ |
| III-147 | $C_6H_5$ | $C_6H_5$ |
| III-148 | 4-$C_6H_4$OH | H |
| III-149 | H | 4-$C_6H_4$OH |
| III-150 | 3,4-$C_6H_3(OH)_2$ | H |
| III-151 | H | 3,4-$C_6H_3(OH)_2$ |
| III-152 | 4-$C_6H_4$F | $C_6H_5$ |
| III-153 | $C_6H_5$ | 4-$C_6H_4$F |
| III-154 | 4-$C_6H_4$Br | $C_6H_5$ |
| III-155 | $C_6H_5$ | 4-$C_6H_4$Br |
| III-156 | 4-$C_6H_4$OPh | $C_6H_5$ |
| III-157 | $C_6H_5$ | 4-$C_6H_4$OPh |
| III-158 | 4-$C_6H_4$OH | $C_6H_5$ |
| III-159 | $C_6H_5$ | 4-$C_6H_4$OH |
| III-160 | $C_5H_4$N (pyr) | $C_5H_4$N (pyr) |
| III-161 | 4-$C_6H_4$F | 4-$C_6H_4$F |
| III-162 | 3-$C_6H_4$F | 3-$C_6H_4$F |
| III-163 | 4-$C_6H_4$OMe | 4-$C_6H_4$OMe |
| III-164 | 3-$C_6H_4$OMe | 3-$C_6H_4$OMe |
| III-165 | 4-$C_6H_4$OH | 4-$C_6H_4$OH |
| III-166 | 3-$C_6H_4$OH | 3-$C_6H_4$OH |
| III-167 | 3,4-$C_6H_3(OH)_2$ | 3,4-$C_6H_3(OH)_2$ |
| III-168 | $Y_1$ and $Y_2$ taken together to form a phenathrolinyl group. | |

Additional exemplary pteridines have the structure

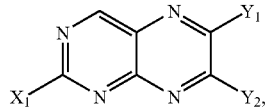

wherein $X_1$=OR, wherein R is —H, aryl or substituted aryl, and $Y_1$ and $Y_2$ include but are not limited to the following structures:

| Structure | Y₁ | Y₂ |
|---|---|---|
| III-169 | C₆H₅ | H |
| III-170 | H | C₆H₅ |
| III-171 | C₆H₅ | C₆H₅ |
| III-172 | 4-C₆H₄OH | H |
| III-173 | H | 4-C₆H₄OH |
| III-174 | 3,4-C₆H₃(OH)₂ | H |
| III-175 | H | 3,4-C₆H₃(OH)₂ |
| III-176 | 4-C₆H₄F | C₆H₅ |
| III-177 | C₆H₅ | 4-C₆H₄F |
| III-178 | 4-C₆H₄Br | C₆H₅ |
| III-179 | C₆H₅ | 4-C₆H₄Br |
| III-180 | 4-C₆H₄OPh | C₆H₅ |
| III-181 | C₆H₅ | 4-C₆H₄OPh |
| III-182 | 4-C₆H₄OH | C₆H₅ |
| III-183 | C₆H₅ | 4-C₆H₄OH |
| III-184 | C₅H₄N (pyr) | C₅H₄N (pyr) |
| III-185 | 4-C₆H₄F | 4-C₆H₄F |
| III-186 | 3-C₆H₄F | 3-C₆H₄F |
| III-187 | 4-C₆H₄OMe | 4-C₆H₄OMe |
| III-188 | 3-C₆H₄OMe | 3-C₆H₄OMe |
| III-189 | 4-C₆H₄OH | 4-C₆H₄OH |
| III-190 | 3-C₆H₄OH | 3-C₆H₄OH |
| III-191 | 3,4-C₆H₃(OH)₂ | 3,4-C₆H₃(OH)₂ |
| III-192 | Y₁ and Y₂ taken together to form aphenathrolinyl group. | |

In further embodiments, exemplary pteridines have the structure:

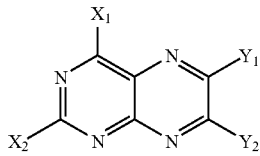

wherein $X_1=X_2=$Cl or NHR, wherein R is H, (CH₂)₂NHEt, (CH₂)₃morpholyn-1-yl, (CH₂)₃(N-methylpiperazinyn-1-yl); $Y_1=$CH₂glycinyl, CH₂NHethoxy, CH₂NHCH₂alkyl, CH₂NHCH₂t-Bu, CH₂NHCH₂aryl, CH₂NHCH₂substituted aryl, CH₂NHCH₂heteroaryl, CH₂NHCH₂substituted heteroaryl with substituents being OH, and OMe, and Y₂ includes but is not limited to the following structures:

| Structure | Y₂ |
|---|---|
| III-193 | C₆H₅ |
| III-194 | H |
| III-195 | 4-C₆H₄OH |
| III-196 | 3-C₆H₄OH |
| III-197 | 2-C₆H₄OH |
| III-198 | naphthyl |
| III-199 | isonaphthyl |
| III-200 | 4-tBuphenyl |
| III-201 | biphenyl |
| III-202 | 2,3-di-methylphenyl |
| III-203 | fluorenyl |
| III-204 | oxophenyl |
| III-205 | thioindole |
| III-206 | C₅H₄N (pyr) |
| III-207 | 4-C₆H₄F |
| III-208 | 3-C₆H₄F |
| III-209 | 4-C₆H₄OMe |
| III-210 | 3-C₆H₄OMe |
| III-211 | 2-C₆H₄OMe. |

Additional exemplary compounds of structure (III) include compounds having the structure:

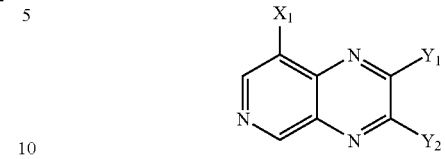

wherein $X_1=$NHR, wherein R is H, aryl or substituted aryl, and Y₁ and Y₂ include but are not limited to the following structures:

| Structure | Y₁ | Y₂ |
|---|---|---|
| III-212 | C₆H₅ | H |
| III-213 | H | C₆H₅ |
| III-214 | C₆H₅ | C₆H₅ |
| III-215 | 4-C₆H₄OH | H |
| III-216 | H | 4-C₆H₄OH |
| III-217 | 3,4-C₆H₃(OH)₂ | H |
| III-218 | H | 3,4-C₆H₃(OH)₂ |
| III-219 | 4-C₆H₄F | C₆H₅ |
| III-220 | C₆H₅ | 4-C₆H₄F |
| III-221 | 4-C₆H₄Br | C₆H₅ |
| III-222 | C₆H₅ | 4-C₆H₄Br |
| III-223 | 4-C₆H₄OPh | C₆H₅ |
| III-224 | C₆H₅ | 4-C₆H₄OPh |
| III-225 | 4-C₆H₄OH | C₆H₅ |
| III-226 | C₆H₅ | 4-C₆H₄OH |
| III-227 | C₅H₄N (pyr) | C₅H₄N (pyr) |
| III-228 | 4-C₆H₄F | 4-C₆H₄F |
| III-229 | 3-C₆H₄F | 3-C₆H₄F |
| III-230 | 4-C₆H₄OMe | 4-C₆H₄OMe |
| III-231 | 3-C₆H₄OMe | 3-C₆H₄OMe |
| III-232 | 4-C₆H₄OH | 4-C₆H₄OH |
| III-233 | 3-C₆H₄OH | 3-C₆H₄OH |
| III-234 | 3,4-C₆H₃(OH)₂ | 3,4-C₆H₃(OH)₂ |
| III-235 | Y₁ and Y₂ taken together to form aphenathrolinyl group. | |

Still further exemplary compounds of structure (III) include the following:

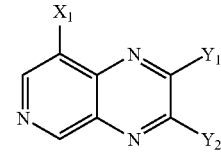

wherein $X_1=$OR, wherein R is H, aryl or substituted aryl, and Y₁ and Y₂ include but are not limited to the following structures:

| Structure | Y₁ | Y₂ |
|---|---|---|
| III-236 | C₆H₅ | H |
| III-237 | H | C₆H₅ |
| III-238 | C₆H₅ | C₆H₅ |
| III-239 | 4-C₆H₄OH | H |
| III-240 | H | 4-C₆H₄OH |
| III-241 | 3,4-C₆H₃(OH)₂ | H |
| III-242 | H | 3,4-C₆H₃(OH)₂ |

-continued

| Structure | Y₁ | Y₂ |
| --- | --- | --- |
| III-243 | 4-C₆H₄F | C₆H₅ |
| III-244 | C₆H₅ | 4-C₆H₄F |
| III-245 | 4-C₆H₄Br | C₆H₅ |
| III-246 | C₆H₅ | 4-C₆H₄Br |
| III-247 | 4-C₆H₄OPh | C₆H₅ |
| III-248 | C₆H₅ | 4-C₆H₄OPh |
| III-249 | 4-C₆H₄OH | C₆H₅ |
| III-250 | C₆H₅ | 4-C₆H₄OH |
| III-251 | C₅H₄N (pyr) | C₅H₄N (pyr) |
| III-252 | 4-C₆H₄F | 4-C₆H₄F |
| III-253 | 3-C₆H₄F | 3-C₆H₄F |
| III-254 | 4-C₆H₄OMe | 4-C₆H₄OMe |
| III-255 | 3-C₆H₄OMe | 3-C₆H₄OMe |
| III-256 | 4-C₆H₄OH | 4-C₆H₄OH |
| III-257 | 3-C₆H₄OH | 3-C₆H₄OH |
| III-258 | 3,4-C₆H₃(OH)₂ | 3,4-C₆H₃(OH)₂ |
| III-259 | Y₁ and Y₂ taken together to form a phenathrolinyl group. | |

Compounds of structure (III) also include the following:

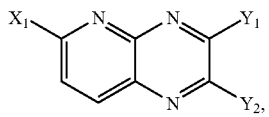

wherein X₁=NHR, wherein R is H, aryl or substituted aryl, and Y₁ and Y₂ include but are not limited to the following structures:

| Structure | Y₁ | Y₂ |
| --- | --- | --- |
| III-260 | C₆H₅ | H |
| III-261 | H | C₆H₅ |
| III-262 | C₆H₅ | C₆H₅ |
| III-263 | 4-C₆H₄OH | H |
| III-264 | H | 4-C₆H₄OH |
| III-265 | 3,4-C₆H₃(OH)₂ | H |
| III-266 | H | 3,4-C₆H₃(OH)₂ |
| III-267 | 4-C₆H₄F | C₆H₅ |
| III-268 | C₆H₅ | 4-C₆H₄F |
| III-269 | 4-C₆H₄Br | C₆H₅ |
| III-270 | C₆H₅ | 4-C₆H₄Br |
| III-271 | 4-C₆H₄OPh | C₆H₅ |
| III-272 | C₆H₅ | 4-C₆H₄OPh |
| III-273 | 4-C₆H₄OH | C₆H₅ |
| III-274 | C₆H₅ | 4-C₆H₄OH |
| III-275 | C₅H₄N (pyr) | C₅H₄N (pyr) |
| III-276 | 4-C₆H₄F | 4-C₆H₄F |
| III-277 | 3-C₆H₄F | 3-C₆H₄F |
| III-278 | 4-C₆H₄OMe | 4-C₆H₄OMe |
| III-279 | 3-C₆H₄OMe | 3-C₆H₄OMe |
| III-280 | 4-C₆H₄OH | 4-C₆H₄OH |
| III-281 | 3-C₆H₄OH | 3-C₆H₄OH |
| III-282 | 3,4-C₆H₃(OH)₂ | 3,4-C₆H₃(OH)₂ |
| III-283 | Y₁ and Y₂ taken together to form a phenathrolinyl group. | |

Still further exemplary compounds of structure (III) include;

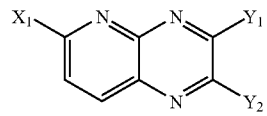

wherein X₁=OR, wherein R is H, aryl or substituted aryl, and Y₁ and Y₂ include but are not limited to the following structures:

| Structure | Y₁ | Y₂ |
| --- | --- | --- |
| III-284 | C₆H₅ | H |
| III-285 | H | C₆H₅ |
| III-286 | C₆H₅ | C₆H₅ |
| III-287 | 4-C₆H₄OH | H |
| III-288 | H | 4-C₆H₄OH |
| III-289 | 3,4-C₆H₃(OH)₂ | H |
| III-290 | H | 3,4-C₆H₃(OH)₂ |
| III-291 | 4-C₆H₄F | C₆H₅ |
| III-292 | C₆H₅ | 4-C₆H₄F |
| III-293 | 4-C₆H₄Br | C₆H₅ |
| III-294 | C₆H₅ | 4-C₆H₄Br |
| III-295 | 4-C₆H₄OPh | C₆H₅ |
| III-296 | C₆H₅ | 4-C₆H₄OPh |
| III-297 | 4-C₆H₄OH | C₆H₅ |
| III-298 | C₆H₅ | 4-C₆H₄OH |
| III-299 | C₅H₄N (pyr) | C₅H₄N (pyr) |
| III-300 | 4-C₆H₄F | 4-C₆H₄F |
| III-301 | 3-C₆H₄F | 3-C₆H₄F |
| III-302 | 4-C₆H₄OMe | 4-C₆H₄OMe |
| III-303 | 3-C₆H₄OMe | 3-C₆H₄OMe |
| III-304 | 4-C₆H₄OH | 4-C₆H₄OH |
| III-305 | 3-C₆H₄OH | 3-C₆H₄OH |
| III-306 | 3,4-C₆H₃(OH)₂ | 3,4-C₆H₃(OH)₂ |
| III-307 | Y₁ and Y₂ taken together to form a phenathrolinyl group. | |

Additional exemplary compounds of structure (III) include quinoxalines having the structure:

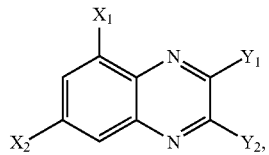

wherein X₁=NHR and X₂=NHR, wherein R is H, aryl or substituted aryl, and Y₁ and Y₂ include but are not limited to the following structures:

| Structure | Y₁ | Y₂ |
| --- | --- | --- |
| III-308 | C₆H₅ | H |
| III-309 | H | C₆H₅ |
| III-310 | C₆H₅ | C₆H₅ |
| III-311 | 4-C₆H₄OH | H |
| III-312 | H | 4-C₆H₄OH |
| III-313 | 3,4-C₆H₃(OH)₂ | H |
| III-314 | H | 3,4-C₆H₃(OH)₂ |
| III-315 | 4-C₆H₄F | C₆H₅ |
| III-316 | C₆H₅ | 4-C₆H₄F |

-continued

| Structure | Y$_1$ | Y$_2$ |
|---|---|---|
| III-317 | 4-C$_6$H$_4$Br | C$_6$H$_5$ |
| III-318 | C$_6$H$_5$ | 4-C$_6$H$_4$Br |
| III-319 | 4-C$_6$H$_4$OPh | C$_6$H$_5$ |
| III-320 | C$_6$H$_5$ | 4-C$_6$H$_4$OPh |
| III-321 | 4-C$_6$H$_4$OH | C$_6$H$_5$ |
| III-322 | C$_6$H$_5$ | 4-C$_6$H$_4$OH |
| III-323 | C$_5$H$_4$N (pyr) | C$_5$H$_4$N (pyr) |
| III-324 | 4-C$_6$H$_4$F | 4-C$_6$H$_4$F |
| III-325 | 3-C$_6$H$_4$F | 3-C$_6$H$_4$F |
| III-326 | 4-C$_6$H$_4$OMe | 4-C$_6$H$_4$OMe |
| III-327 | 3-C$_6$H$_4$OMe | 3-C$_6$H$_4$OMe |
| III-328 | 4-C$_6$H$_4$OH | 4-C$_6$H$_4$OH |
| III-329 | 3-C$_6$H$_4$OH | 3-C$_6$H$_4$OH |
| III-330 | 3,4-C$_6$H$_3$(OH)$_2$ | 3,4-C$_6$H$_3$(OH)$_2$ |
| III-331 | Y$_1$ and Y$_2$ taken together to form a phenathrolinyl group. | |

Additional quinoxalines contemplated for use in the practice of the invention include the following:

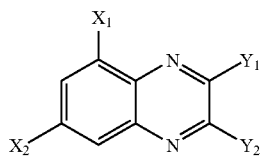

wherein X$_1$=X$_2$=OR, wherein R is —H, aryl or substituted aryl, and Y$_1$ and Y$_2$ include but are not limited to the following structures:

| Structure | Y$_1$ | Y$_2$ |
|---|---|---|
| III-332 | C$_6$H$_5$ | H |
| III-333 | H | C$_6$H$_5$ |
| III-334 | C$_6$H$_5$ | C$_6$H$_5$ |
| III-335 | 4-C$_6$H$_4$OH | H |
| III-336 | H | 4-C$_6$H$_4$OH |
| III-337 | 3,4-C$_6$H$_3$(OH)$_2$ | H |
| III-338 | H | 3,4-C$_6$H$_3$(OH)$_2$ |
| III-339 | 4-C$_6$H$_4$F | C$_6$H$_5$ |
| III-340 | C$_6$H$_5$ | 4-C$_6$H$_4$F |
| III-341 | 4-C$_6$H$_4$Br | C$_6$H$_5$ |
| III-342 | C$_6$H$_5$ | 4-C$_6$H$_4$Br |
| III-343 | 4-C$_6$H$_4$OPh | C$_6$H$_5$ |
| III-344 | C$_6$H$_5$ | 4-C$_6$H$_4$OPh |
| III-345 | 4-C$_6$H$_4$OH | C$_6$H$_5$ |
| III-346 | C$_6$H$_5$ | 4-C$_6$H$_4$OH |
| III-347 | C$_5$H$_4$N (pyr) | C$_5$H$_4$N (pyr) |
| III-348 | 4-C$_6$H$_4$F | 4-C$_6$H$_4$F |
| III-349 | 3-C$_6$H$_4$F | 3-C$_6$H$_4$F |
| III-350 | 4-C$_6$H$_4$OMe | 4-C$_6$H$_4$OMe |
| III-351 | 3-C$_6$H$_4$OMe | 3-C$_6$H$_4$OMe |
| III-352 | 4-C$_6$H$_4$OH | 4-C$_6$H$_4$OH |
| III-353 | 3-C$_6$H$_4$OH | 3-C$_6$H$_4$OH |
| III-354 | 3,4-C$_6$H$_3$(OH)$_2$ | 3,4-C$_6$H$_3$(OH)$_2$ |
| III-355 | Y$_1$ and Y$_2$ taken together to form a phenathrolinyl group. | |

Still further exemplary quinoxalines include:

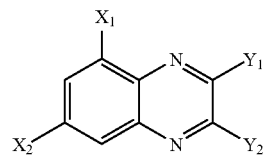

wherein when X$_1$=OR and X$_2$=NHR, wherein R is H, aryl or substituted aryl, and Y$_1$ and Y$_2$ include but are not limited to the following structures:

| Structure | Y$_1$ | Y$_2$ |
|---|---|---|
| III-356 | C$_6$H$_5$ | H |
| III-357 | H | C$_6$H$_5$ |
| III-358 | C$_6$H$_5$ | C$_6$H$_5$ |
| III-359 | 4-C$_6$H$_4$OH | H |
| III-360 | H | 4-C$_6$H$_4$OH |
| III-361 | 3,4-C$_6$H$_3$(OH)$_2$ | H |
| III-362 | H | 3,4-C$_6$H$_3$(OH)$_2$ |
| III-363 | 4-C$_6$H$_4$F | C$_6$H$_5$ |
| III-364 | C$_6$H$_5$ | 4-C$_6$H$_4$F |
| III-365 | 4-C$_6$H$_4$Br | C$_6$H$_5$ |
| III-366 | C$_6$H$_5$ | 4-C$_6$H$_4$Br |
| III-367 | 4-C$_6$H$_4$OPh | C$_6$H$_5$ |
| III-368 | C$_6$H$_5$ | 4-C$_6$H$_4$OPh |
| III-369 | 4-C$_6$H$_4$OH | C$_6$H$_5$ |
| III-370 | C$_6$H$_5$ | 4-C$_6$H$_4$OH |
| III-371 | C$_5$H$_4$N (pyr) | C$_5$H$_4$N (pyr) |
| III-372 | 4-C$_6$H$_4$F | 4-C$_6$H$_4$F |
| III-373 | 3-C$_6$H$_4$F | 3-C$_6$H$_4$F |
| III-374 | 4-C$_6$H$_4$OMe | 4-C$_6$H$_4$OMe |
| III-375 | 3-C$_6$H$_4$OMe | 3-C$_6$H$_4$OMe |
| III-376 | 4-C$_6$H$_4$OH | 4-C$_6$H$_4$OH |
| III-377 | 3-C$_6$H$_4$OH | 3-C$_6$H$_4$OH |
| III-378 | 3,4-C$_6$H$_3$(OH)$_2$ | 3,4-C$_6$H$_3$(OH)$_2$ |
| III-379 | Y$_1$ and Y$_2$ taken together to form a phenathrolinyl group. | |

Additional exemplary quinoxalines have the structure:

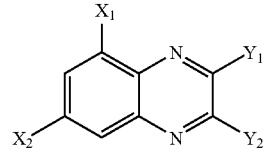

wherein X$_1$=NHR and X$_2$=OR, wherein R is H, aryl or substituted aryl, and Y$_1$ and Y$_2$ include but are not limited to the following structures:

| Structure | Y$_1$ | Y$_2$ |
|---|---|---|
| III-380 | C$_6$H$_5$ | H |
| III-381 | H | C$_6$H$_5$ |
| III-382 | C$_6$H$_5$ | C$_6$H$_5$ |
| III-383 | 4-C$_6$H$_4$OH | H |
| III-384 | H | 4-C$_6$H$_4$OH |
| III-385 | 3,4-C$_6$H$_3$(OH)$_2$ | H |
| III-386 | H | 3,4-C$_6$H$_3$(OH)$_2$ |
| III-387 | 4-C$_6$H$_4$F | C$_6$H$_5$ |
| III-388 | C$_6$H$_5$ | 4-C$_6$H$_4$F |
| III-389 | 4-C$_6$H$_4$Br | C$_6$H$_5$ |

-continued

| Structure | Y₁ | Y₂ |
|---|---|---|
| III-390 | C₆H₅ | 4-C₆H₄Br |
| III-391 | 4-C₆H₄OPh | C₆H₅ |
| III-392 | C₆H₅ | 4-C₆H₄OPh |
| III-393 | 4-C₆H₄OH | C₆H₅ |
| III-394 | C₆H₅ | 4-C₆H₄OH |
| III-395 | C₅H₄N (pyr) | C₅H₄N (pyr) |
| III-396 | 4-C₆H₄F | 4-C₆H₄F |
| III-397 | 3-C₆H₄F | 3-C₆H₄F |
| III-398 | 4-C₆H₄OMe | 4-C₆H₄OMe |
| III-399 | 3-C₆H₄OMe | 3-C₆H₄OMe |
| III-400 | 4-C₆H₄OH | 4-C₆H₄OH |
| III-401 | 3-C₆H₄OH | 3-C₆H₄OH |
| III-402 | 3,4-C₆H₃(OH)₂ | 3,4-C₆H₃(OH)₂ |
| III-403 | Y₁ and Y₂ taken together to form a phenathrolinyl group. | |

Still further exemplary quinoxalines have the structure:

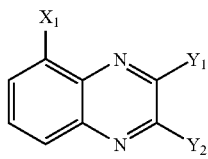

wherein $X_1$=NHR, wherein R is H, aryl or substituted aryl, and $Y_1$ and $Y_2$ include but are not limited to the following structures:

| Structure | Y₁ | Y₂ |
|---|---|---|
| III-404 | C₆H₅ | H |
| III-405 | H | C₆H₅ |
| III-406 | C₆H₅ | C₆H₅ |
| III-407 | 4-C₆H₄OH | H |
| III-408 | H | 4-C₆H₄OH |
| III-409 | 3,4-C₆H₃(OH)₂ | H |
| III-410 | H | 3,4-C₆H₃(OH)₂ |
| III-411 | 4-C₆H₄F | C₆H₅ |
| III-412 | C₆H₅ | 4-C₆H₄F |
| III-413 | 4-C₆H₄Br | C₆H₅ |
| III-414 | C₆H₅ | 4-C₆H₄Br |
| III-415 | 4-C₆H₄OPh | C₆H₅ |
| III-416 | C₆H₅ | 4-C₆H₄OPh |
| III-417 | 4-C₆H₄OH | C₆H₅ |
| III-418 | C₆H₅ | 4-C₆H₄OH |
| III-419 | C₅H₄N (pyr) | C₅H₄N (pyr) |
| III-420 | 4-C₆H₄F | 4-C₆H₄F |
| III-421 | 3-C₆H₄F | 3-C₆H₄F |
| III-422 | 4-C₆H₄OMe | 4-C₆H₄OMe |
| III-423 | 3-C₆H₄OMe | 3-C₆H₄OMe |
| III-424 | 4-C₆H₄OH | 4-C₆H₄OH |
| III-425 | 3-C₆H₄OH | 3-C₆H₄OH |
| III-426 | 3,4-C₆H₃(OH)₂ | 3,4-C₆H₃(OH)₂ |
| III-427 | Y₁ and Y₂ taken together to form a phenathrolinyl group. | |

Additional exemplary quinoxalines have the structure:

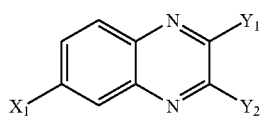

wherein $X_1$=NHR, wherein R is H, aryl or substituted aryl, and $Y_1$ and $Y_2$ include but are not limited to the following structures:

| Structure | Y₁ | Y₂ |
|---|---|---|
| III-428 | C₆H₅ | H |
| III-429 | H | C₆H₅ |
| III-430 | C₆H₅ | C₆H₅ |
| III-431 | 4-C₆H₄OH | H |
| III-432 | H | 4-C₆H₄OH |
| III-433 | 3,4-C₆H₃(OH)₂ | H |
| III-434 | H | 3,4-C₆H₃(OH)₂ |
| III-435 | 4-C₆H₄F | C₆H₅ |
| III-436 | C₆H₅ | 4-C₆H₄F |
| III-437 | 4-C₆H₄Br | C₆H₅ |
| III-438 | C₆H₅ | 4-C₆H₄Br |
| III-439 | 4-C₆H₄OPh | C₆H₅ |
| III-440 | C₆H₅ | 4-C₆H₄OPh |
| III-441 | 4-C₆H₄OH | C₆H₅ |
| III-442 | C₆H₅ | 4-C₆H₄OH |
| III-443 | C₅H₄N (pyr) | C₅H₄N (pyr) |
| III-444 | 4-C₆H₄F | 4-C₆H₄F |
| III-445 | 3-C₆H₄F | 3-C₆H₄F |
| III-446 | 4-C₆H₄OMe | 4-C₆H₄OMe |
| III-447 | 3-C₆H₄OMe | 3-C₆H₄OMe |
| III-448 | 4-C₆H₄OH | 4-C₆H₄OH |
| III-449 | 3-C₆H₄OH | 3-C₆H₄OH |
| III-450 | 3,4-C₆H₃(OH)₂ | 3,4-C₆H₃(OH)₂ |
| III-451 | Y₁ and Y₂ taken together to form a phenathrolinyl group. | |

Still further exemplary quinoxalines have the structure:

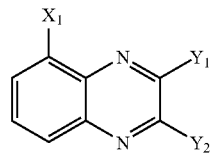

wherein $X_1$=OR, wherein R is H, aryl or substituted aryl, and $Y_1$ and $Y_2$ include but are not limited to the following structures:

| Structure | Y₁ | Y₂ |
|---|---|---|
| III-452 | C₆H₅ | H |
| III-453 | H | C₆H₅ |
| III-454 | C₆H₅ | C₆H₅ |
| III-455 | 4-C₆H₄OH | H |
| III-456 | H | 4-C₆H₄OH |
| III-457 | 3,4-C₆H₃(OH)₂ | H |
| III-458 | H | 3,4-C₆H₃(OH)₂ |
| III-459 | 4-C₆H₄F | C₆H₅ |
| III-460 | C₆H₅ | 4-C₆H₄F |
| III-461 | 4-C₆H₄Br | C₆H₅ |
| III-462 | C₆H₅ | 4-C₆H₄Br |
| III-463 | 4-C₆H₄OPh | C₆H₅ |
| III-464 | C₆H₅ | 4-C₆H₄OPh |
| III-465 | 4-C₆H₄OH | C₆H₅ |
| III-466 | C₆H₅ | 4-C₆H₄OH |
| III-467 | C₅H₄N (pyr) | C₅H₄N (pyr) |
| III-468 | 4-C₆H₄F | 4-C₆H₄F |
| III-469 | 3-C₆H₄F | 3-C₆H₄F |
| III-470 | 4-C₆H₄OMe | 4-C₆H₄OMe |
| III-471 | 3-C₆H₄OMe | 3-C₆H₄OMe |
| III-472 | 4-C₆H₄OH | 4-C₆H₄OH |
| III-473 | 3-C₆H₄OH | 3-C₆H₄OH |
| III-474 | 3,4-C₆H₃(OH)₂ | 3,4-C₆H₃(OH)₂ |
| III-475 | Y₁ and Y₂ taken together to form a phenathrolinyl group. | |

Further exemplary quinoxalines have the structure:

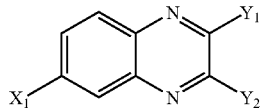

wherein $X_1$=OR, wherein R is H, aryl or substituted aryl, and $Y_1$ and $Y_2$ include but are not limited to the following structures:

| Structure | $Y_1$ | $Y_2$ |
|---|---|---|
| III-476 | $C_6H_5$ | H |
| III-477 | H | $C_6H_5$ |
| III-478 | $C_6H_5$ | $C_6H_5$ |
| III-479 | 4-$C_6H_4$OH | H |
| III-480 | H | 4-$C_6H_4$OH |
| III-481 | 3,4-$C_6H_3(OH)_2$ | H |
| III-482 | H | 3,4-$C_6H_3(OH)_2$ |
| III-483 | 4-$C_6H_4$F | $C_6H_5$ |
| III-484 | $C_6H_5$ | 4-$C_6H_4$F |
| III-485 | 4-$C_6H_4$Br | $C_6H_5$ |
| III-486 | $C_6H_5$ | 4-$C_6H_4$Br |
| III-487 | 4-$C_6H_4$OPh | $C_6H_5$ |
| III-488 | $C_6H_5$ | 4-$C_6H_4$OPh |
| III-489 | 4-$C_6H_4$OH | $C_6H_5$ |
| III-490 | $C_6H_5$ | 4-$C_6H_4$OH |
| III-491 | $C_5H_4N$ (pyr) | $C_5H_4N$ (pyr) |
| III-492 | 4-$C_6H_4$F | 4-$C_6H_4$F |
| III-493 | 3-$C_6H_4$F | 3-$C_6H_4$F |
| III-494 | 4-$C_6H_4$OMe | 4-$C_6H_4$OMe |
| III-495 | 3-$C_6H_4$OMe | 3-$C_6H_4$OMe |
| III-496 | 4-$C_6H_4$OH | 4-$C_6H_4$OH |
| III-497 | 3-$C_6H_4$OH | 3-$C_6H_4$OH |
| III-498 | 3,4-$C_6H_3(OH)_2$ | 3,4-$C_6H_3(OH)_2$ |
| III-499 | $Y_1$ and $Y_2$ taken together to form a phenathrolinyl group. | |

Still further exemplary compounds of structure (III) include:

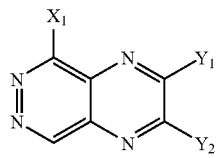

wherein $X_1$=NHR, wherein R is H, aryl or substituted aryl, and $Y_1$ and $Y_2$ include but are not limited to the following structures:

| Structure | $Y_1$ | $Y_2$ |
|---|---|---|
| III-500 | $C_6H_5$ | H |
| III-501 | H | $C_6H_5$ |
| III-502 | $C_6H_5$ | $C_6H_5$ |
| III-503 | 4-$C_6H_4$OH | H |
| III-504 | H | 4-$C_6H_4$OH |
| III-505 | 3,4-$C_6H_3(OH)_2$ | H |
| III-506 | H | 3,4-$C_6H_3(OH)_2$ |
| III-507 | 4-$C_6H_4$F | $C_6H_5$ |
| III-508 | $C_6H_5$ | 4-$C_6H_4$F |
| III-509 | 4-$C_6H_4$Br | $C_6H_5$ |
| III-510 | $C_6H_5$ | 4-$C_6H_4$Br |
| III-511 | 4-$C_6H_4$OPh | $C_6H_5$ |
| III-512 | $C_6H_5$ | 4-$C_6H_4$OPh |
| III-513 | 4-$C_6H_4$OH | $C_6H_5$ |
| III-514 | $C_6H_5$ | 4-$C_6H_4$OH |
| III-515 | $C_5H_4N$ (pyr) | $C_5H_4N$ (pyr) |
| III-516 | 4-$C_6H_4$F | 4-$C_6H_4$F |
| III-517 | 3-$C_6H_4$F | 3-$C_6H_4$F |
| III-518 | 4-$C_6H_4$OMe | 4-$C_6H_4$OMe |
| III-519 | 3-$C_6H_4$OMe | 3-$C_6H_4$OMe |
| III-520 | 4-$C_6H_4$OH | 4-$C_6H_4$OH |
| III-521 | 3-$C_6H_4$OH | 3-$C_6H_4$OH |
| III-522 | 3,4-$C_6H_3(OH)_2$ | 3,4-$C_6H_3(OH)_2$ |
| III-523 | $Y_1$ and $Y_2$ taken together to form a phenathrolinyl group. | |

Additional compounds of structure (III) include the following:

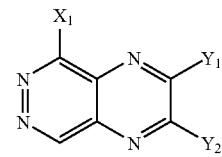

wherein $X_1$=OR, wherein R is H, aryl or substituted aryl, and $Y_1$ and $Y_2$ include but are not limited to the following structures:

| Structure | $Y_1$ | $Y_2$ |
|---|---|---|
| III-524 | $C_6H_5$ | H |
| III-525 | H | $C_6H_5$ |
| III-526 | $C_6H_5$ | $C_6H_5$ |
| III-527 | 4-$C_6H_4$OH | H |
| III-528 | H | 4-$C_6H_4$OH |
| III-529 | 3,4-$C_6H_3(OH)_2$ | H |
| III-530 | H | 3,4-$C_6H_3(OH)_2$ |
| III-531 | 4-$C_6H_4$F | $C_6H_5$ |
| III-532 | $C_6H_5$ | 4-$C_6H_4$F |
| III-533 | 4-$C_6H_4$Br | $C_6H_5$ |
| III-534 | $C_6H_5$ | 4-$C_6H_4$Br |
| III-535 | 4-$C_6H_4$OPh | $C_6H_5$ |
| III-536 | $C_6H_5$ | 4-$C_6H_4$OPh |
| III-537 | 4-$C_6H_4$OH | $C_6H_5$ |
| III-538 | $C_6H_5$ | 4-$C_6H_4$OH |
| III-539 | $C_5H_4N$ (pyr) | $C_5H_4N$ (pyr) |
| III-540 | 4-$C_6H_4$F | 4-$C_6H_4$F |
| III-541 | 3-$C_6H_4$F | 3-$C_6H_4$F |
| III-542 | 4-$C_6H_4$OMe | 4-$C_6H_4$OMe |
| III-543 | 3-$C_6H_4$OMe | 3-$C_6H_4$OMe |
| III-544 | 4-$C_6H_4$OH | 4-$C_6H_4$OH |
| III-545 | 3-$C_6H_4$OH | 3-$C_6H_4$OH |
| III-546 | 3,4-$C_6H_3(OH)_2$ | 3,4-$C_6H_3(OH)_2$ |
| III-547 | $Y_1$ and $Y_2$ taken together to form a phenathrolinyl group. | |

Still further exemplary compounds of structure (III) include:

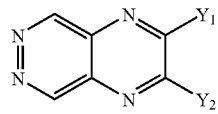

wherein $Y_1$ and $Y_2$ include but are not limited to the following structures:

| Structure | $Y_1$ | $Y_2$ |
|---|---|---|
| III-547 | $C_6H_5$ | H |
| III-548 | $C_6H_5$ | $C_6H_5$ |
| III-549 | $4-C_6H_4OH$ | H |
| III-550 | $3,4-C_6H_3(OH)_2$ | H |
| III-551 | $4-C_6H_4F$ | $C_6H_5$ |
| III-552 | $4-C_6H_4Br$ | $C_6H_5$ |
| III-553 | $4-C_6H_4OPh$ | $C_6H_5$ |
| III-554 | $C_6H_5$ | $4-C_6H_4OH$ |
| III-555 | $C_5H_4N$ (pyr) | $C_5H_4N$ (pyr) |
| III-556 | $4-C_6H_4F$ | $4-C_6H_4F$ |
| III-557 | $3-C_6H_4F$ | $3-C_6H_4F$ |
| III-558 | $4-C_6H_4OMe$ | $4-C_6H_4OMe$ |
| III-559 | $3-C_6H_4OMe$ | $3-C_6H_4OMe$ |
| III-560 | $4-C_6H_4OH$ | $4-C_6H_4OH$ |
| III-561 | $3-C_6H_4OH$ | $3-C_6H_4OH$ |
| III-562 | $3,4-C_6H_3(OH)_2$ | $3,4-C_6H_3(OH)_2$ |
| III-563 | $Y_1$ and $Y_2$ taken together to form a phenathrolinyl group. | |

Additional exemplary compounds of structure (III) include:

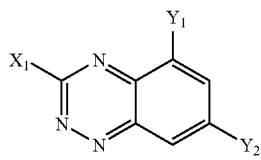

wherein $X_1$=NHR, wherein R is H, aryl, substituted aryl, or aroyl, $Y_1$=NHR, or R, wherein R=H, alkyl or branched alkyl, and $Y_2$ includes but is not limited to the following structures:

| Structure | $Y_2$ |
|---|---|
| III-564 | $C_6H_5$ |
| III-565 | H |
| III-566 | $4-C_6H_4OH$ |
| III-567 | $3-C_6H_4OH$ |
| III-568 | $2-C_6H_4OH$ |
| III-569 | naphthyl |
| III-570 | isonaphthyl |
| III-571 | 4-tBuphenyl |
| III-572 | biphenyl |
| III-573 | 2,3-diMephenyl |
| III-574 | fluorenyl |
| III-575 | oxophenyl |
| III-576 | thioindole |
| III-577 | $C_5H_4N$ (pyr) |
| III-578 | $4-C_6H_4F$ |
| III-579 | $3-C_6H_4F$ |
| III-580 | $4-C_6H_4OMe$ |
| III-581 | $3-C_6H_4OMe$ |
| III-582 | $2-C_6H_4OMe$ |

Still further exemplary compounds of structure (III) include asymmetric triazines, such as:

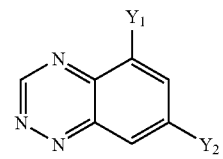

wherein $Y_1$=NHR or R, wherein R=H, alkyl or branched alkyl, and $Y_2$ includes but is not limited to the following structures:

| Structure | $Y_2$ |
|---|---|
| III-583 | $C_6H_5$ |
| III-584 | H |
| III-585 | $4-C_6H_4OH$ |
| III-586 | $3-C_6H_4OH$ |
| III-587 | $2-C_6H_4OH$ |
| III-588 | naphthyl |
| III-589 | isonaphthyl |
| III-590 | 4-tBuphenyl |
| III-591 | biphenyl |
| III-592 | 2,3-diMephenyl |
| III-593 | fluorenyl |
| III-594 | oxophenyl |
| III-595 | thioindole |
| III-596 | $C_5H_4N$ (pyr) |
| III-597 | $4-C_6H_4F$ |
| III-598 | $3-C_6H_4F$ |
| III-599 | $4-C_6H_4OMe$ |
| III-600 | $3-C_6H_4OMe$ |
| III-601 | $2-C_6H_4OMe$ |

In yet another embodiment of the invention, compounds are provided having structure (IV):

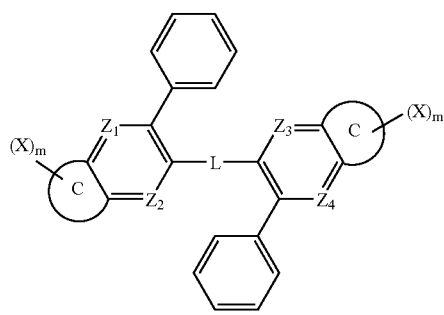

IV wherein:
L is an arylene, substituted arylene, oxyarylene, or substituted oxyarylene linking moiety,
C is 5- or 6-membered aromatic or heteroaromatic ring, each X is independently OR, NR$_2$, or SR, wherein R is H or lower alkyl, Z$_1$–Z$_4$ are each independently CH or N, and m is 1 to 4.

In some embodiments, the linking moiety L is an arylene moiety, and Z is N, as exemplified by the following structures:

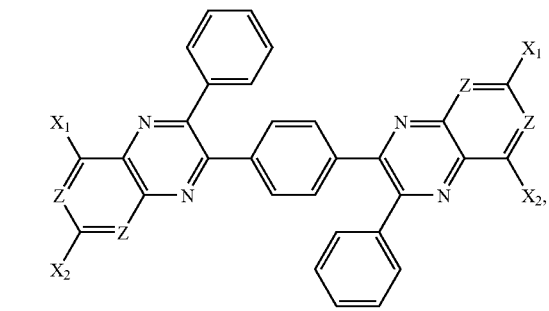

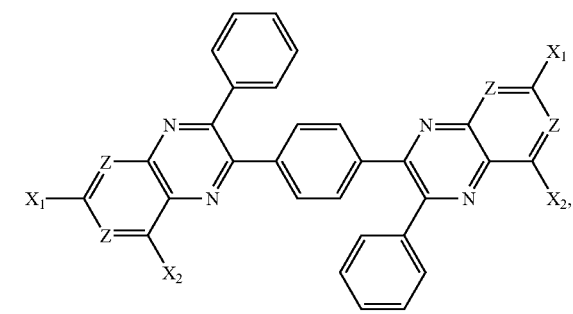

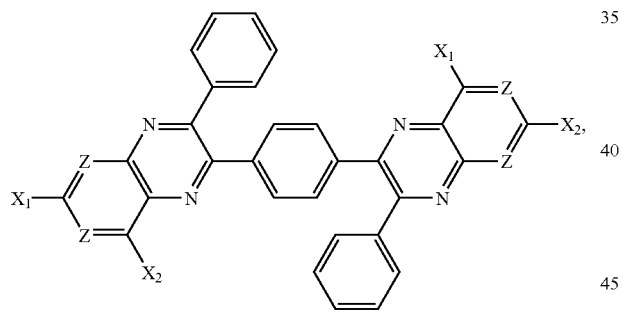

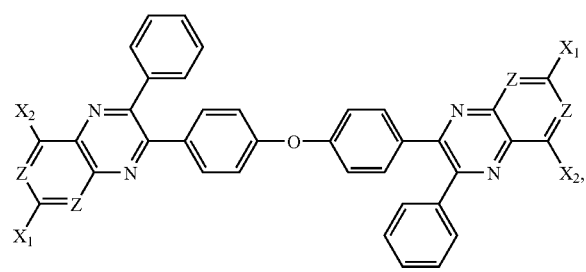

wherein, Z=N or CH, X$_1$=H or OH, and X$_2$=NH$_2$ or OH.

In another embodiment, the linking moiety L is an oxyarylene moiety, as exemplified by the following structures:

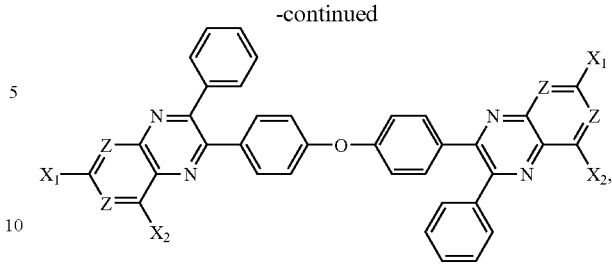

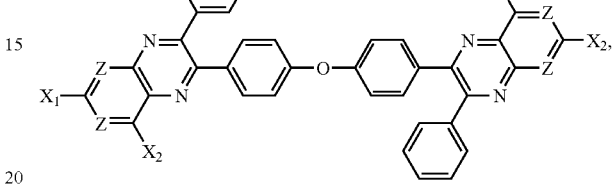

wherein, Z=N or CH, X$_1$=H or OH, and X$_2$=NH$_2$ or OH.

In still another embodiment, compounds are provided having the structure (V):

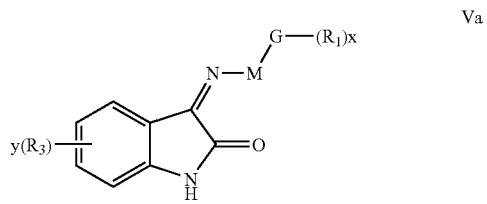

Va

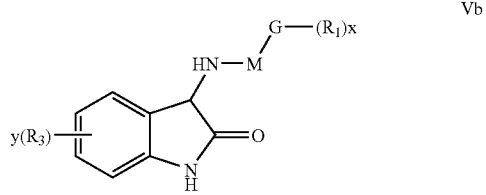

Vb wherein:

R$_1$, x, and y are as defined above,

R$_3$ is —H, —SO$_3$H, or —SO$_2$NMe$_2$,

M is NH, CO, SO$_2$, (CH$_2$)p, wherein p is 0 to 2,

G is aryl or heteroaryl, and x and y are each independently 0–4.

In an additional embodiment, there are provided bis-pteridine compounds. An exemplary bis-pteridine compound according to the invention has the structure:

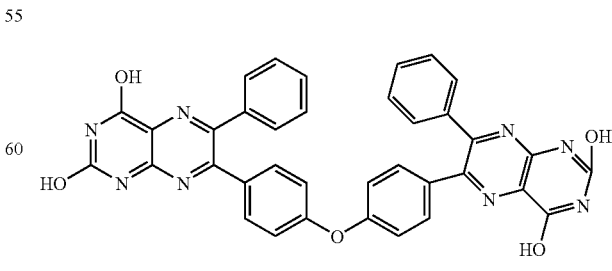

As used herein, the term "heterocyclic", when used to describe an aromatic ring, means that the aromatic ring contains at least one heteroatom. As used herein, the term "heteroatom" refers to N, O, S, and the like.

As used herein, the term "alkyl" refers to a monovalent straight or branched chain hydrocarbon group having from one to about 12 carbon atoms, including methyl, ethyl, n-propyl, isopropyl, n-butyl, isobutyl, tert-butyl, n-hexyl, and the like.

As used herein, "substituted alkyl" refers to alkyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, —C(O)H, acyl, oxyacyl, carboxyl, sulfonyl, sulfonamide, sulfuryl, and the like.

As used herein, "lower alkyl" refers to alkyl groups having from 1 to about 6 carbon atoms.

As used herein, "alkenyl" refers to straight or branched chain hydrocarbyl groups having one or more carbon-carbon double bonds, and having in the range of about 2 up to 12 carbon atoms, and "substituted alkenyl" refers to alkenyl groups further bearing one or more substituents as set forth above.

As used herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic rings containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein, "alkoxy" refers to the moiety —O-alkyl-, wherein alkyl is as defined above, and "substituted alkoxy" refers to alkoxyl groups further bearing one or more substituents as set forth above.

As used herein, "cycloalkyl" refers to ring-containing alkyl groups containing in the range of about 3 up to 8 carbon atoms, and "substituted cycloalkyl" refers to cycloalkyl groups further bearing one or more substituents as set forth above.

As used herein, "heterocyclic", when not used with reference to an aromatic ring, refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "alkylaryl" refers to alkyl-substituted aryl groups and "substituted alkylaryl" refers to alkylaryl groups further bearing one or more substituents as set forth above.

As used herein, "arylalkyl" refers to aryl-substituted alkyl groups and "substituted arylalkyl" refers to arylalkyl groups further bearing one or more substituents as set forth above.

As used herein, "arylalkenyl" refers to aryl-substituted alkenyl groups and "substituted arylalkenyl" refers to arylalkenyl groups further bearing one or more substituents as set forth above.

As used herein, "arylalkynyl" refers to aryl-substituted alkynyl groups and "substituted arylalkynyl" refers to arylalkynyl groups further bearing one or more substituents as set forth above.

As used herein, divalent aromatic groups having in the range of 6 up to 14 carbon atoms and "substituted arylene" refers to arylene groups further bearing one or more substituents as set forth above.

As used herein, "oxyarylene" refers to the moiety "O-arylene", wherein arylene is as defined above and "substituted oxyarylene" refers to oxyarylene groups further bearing one or more substituents as set forth above.

Invention compounds can be prepared by a variety of methods well-known to those skilled in the art. For example, Scheme A illustrates three exemplary syntheses for invention compounds of structure (I).

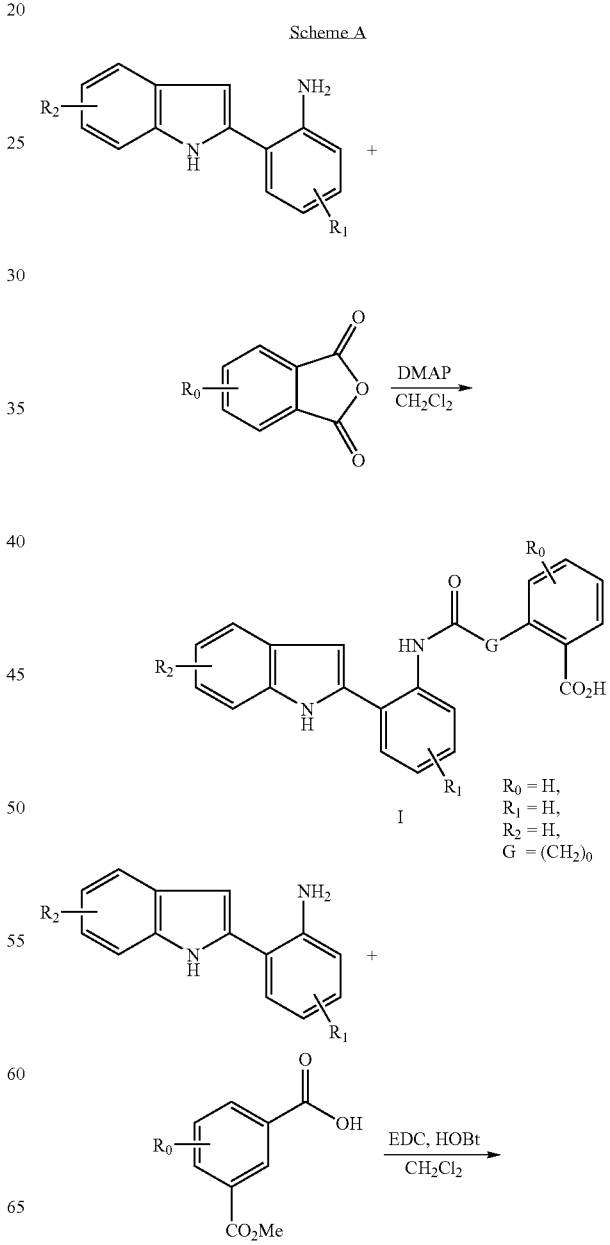

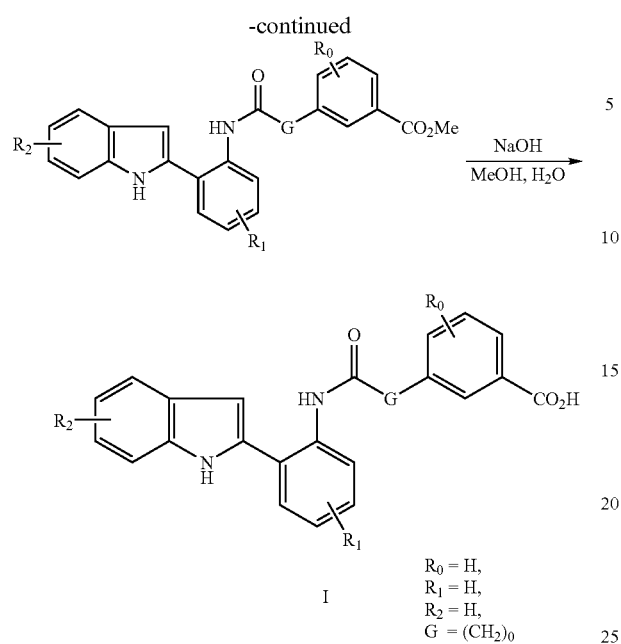
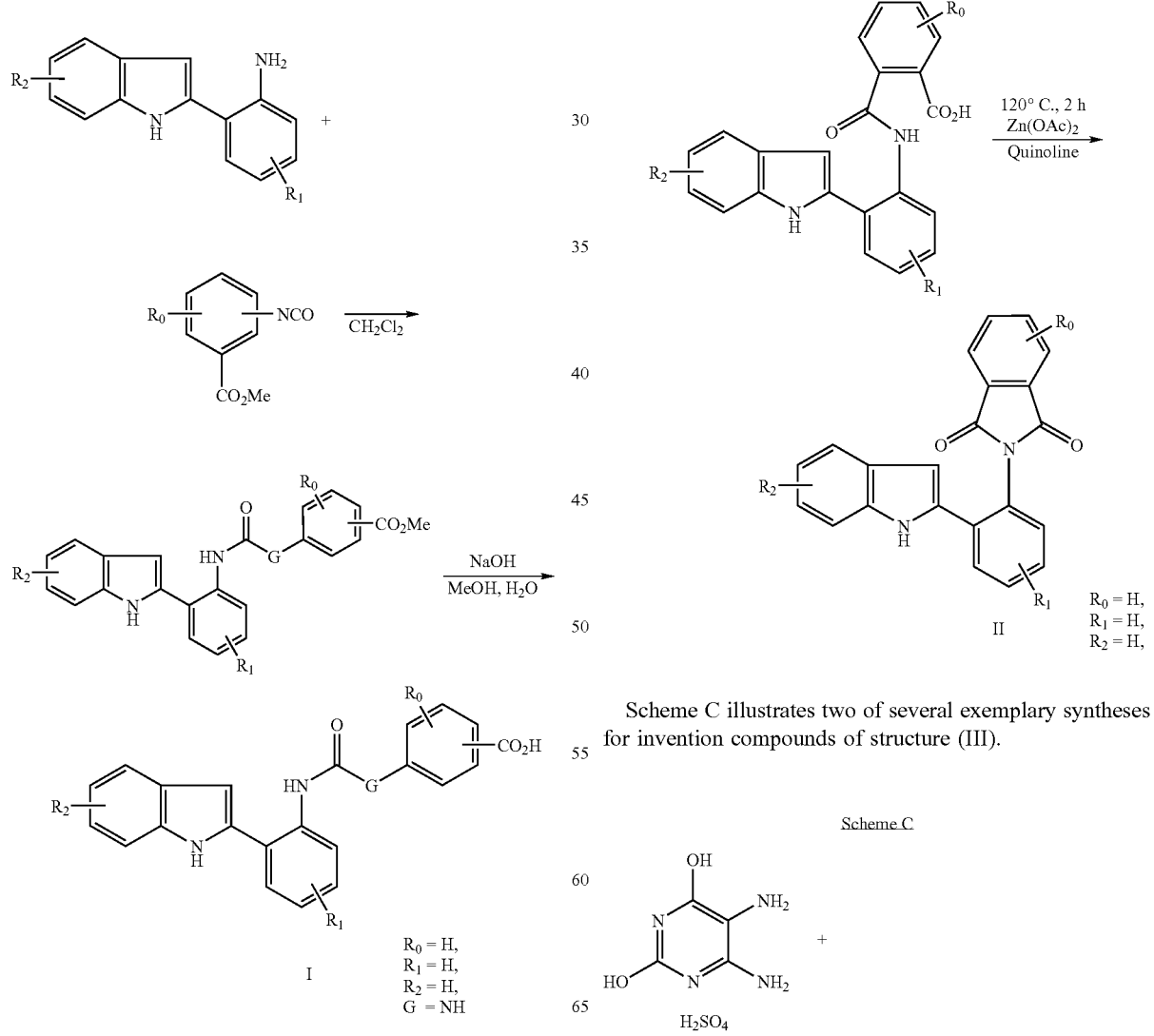
Scheme B illustrates an exemplary synthesis for invention compounds of structure (II).
Scheme C illustrates two of several exemplary syntheses for invention compounds of structure (III).

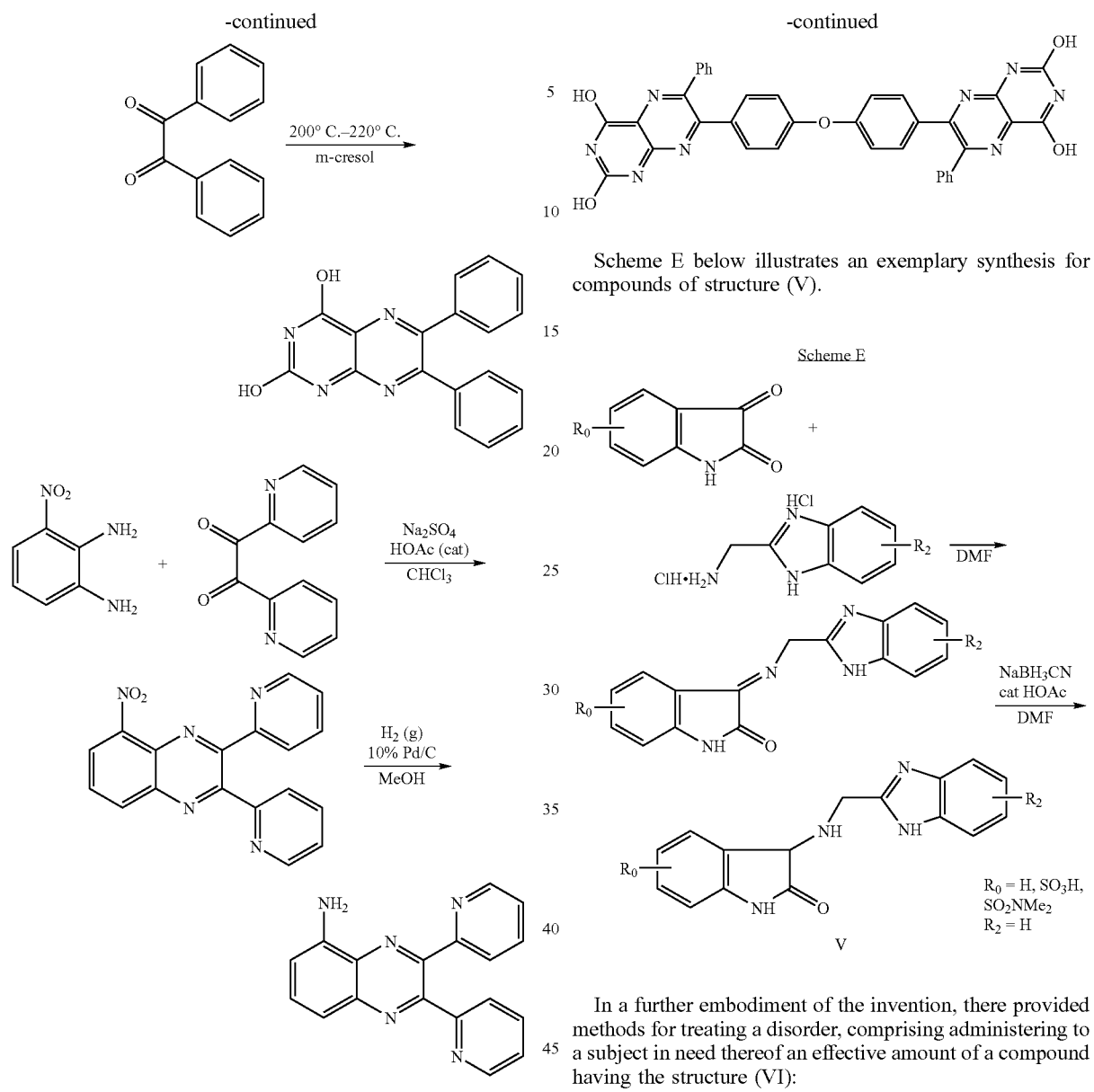

Scheme E below illustrates an exemplary synthesis for compounds of structure (V).

In a further embodiment of the invention, there provided methods for treating a disorder, comprising administering to a subject in need thereof an effective amount of a compound having the structure (VI):

wherein:
A and B are each independently 5- or 6-membered aromatic rings, wherein at least one of A and B is an aromatic heterocyclic ring having at least one heteroatom in the heterocyclic ring,
each X is independently OR, $NR_2$, or SR, wherein R is H or lower alkyl,
each Y is independently hydrogen, alkyl, substituted alkyl, alkenyl substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted Scheme D illustrates an exemplary synthesis for invention compounds of structure (IV).

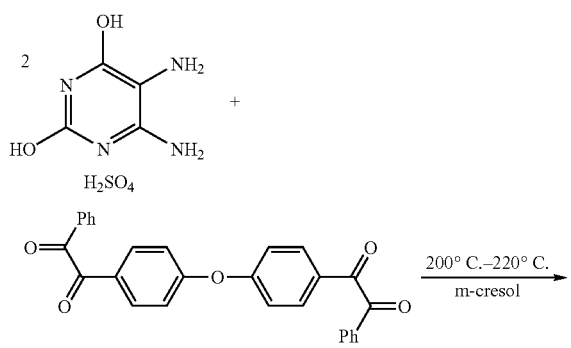

alkylaryl, arylalkyl, substituted arylalkyl, arylalkenyl, substituted arylalkenyl, arylalkynyl, substituted arylalkynyl, aroyl, substituted aroyl, acyl, or substituted acyl, with the proviso that at least one Y is not hydrogen, or when n is 2, each Y is taken together to form a fused aromatic ring system comprising at least one aromatic ring, and m and n are each independently 1 to 4, thereby treating the disorder.

Rings A and B taken together may form a variety of fused aromatic heterocyclic groups suitable for use in the practice of the present invention. For example, rings A and B taken together may form aromatic heterocycles such as quinoxaline, pteridine, benzoxazine, benzoxazole, benzimidazole, 1,2-benzodiazole, indole, isoindole, quinoline, isoquinoline, phthalazine, naphthyridine, quinazoline, cinnoline, purine, benzothiazole, benzofuran, isobenzofuran, benzothiophene, chromene, and the like. In one embodiment, rings A and B taken together form a quinoxaline. In a further embodiment, rings A and B taken together form a pteridine. In a still further embodiment, rings A and B taken together form a benzimidazole.

Quinoxalines contemplated for use in the methods of the present invention have the structure:

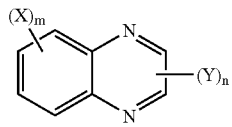

wherein:
each X is independently H, OR, NR$_2$, or SR, wherein R is H or lower alkyl,
each Y is independently hydrogen, alkyl, substituted alkyl, alkenyl substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, with the proviso that at least one Y is not hydrogen, or
when n is 2, each Y is taken together to form a fused aromatic ring system comprising at least one aromatic ring,
m is 1 to 4, and
n is 1 or 2.

In one embodiment, quinoxalines contemplated for use in the methods of the present invention have the structure:

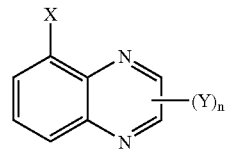

wherein:
X is OR, NR$_2$, or SR, wherein R is H or lower alkyl,
Y is aryl, substituted aryl, heteroaryl, or substituted heteroaryl, and
n is 1 or 2.

Pteridines contemplated for use in the methods of the present invention have the structure:

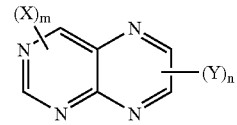

wherein:
each X is independently H, OR, NR$_2$, or SR, wherein R is H or lower alkyl,
each Y is independently hydrogen, alkyl, substituted alkyl, alkenyl substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, with the proviso that at least one Y is not hydrogen, or
when n is 2, each Y is taken together to form a fused aromatic ring system comprising at least one aromatic ring, and
m and n are each independently 1 or 2.

In one embodiment, pteridines contemplated for use in the methods of the present invention have the structure:

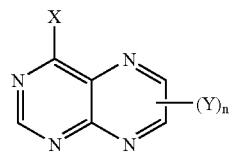

wherein:
X is OR, NR$_2$, or SR, wherein R is H or lower alkyl,
Y is aryl, substituted aryl, heteroaryl, or substituted heteroaryl, and
n is 1 or 2.

Benzimidazoles, oxazoles, or thiazoles contemplated for use in the methods of the present invention have the structure:

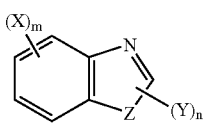

wherein:
Z is N, O, or S,
each X is independently H, OR, NR$_2$, or SR, wherein R is H or lower alkyl,
each Y is independently hydrogen, alkyl, substituted alkyl, alkenyl substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, with the proviso that at least one Y is not hydrogen, or when n is 2, each Y is taken together to form a fused aromatic ring system comprising at least one aromatic ring, and m is 1 to 4, and n is 1 or 2.

In one embodiment, benzimidazoles contemplated for use in the methods of the present invention have the structure:

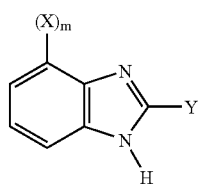

wherein:
each X is independently H, OR, NR$_2$, or SR, wherein R is H or lower alkyl,
Y is aryl, substituted aryl, heteroaryl, or substituted heteroaryl, and
m is 1–4.

In a further embodiment of the invention, there are provided methods for treating a disorder such as those associated with vascular permeability and/or angiogenesis and/or other aspects of compromised vasculostasis including administering to a subject in need thereof an effective amount of a compound having structure (VII):

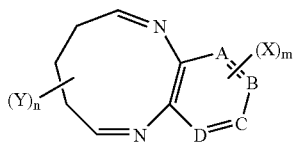

wherein:
A, B, C, and D are each independently C, N, O, or S,
each X is independently H, OR, NR$_2$, or SR, wherein R is H or lower alkyl,
each Y is independently hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, with the proviso that at least one Y is not hydrogen, and
m and n are each independently 1 to 4, thereby treating the disorder.

In one aspect of this embodiment, the compound has the structure:

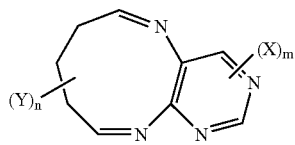

wherein:
each X is independently H, OR, NR$_2$, or SR, wherein R is H or lower alkyl,
each Y is independently aryl or substituted aryl,
m is 1 or 2, and
n is 1–4.

In a further aspect of this embodiment, the compound has the structure:

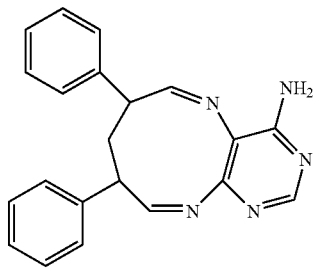

In one embodiment, the present invention is based on the discovery that a combination therapy including interleukin-2 (IL-2) and chemical compounds described herein, some of which are effective kinase inhibitors, administered during IL-2 therapy, mitigates or lessens the adverse effects of IL-2. While not wanting to be bound by a particular theory, it is likely that the effect occurs while preserving or enhancing the beneficial effect of IL-2 such that the disease or disorder is treated. While IL-2 is described in the present application as an illustrative example, it should be understood that the invention includes combination therapy including a compound of the invention, including but not limited to vasculostatic agents, such as tyrosine, serine or threonine kinase inhibitors, for example, Src-family inhibitors, and immunomodulatory molecules. In particular, such immunomodulatory molecules include those that result in vascular leakage. Cytokines, and in particular IL-2, are examples of such immunomodulatory molecules.

Such inhibitors, in combination with IL-2, are effective in blocking vascular leakage typically associated with IL-2 administration. Thus, compositions and methods are provided for treating disorders associated with VLS. In one embodiment, the invention provides a composition containing a therapeutically effective amount of IL-2 and a vasculostatic agent or compound as described herein in a pharmaceutically acceptable carrier.

Some of the compounds are kinase inhibitors, such as Src-family tyrosine kinases, and therefore are useful in treating a wide variety of disorders resulting from aberrant kinase activity, in addition to treating disorders associates with IL-2 administration. Kinase-associated disorders are those disorders which result from aberrant kinase activity, and/or which are alleviated by the inhibition of one or more enzymes within a kinase family. For example, Lck inhibitors are of value in the treatment of a number of such disorders (e.g., the treatment of autoimmune diseases), as Lck inhibition blocks T cell activation. Similarly, Src family inhibitors are of value in treating a variety of cancers as Src inhibition impacts tumor cell invasion, metastases and survival.

The compounds and methods of the present invention, either when administered alone or in combination with other agents described herein (e.g., chemotherapeutic agents or protein therapeutic agents) are useful in treating a variety of disorders associated with compromised vasculostasis including but not limited to, for example: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), cancer, pleural effusions, rheumatoid arthritis, diabetic retinopathy, retinitis pigmentosa, and retinopathies, including diabetic retinopathy and retinopathy of prematurity, inflammatory diseases, restenosis, edema (including edema associated with pathologic situations such as cancers and edema induced by medical interventions such as chemotherapy), asthma, acute or adult respiratory distress syndrome (ARDS), lupus, vascular leakage, transplant (such as organ transplant, acute transplant or heterograft or homograft (such as is employed in burn treatment)) rejection; protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus crythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kinases such as Src-family kinases are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener's granulomatosis, and Behcet's disease; scleroderma; preeclampsia; thalassemia; Kaposi's sarcoma; von Hippel Lindau disease; and the like.

"Treating cancer" as used herein refers to providing a therapeutic benefit to the cancer patient, e.g. the therapy extends the mean survival time of patients, increases the percentage of patients surviving at a given timepoint, extends the mean time to disease progression, reduces or stabilizes tumor burden or improves quality of life for the patient or any of the above, for example. While not wanting to be bound by a particular theory, some of the compounds of the inventin may be cytostatic and therefore have activity directly on the tumor cells.

As used herein, "kinase" refers to any enzyme that catalyze the addition of phosphate groups to a protein residue, for example serine and threonine kinases catalyze the addition of phosphate groups to serine and threonine residues.

As used herein, the terms "Src kinase" or "Src kinase family" or "Src family" refer to the related homologs or analogs belonging to the mammalian family of Src kinases, including, for example, the widely expressed c-Src, Fyn, Yes and Lyn kinases and the hematopoietic-restricted kinases Hck, Fgr, Lck and Blk. As used herein, the terms "Src kinase signaling pathway" or "Src cascade" refer to both the upstream and downstream components of the Src signaling cascade.

Src-family tyrosine kinases other than Lck, such as Hck and Fgr, are important in the Fc gamma receptor induced respiratory burst of neutrophils as well as the Fc gamma receptor responses of monocytes and macrophages. The compositions and methods of the present invention may be useful in inhibiting the Fc gamma induced respiratory burst response in neutrophils, and may also be useful in inhibiting the Fc gamma dependent production of TNF alpha. The ability to inhibit Fc gamma receptor dependent neutrophil, monocyte and macrophage responses would result in additional anti-inflammatory activity for the compounds employed in invention methods. This activity would be especially of value, for example, in the treatment of inflammatory diseases, such as arthritis or inflammatory bowel disease. The compositions and methods of the present invention may also be useful in the treatment of autoimmune glomerulonephritis and other instances of glomerulonephritis induced by deposition of immune complexes in the kidney that trigger Fc gamma receptor responses and which can lead to kidney damage.

In addition, certain Src-family tyrosine kinases, such as Lyn and Src, may be important in the Fc epsilon receptor induced degranulation of mast cells and basophils that plays an important role in asthma, allergic rhinitis, and other allergic disease. Fc epsilon receptors are stimulated by IgE-antigen complexes. Compounds employed in the methods of the present invention may inhibit the Fc epsilon induced degranulation responses. The ability to inhibit Fc epsilon receptor dependent mast cell and basophil responses may result in additional anti-inflammatory activity for the present compounds beyond their effect on T cells.

The present invention also provides articles of manufacture comprising packaging material and a pharmaceutical composition contained within said packaging material, wherein said packaging material comprises a label which indicates that said pharmaceutical composition can be used for treatment of disorders and wherein said pharmaceutical composition comprises a compound according to the present invention. Thus, in one aspect, the invention provides a pharmaceutical composition including both a therapeutic and a compound of the invention (e.g, as shown in FIG. 1), wherein the compound is present in a concentration effective to reduce vascular leakage associated with indications or therapeutics which have vascular leak as a side-effect. For example, administration of a compound of the invention in conjunction with IL-2, immunotoxins, antibodies or chemotherapeutics. In these cases, IL-2, immunotoxin, antibody or chemotherapeutic concentration can be determined by one of skill in the art according to standard treatment regimen or as determined by an in vivo animal assay, for example.

The present invention also provides pharmaceutical compositions comprising IL-2, immunotoxin, antibody or chemotherapeutic and at least one invention compound in an amount effective for inhibiting vascular permeability, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the invention include amine salts formed by the protonation of an amino group with inorganic acids such as hydrochloric acid, hydrobromic acid, hydroiodic acid, sulfuric acid, phosphoric acid, and the like. Salts of the invention also include amine salts formed by the protonation of an amino group with suitable organic acids, such as p-toluenesulfonic acid, acetic acid, and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs of the invention compounds are included in the present invention.

Invention pharmaceutical compositions may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The term "therapeutically effective amount" means the amount of the compound or pharmaceutical composition that will elicit the biological or medical response of a tissue, system, animal or human that is being sought by the researcher, veterinarian, medical doctor or other clinician, e.g., restoration or maintainance of vasculostasis or prevention of the compromise or loss or vasculostasis; reduction of tumor burden; reduction of morbidity and/or mortality.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or pharmaceutical composition to the subject in need of treatment.

The pharmaceutical compositions for the administration of the compounds of this embodiment either alone or in combination with IL-2, immunotoxin, antibody or chemotherapeutic may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or coslvent or complexing agent or dispersing agent or excipient or combination thereof, for example 1,3-butane diol, polyethylene glycols, polypropylene glycols, ethanol or other alcohols, povidones, Tweens, sodium dodecyle sulfate, sodium deoxycholate,dimethylacetamide, polysorbates, poloxamers, cyclodextrins, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles).

In one aspect, the invention compounds are administered in combination with an antiinflammatory, antihistamines, chemotherapeutic agent, immunomodulator, therapeutic antibody or a protein kinase inhibitor, e.g., a tyrosine kinase inhibitor, to a subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomicin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecoline, etoposide, taxane, anthracycline antibiotic, doxorubicin, daunorubicin, carminomycin, epirubicin, idarubicin, mithoxanthrone, 4-demethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methtrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase 1 (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase, and hydroxyurea, etc.; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

The pharmaceutical composition and method of the present invention may further comprise other therapeutically active compounds as noted herein which are usually applied in the treatment of the above mentioned pathological conditions. Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

Other agents that may be administered in combination with invention compounds include protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay.

The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

The term antibody as used in this invention is meant to include intact molecules of polyclonal or monoclonal antibodies, as well as fragments thereof, such as Fab and F(ab')$_2$, Fv and SCA fragments which are capable of binding an epitopic determinant.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which involve compromised vasculostasis an appropriate dosage level will generally be about 0.01 to 500 mg per kg patient body weight per day which can be administered in single or multiple doses. Preferably, the dosage level will be about 0.01 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day or 1.0 mg/kg per day. Within this range the dosage may be 0.05 to 0.5, 0.5 to 5 or 5 to 50 mg/kg per day for example. The Examples section shows that one of the exemplary compounds was preferred at 0.1 mg/kg/day while another was effective at about 1.0 mg/kg/day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. There may be a period of no administration followed by another regimen of administration. Preferably, administration of the compound is closely associated with the schedule of IL-2 administration. For example, administration can be prior to, simultaneously with or immediately following IL-2 administration It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Another embodiment described herein is based on the discovery that a compound that is a vasculostatic agent alone or in combination with an effective amount of therapeutic antibody (or therapeutic fragment thereof), chemotherapeutic or immunotoxic agent, is an effective therapeutic regimen for treatment of tumors, for example. While doxorubicin, docetaxel, or taxol are described in the present application as illustrative examples of chemotherapeutic agents, it should be understood that the invention includes combination therapy including a compound of the invention, including but not limited to vasculostatic agents, such as tyrosine, serine or threonine kinase inhibitors, for example, Src-family inhibitors, and any chemotherapeutic agent or therapeutic antibody.

Such vasculostatic agents, in combination with chemotherapeutic agents or therapeutic antibodies are effective in blocking vascular permeability and/or vascular leakage and/or angiogenesis. In one embodiment, the invention provides a composition containing a therapeutically effective amount of a chemotherapeutic agent and a vasculostatic agent in a pharmaceutically acceptable carrier.

In one embodiment, the invention provides a method for reducing the tumor burden in a subject, comprising administering to a subject in need thereof an effective amount of chemotherapeutic agent in combination with a compound that is a vasculostatic agent. In an illustrative example, the method includes use of at least one of the invention compounds e.g., as set forth in Structures I, II, III, IIIa, IV, V, VI or VII or any combination thereof, with the chemotherapeutic agent. In one aspect, the compound is set forth in FIG. 1. It should be understood that the tumor burden in a subject can be reduced prior to treatment with a compound of the invention through surgical resection, chemotherapy, radiation treatment or other methods known to those of skill in the art.

The compounds according to this invention may contain one or more asymmetric carbon atoms and thus occur as racemates and racemic mixtures, single enantiomers, diastereomeric mixtures and individual diastereomers. The term "stereoisomer" refers to a chemical compounds which differ from each other only in the way that the different groups in the molecules are oriented in space. Stereoisomers have the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. All such isomeric forms of these compounds are included in the present invention.

Each stereogenic carbon may be of R or S configuration. Although the specific compounds exemplified in this application may be depicted in a particular configuration, compounds having either the opposite stereochemistry at any given chiral center or mixtures thereof are also envisioned. When chiral centers are found in the derivatives of this invention, it is to be understood that this invention encompasses all possible stereoisomers. The terms "optically pure compound" or "optically pure isomer" refers to a single stereoisomer of a chiral compound regardless of the configuration of the compound.

Several illustrative compounds employed in the methods of the present invention are inhibitors of kinases and therefore are useful in treating a wide variety of disorders resulting from aberrant kinase activity. Examples of kinases include Src-family tyrosine kinases and their associated disorders, which result from aberrant tyrosine kinase activity, and/or which are alleviated by the inhibition of one or more of the enzymes within the Src family. For example, Src inhibitors are of value in the treatment of cancer, as Src inhibition blocks tumor cell migration and survival. Many compounds of the invention are also broad spectrum kinase inhibitors and inhibit other kinases in addition to Src-family tyrosine kinases or non-Src family kinases.

Cancers that may be treated by compounds of the invention alone or as a combination therapy of the invention include but are not limited to a carcinoma or a sarcoma, including one or more specific types of cancer, e.g., an alimentary/gastrointestinal tract cancer, a liver cancer, a skin cancer, a breast cancer, an ovarian cancer, a prostate cancer, a lymphoma, a leukemia, a kidney cancer, a lung cancer, a muscle cancer, a bone cancer, bladder cancer or a brain cancer.

The present invention also provides articles of manufacture comprising packaging material and a pharmaceutical composition contained within said packaging material, wherein said packaging material comprises a label which indicates that said pharmaceutical composition can be used for treatment of disorders and wherein said pharmaceutical composition comprises a compound according to the present invention. Thus, in one aspect, the invention provides a pharmaceutical composition including both a chemotherapeutic agent, immunotoxin or therapeutic antibody and a compound of the invention (e.g, as shown in FIG. 1), wherein the compound is present in a concentration effective to reduce tumor burden, for example. In one aspect, the invention provides a pharmaceutical composition including a compound of the invention, wherein the compound is present in a concentration effective to reduce vascular permeability, for example. The concentration can be determined by one of skill in the art according to standard treatment regimen or as determined by an in vivo animal assay, for example.

Pharmaceutical compositions employed as a component of invention articles of manufacture can be used in the form of a solid, a solution, an emulsion, a dispersion, a micelle, a liposome, and the like, wherein the resulting composition contains one or more of the compounds described above as an active ingredient, in admixture with an organic or inorganic carrier or excipient suitable for enteral or parenteral applications. Compounds employed for use as a component of invention articles of manufacture may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

The present invention also provides pharmaceutical compositions including at least one invention compound in an amount effective for treating a tumor, or cancer, alone or in combination with a chemotherapeutic agent, immunotoxin, immunomodulator or therapeutic antibody and a pharmaceutically acceptable vehicle or diluent. Similarly, the present invention provides pharmaceutical compositions including at least one invention compound capable of treating a disorder associated with vasculostasis in an amount effective therefore. The compositions of the present invention may contain other therapeutic agents as described herein and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The terms "administration of" and or "administering a" compound should be understood to mean providing a compound of the invention or pharmaceutical composition to the subject in need of treatment. For example, administration of the vasculostatic agent can be prior to, simultaneously with, or after administration of an invention compound or other agent. In the Examples provided herein, typically the compounds of the invention are co-administered at the same time as a chemotherapeutic agent.

While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomicin; microtubule inhibitors such as taxol (paclitaxol), and the like. Other chemotherapeutic agents include, for example, a vinca alkaloid, mitomycin-type antibiotic, bleomycin-type antibiotic, antifolate, amsacrine, carmustine, cyclophosphamide, cytarabine, etoposide, lovastatin, melphalan, topetecan, oxalaplatin, chlorambucil, methtrexate, lomustine, thioguanine, asparaginase, vinblastine, vindesine, tamoxifen, mechlorethamine, colchicine, demecoline, etoposide, taxane, anthracycline antibiotic, doxorubicin, daunorubicin, carminomycin, epirubicin, idarubicin, mithoxanthrone, 4-demethoxy-daunomycin, 11-deoxydaunorubicin, 13-deoxydaunorubicin, adriamycin-14-benzoate, adriamycin-14-octanoate or adriamycin-14-naphthaleneacetate.

Compounds, their prodrugs, or metabolites employed in the methods of the present invention are vasculostatic agents such as inhibitors of vascular permeability and/or vascular leakage and/or angiogenesis. In addition, several illustrative compounds employed in the methods of the present invention are inhibitors of kinases and therefore are useful in treating a wide variety of disorders resulting from aberrant kinase activity. Kinase-associated disorders are those disorders which result from aberrant kinase activity, and/or which are alleviated by the inhibition of one or more of the kinases.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The Examples set out below include representative examples of aspects of the present invention. The Examples are not meant to limit the scope of the invention but rather serve exemplery purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLE 1

Syntheses of Vasculostatic Agents

Experimentals

General Analytical Methods

All solvents are used without further purification. Reactions are usually run without an inert gas atmosphere unless specified otherwise. All $^1$H NMR are run on a 500 MHz Bruker NMR. Chemical shifts are reported in delta ($\delta$) units, parts per million (ppm) downfield from tetramethylsilane. Coupling constants are reported in hertz (Hz). A Water LC/MS system is used in identity and purity analysis. This system includes a 2795 separation module, a 996 photodiode array detector and a ZQ2000 mass spectrometer. A Zorbax SB column (150×4.6 mm 3.5µ, Agilent Technologies) is used for the LC. Column temperature is 40° C. Compounds are separated using gradient elution with mobile phases of water (0.05% TFA (A)) and acetonitrile (0.05% TFA (B)). Flow rate is 1 mL/min. The gradient program used in separation is 0–15 min: 5–60% B; 15–15.5 min: 60–100% B; 15.5–17 min: 100% B.

The following gradient programs were used based on the hydrophobicity of the analyzed sample: (1) 0–15 min: 30–70% B; 15–15.5 min: 70–90% B; 15.5–17 min: 90% B for the compounds: 4-Hydroxy-N-(2-(1H-indol-2-yl)-phenyl)-benzamide; 3,4-Dihydroxy-N-(2-(1H-indol-2-yl)-phenyl)-benzamide; N-(2-(1H-Indol-2-yl)-phenyl)-2-phenyl-acetamide; 2-(3,4-Dihydroxy-phenyl)-N-(2-(1H-indol-2-yl)-phenyl)-acetamide; N-(2-(1H-Indol-2-yl)-phenyl)-3-phenyl-propionamide; 3-(4-Hydroxy-phenyl)-N-(2-(1H-indol-2-yl)-phenyl)-propionamide; N-(2-(1H-Indol-2-yl)-phenyl)-3-(2-methoxy-phenyl)-propionamide; 3-(3,4-Dihydroxy-phenyl)-N-(2-(1H-indol-2-yl)-phenyl)-propionamide; (2) 0–15 min: 30–50% B; 15–15.5 min: 50–90% B; 15.5–17 min: 90% B for compound N-(2-(2,3-Dihydro-1H-indol-2-yl)-phenyl)-2-hydroxy-benzamide. (3) 0–15 min: 20–40% B; 15–15.5 min: 40–90% B; 15.5–17 min: 90% B for compound 4-(4-amino-6-(3,4-dihydroxyphenyl)pteridin-7-yl)benzene-1,2-diol. (4) 0–15 min: 5–60% B; 15–15.5 min: 60–90% B; 15.5–17 min: 90% B for compound 2-(4-Hydroxy-phenyl)-N-(2-(1H-indol-2-yl)-phenyl)-acetamide. (5) 0–15 min: 40–100% B; 15.–17 min: 100% B for compounds N-(2-(1H-Indol-2-yl)-phenyl)-2-(2-methoxy-phenyl)-acetamide and 2-Benzo(1,3)dioxol-5-yl-N-(2-(1H-indol-2-yl)-phenyl)-acetamide.

The mass spectrometer is equipped with an electrospray probe. Source temperature is 120° C. All of the compounds are identified using the positive mode with mass scan range from 100 to 800.

General Procedure for Indoles 2-(2-Aminophenyl) indole and the starting material acid (2 equiv) were dissolved in acetonitrile. To the solution were added 2 equiv of EDC (dimethylaminopropyl ethylcarbodiimide hydrochloride) as powder. The mixture was stirred at either room temperature (23° C.) or at slightly elevated temperature (50° C.) for 3 to 16 hours.

The solvent was removed and the residue dissolved in methanol:ethylacetate (5–10%). The solution was extracted with 1 M HCl as well as saturated sodium bicarbonate solution. The aqueous phases were re-extracted with EtOAc, respectively. The combined organic phases were dried over magnesium sulfate. The product was purified by column chromatography (silica, typically using EtOAc-hexanes as mobile phase) and/or crystallization from different solvents including methanol and acetonitrile.

2-(4-Hydroxy-phenyl)-N-[2-(1H-indol-2-yl)-phenyl]-acetamide

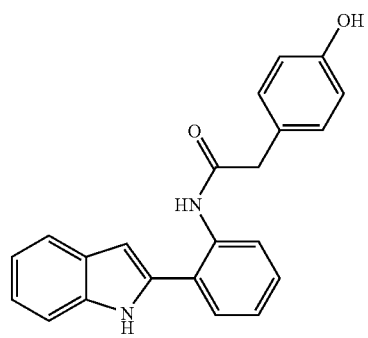

1 g (4.8 mmol) 2-(2-Aminophenyl) indole was dissolved in 200 ml acetonitrile. 1.46 g (9.6 mmol, 2 eq) of 4-hydroxyphenylacetic acid were dissolved in 50 ml acetonitrile and added to the solution. To the mixture were added 1.84 g (9.6 mmol, 2 eq) of EDC (dimethylaminopropyl ethylcarbodiimide hydrochloride). The reaction mixture was stirred at 23° C. for 16 hours. The solvent was removed and the residue was dissolved in 100 ml ethylacetate:methanol (10:1). It was extracted twice with 100 ml of aqueous 1M HCl as well as 100 ml of aqueous, saturated sodium bicarbonate solution. The aqueous phases were re-extracted with EtOAc, respectively. The combined organic phases were dried over magnesium sulfate. The crude product was chromatographed on silica using a ethylacetate/hexane gradient (10%–50%) to obtain 1.23 g of the amide as a pink colored powder in an overall yield of 75%. 100% Purity by LC/MS (230 DAD) Mass-spec [M+H$^+$]=343.9 $^1$H NMR (MeOH-d4): 3.60 s (2H), 6.10 s (1H), 6.70 d, 8 Hz (2H), 7.03 t, 8 Hz (1H), 7.09–7.13 m (3H), 7.25 t, 7 Hz (1H), 7.34 m (2H), 7.49 d, 8 Hz (1H), 7.53 d, 8 Hz (1H), 7.95 d, 8 Hz (1H).

4-Hydroxy-N-(2-(1H-indol-2-yl)-phenyl)-benzamide

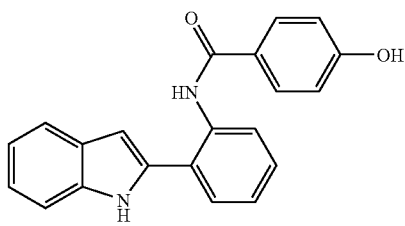

Prepared from 2-(2-aminophenyl) indole and 4-hydroxybenzoic acid in 35% overall yield following procedure 1. The product was chromatographed on silica and crystallized from acetonitrile. 95.6% Purity by LC/MS (230 DAD) Mass-spec (M+H$^+$)=329.8 $^1$H NMR (MeOH-d4): 6.65 s (1H), 6.83 m (2H), 7.01 t, 7 Hz (1H), 7.12 td, 7.1 Hz (1H), 7.34 td, 7.1 Hz (1H), 7.39–7.43 m (2H), 7.51 d, 7 Hz (1H), 7.66 dd, 8.1 Hz (1H), 7.76 m (2H), 7.91 dd, 8.1 Hz (1H).

3,4-Dihydroxy-N-(2-(1H-indol-2-yl)-phenyl)-benzamide

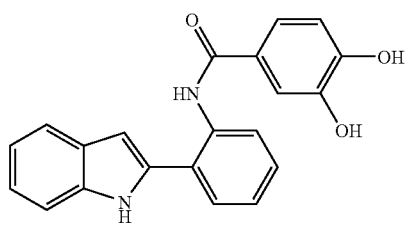

Prepared from 2-(2-aminophenyl) indole and 3,4-dihydroxybenzoic acid in 54% yield following procedure 1. The product was chromatographed on silica. 100% Purity by LC/MS (230 DAD), Mass-spec (M+H$^+$)=345.83, $^1$H NMR (MeOH-d4): 6.645 s (1H), 6.80 d, 8 Hz (1H), 7.02 t, 8 Hz (1H), 7.12 td, 8.1 Hz (1H), 7.23 dd, 8.1 Hz (1H), 7.33–7.36 m (2H), 7.39–7.42 m (2H), 7.52 d, 7 Hz (1H), 7.65 dd, 8.1 Hz (1H), 7.94 d, 8 Hz (1H).

2-Hydroxy-N-(2-(1H-indol-2-yl)-phenyl)-benzamide

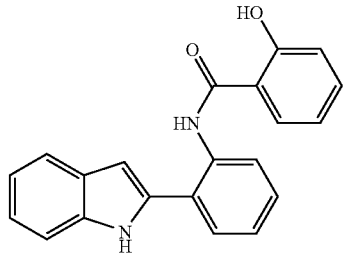

Prepared from 2-(2-aminophenyl) indole and salicylic acid in 46% yield following procedure 1. The compound was chromatographed on silica using an ethylacetate/hexane gradient. % Purity by LC/MS (230 DAD), Mass-spec (M+H$^+$)=329, $^1$H NMR (MeOH-d4): 6.66 s (1H), 6.86 dd, N-[2-(1H-Indol-2-yl)-phenyl]-2-phenyl-acetamide

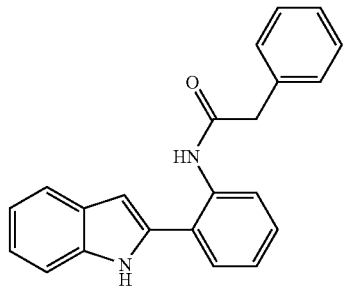

Prepared from 2-(2-aminophenyl) indole and phenylacetic acid in 62% yield following procedure 1. The product was crystallized from methanol. 100% Purity by LC/MS (230 DAD), Mass-spec [M+H$^+$]=327, $^1$H NMR (MeOH-d4): 3.69 s (2H), 6.21 s (1H), 7.03 t, 7 Hz (1H), 7.12 t, 8 Hz (1H), 7.21–7.28 m (6H), 7.33–7.36 m (2H), 7.46 d, 8 Hz (1H), 7.54 dd, 7.1 Hz (1H), 7.89 d, 8 Hz (1H).

N-[2-(1H-Indol-2-yl)-phenyl]-2-(2-methoxy-phenyl)-acetamide

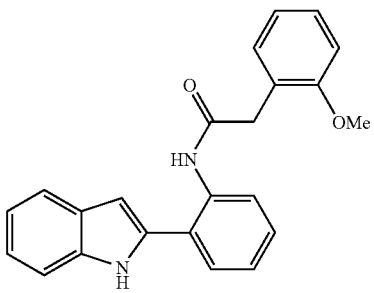

Prepared from 2-(2-aminophenyl) indole and 2-methoxyphenylacetic acid in 53% yield following procedure 1. The product was crystallized from acetonitrile. 100% Purity by LC/MS (230 DAD), Mass-spec [M+H$^+$]=357, $^1$H NMR (MeOH-d4): 3.45 s (3H, OMe), 3.67 s (2H), 6.17 s (1H), 6.75 d, 8 Hz (1H), 6.83 t, 8 Hz (1H), 7.06 t, 8 Hz (1H), 7.14 t, 8 Hz (1H), 7.17–7.21 m (3H), 7.23–7.36 m (2H), 7.49 t, 8 Hz (2H), 8.13 d, 8 Hz (1H).

2-(2-Hydroxy-phenyl)-N-[2-(1H-indol-2-yl)-phenyl]-acetamide

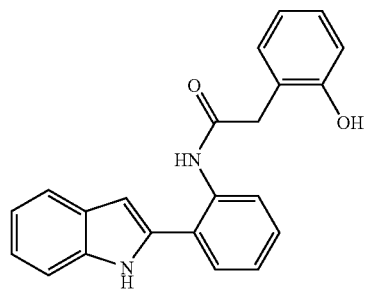

The product was prepared from N-[2-(1H-Indol-2-yl)-phenyl]-2-(2-methoxy-phenyl)-acetamide. Cleavage of the methylether was accomplished using 1.8 eq of BBr$_3$ (1M solution in dichloromethane) at −78° C. to room temperature (23° C.) and subsequent hydrolysis (32% yield). 96% Purity by HPLC (ELSD), Mass-spec [M+H$^+$]=343, $^1$H NMR (MeOH-d4): 3.69 s (2H), 6.25 s (1H), 6.71–6.74 m (2H), 7.01–7.07 m (2H), 7.10–7.13 m (2H), 7.22 t, 7 Hz (1H), 7.31–7.36 m (2H), 7.48 d, 8 Hz (1H), 7.52 dd, 8.1 Hz (1H), 8.08 d, 8 Hz (1H).

2-(3,4-Dihydroxy-phenyl)-N-[2-(1H-indol-2-yl)-phenyl]-acetamide

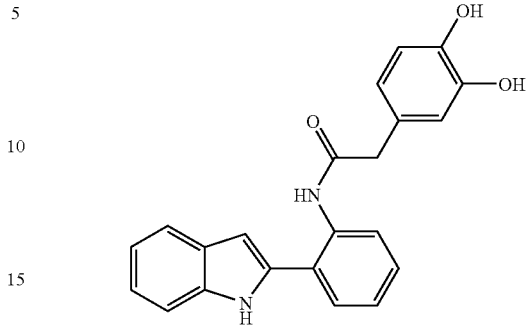

Prepared from 2-(2-aminophenyl) indole and 3,4-dihydroxyphenylacetic acid in 17% yield. The product was chromatographed on silica. 100% Purity by LC/MS (230 DAD), Mass-spec [M+H$^+$]=359, $^1$H NMR (MeOH-d4): 3.56 s (2H), 6.10 s (1H), 6.59 dd, 8, 2 Hz (1H), 6.66 d, 8 Hz (1H), 6.78 d, 2 Hz (1H), 7.03 t, 8 Hz (1H), 7.11 t, 8 Hz (1H), 7.25 t, 8 Hz (1H), 7.31–7.35 m (2H), 7.51 d, 7 Hz (1H), 7.55 dd, 8.1 Hz (1H), 7.99 d, 8 Hz (1H).

2-Benzo[1,3]dioxol-5-yl-N-[2-(1H-indol-2-yl)-phenyl]-acetamide

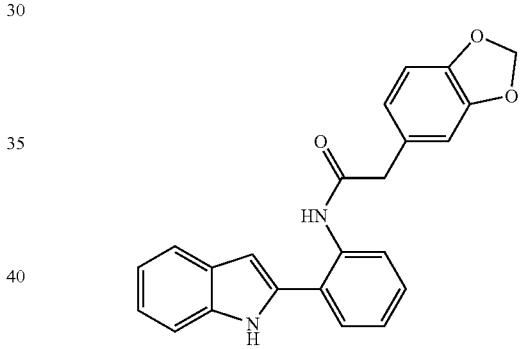

Prepared from 2-(2-aminophenyl) indole and 3,4-(methylenedioxy) phenylacetic acid in 55% yield. The product was purified by crystallization from acetonitrile. 100% Purity by LC/MS (230 DAD), Mass-spec [M+H$^+$]=371, $^1$H NMR (MeOH-d4): 3.61 s (2H), 5.82 s (2H), 6.20 s (1H), 6.66 d, 8 Hz (1H), 6.74 dd, 8.1 Hz (1H), 6.76 d, 1 Hz (1H), 7.03 t, 8 Hz (1H), 7.12 t, 8 Hz (1H), 7.25 t, 8 Hz (1H), 7.33–7.36 m (2H), 7.48 d, 8 Hz (1H), 7.52 d, 8 Hz (1H), 7.99 d, 8 Hz (1H).

N-[2-(1H-Indol-2-yl)-phenyl]-3-phenyl-propionamide

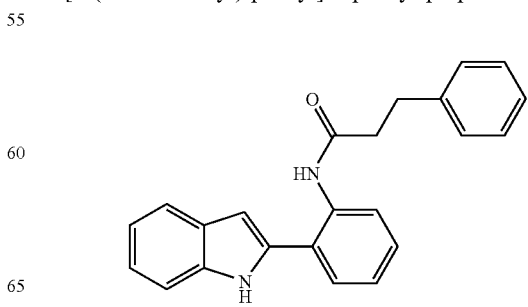

Prepared from 2-(2-aminophenyl) indole and hydrocinnamic acid in 54% yield following procedure 1. The product was crystallized from methanol. 99% Purity by LC/MS (230 DAD), Mass-spec [M+H⁺]=341, ¹H NMR (DMSO-d6): 2.65 t, 7.5 Hz (2H), 2.91 t, 7.5 Hz (2H), 6.50 s (1H), 7.00 t, 7 Hz (1H), 7.10 t, 7 Hz (1H), 7.19–7.34 m (7H), 7.39 d, 8 Hz (1H), 7.51 d, 8 Hz (1H), 7.60–7.62 m (2H), 9.39 s (1H), 11.32 s (1H).

3-(4-Hydroxy-phenyl)-N-[2-(1H-indol-2-yl)-phenyl]-propionamide

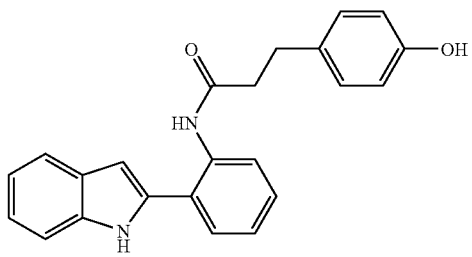

Prepared from 2-(2-aminophenyl) indole and 3-(4-hydroxyphenyl) propionic acid in 55% yield following procedure 1. The product was chromatographed on silica and crystallized from acetonitrile. 100% Purity by LC/MS (230 DAD), Mass-spec [M+H⁺]=357, ¹H NMR (MeOH-d4): 2.61 t, 7.4 Hz (1H), 2.89 t, 7.4 Hz (1H), 6.37 s (1H), 6.72 d, 8 Hz (2H), 7.00–7.06 m (3H), 7.11 t, 7 Hz (1H), 7.27–7.35 m (2H), 7.38 d, 8 Hz (1H), 7.54 d, 7 Hz (1H), 7.58 dd, 7.1 Hz (1H), 7.67 d, 8 Hz (1H).

N-[2-(1H-Indol-2-yl)-phenyl]-3-(2-methoxy-phenyl)-propionamide

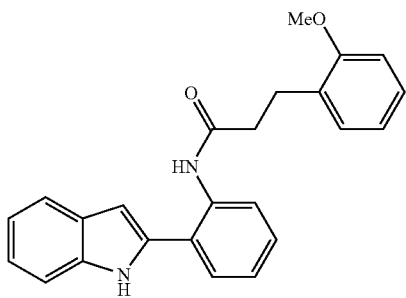

Prepared from 2-(2-aminophenyl) indole and 3-(2-methoxyphenyl) propionic acid in 62% yield following procedure 1. The product was crystallized from acetonitrile. 96% Purity by LC/MS (TIC, DAD), Mass-spec [M+H⁺]=371, ¹H NMR (MeOH-d4): 2.62 t, 7.5 Hz (2H), 2.97 t, 7.5 Hz (2H), 3.74 s (3H, OMe), 6.40 s (1H), 6.81 t, 7 Hz (1H), 6.88 d, 8 Hz (1H), 7.03 t, 8 Hz (1H), 7.10–7.14 m (2H), 7.17 t, 8 Hz (1H), 7.27 t, 7 Hz (1H), 7.33 td, 7.5, 1 Hz (1H), 7.40 d, 8 Hz (1H), 7.54 d, 8 Hz (1H), 7.57 dd, 7.1 Hz (1H), 7.76 d, 8 Hz (1H).

3-(3,4-Dihydroxy-phenyl)-N-[2-(1H-indol-2-yl)-phenyl]-propionamide

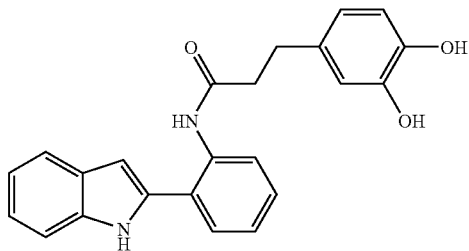

Prepared from 2-(2-aminophenyl) indole and 3,4-dihydroxyhydrocinnamic acid in 19% yield following procedure 1. The product was chromatographed on silica and crystallized from acetonitrile. 100% Purity by LC/MS (230 DAD), Mass-spec [M+H⁺]=373, ¹H NMR (MeOH-d4): 2.60 t, 7.4 Hz (2H), 2.85 t, 7.4 Hz (2H), 6.38 s (1H), 6.55 dd, 8.2 Hz (1H), 6.69 m (2H), 7.02 t, 8 Hz (1H), 7.11 t, 8 Hz (1H), 7.27–7.35 m (2H), 7.38 d, 8 Hz (1H), 7.56 d, 8 Hz (1H), 7.58 dd, 7.1 Hz (1H), 7.70 d, 8 Hz (1H).

2-(4-Hydroxy-phenoxy)-N-[2-(1H-indol-2-yl)-phenyl]-acetamide

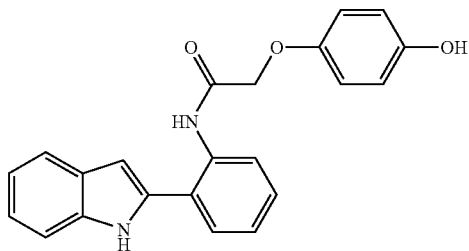

Prepared from 2-(2-aminophenyl) indole and (4-hydroxyphenoxy) acetic acid in 30% yield following procedure 1. The product was crystallized from methanol. 89% Purity by LC/MS (230 DAD), Mass-spec [M+H⁺]=359, ¹H NMR (MeOH-d4): 4.52 s (2H), 6.55 d, 9 Hz (2H), 6.58 s (1H), 6.61 d, 9 Hz (2H), 7.09 t, 8 Hz (1H), 7.18 t, 8 Hz (1H), 7.26 t, 8 Hz (1H), 7.37–7.43 m (2H), 7.56 t, 8 Hz (2H), 8.38 d, 8 Hz (1H).

2-Acetylamino-3-(4-hydroxy-phenyl)-N-[2-(1H-indol-2-yl)-phenyl]-propionamide

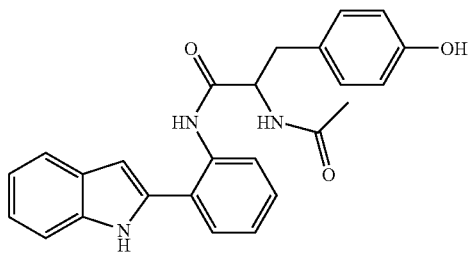

Prepared from 2-(2-aminophenyl) indole and N-acetyl-L-tyrosine in 69% yield following procedure 1. The product was chromatographed on silica. 99% Purity by LC/MS (230 DAD), Mass-spec [M+H⁺]=414, ¹H NMR (MeOH-d4): 1.79 s (3H, COMe), 2.83 dd, 14,9 Hz (1H), 3.14 dd, 14,6 Hz (1H), 4.58 dd, 9,6 Hz (1H), 6.51 s (1H), 6.70 d, 8 Hz (2H), 7.02 t, 7.5 Hz (1H), 7.07 d, 8 Hz (2H), 7.12 td, 8,1 Hz (1H), 7.27 td, 8,1 Hz (1H), 7.33 td, 8,1 Hz (1H), 7.44 d, 8 Hz (1H), 7.56 d, 8 Hz (1H), 7.59 dd, 8,1 Hz (1H), 7.83 d, 8 Hz (1H).

Procedure 2:

N-[2-(1H-Indol-2-yl)-phenyl]-phthalamic acid

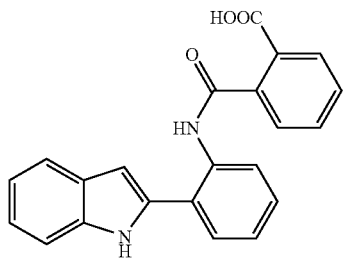

958 mg (4.6 mmol) 2-(2-Aminophenyl) indole and 675 mg (5.52 mmol, 1.2 eq) DMAP (dimethylamino pyridine) were dissolved in 35 ml anhydrous dichloromethane. The mixture was stirred for 10 min. 954 mg (6.44 mmol, 1.4 eq) of phthalic anhydride in 3 ml anhydrous dichloromethane were added and the mixture was stirred at 23° C. for three hours. To the mixture were added 20 ml dichloromethane. It was extracted with 50 ml aqueous 1 M HCl. The aqueous phase was re-extracted with 30 ml dichloromethane. The combined organic phases were dried over magnesium sulfate. The crude product was chromatographed on silica using an ethylacetate/hexane gradient (10%–90%) as mobile phase. The solvent was removed and the product was re-crystallized from ethylacetate:hexane (70:30) to obtain 654 mg of ivory colored crystals in 40% overall yield.

95% Purity by LC/MS (230 DAD), Mass-spec [M+H$^+$]= 357, $^1$H NMR (MeOH-d4): 6.75 s (1H), 6.99 t, 8 Hz (1H), 7.09 t, 7 Hz (1H), 7.35–7.43 m (3H), 7.52–7.57 m (3 H), 7.63 t, 8 Hz (1H), 7.71 d, 8 Hz (1H), 7.84 d, 8 Hz (1H), 8.06 d, 7 Hz (1H).

2-[2-(1H-Indol-2-yl)-phenylcarbamoyl]-nicotinic acid

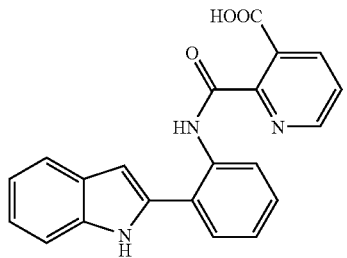

104 mg (0.5 mmol) 2-(2-Aminophenyl) indole and 74 mg (0.6 mmol, 1.2 eq) DMAP (dimethylamino pyridine) were dissolved in 5 ml anhydrous dichloromethane. The mixture was stirred for 10 min. 104 mg (0.7 mmol, 1.4 eq) of 2,3-pyridinedicarboxylic anhydride were added and the mixture was stirred at 23° C. for three hours.

To the mixture were added 20 ml dichloromethane. It was extracted with 20 ml saturated NaCl solution. The aqueous phase was re-extracted with 20 ml dichloromethane. The combined organic phases were dried over magnesium sulfate. The crude product was chromatographed on silica and re-crystallized from acetonitrile. 100% Purity by HPLC (UV, 230 nm), Mass-spec [M+H$^+$]=358, $^1$H NMR (MeOH-d4): 6.80 s (1H), 7.04 t, 7 Hz (1H), 7.14 t, 8 Hz (1H), 7.31 t, 7 Hz (1H), 7.42 t (2H), 7.57 d, 8 Hz (1H), 7.61 dd, 8.5 Hz (1H), 7.67 dd, 8.1 Hz (1H), 8.13 dd, 8.1 Hz (1H), 8.30 d, 8 Hz (1H), 8.61 dd, 5.1 Hz (1H).

3,4,5-trihydroxy-N-[2-(1H-indol-2-yl)-phenyl]-benzamide

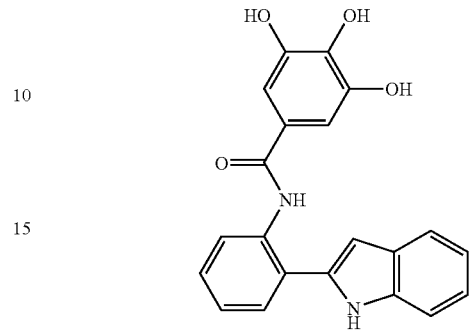

A 25-mL one-necked recovery flask equipped with a stirring bar and a septum was charged with gallic acid (176 mg; 1.03 mmol; 1.00 equiv). A clear, colorless solution was formed on addition of 5 mL of dichloromethane. Solid EDC (197 mg; 1.03 mmol; 1.00 equiv) and 2-(2-aminophenyl) indole (194 mg; 0.932 mmol; 0.904 equiv) were added sequentially as solids. The reaction was worked up after 24 h by extraction with 10 mL of NaHCO3 (satd aq). The organic layer was dried (anhydrous sodium sulfate), filtered and concentrated by rotary evaporation to yield a yellow oily paste. The crude was purified using DCM-MeOH (19:1) to yield a light yellow solid (230 mg; 68%).

Representative Syntheses of Compounds of Structure II

Compound II-1

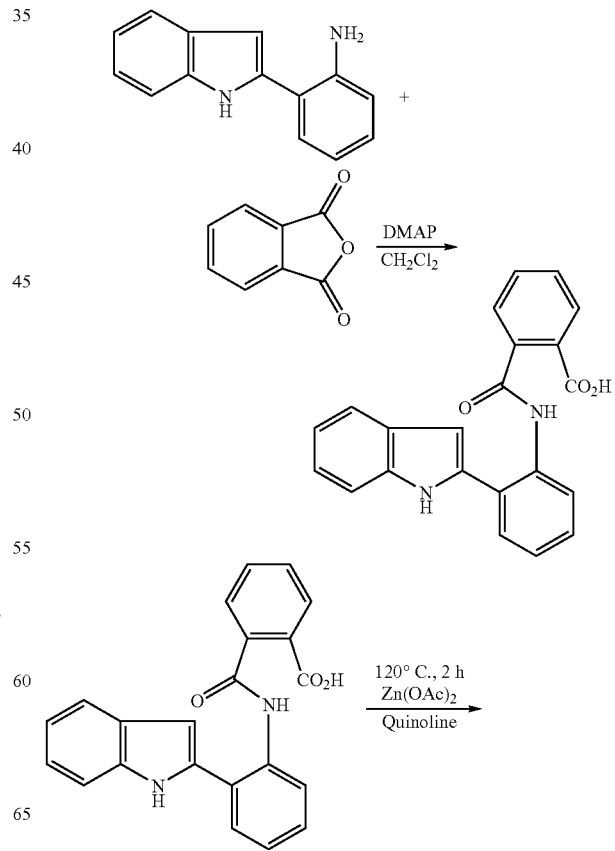

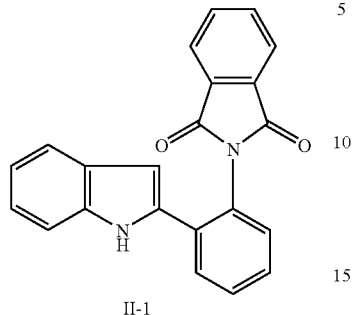

II-1

A 100-mL, one-necked, round bottomed flask with a magnetic stirring bar and a septum was charged with 2-(2-aminophenyl) indole (210 mg; 1.01 mmol). The indole was dissolved in ca. 7 mL of dichloromethane to give a very pale yellow solution. DMAP (143 mg; 1.17 mmol; 1.16 equiv) and phthalic anhydride (179 mg; 1.21 mmol; 1.20 equiv) were added sequentially each dissolving completely with a resulting yellow solution. The solution was stirred at room temperature, and the reaction was followed by TLC, and showed complete conversion in ca. 30 min as indicated by the disappearance of the 2-(2-aminophenyl) indole. The reaction mixture was poured into a 125-mL separatory funnel and extracted with 15 mL HCl (aq, ca. 1 M). The aqueous layer was washed with 2×5 mL CH$_2$Cl$_2$, and the combined organic layer was dried (anhydrous Na$_2$SO$_4$), filtered, and concentrated by rotary evaporation to yield a canary yellow foamy solid (0.377 g) of N-[2-(1H-indol-2-yl)-phenyl]phthalamic acid. MS (M+H$^+$: calcd 357; found 357).

A 5-mL reaction vial with a stirring vane and a teflon stopper was charged with N-(2-(1H-indol-2-yl)-phenyl)phthalamic acid, (140 mg; 0.393 mmol) and 0.500 mL of quinoline. To the solution, which was a dark brown-black, was added zinc acetate dihydrate (98.0 mg; 0.464 mmol; 1.16 equiv) and the resulting solution was heated to 120° C. for ca. 2 h. On adding 1 mL of ethyl acetate, a light tan solid resulted. The solid was washed with 4×10 mL 1 M HCl, then with 10 mL ethylacetate-hexane (1:1), followed by 10 mL ethyl acetate. The solid was dried in a vacuum dessicator over phosphorus pentoxide to yield 80.1 mg (71%) of a light tan solid. MS (M+H$^+$: calcd 339; found 339).

Pteridine, and Substituted Pteridine Syntheses

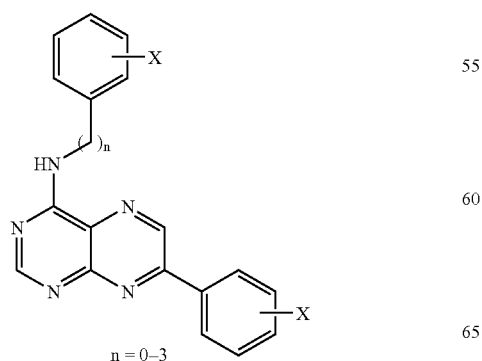

n = 0–3

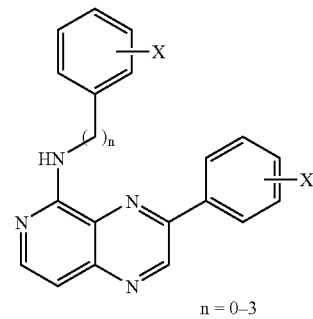

n = 0–3

X = H, OH, OMe, Hal

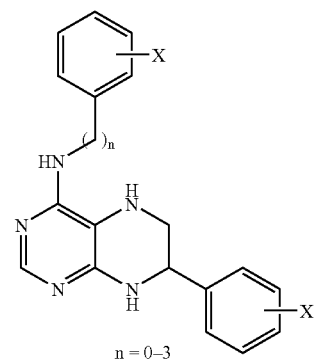

n = 0–3

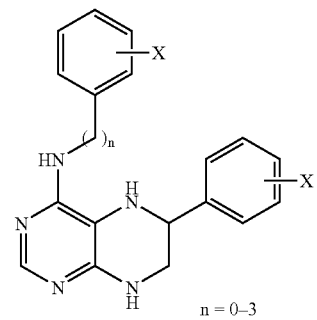

n = 0–3

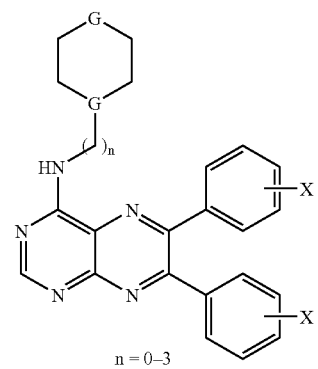

n = 0–3

Experimental Procedure 6,7-(4,4'-Dihydroxyphenyl)-pteridin-4-yl-3-morpholin-4-yl-propyl)-amine hydrochloride salt

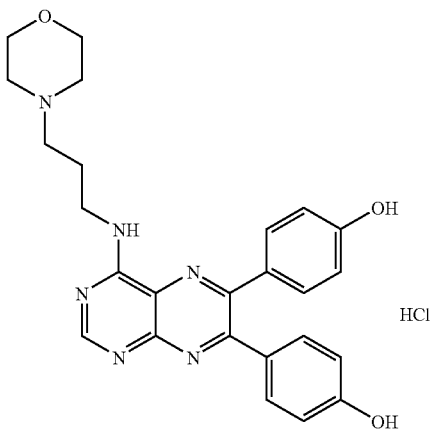

1.19 g (3.59 mmol) of 6,7-bis(4-hydroxyphenyl)-pteridin-4-ylamine was dissolved in 10 mL of N-(3-aminopropyl)morpholine and 0.697 g (7.18 mmol, 2.0 eq.) of sulfamic acid was added. The reaction mixture was heated at 160° C. for 18 hrs. Then it was cooled down to r.t., diluted with 20 mL of methanol and added dropwise to 1 L of diethyl ether. The resulting oil was purified by prep-HPLC, fractions were collected and solvent was removed in vacuo to give red oily residue, which was dissolved in 20 mL of methanol. 5 g of Amberlite chloride-exchange resin was added to the methanol solution. The reaction mixture was left to stir at r.t. overnight, then it was filtered and resin was washed with methanol. The methanol washes were combined, solvent was removed in vacuo. The resulting residue was re-dissolved in 2 mL of methanol and added dropwise to 45 mL of diethyl ether. The formed bright-yellow precipitate was centrifuged down, washed with 40 mL of diethyl ether twice and dried in vacuo to give 281.0 mg (26.2% overall) of the product as a yellow solid. Mass-spec [ES+]=459.2. 100% purity by LC/MS (230 DAD). $^1$H NMR (MeOH-d4) 2.28–2.31 (2H, m), 3.14–3.17 (2H, m), 3.30–3.35 (2H, m), 3.51–3.53 (2H, m), 3.80–3.84 (2H, m), 3.97–4.00 (2H, m), 4.04–4.06 (2H, m), 6.77–6.82 (4H, dd), 7.49–7.54 (4H, dd), 8.84 (1H, s).

Acetic acid 4-[7-(4-acetoxy-phenyl)-4-amino-pteridin-6-yl]-phenyl ester

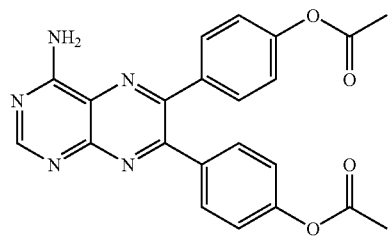

662.6 mg (2.0 mmol) of 6,7-bis(4-hydroxyphenyl)-pteridin-4-ylamine was dissolved in 20 ml of trifluoroacetic acid. 1.0 mL (14.06 mmol, 7.0 eq) of acetyl chloride was added via syringe to this mixture. Upon heating to 80° C. bubbling of the reaction mixture and evolution of HCl gas was observed. The reaction mixture was heated at 80° C. for 40 min, at which point LC/MS indicated a complete conversion of the starting material to the di-acetate. Solvent was removed in vacuo to give bright-yellow oil, which upon standing solidified. 40 mL of diethyl ether was added, the solid was crushed with spatula, centrifuged down, washed with 45 mL of diethyl ether twice and dried in vacuo to give 1.034 g (97.7%) of the product as a light-yellow solid. 97.5% purity by LC/MS (230 DAD). Mass-spec [ES+]= 416.5. $^1$H NMR (DMSO-d6) 2.280 (3H, s), 2.284 (3H, s), 7.16–7.21 (4H, dd), 7.56–7.62 (4H, dd), 8.80 (1H, s), 9.46 (1H, br.s), 9.52 (1H, br, s).

Acetic acid 4-[2-(4-acetoxy-phenyl)-6-amino-pyrido[2,3-b]pyrazin-3-yl]-phenyl ester

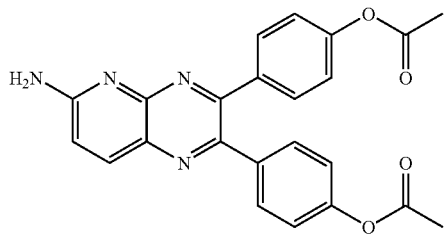

201.0 mg (0.5 mmol) of 2,3-bis(4-hydroxyphenyl)-pyrido[2,3-b]pyrazin-6-ylamine was dissolved in 10 ml of trifluoroacetic acid. 0.355 mL (5.0 mmol, 10.0 eq) of acetyl chloride was added via syringe to this mixture. Upon heating to 80° C. bubbling of the reaction mixture and evolution of HCl gas was observed. The reaction mixture was heated at 80° C. for 1 hr, at which point LC/MS indicated a complete conversion of the starting material to the di-acetate. Solvent was removed in vacuo to give brown solid. The solid was dissolved in 3.0 mL of methanol and this solution was added to 40 mL of diethyl ether. Upon standing for about an hour a brown precipitate was formed. It was centrifuged down, washed with 45 mL of diethyl ether twice and dried in vacuo to give 191.9 mg (79.0%) of the product as a light-brown solid. 98% purity by LC/MS (230 DAD). Mass-spec [ES+]= 415.5. $^1$H NMR (MeOH-d4) 2.28 (6H, s), 7.10–7.12 (4H, d), 7.24–7.26 (1H, d), 7.48–7.50 (2H, d), 7.54–7.56 (2H, d), 8.24–8.26 (1H, d).

Synthesis of 4-substituted 6-phenyl-pteridin-4-yl-amines

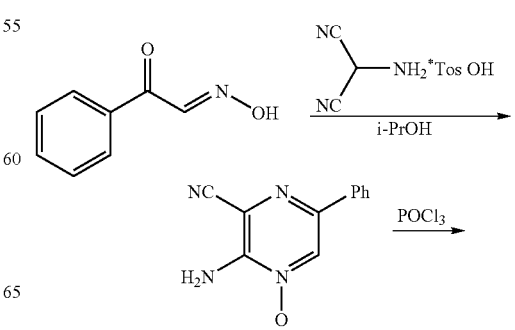

-continued

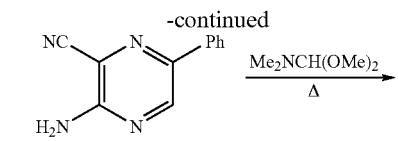

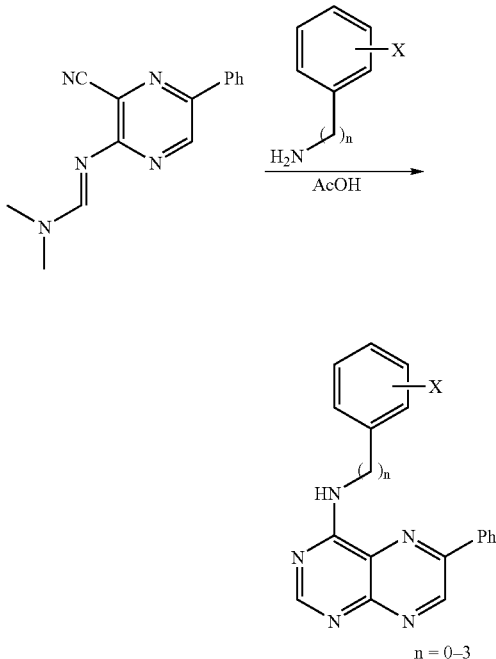

n = 0–3

General Procedure 0.55 mmol of amine was suspended in 4 mL of acetic acid. The mixture was brought to reflux and 0.5 mmol of N'-(3-cyano-5-phenyl-pyrazin-2-yl)-N,N'-dimethyl-formamidine was added to the solution. The reaction was refluxed for 2–5 hours. The progress of the reaction was monitored by LC/MS. After the reaction had completed, the reaction mixture was cooled down to ambient temperature and acetic acid was removed in vacuo. 5 mL of methanol was added to the resulting residue and it was crushed with a spatula into a fine suspension. The suspension was added to 45 mL of diethyl ether. The solid was centrifuged down, washed with 45 mL of diethyl ether twice and dried in vacuo to give the product as a solid.

(3,4-Dimethoxy-phenyl)-(6-phenyl-pteridine-4-yl)-amine

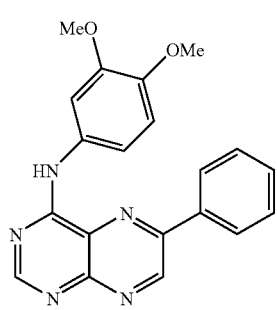

95.7% yield. 100% purity by LC/MS (230 DAD). Mass-spec [ES+]=360.9. $^1$H NMR (DMSO-d6) 3.79 (3H, s), 3.81 (3H, s), 7.02–7.03 (1H, d), 7.56–7.63 (5H, m), 8.58–8.60 (2H, m), 8.71 (1H, s), 9.80 (1H, s), 10.27 (1H, s).

(3-Chloro-4,6-dimethoxy-phenyl)-(6-phenyl-pteridin-4-yl)-amine

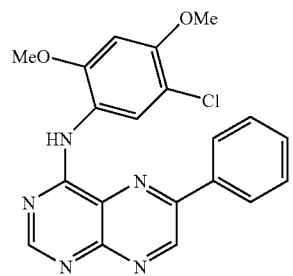

96% purity by LC/MS (230 DAD). Mass-spec [ES+]=394.9. $^1$H NMR (DMSO-d6) 3.92 (3H, s), 3.97 (3H, s), 6.96 (1H, s), 7.59–7.65 (3H, m), 8.29 (1H, s), 8.42–8.43 (2H, d), 8.74 (1H, s), 9.80 (1H, s), 9.89 (1H, s).

(3-Hydroxy-4-methoxy-phenyl)-(6-phenyl-pteridin-4-yl)-amine

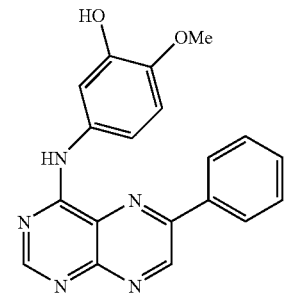

79.5% yield. 100% purity by LC/MS (230 DAD). Mass-spec [ES+]=346.9. $^1$H NMR (DMSO-d6) 3.79 (3H, s), 6.97–6.98 (1H, d), 7.29–7.31 (1H, dd), 7.46–7.47 (1H, d), 7.58–7.62 (3H, m), 8.58–8.60 (2H, m), 8.69 (1H, s), 9.15 (1H, s), 9.78 (1H, s), 10.2 (1H, s).

(4-Hydroxy-phenyl)-(6-phenyl-pteridin-4-yl)-amine

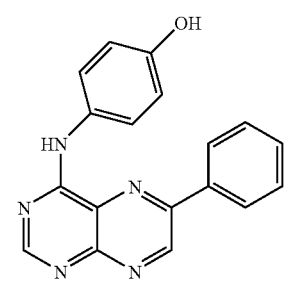

86.0% yield. 98% purity by LC/MS (230 DAD). Mass-spec [ES+]=316.8. $^1$H NMR (DMSO-d6) 6.82–6.84 (2H, d), 7.57–7.62 (3H, m), 7.65–7.67 (2H, d), 8.58 (2H, m), 8.63 (1H, s), 9.45 (1H, s), 9.78 (1H, s), 10.26 (1H, s).

(2,5-Dimethyl-4-hydroxy-phenyl)-(6-phenyl-pteridin-4-yl)-amine

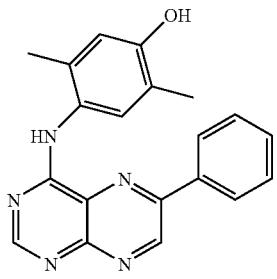

76.8% yield. 100% purity by LC/MS (230 DAD). Mass-spec [ES+]=344.9. ¹H NMR (DMSO-d6) 2.12 (6H, s), 6.73 (1H, s), 7.12 (1H, s), 7.55–7.60 (3H, m), 8.54 (1H, s), 8.57–8.58 (2H, m), 9.29 (1H, s), 9.78 (1H, s), 10.16 (1H, s).

2-Hydroxy-5-(6-phenyl-pteridin-4-ylamino)-benzene-sulfonic acid

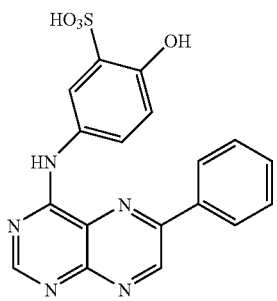

70.1% yield. 83% purity by LC/MS (230 DAD). Mass-spec [ES+]=396.8. ¹H NMR (DMSO-d6) 7.17–7.19 (1H, dd), 7.58–7.63 (3H, m), 7.80–7.82 (1H, dd), 7.993–7.999 (1H, d), 8.61–8.63 (2H, m), 8.73 (1H, s), 9.80 (1H, s), 10.51–10.53 (3H, m).

2-Diethylaminomethyl-4-(6-phenyl-pteridin-4-ylamino)-phenol

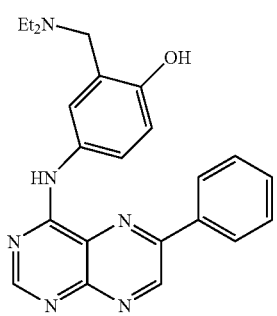

94.3% yield. 98.8% purity by ELSD. Mass-spec [ES+]=402.0. ¹H NMR (DMSO-d6) 1.28–1.31 (6H, t), 3.11–3.16 (4H, m), 4.25–4.26 (2H, d), 7.07–7.09 (1H, d), 7.58–7.63 (3H, m), 7.75–7.77 (1H, dd), 7.89–7.90 (1H, d), 8.57–8.59 (2H, m), 8.67 (1H, s), 9.81 (1H, s), 10.39 (1H, s), 10.5 (1H, s)

5-(6-Phenyl-pteridin-4-ylamino)-quinolin-8-ol hydrochloride salt

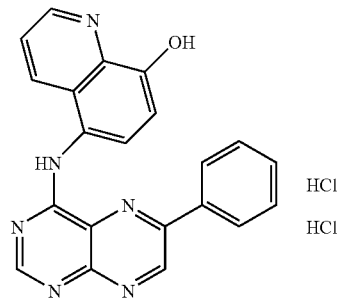

79.9% yield. 85% purity by LC/MS (230 DAD). Mass-spec [ES+]=367.7. ¹H NMR (DMSO-d6) 7.39–7.40 (1H, m), 7.61–7.72 (3H, m), 7.73–7.77 (2H, m), 8.60–8.67 (4H, m), 9.01–9.02 (1H, m), 9.92 (1H, s), 11.58 (1H, br.s.)

Benzyl-(6-phenyl-pteridin-4-yl)-amine

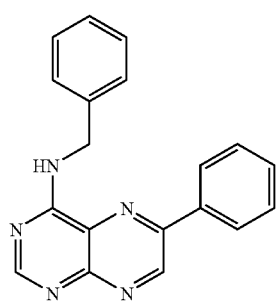

50.5% yield. 95.2% purity by LC/MS (230 DAD). Mass-spec [ES+]=314.2. ¹H NMR (MeOH-d4) 4.87 (2H, s), 7.24–7.26 (1H, m), 7.30–7.33 (2H, m), 7.43–7.44 (2H, m), 7.51–7.54 (3H, m), 8.30–8.32 (2H, m), 8.58 (1H, s), 9.56 (1H, s).

4-[(6-phenyl-pteridin-4-ylamino)-methyl]-benzene-1,2-diol

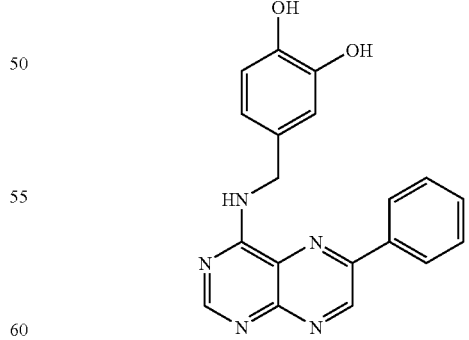

39.8% yield. 100% purity by LC/MS (230). Mass-spec [ES+]=346.2. ¹H NMR (DMSO-d6) 5.56 (2H, s), 6.68–6.70 (1H, d), 6.75–6.77 (1H, dd), 6.875–6.879 (1H, d), 7.62–7.64 (3H, m), 8.53–8.55 (2H, m), 8.97 (1H, s), 9.12 (1H, s), 9.24 (1H, s), 9.89 (1H, s), 10.48 (1H, s), 10.54 (1H, s).

Indan-2-yl-(6-phenyl-pteridin-4-yl)-amine

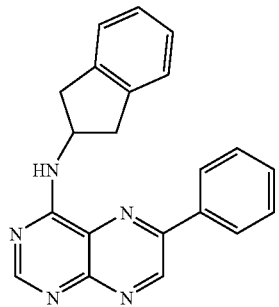

53.9% yield. 96.6% purity by LC/MS. Mass-spec [ES+]= 340.2. ¹H NMR (DMSO-d6) 3.21–3.26 (2H, dd), 3.35–3.40 (2H, dd), 5.13–5.18 (1H, m), 7.17–7.19 (2H, m), 7.25–7.27 (2H, m), 7.55–7.59 (3H, m), 8.47–8.49 (2H, m), 8.65 (1H, s), 8.94–8.96 (1H, d), 9.72 (1H, s).

2-(3,4-Dimethoxy-phenyl)-ethyl]-(6-phenyl-pteridin-4-yl)-amine

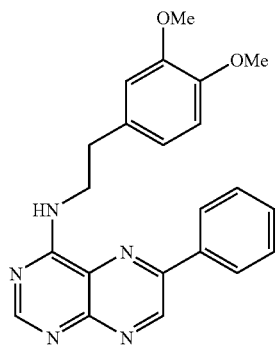

66.5% yield. 95.5% purity by LC/MS (230 DAD). Mass-spec [ES+]=388.2. ¹H NMR (MeOH-d4) 2.98–3.01 (2H, t), 3.76 (3H, s), 3.78 (3H, s), 3.90–3.93 (2H, t), 6.85–6.88 (2H, m), 6.93–6.93 (1H, m), 7.55–7.57 (3H, m), 8.27–8.29 (2H, m), 8.58 (1H, s), 9.56 (1H, s)

Synthesis of 4-substituted 7-phenyl-pteridin-4-yl-amines

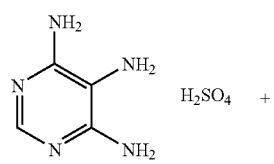

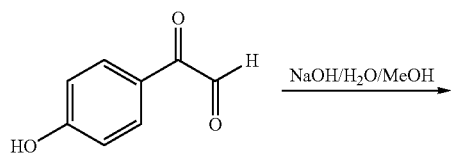

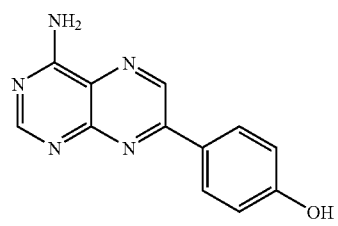

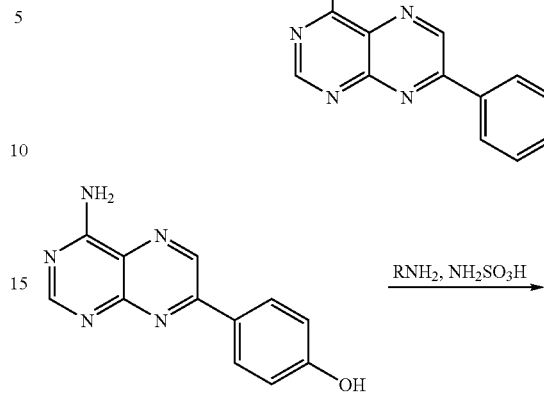

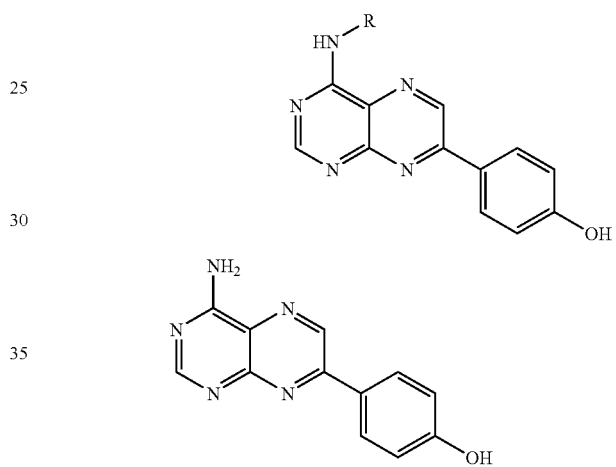

4-(4-Amino-pteridin-7-yl)-phenol 1N aqueous NaOH was added to a suspension of 1.33 g (5.95 mmol) of 4,5,6-triaminopyrimidine sulfate in 20 mL of water until pH reached 8. To this solution was added a solution of 1.0 g (5.95 mmol) of 4-hydroxyphenylglyoxal in 20 mL of methanol. The reaction mixture was left to stir at ambient temperature for 18 hrs. Formation of a yellow precipitate was observed. It was collected, washed with 20 mL of water, 20 mL of methanol, 45 mL of diethyl ether 3 times and dried in vacuo to give 1.513 g of the product as a light-yellow solid. 100% yield. 97.5% purity by LC/MS (230 DAD). Mass-spec [ES+]=. ¹H NMR (DMSO-d6) 6.95–6.98 (2H, d), 8.31 (1H, br.s.), 8.19 (1H, br.s.), 8.21–8.24 (2H, d), 8.51 (1H, s), 9.34 (1H, s).

239.2 mg (1.0 mmol) of 4-(4-amino-pteridin-7-yl)-phenol was suspended in 3 mL of amine and 194.2 mg (2.0 mmol) of sulfamic acid was added to this mixture. The reaction mixture was heated at 160–180° C. for 18 hrs. Then it was cooled down to ambient temperature and dissolved in 5–10 mL of methanol. Methanol solution was added dropwise to 45 mL of diethyl ether, the mixture was vortexed and centrifuged down. Solvent was decanted and the residue was purified by prep-HPLC.

4-(4-Benzylamino-pteridin-7-yl)-phenol

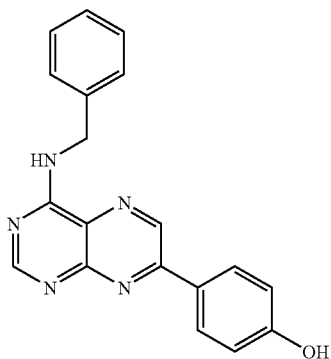

79% yield. 98.5% purity by LC/MS (230 DAD). Mass-spec [ES+]=330.2. $^1$H NMR (DMSO-d6) 4.77–4.78 (2H, d), 6.97–6.98 (2H, d), 7.24–7.26 (1H, m), 7.30–7.33 (2H, m), 7.43–7.44 (2H, m), 8.23–8.24 (2H, d), 8.58 (1H, s), 9.37 (1H, s).

Substituted (6-phenyl-5,6,7,8-tetrahydro-pteridin-4-yl)-amines and (7-phenyl-5,6,7,8-tetrahydro-pteridin-4-yl)-amines

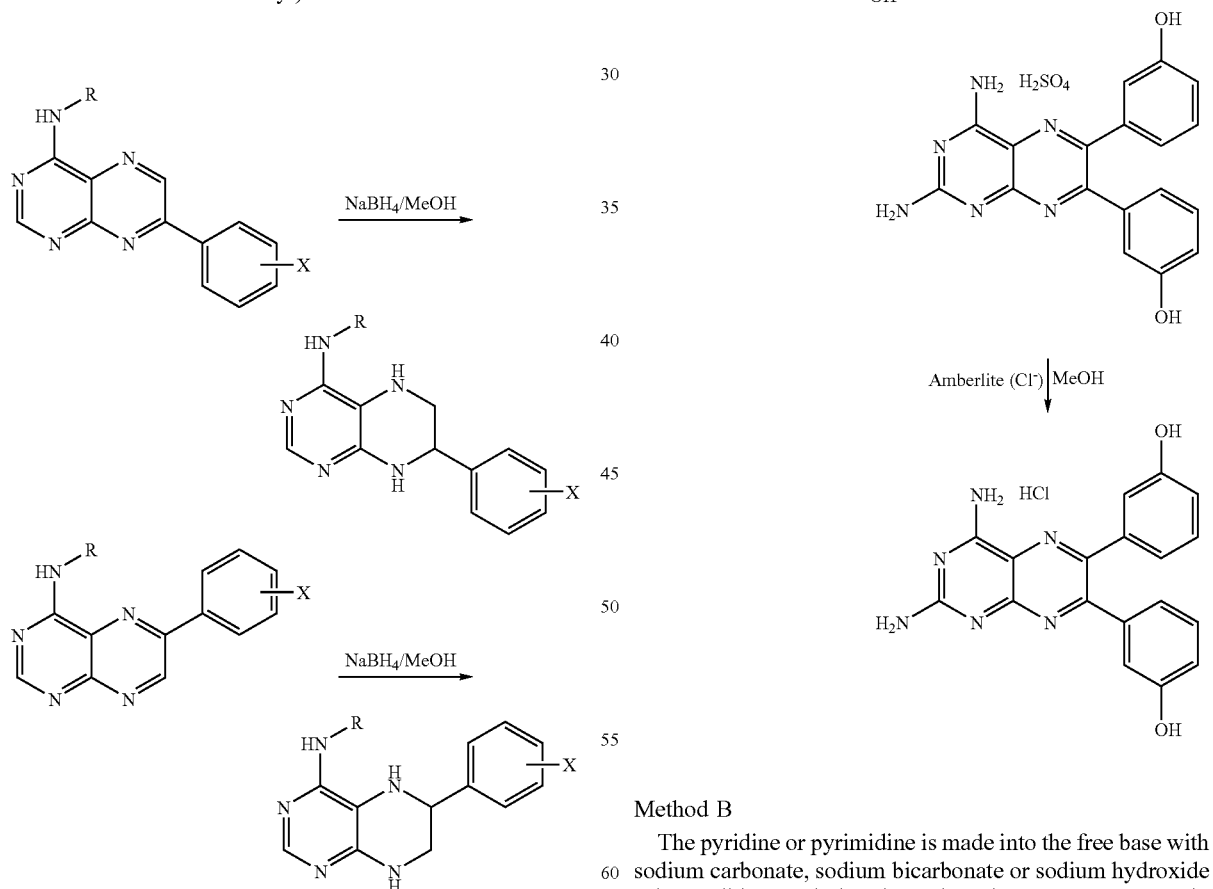

General Procedure

To a stirred solution of the pteridine (5.0 mmol) in 15 mL of dry methanol was added sodium borohydride (5 mmol) at room temperature. The reaction mixture was stirred for 30 min and then neutralized with acetic acid. Solvent was removed in vacuo and the residue was washed with water, cold methanol, diethyl ether and dried in vacuo. The resulting solid was purified by reverse phase prep-HPLC.

6,7-disubstituted pteridines; Method A.

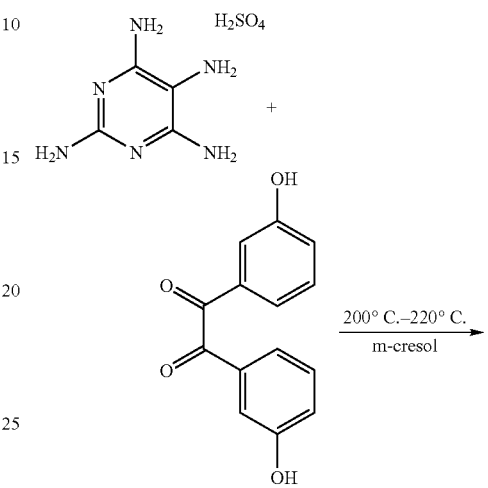

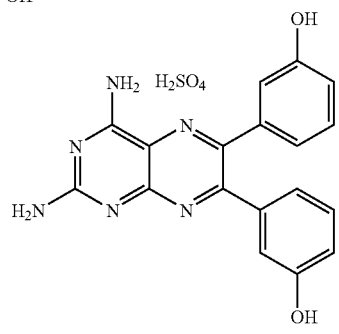

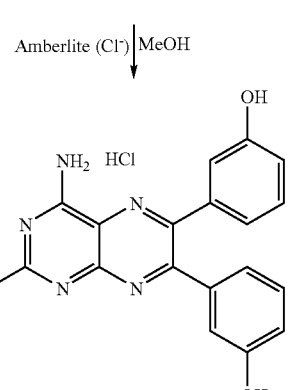

Method B

The pyridine or pyrimidine is made into the free base with sodium carbonate, sodium bicarbonate or sodium hydroxide using solid or solution by using the correct amount in equivalents to neutralize the acid or by adjusting the pH to neutral to slightly basic (ca. 7–9). The benzil or glyoxal is added and the solution is heated for 1 h–5 h. The free base formed precipitates out of solution and is washed successively with water, methanol and then ether. The solid is vacuum dessicator dried.

This reaction was carried out by method A by using 23.5 mg of the pyrimidine and 22.5 mg of pyridyl. The reaction mixture was heated for 1 h. The product was precipitated into 5 mL of 1:1 EtOAc-ether, filtered and washed with 50 mL of ether. M+H calcd and found 400.

6,7-bis(3-hydroxyphenyl)-pteridine-2,4,-diamine 5-mL reaction vial with a stirring vane and a teflon cap was charged with 3,3'-dihydroxybenzil (Midori Kagaku Co Ltd; 121 mg; 0.500 mmol) and 0.700 mL of m-cresol (Acros) which gives a dull-yellow solution on warming to ca. 50° C. The clear solution is treated with 2,4,5,6-tetraaminopyrimidine sulfate (Aldrich; 119 mg; 0.500 mmol; 1.00 equiv) which is insoluble in the reaction solution at room temperature and goes into solution on heating to ca. 200° C. to give an almost completely homogeneous dark greenish solution in about 30 min–45 min. Heating between 200° C. and 220° C. for an additional 1.5 h, followed by cooling to room temperature, and precipitation by pouring into 40 mL of anhydrous diethyl ether resulted in a greenish-yellow precipitate. The solid was centrifuged, the supernatant decanted, the solid precipitate was washed with 5×40 mL of diethyl ether and dried in a vacuum dessicator to yield 0.275 g (124%)[1] of a yellow-green solid. The only obvious major impurity is the reaction solvent, m-cresol. MS (M+H$^+$: calcd 347; found 347).

In case purified 6,7-bis(3-hydroxyphenyl)-pteridine-2,4-diamine is required, the crude 3-[2,4-diamino-6-(3-hydroxyphenyl)pteridin-7-yl]phenol may be dissolved in methanol, and an aqueous solution of 2.0 equiv.–2.2 equiv. of sodium bicarbonate (or excess sodium bicarbonate) may be added to neutralize the acid making sure the pH is between 6 and 8 to ensure free-base. The free-base precipitates out of the methanol-water mixture within a few seconds. In case, precipitation does not occur, excess methanol ensures precipitation. The yellowish solid may be isolated and washed with acetonitrile-water or isopropanol-water mixtures and then with methanol-ether, and then ether (×3). The product is dried and stored as the free base, 6,7-bis(3-hydroxyphenyl)-pteridine-2,4-diamine.

In case the purified sulfate is required, the free base is protonated in MeOH by adding a conc. aqueous sulfuric acid (1.0 equiv) to a slurry of the compound in MeOH. The homogeneous protonated product is precipitated out by adding ether to the methanol.

6-pyridin-2-yl-7-pyridin-3-ylpteridin-4-amine sulfate salt

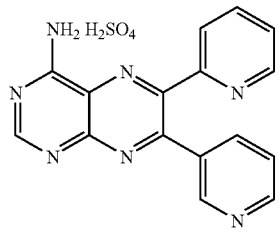

A 5-mL reaction vial with a stirring vane and a teflon cap was charged with pyridyl (22.5 mgl) and 0.500 mL of m-cresol (Acros) which gives a dull-yellow solution on warming to ca. 50° C. The clear solution is treated with 2,4,5-triaminopyrimidine sulfate (Aldrich; 23.5 mg) which is insoluble in the reaction solution at room temperature and goes into solution on heating to ca. 200° C. to give an almost completely homogeneous dark solution in about 30 min–45 min. Heating between 200° C. and 220° C. for an additional 0.5 h, followed by cooling to room temperature, and precipitation by pouring into 40 mL of anhydrous diethyl ether resulted in a dull yellow precipitate. The solid was centrifuged, the supernatant decanted, the solid precipitate was washed with 4×40 mL of diethyl ether and dried in a vacuum dessicator to yield a yellow solid. MS (M+H$^+$: calcd 302; found 302).

6,7-bis(3,4-dihydroxyphenyl)pteridine-2,4-diol

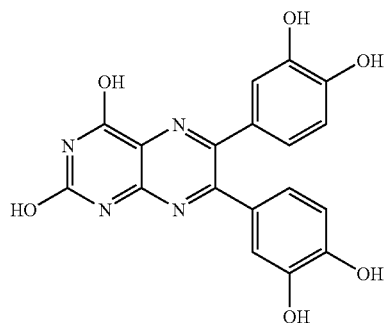

A 5-mL reaction vial with a stirring vane and a teflon cap was charged with 3,3',4,4'-tetrahydroxybenzil (137 mg; 0.500 mmol) and 1.00 mL of m-cresol (Acros) which gives a yellow-brown slurry warming to ca. 50° C. The suspension is treated with sulfate 5,6-diamino-2,4-dihydroxypyrimidine sulfate (120 mg; 0.500 mmol; 1.00 equiv) which is insoluble in the reaction solution at room temperature and goes into solution on heating to ca. 200° C. to give homogeneous dark solution. Heating between 200° C. and 220° C. for an additional 2 h, followed by cooling to room temperature, and precipitation by pouring into 40 mL of anhydrous diethyl ether resulted in a light yellow precipitate. The solid was centrifuged, the supernatant decanted, the solid precipitate was washed with 4×40 mL of diethyl ether and dried in a vacuum dessicator to yield a yellow solid. MS (M+H$^+$: calcd 381; found 381).

6,7-bis(3-hydroxyphenyl)-pteridine-2,4-diamine dihydrochloride salt

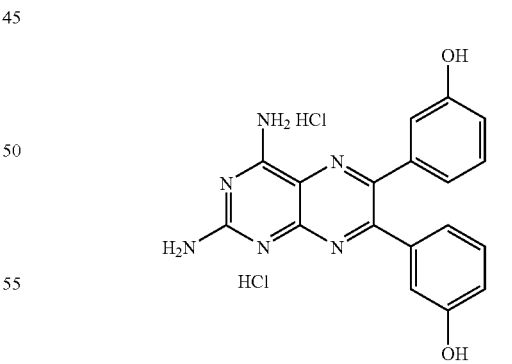

A 125-mL amber-bottle with a stirring bar and a septum was charged with crude 6,7-bis(3-hydroxyphenyl)-pteridine-2,4-diamine (135 mg; 0.304 mmol) and 5 mL of methanol. To the resulting dark brownish-green solution was added Amberlite (Cl$^-$) resin (GFS Chemical; 5.20 g). The heterogeneous mixture was stirred gently for ca. 16 h. with an apparent visual lightening of the solution. The solution was filtered to remove the resin beads, which were rinsed with 5×8 mL of MeOH. The light brown solution was concentrated on a rotary evaporator to yield 133 mg of dark brown oil. The oil was redissolved in ca. 2 mL of MeOH, and added to 40 mL of diethyl ether to yield a flocculent yellow precipitate that was isolated by centrifuging and decanting the supernatant. The solid was washed with 4×40 mL of diethyl ether, and dried in a vacuum dessicator to yield a greenish-yellow product (94.0 mg; 0.246 mmol; 81% for two steps). 98% purity by LC/MS (230 DAD). Mass-spec [ES$^+$]=347.7. $^1$H NMR (DMSO-d6) 6.78–6.87 (4H, m), 6.92–6.95 (2H, m), 7.12–7.16 (2H, m), 7.82 (1H, br.s), 8.68 (1H, br.s), 9.15 (1H, s), 9.25 (1H, s), 9.58 (1H, s), 9.72 (1H, s). C, N analysis: $C_{18}H_{16}Cl_2N_6O_2$ (Calcd.: C, 51.56; N, 20.04; Found: C, 51.64; N, 19.93).

Method B

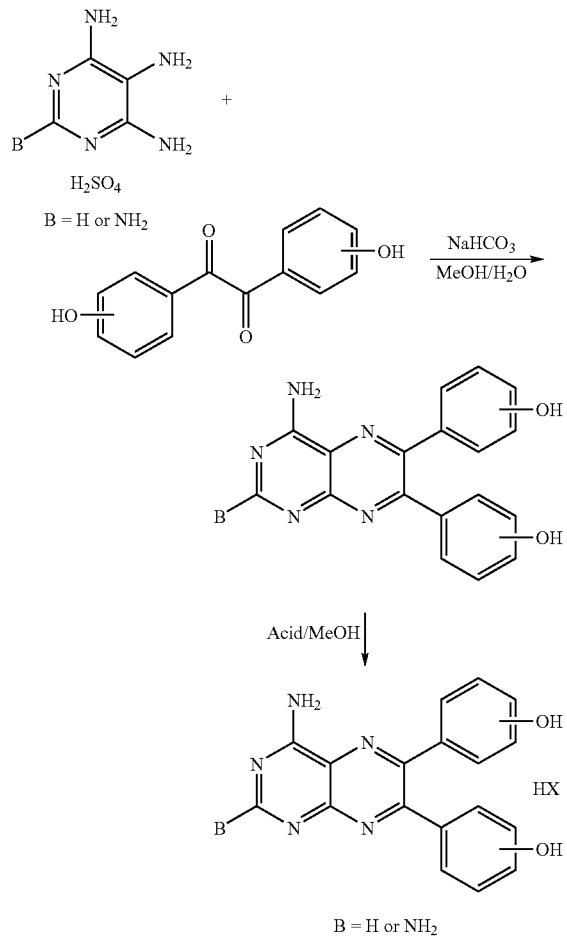

6,7-bis(3-hydroxyphenyl)-pteridine-2,4-diamine 4.76 g (20.0 mmol) of 2,4,5,6-tetraaminopyrimidine sulfate was added in small portions to a solution of 3.36 g (40.0 mmol) sodium bicarbonate in 100 mL of water with vigorous stirring. A brisk evolution of $CO_2$ gas was observed. The resulting suspension was heated to 80° C. and 4.84 g (20.0 mmol) of 3,3'-dihydroxybenzil was added to the mixture. The reaction mixture was refluxed for 3 hours, at which point a bright-yellow precipitate was formed in abundance.

The precipitate was filtered, washed with water, then with methanol, followed by diethyl ether and dried in vacuo to give 6.46 g (93.3% yield) of a bright-yellow solid. 98.10% purity by LC/MS (230 DAD). Mass-spec [ES$^+$]=347.7. $^1$H NMR (DMSO-d6) 6.64 (2H, br.s.), 6.69–6.82 (4H, m), 6.86–6.89 (2H, m), 7.06–7.11 (2H, m), 7.57 (1H, br.s), 7.65 (1H, br.s), 9.38 (1H, s), 9.49 (1H, s).

6,7-bis(3-hydroxyphenyl)-pteridine-2,4-diamine methanesulfonate salt

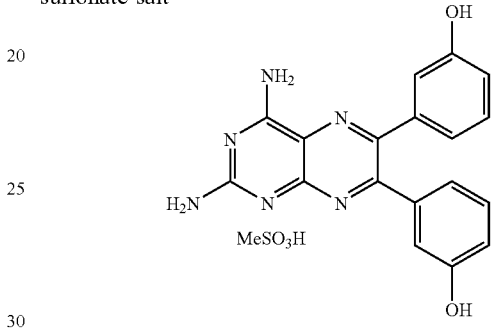

2.66 g (7.68 mmol) of 6,7-bis(3-hydroxyphenyl)-pteridine-2,4-diamine was added to a solution of 1.55 g (16.13 mmol) of methanesulfonic acid in 20 mL of MeOH with stirring. Pteridine immediately dissolved to give a dark-greenish solution. The reaction mixture was stirred for 30 min and then added dropwise to 400 mL of diethyl ether with vigorous stirring. The formed yellow precipitate was collected, washed repeatedly with ether and dried in vacuo to give 3.36 g (99.1% yield) of the product as a light-yellow powder. 95.5% purity by LC/MS (230 DAD). Mass-spec [ES$^+$]=347. $^1$H NMR (MeOH-d4) 2.71 (3H, s), 6.80–6.85 (2H, m), 6.90–6.92 (2H, m), 6.95 (1H, m), 7.00 (1H, m), 7.12–7.16 (2H, m).

6,7-bis(3-hydroxyphenyl)-pteridine-2,4-diamine Dihydrobromide Salt

The salt is made by making a HBr containing solution of methanol using methanol and acetyl bromide (10 equiv–12 equiv) at −78° C., and adding the free base to this solution so that the resulting solution concentration is below 0.4 M. The light yellow solution is stirred for ca. 30 min–60 min, concentrated by rotary evaporation to a yellow solid and then washed with ether, or with ether-hexanes, and dried in a vacuum dessicator

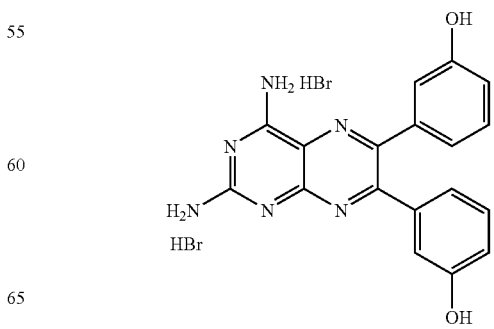

98.8% Purity by LC/MS (230 DAD). Mass-spec [ES⁺]= 347. ¹H NMR (MeOH-d4) 6.81–6.86 (2H, m), 6.92–6.95 (2H, m), 6.96–7.01 (2H, m), 7.13–7.18 (2H, m). Elemental analysis; calcd: C, 42.54; H, 3.17; N, 16.54; found: C, 43.11; H, 3.47; N, 16.47

6,7-bis(3-hydroxyphenyl)-pteridin-4-ylamine

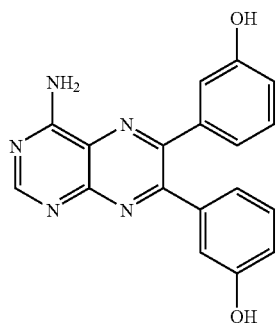

2.23 g (10.0 mmol) of 4,5,6-triaminopyrimidine sulfate was added in small portions to a solution of 1.68 g (20.0 mmol) sodium bicarbonate in 50 mL of water with vigorous stirring. A brisk evolution of $CO_2$ gas was observed. The resulting suspension was heated to 80° C. and 2.42 g (10 mmol) of 3,3'-dihydroxybenzil was added to the mixture. The reaction mixture was refluxed for 1 hour, during which time the starting materials completely dissolved and the product precipitated out as a light-yellow solid.

The precipitate was collected, washed with water, then with methanol, followed by diethyl ether and dried in vacuo to give 3.14 g (94.8% yield) of the product as a light-yellow solid. 100% purity by LC/MS (230 DAD). Mass-spec [ES⁺]= 332.8. ¹H NMR (DMSO-d6) 6.77–6.83 (3H, m), 6.91–6.92 (1H, d), 6.90–6.99 (2H, m), 7.11–7.15 (2H, m), 8.17 (1H, br.s), 8.25 (1H, br.s.), 8.56 (1H, s), 9.55 (2H, br.s).

6,7-bis(3-hydroxyphenyl)-pteridin-4-ylamine hydrochloride salt

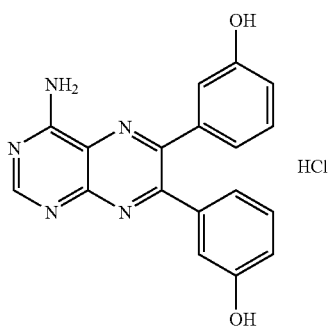

4.4 g (13.27 mmol) of 6,7-bis(3-hydroxyphenyl)-pteridin-4-ylamine was suspended in 35 ml of MeOH. A solution of 2.61 g of aq. HCl (26.55 mmol, 12.1 N) in 5 mL of MeOH was added to the suspension. The reaction mixture became homogeneous within 5 min of stirring. It was left to stir for 30 min and then added dropwise to 400 mL of diethyl ether with vigorous stirring. The resulting precipitate was collected, washed repeatedly with ether and dried in vacuo to give 4.62 g (94.7% yield) of the product as a bright-yellow solid. 98.3% purity by LC/MS (230 DAD). Mass-spec [ES⁺]=332.8. ¹H NMR (MeOH) 6.88–6.90 (2H, m), 6.99–7.02 (2H, m), 7.04–7.08 (2H, m), 7.17–7.20 (2H, m), 8.79 (1H, s).

6,7-bis(3-hydroxyphenyl)-pteridin-4-ylamine methanesulfonate salt

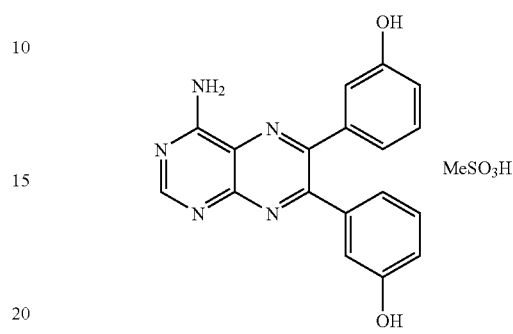

1.308 g (13.63 mmol) of methanesulfonic acid in 10 mL of MeOH was added to the suspension of 2.15 g (6.48 mmol) of 6,7-bis(3-hydroxyphenyl)-pteridin-4-ylamine in 10 mL of MeOH. The mixture became homogeneous and orange-red in color. It was stirred for 30 min and then added dropwise to 400 mL of diethyl ether with vigorous stirring. The formed yellow precipitate was collected, washed with diethyl ether and dried in vacuo to give 2.69 g (97.11% yield) of the product as a light-yellow powder. Mass-spec [ES⁺]=332.8. ¹H NMR (MeOH-d4) 2.70 (3H, s), 6.86–6.90 (2H, m), 6.99–7.01 (2H, m), 7.04–7.08 (2H, m), 7.16–7.21 (2H, m), 8.80 (1H, s).

6,7-bis(4-hydroxyphenyl)-pteridin-4-ylamine

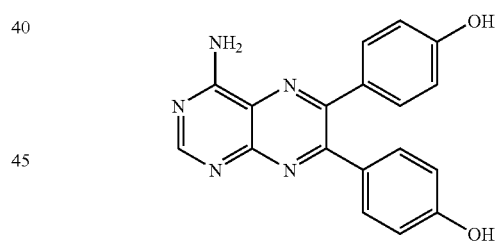

1.5 mmol of the sulfate salt (6,7-bis(4-hydroxyphenyl)-pteridin-4-ylamine sulfate salt as 1:1 complex with m-cresol) was dissolved in 10 mL of 1:1 solution of MeOH/$H_2O$. 2.0 eq. of solid $NaHCO_3$ were added to this solution. A brisk evolution of $CO_2$ was observed and a light-yellow precipitate started to form in ~10–15 min of stirring. The mixture was left to stir overnight and a yellow precipitate was formed in abundance. 20 mL of water was added, the formed precipitate was filtered, washed twice with water to remove $Na_2SO_4$, washed with cold MeOH, washed repeatedly with $Et_2O$ and dried in vacuo to give the product in 81.3% yield over two steps (reaction in m-cresol and free base synthesis). 95.5% purity by LC/MS (230 DAD). Mass-spec [ES⁺]=332.8. ¹H NMR (DMSO-d6) 6.72–6.76 (4H, dd), 7.35–7.42 (4H, dd), 8.06 (1H, br.s), 8.14 (1H, br.s), 8.50 (1H, s), 9.77 (1H, br.s), 9.87 (1H, br.s)

6,7-bis(4-hydroxyphenyl)-pteridin-4-ylamine sulfate salt

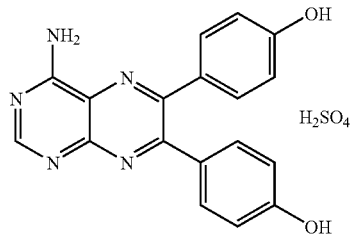

1.97 g of 6,7-bis(4-hydroxyphenyl)-pteridin-4-ylamine was added to a solution of 0.585 g of concentrated sulfuric acid in 50 mL of MeOH. The homogeneous mixture was left to stir at ambient temperature for 2 hours, then it was added dropwise to 400 mL of diethyl ether. The formed orange precipitate was collected, washed repeatedly with ether and dried in vacuo to give 2.36 g (92.5% yield) of the product as a light-orange fluffy powder. 100% purity by LC/MS (230 DAD). Mass-spec [ES$^+$]=332.8. $^1$H NMR (MeOH-d4) 6.77–6.80 (4H, m), 7.48–7.53 (4H, m), 8.73 (1H, s). $^1$H NMR (DMSO-d6) 6.76–6.81 (4H, dd), 7.41–7.47 (4H, dd), 8.84 (1H, s), 9.85 (1H, s), 10.01 (1H, s), 9.94 (1H, br.s), 10.15 (1H, br.s).

6,7-bis(3,4-dihydroxyphenyl)-pteridine-2,4-diamine

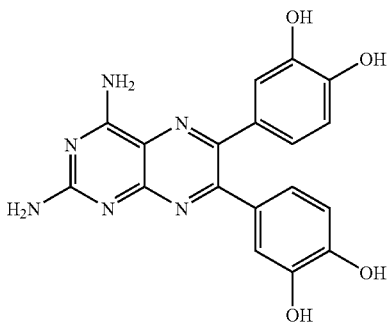

105.0 mg (0.253 mmol) of 6,7-bis(3,4-dihydroxyphenyl)-pteridine-2,4-diamine dihydrochloride salt was dissolved in 3 mL of water and 42.53 mg of solid NaHCO3 was added to this solution. The reaction mixture was stirred for 30 min. A slurry of yellow precipitate was formed, it was centrifuged down and solvent was decanted. The dark-yellow residue was dissolved in 3 mL of MeOH and added dropwise to 40 mL of diethyl ether. The formed yellow precipitate was collected, washed with ether and dried in vacuo to give 92.5 mg (96.5% yield) of the product as a yellow, fluffy powder. 97% purity by LC/MS (230 DAD). Mass-spec [M+H$^+$]= 379.3. $^1$H NMR (MeOH-d4) 6.68–6.73 (2H, dd), 6.79–6.81 (1H, dd), 6.84–6.86 (1H, dd), 6.93 (1H, d), 7.03 (1H, d).

6,7-bis(3,4-dihydroxyphenyl)-pteridine-2,4-diamine dihydrochloride salt

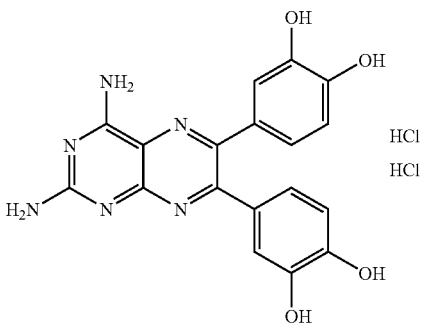

Mass-spec [ES$^+$]=379.8. $^1$H NMR (MeOH-d4) 6.70 (1H, d), 6.75 (1H, d), 6.88 (1H, dd), 6.93 (1H, dd), 6.95 (1H, d), 7.08 (1H, d).

6,7-bis(3,4-dihydroxyphenyl)-pteridin-4-ylamine hydrochloride salt or 4-[4-amino-6-(3,4-dihydroxyphenyl)pteridin-7-yl]benzene-1,2-diol hydrochloride salt A 5-mL reaction vial with a stirring vane and a teflon cap was charged with 3,3',4,4'-tetrahydroxybenzil (Midori Kagaku Co Ltd; 548 mg; 2.00 mmol), 4,5,6-triaminopyrimidine sulfate and 3.00 mL of m-cresol. The heterogeneous mixture was heated, it first goes orange while dissolving at ca. 150° C. and then on heating at 200° C.–220° C. for ca. 2 h goes to a dark blood-red solution. The clear solution is heated for an additional 30 min, followed by cooling to room temperature, and precipitation by pouring into 40 mL of anhydrous diethyl ether resulted in a dark red-orange precipitate. The solid was centrifuged, washed with 5×40 mL of diethyl ether and dried in a vacuum dessicator to yield 1.20 g (128%)[1] of an orange-red solid. The only obvious major impurity is the reaction solvent, m-cresol.

Mass-spec [ES+]=364.8. $^1$H NMR (MeOH-d4) 6.73 (1H, d), 6.78 (1H, d), 7.00–7.02 (2H, dd), 7.07 (1H, d), 7.16 (1H, d). 8.71 (1H, s).

6,7-bis(3,4-dihydroxyphenyl)-pteridin-4-ylamine or 4-[4-amino-6-(3,4-dihydroxyphenyl)pteridin-7-yl]benzene-1,2-diol

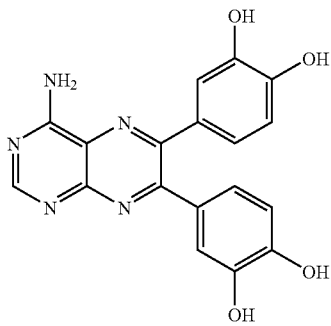

Mass-spec [ES+]=364.8. $^1$H NMR (MeOH-d4) 6.70–6.75 (2H, dd), 6.91–6.95 (2H, dd), 7.03 (1H, d), 7.12 (1H, d), 8.49 (1H, s). $^1$H NMR (DMSO-d6) 6.63–6.68 (2H, dd), 6.74–6.76 (1H, dd), 6.85–6.87 (1H, dd), 7.00 (1H, d), 7.06 (1H, d), 7.93 (2H, br.s), 8.47 (1H, s).

6,7-bis(3,4-dihydroxyphenyl)-pteridin-4-ylamine methanesulfonate salt or 4-[4-amino-6-(3,4-dihydroxyphenyl)pteridin-7-yl]benzene-1,2-diol methanesulfonate salt

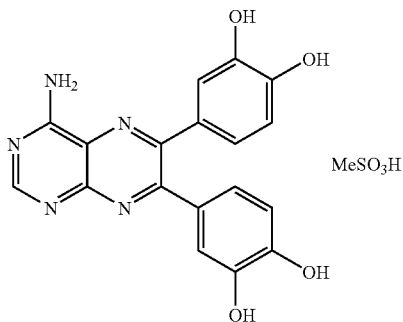

98.07% purity by LC/MS (230 DAD). Mass-spec [ES+]=364.8. $^1$H NMR (MeOH-d4) 2.69 (3H, s), 6.73–6.79 (2H, dd), 7.00–7.04 (2H, dd), 7.08 (1H, d), 7.17 (1H, d), 8.81 (1H, s).

4-(2,4-diaminopteridin-6-yl)phenol

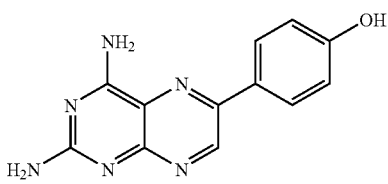

A 50-mL recovery flask fitted with a stirring bar, a reflux condensor and a heating mantle was charged with 1 mmol of each of hydroxylamine hydrochloride and 4-hydroxyphenylglyoxal. The substances were dissolved in methanol (5 mL). To this yellow solution was added the 2,4,5,6-tetraminopyrimidine sulfate and 20 mL of water. The heterogeneous solution was heated to reflux for 2 h. A yellow precipitate that was formed. The solution was cooled, the reaction mixture was made slightly basic NaOH (4 M, aqueous) to a pH of ca. 8. The precipitated free base was isolated and washed sequentially with water (2×40 mL), methanol (1×40 mL) and ether (1×40 mL) and drying in a vacuum dessicator.

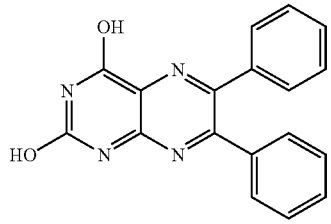

A 5-mL reaction vial with a stirring vane and a teflon cap was charged with benzil (420 mg; 2.00 mmol) and 2.00 mL of m-cresol (Acros) which gives a dull-yellow solution on warming to ca. 50° C. The clear solution is treated with 5,6-diamino-2,4-dihydroxypyrimidine sulfate (Aldrich; 482 mg; 2.00 mmol; 1.00 equiv) which is insoluble in the reaction solution at room temperature and goes into solution on heating to ca. 200° C. to give an almost completely homogeneous dark solution in about 30 min–45 min. Heating between 200° C. and 220° C. for an additional 1.5 h, followed by cooling to room temperature, and precipitation by pouring into 40 mL of anhydrous diethyl ether resulted in a dull yellow precipitate. The solid was centrifuged, the supernatant decanted, the solid precipitate was washed with 4×40 mL of diethyl ether and dried in a vacuum dessicator to yield 960 mg (99%) of a yellow solid. MS (M+H+: calcd 317; found 317).

4-(2,4-Diamino-pteridin-6-yl)-phenol (M+H)+ calcd and found 255; LC (UV-PDA 230 nm) 98% purity.; $^1$H NMR (500 MHz; DMSO-d$_6$): δ 9.89 (br s, 1 H), 9.24 (s, 1 H), 8.15 (d, J=8.5 Hz, 2 H), 7.70 (br. s, 1 H), 7.65 (br. s, 1 H) 6.88 (d, J=8.5 Hz, 2 H), 6.57 (br s, 2 H)

2,3-Diphenyl-pyrido[3,4-b]pyrazin-8-ylamine hydrochloride salt

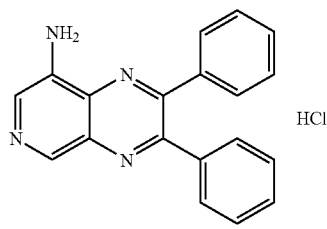

60.0 mg (0.37 mmol) of 3,4,5-triaminopyrimidine hydrochloride and 86.3 mg (0.41 mmol) of benzil were heated at 190° C. in 1.0 mL of m-cresol for 1 hr. Then the mixture was cooled down to r.t., mixed with 35 mL of diethyl ether. The formed brown precipitate was collected, washed repeatedly with ether and dried in vacuo to give 51.1 mg (45.8% yield) of the product as a brown powder. Mass-spec [M+H+]= 299.2. 1H NMR (MeOH-d4) 7.38–7.41 (3H, m), 7.45–7.49 (3H, m), 7.58–7.60 (2H, m), 7.66–7.68 (2H, m), 8.05 (1H, s), 8.85 (1H, s).

2,3-Bis(4-hydroxyphenyl)-pyrido[3,4-b]pyrazin-8-ylamine hydrochloride salt

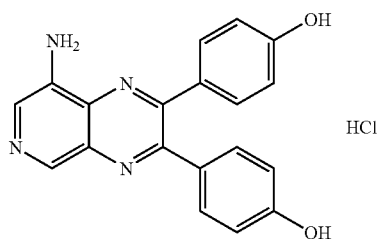

60.0 mg (0.37 mmol) of 3,4,5-triaminopyrimidine hydrochloride and 99.6 mg (0.41 mmol) of 4,4'-dihydroxybenzil were heated at 190° C. in 1.0 mL of m-cresol for 1 hr. Then the mixture was cooled down to r.t., mixed with 35 mL of diethyl ether. The formed brown precipitate was collected, washed repeatedly with ether and dried in vacuo to give 91.3 mg (66.6% yield) of the product as a dark-green powder. Mass-spec [M+H$^+$]=331.4. $^1$H NMR (MeOH-d4) 6.78–6.81 (4H, d), 7.49–7.51 (2H, d), 7.60–7.62 (2H, d), 7.95 (1H, s), 8.71 (1H, s).

2,3-Bis(3-hydroxyphenyl)-pyrido[3,4-b]pyrazin-8-ylamine hydrochloride salt

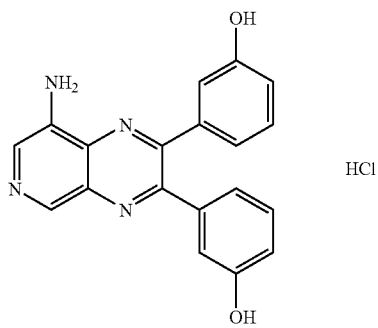

60.0 mg (0.37 mmol) of 3,4,5-triaminopyrimidine hydrochloride and 99.6 mg (0.41 mmol) of 3,3'-hydroxybenzil were heated at 190° C. in 1.0 ml of m-cresol for 1 hr. Then the mixture was cooled down to r.t., mixed with 35 ml of diethyl ether. The formed brown precipitate was collected, washed repeatedly with ether and dried in vacuo to give 93.9 mg (68.5% yield) of the product as a greenish-brown powder. Mass-spec [M+H$^+$]=331.4. $^1$H NMR (MeOH-d4) 6.88–6.91 (2H, m), 6.99–7.01 (1H, m), 7.07–7.10 (2H, m), 7.13–7.14 (1H, m), 7.18–7.22 (2H, m), 8.03 (1H, s), 8.82 (1H, s).

2,3-Bis(3,4-dihydroxyphenyl)-pyrido[3,4-b]pyrazin-8-ylamine hydrochloride salt

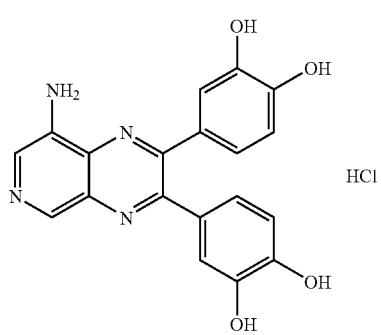

60 mg (0.37 mmol) of 3,4,5-triamnopyridine hydrochloride and 112.6 mg (0.41 mmol) of 3,3',4,4'-tetrahydroxybenzil were dissolved in 1 mL of m-cresol. The reaction mixture was heated at 190° C. for 1 hr, at which point the mixture became homogeneous and dark-brown in color. The reaction was cooled to r.t. and mixed with 35 mL of diethyl ether. The formed brown precipitate was vortexed, collected, washed repeatedly with diethyl ether and dried in vacuo to give 111.0 mg (82% yield) of the product. Mass-spec [M+H$^+$]=363.2. $^1$H NMR (MeOH-d4) 6.76–6.78 (2H, d), 6.98–7.00 (1H, dd), 7.11 (1H, dd), 7.13 (1H, d), 7.21 (1H, dd), 7.94 (1H, s), 8.68 (1H, s).

2,3-bis(3-hydroxyphenyl)-pyrido[2,3-b]pyrazin-6-ylamine dihydrochloride salt

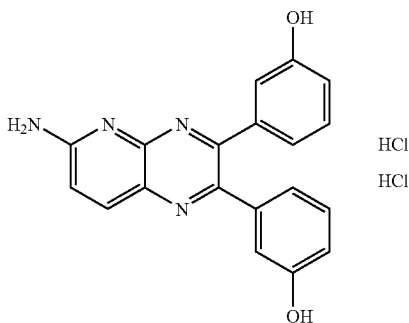

197.0 mg (1.0 mmol) of 2,3,6-triaminopyrimidine dihydrochloride and 242.4 mg (1.0 mmol) of 3,3'-dihydroxybenzil were dissolved in 3.0 mL of 1:1 mixture of dioxane-water. The reaction mixture was refluxed for 3 hours and then solvent was removed in vacuo. The resulting greenish solid was dissolved in 3 mL of MeOH and this solution was added to 40 mL of diethyl ether with vigorous stirring. The formed precipitate was collected, washed with diethyl ether and dried in vacuo to give 342.9 mg (85.0% yield) of the product as a light-green powder. 99.0% purity by LC/MS (230 DAD). Mass-spec [ES$^+$]=331.8. $^1$H NMR (MeOH-d4) 6.83–6.85 (2H, m), 6.88–6.90 (1H, m), 6.95–6.97 (2H, m), 7.02–7.03 (1H, m), 7.14–7.18 (2H, m), 7.36–7.38 (1H, d), 8.43–8.46 (1H, d).

2,3-bis(4-hydroxyphenyl)-pyrido[2,3-b]pyrazin-6-ylamine dihydrochloride salt

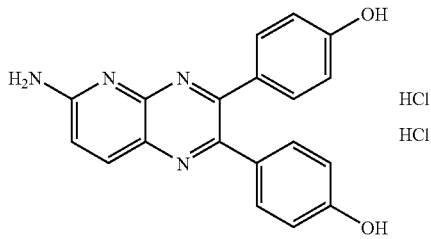

1.97 g (10.0 mmol) of 2,3,6-triaminopyrimidine dihydrochloride and 2.42 g (10.0 mmol) of 4,4'-dihydroxybenzil were dissolved in 30 mL of 1:1 mixture of dioxane-water. The reaction mixture was refluxed for 6 hours and then solvent was distilled off. The resulting dark-brown solid was suspended in 20 mL of MeOH and this suspension was added to 400 mL of diethyl ether with vigorous stirring. The formed dark-brown precipitate was collected, washed with diethyl ether and dried in vacuo to give 3.35 g (83.1% yield) of the product as a brown fluffy powder. 92.6% purity by LC/MS (230 DAD). Mass-spec [ES+]=331.8. $^1$H NMR (MeOH-d4) 6.72–5.77 (4H, m), 7.29–7.33 (3H, m), 7.40–7.42 (1H, m), 7.41 (1H, d), 8.35 (1H, d).

Phosphate ester of 4,4'-dihydroxybenzil

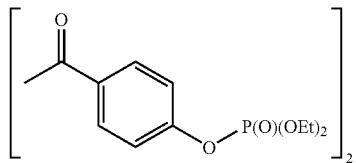

A 50-mL one-necked round-bottomed flask with a stirring bar and a septum was charged with 4,4'-dihydroxybenzil (512 mg; 2.11 mmol; 1.00 equiv) and acetonitrile (8 mL). To this partially dissolved mixture was added triethylamine (1.06 g; 14.9 mmol; 7.06 equiv), dimethylaminopyridine (DMAP) (478 mg; 3.91 mmol; 1.85 equiv) and dichloromethane (DCM) as co-solvent. The reaction mixture was stirred for 3 d at room temperature after which it was concentrated by rotary evaporation to yield a yellow-white slurry. This oily slurry was partitioned between sodium bicarbonate (satd. aq) and dichloromethane (DCM). The aqueous layer was rewashed with 2×5 mL DCM, followed by extraction of the combined organics with 10 mL of 1 M HCl. The DCM layer was dried (anhyd. MgSO$_4$), filtered and concentrated by rotary evaporation to yield the desired material as a light yellow slightly viscous oil. The compound does not require any purification but is easily purified by column chromatography using DCM-EtOAc (1:1). The chromatographically purified material is a yellow oil (911 mg; 89%).

$^1$H NMR (500 MHz; DMSO-d$_6$): δ 8.01 (d, J=8.6 Hz, 4 H), 7.45 (d, J=8.5 Hz, 4 H), 4.21–4.18 (m, 8 H), 1.28 (app t, J=5.0 Hz, 12 H)

The compound was made by the method B in the pteridine synthesis by using the pyrimidine and the phosphate ester of the 4,4'-dihydroxybenzil.

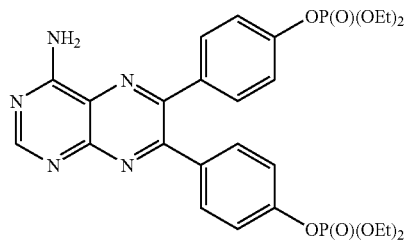

The compound was purified by passing through a plug of silica using ethyl acetate. (M+H)+: calcd. 604; found 604. LC purity 96% (DAD at 230 nm).

$^1$H NMR (500 MHz; DMSO-d$_6$); δ 8.58 (s, 1 H), 8.30 (br s, 2 H), 7.58 (d, J=6.8 Hz), 7.54 (d, J=6.8 Hz, 2 H), 7.23 (d, J=8.8 Hz, 2 H), 7.20 (d, J=8.9 Hz, 2 H), 4.17–4.14 (m, 8 H), 1.26 (app t, J=6.9 Hz, 12 H)

Phosphate Ester Deprotected

The above diethylester compound was deprotected in acetonitrile using TMSBr. The reaction was completed by adding water and then concentration by rotary evaporation and drying of the solid.

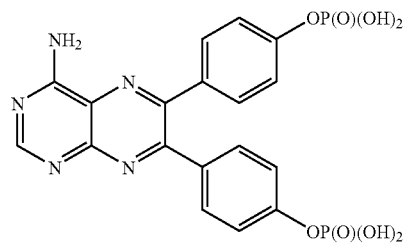

$^1$H NMR (500 MHz; methanol-d4); δ 8.39 (s, 1 H), 7.31 (d, J=6.8 Hz, 2 H), 7.26 (d, J=6.7 Hz, 2 H), 6.31 (app t, J=6.8 Hz, 4 H)

Phosphate Ester of Pyridopyrazine

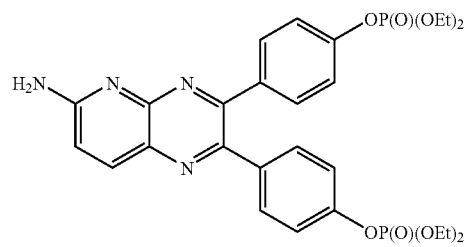

$^1$H NMR (500 MHz; DMSO-d$_6$): δ 8.05 (d, J=9.0 Hz, 1 H), 7.46 (d, J=8.7 Hz, 2 H), 7.43 (d, J=8.6 Hz, 2 H), 7.24 (br s, 2 H), 7.17 (app t, J=7.7 Hz, 4 H), 7.10 (d, J=9.0 Hz, 1 H), 4.17–4.13 (m, 8 H), 1.26 (app t, J=5.0 Hz, 12 H)

Phosphate Ester Deprotected

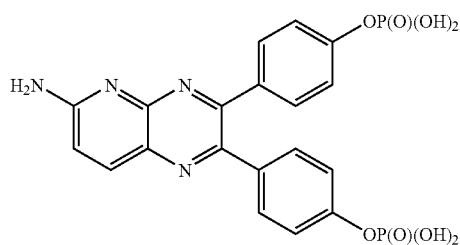

This compound was made in a similar fashion to the one described above.

$^1$H NMR (500 MHz; methanol-d$_4$); δ 8.05 (d, J=9.0 Hz, 1 H), 7.46 (d, J=8.7 Hz, 2 H), 7.43 (d, J=8.6 Hz, 2 H), 7.24 (br s, 2 H), 7.17 (app t, J=7.7 Hz, 4 H), 7.10 (d, J=9.0, 2 H).

Long Chain Ester of Pteridine

The benzil was modified using an acid chloride with DMAP as base in DCM. The modified Benzil was then condensed with the pyrimidine to yield the product below.

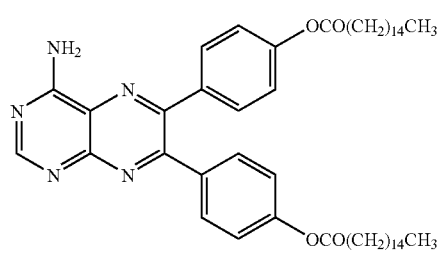

4-(4-amino-pteridin-7-yl)-benzene-1,2-diol

This compound is made by stirring a 1:1 ratio of the appropriate glyoxal with the free base of the pyrimidine in water at a pH of 7 for ca. 3 h. The product is isolated by filtering the precipitated free base, washing sequentially with water (2×40 mL), methanol (1×40 mL) and ether (2×40 mL) and drying in a vacuum dessicator.

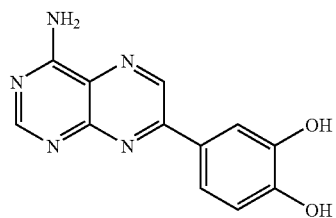

$^1$H NMR (500 MHz; DMSO-d$_6$): δ 9.72 (s, 1 H), 9.40 (br s, 1 H), 9.28 (s, 1 H), 8.51 (s, 1 H), 8.17 (br s, 1 H), 8.12 (br s, 1 H), 7.80 (d, J=2.3 Hz, 1 H), 7.71 Hz, (dd, J=8.4 Hz, J=2.3 Hz, 1 H), 6.92 (d, J=8.3 Hz, 1 H).

4-(2,4-diamino-pteridin-7-yl)-benzene-1,2-diol

This compound is made by stirring a 1:1 ratio of the appropriate glyoxal with the free base of the pyrimidine in water at a pH of 7 for ca. 3 h. The product is isolated by filtering the precipitated free base, washing sequentially with water (2×40 mL), methanol (1×40 mL) and ether (2×40 mL) and drying in a vacuum dessicator.

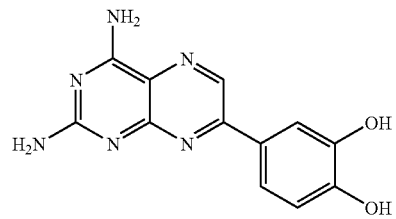

$^1$H NMR (500 MHz; DMSO-d$_6$): δ 8.71 (s, 1 H), 7.64 (d, J=2.3 Hz, 1 H), 7.56–7.53 (br s, 2 H), 7.53 (dd, J=8.3 Hz, 2.1 Hz, 1 H), 6.84 (d, J=8.3 Hz, 1 H), 6.52 (br s, 2 H)

4-(4-amino-pteridin-7-yl)-phenol

This compound is made by stirring a 1:1 ratio of the appropriate glyoxal with the free base of the pyrimidine in water at a pH of 7 for ca. 3 h. The product is isolated by filtering the precipitated free base, washing sequentially with water (2×40 mL), methanol (1×40 mL) and ether (2×40 mL) and drying in a vacuum dessicator.

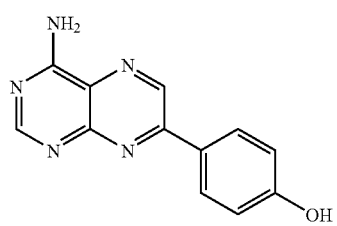

$^1$H NMR (500 MHz; DMSO-d$_6$): δ 10.2 (br s, 1 H), 9.34 (s, 1 H), 8.52 (s, 1 H), 8.23 (d, J=6.8 Hz, 2 H), 8.19 (br s, 1 H), 8.13 (br s, 1 H), 6.97 (d, J=8.8 Hz, 2 H)

4-(2,4-diamino-pteridin-7-yl)-phenol

This compound is made by stirring a 1:1 ratio of the appropriate glyoxal with the free base of the pyrimidine in water at a pH of 7 for ca. 3 h. The product is isolated by filtering the precipitated free base, washing sequentially with water (2×40 mL), methanol (1×40 mL) and ether (2×40 mL) and drying in a vacuum dessicator.

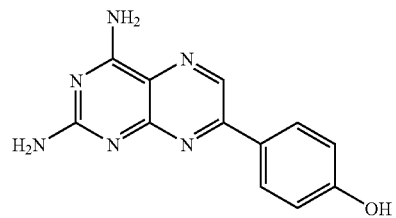

$^1$H NMR (500 MHz; DMSO-d$_6$): δ 10.0 (br s, 1 H), 8.81 (s, 1 H), 8.09 (d, J=8.5 Hz, 2 H), 7.62 (br s, 1 H), 7.55 (br s, 1 H), 6.91 (d, J=8.5 Hz, 2 H), 6.57 (br s, 2 H)

4-phenyl-pteridin-4-yl-amine

This compound was prepared by heating ammonium acetate with the appropriate pyrazine in acetic acid for an hour. The product is isolated by concentrating the solution by rotary evaporation and washing with ether.

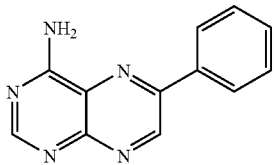

¹H NMR (500 MHz; DMSO-d₆): δ 9.73 (s, 1 H), 8.54 (s, 1 H), 8.49 (dd, J=8.2 Hz, J=1.9 Hz, 2 H), 8.46 (br s, 1 H), 8.31 (br s, 1H), 7.60–7.55 (m, 3 H)

Experimental Procedure

4-[2-(6-Phenyl-pteridin-4-ylamino)-ethyl]benzene-1,2-diol

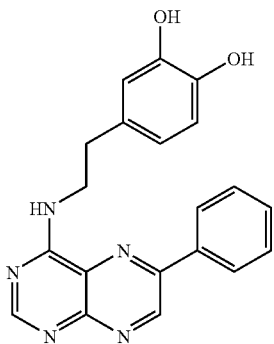

To a suspension of 3-hydroxytyramine hydrochloride (189.6 mg, 1.0 mmol) in 4 mL of glacial acetic acid was added N'-(3-cyano-5-phenyl-pyrazin-2-yl)-N,N'-dimethyl-formamidine (251.3 mg, 1.0 mmol). The reaction was refluxed for 1.5 hours. The progress of the reaction was monitored by LC/MS. After the reaction had completed, the reaction mixture was cooled down to ambient temperature and acetic acid was removed in vacuo. 5 mL of methanol was added to the resulting residue and it was crushed with a spatula into a fine suspension. 10 mL of 1:1 mixture of acetonitrile/water was added to the suspension. The solid was centrifuged down, washed with 20 mL of 1:1 mixture of acetonitrile/water twice, 10 mL of methanol, 40 mL of diethyl ether and dried in vacuo to give the product as a greenish-yellow solid. 58.5% yield. 96.9% purity by LC/MS (230 DAD). Mass-spec [ES+]=360.5. ¹H NMR (DMSO-d6) 2.80–2.83 (m, 2H), 3.72–3.76 (m, 2H), 6.52–6.54 (dd, 1H), 6.65–6.67 (d, 1H), 6.68–6.69 (d, 1H), 7.56–7.61 (m, 3H), 8.45–8.47 (m, 2H), 8.63 (s, 1H), 8.68 (br.s, 1H), 8.80 (br.s, 1H), 8.91–8.94 (t, 1H), 9.72 (s, 1H). UV λ$_{max}$=239, 209, 279.

4-[(Phenyl-pteridin-4-ylamino)-methyl]-benzene-1,2-diol

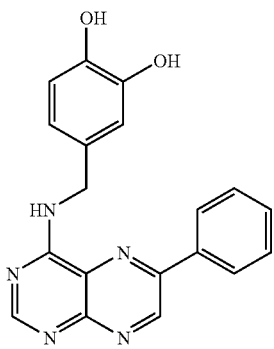

To a suspension of 3,4-dihydroxybenzylamine hydrobromide (220.1 mg, 1.0 mmol) in 4 mL of glacial acetic acid was added N'-(3-cyano-5-phenyl-pyrazin-2-yl)-N,N'-dimethyl-formamidine (251.3 mg, 1.0 mmol). The reaction was refluxed for 4 hours. The progress of the reaction was monitored by LC/MS. After the reaction had completed, the reaction mixture was cooled down to ambient temperature and acetic acid was removed in vacuo. 5 mL of methanol was added to the resulting residue and it was crushed with a spatula into a fine suspension. The suspension was added to 45 mL of diethyl ether. The solid was centrifuged down, washed with 45 mL of diethyl ether twice and dried in vacuo to give the product as a yellow solid. The product was purified by prep-HPLC, the major product was collected and solvent was removed in vacuo. 99.6% purity by LC/MS (230 DAD). Mass-spec [ES+]=346.5. ¹H NMR (DMSO-d6) 5.56 (s, 2H), 6.68–6.70 (d, 1H), 6.75–6.77 (dd, 1H), 6.87–6.87 (d, 1H), 7.62–7.64 (m, 3H), 8.53–8.55 (m, 2H), 8.97 (s, 1H), 9.12 (s, 1H), 9.24 (s, 1H), 9.89 (s, 1H), 10.48 (br.s, 1H), 10.54 (br.s, 1H). UV λ$_{max}$=245, 278, 210.

2,3-Bis(3,4-dihydroxyphenyl)-pyrido[2,3-b]pyrazin-6-ylamine dihydrochloride salt

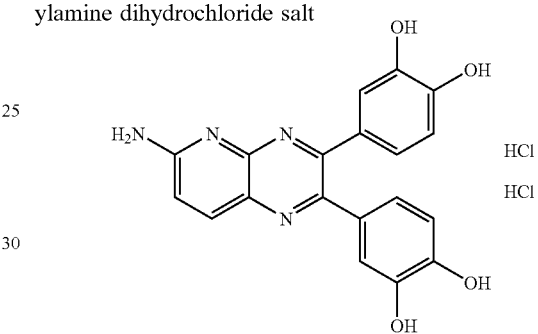

107.07 mg (1.0 mmol) of 2,3,6-triaminopyrimidine dihydrochloride and 274.23 mg (1.0 mmol) of 3,3',4,4'-tetrahydroxybenzil were dissolved in 4 mL of 1:1 mixture of dioxane-water. The reaction was refluxed for 8 hours. Then solvent was removed in vacuo. The dark-yellow residue was dissolved in 2 mL of methanol and this solution was added dropwise to 40 mL of diethyl ether. The formed dark-yellow precipitate was collected, washed with ether and dried in vacuo to give 370.0 mg (85% yield) of the product. 100% purity by LC/MS (230 DAD). Mass-spec [ES+]=363.8. 1H NMR (MeOH-d4) 6.70–6.75 (2H, dd), 6.81–6.92 (2H, dd), 6.96–7.07 (2H, dd), 7.27 (1H, d), 8.34 (1H, d).

2,3-Bis(3-hydroxyphenyl)quinoxalin-6-ylamine dihydrochloride salt

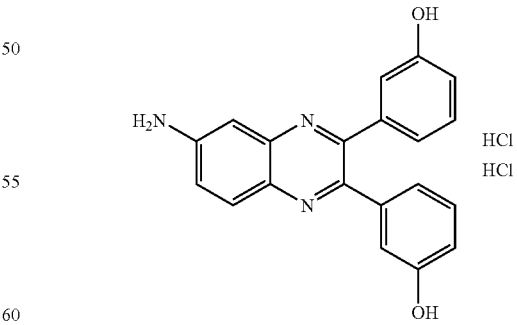

40.4 mg (0.206 mmol) of 1,2,4-benzenetriamine dihydrochloride and 50 mg (0.20 mmol) of 3,3'-dihydroxybenzil were dissolved in 2 mL of 1:1 mixture of dioxane-water. The reaction was refluxed for 3 hours. Then solvent was removed in vacuo. The residue was dissolved in 2 mL of methanol and this solution was added dropwise to 40 mL of diethyl ether. The formed dark-red precipitate was collected, washed with ether and dried in vacuo to give 69.8 mg (92.6% yield) of the product. 97.6% purity by LC/MS (230 DAD). Mass-spec [ES+]=330.8. $^1$H NMR (500 MHz, MeOH-d4) 6.81–6.87 (2H, m), 6.96–6.98 (4H, m), 7.10 (1H, m), 7.13–7.16 (1H, t), 7.28–7.31 (1H, t), 7.56–7.58 (1H, m), 8.04–8.06 (1H, d).

2,3-Bis(4-hydroxyphenyl)quinoxalin-6-ylamine dihydrochloride salt

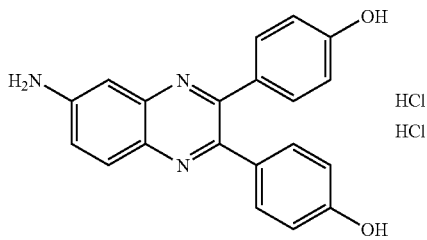

98.04 mg (0.5 mmol) of 1,2,4-benzenetriamine dihydrochloride and 121.2 mg (0.5 mmol) of 4,4'-dihydroxybenzil were dissolved in 2 ml of 1:1 mixture of dioxane-water. The reaction was refluxed for 3 hours. Then solvent was removed in vacuo. The residue was dissolved in 2 ml of methanol and this solution was added dropwise to 40 ml of diethyl ether. The formed dark-red precipitate was collected, washed with ether and dried in vacuo to give 168.3 mg (83.7% yield) of the product. 98.7% purity by LC/MS (230 DAD). Mass-spec [ES+]=330.8. $^1$H NMR (500 MHz, MeOH-d4) 6.76–6.77 (2H, d), 6.87–6.89 (2H, d), 7.05–7.06 (1H, d), 7.29–7.31 (2H, d), 7.38–7.40 (2H, d), 7.50–7.52 (1H, m), 7.99–8.01 (1H, d).

2,3-Bis(3,4-dihydroxyphenyl)quinoxalin-6-ylamine dihydrochloride salt

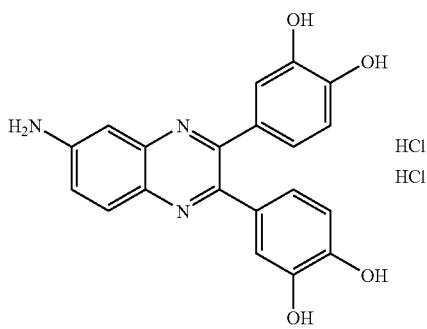

98.0 mg (0.5 mmol) of 1,2,4-benzenetriamine dihydrochloride and 137.1 mg (0.5 mmol) of 3,3',4,4'-tetrahydroxybenzil were dissolved in 3 ml of MeOH. The reaction was refluxed for 6 hours. Then the reaction mixture was cooled to r.t. and added dropwise to 40 ml of diethyl ether. The formed dark-red precipitate was collected, washed with ether and dried in vacuo to give 184.0 mg (84.7% yield) of the product. 97.7% purity by LC/MS (230 DAD). Mass-spec [ES+]=362.8. $^1$H NMR (MeOH-d4) 6.73–6.75 (1H, d), 6.78–6.80 (1H, m), 6.88–6.89 (1H, m), 6.94–6.97 (3H, m), 7.03 (1H, d), 7.49–7.51 (1H, dd), 7.97–7.99 (1H, d).

2-Hydroxy-5-(6-phenyl-pteridin-4-ylamino)-benzenesulfonic acid

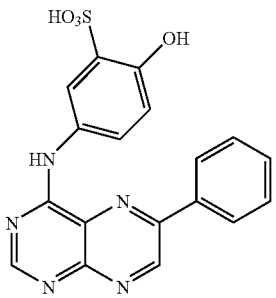

70.1% yield. 83% purity by LC/MS (230 DAD). Mass-spec [ES+]=396.8. $^1$H NMR (DMSO-d6) 7.17–7.19 (1H, dd), 7.58–7.63 (3H, m), 7.80–7.82 (1H, dd), 7.993–7.999 (1H, d), 8.61–8.63 (2H, m), 8.73 (1H, s), 9.80 (1H, s), 10.51–10.53 (3H, m).

5-(6-Phenyl-pteridin-4-ylamino)-quinolin-8-ol hydrochloride salt

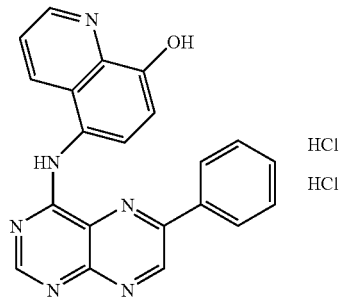

79.9% yield. 85% purity by LC/MS (230 DAD). Mass-spec [ES+]=367.7. $^1$H NMR (DMSO-d6) 7.39–7.40 (1H, m), 7.61–7.72 (3H, m), 7.73–7.77 (2H, m), 8.60–8.67 (4H, m), 9.01–9.02 (1H, m), 9.92 (1H, s), 11.58 (1H, br.s.)

General Procedure

Scheme A:

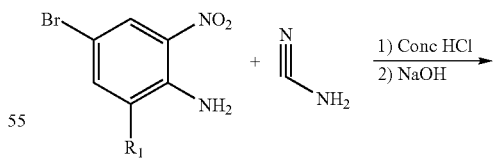

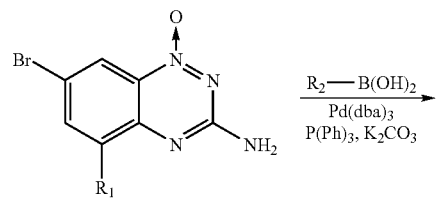

243; $^1$H NMR (DMSO-$d_6$): δ 7.48 (d, J=9.02 Hz, 1 H), 7.89 (dd, $J_1$=9.02 Hz, $J_2$=2.14 Hz, 1 H), 8.26 (d, J=2.14 Hz, 1 H).

7-Bromo-5-methyl-benzo[1,2,4]triazin-3-ylamine-1-oxide

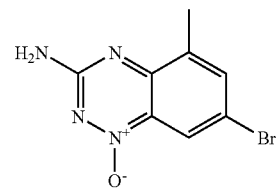

4-Bromo-2-methyl-6-nitro-phenylamine (1 g, 4.33 mmol) was mixed with cynamide (0.5 g, 12 mmol) and 5 g pyridine HCl in a 20 ml vial. The mixture was heated to reflux overnight. The mixture was cooled down to room temperature and 10% NaOH was carefully added. The resulted mixture was heated at 100° C. for 2 hours then cool down to room temperature. After filtration, the precipitate was washed several times with water, acetone and ditheylether to remove the starting material. 0.4 g product was obtained. Yield: 36%. ESI-MS: [M+H]$^+$, 255, 257; $^1$H NMR (DMSO-$d_6$): δ 2.45 (s, 3 H), 7.81 (d, J=1.97 Hz, 1 H), 8.26 (d, J=1.97 Hz, 1 H).

7-Benzo[1,3]dioxol-5-yl-benzo[1,2,4]triazin-3-ylamine-1-oxide

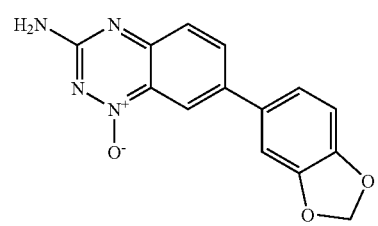

To a solution of 7-Bromo-benzo[1,2,4]triazin-3-ylamine-1-oxide (50 mg, 0.21 mmol) dissolved in 6 ml N,N-Dim- -continued

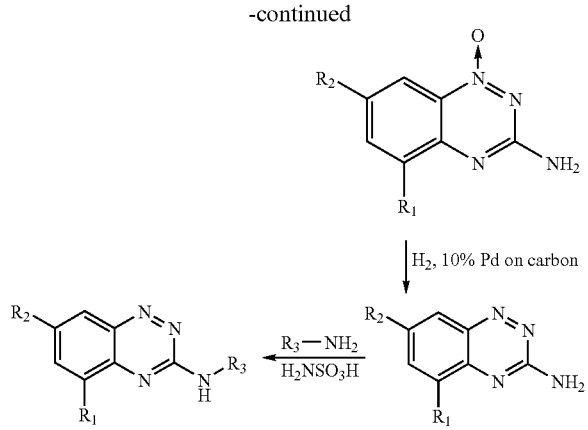

Scheme B:

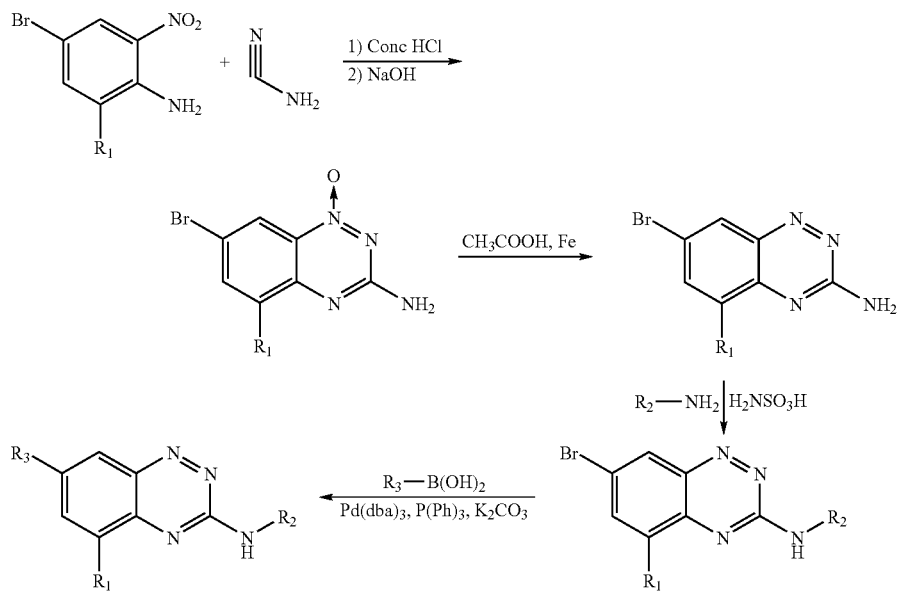

7-Bromo-benzo[1,2,4]triazin-3-ylamine-1-oxide

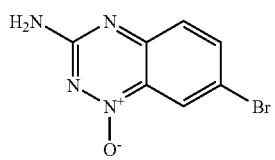

4-Bromo-2-nitro-phenylamine (2.48 g, 11.4 mmol) was mixed with cynamide (1.51 g, 36 mmol) in a 20 mL vial. The mixture was heated to 100° C. till the mixture was totally melted. The mixture was cooled down to room temperature and 6.5 ml concentrated HCl was added. The mixture was heated at 100° C. for 40 minutes and cool down in ice water. 6.5 ml 14M NaOH was carefully added to the above reaction mixture. The resulted mixture was heated at 100° C. for 2 hours then cool down to room temperature. After filtration, the precipitate was washed several times with water, methanol and ditheylether to remove the starting material. 0.739 g product was obtained. Yield: 27%. ESI-MS: [M+H]$^+$, 241, ethylacetamide in a 20 ml vial, 3,4-(Methylenedioxy) phenylboronic acid (68.6 mg, 0.41 mmol) dissolved in 1 ml ethanol and potassium carbonate (32.4 mg, 0.3 mmol) dissolved in 1 ml water were added. Triphenylphosphine (9 mg, 0.034 mmol) and tris(dibenzylideneacetone) dipalladium (0) (9 mg, 9.83 mmol) were added to the mixture. The mixture was reflux overnight. The crude product was poured into 50 ml saturated $NaHCO_3$ solution, and $CH_2Cl_2$ was used to extract the product. Solvent in the organic phase was removed under vacuum. The resulted residue was purified by preparative HPLC. 20 mg 7-Benzo[1,3]dioxol-5-yl-benzo[1,2,4]triazin-3-ylamine-1-oxide was isolated. Yield: 34.5%; ESI-MS: [M+H]$^+$, 283; $^1$H NMR (DMSO-d$_6$): δ 6.09 (s, 2 H), 7.04 (d, J=8.12 Hz, 1H), 7.27 (dd, J$_1$=7.88 Hz, J$_2$=1.58 Hz, 1H), 7.37 (s, 1 H), 7.58 (d, J=8.12 Hz, 1 H), 8.10 (dd, J$_1$=8.86 Hz, J$_2$=1.86 Hz, 1 H), 8.25 (d, J=1.86 Hz, 1 H).

7-Benzo[1,3]dioxol-5-yl-benzo[1,2,4]triazin-3-ylamine

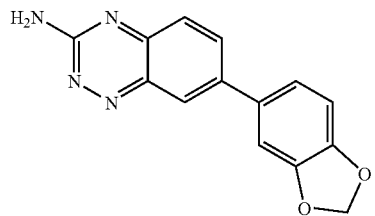

10 mg 7-Benzo[1,3]dioxol-5-yl-benzo[1,2,4]triazin-3-ylamine-1-oxide was dissolved in in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 5 mg 7-(2,6-Dimethyl-phenyl)-benzo[1,2,4]triazin-3-ylamine was obtained. Yield: 53%; ESI-MS: [M+H]$^+$, 267; $^1$H NMR (DMSO-d$_6$): δ 6.09 (s, 2 H), 7.04 (d, J=8.00 Hz, 1H), 7.33 (dd, J$_1$=7.91 Hz, J$_2$=1.76 Hz, 1H), 7.46 (d, J=1.51 Hz, 1 H), 7.58 (d, J=8.84 Hz, 1 H), 8.12 (dd, J$_1$=8.84 Hz, J$_2$=1.96 Hz, 1 H), 8.39 (d, J=1.96 Hz, 1 H).

7-(2,6-Dimethyl-phenyl)-benzo[1,2,4]triazin-3-ylamine

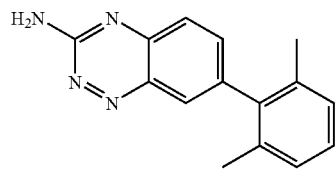

To a solution of 7-Bromo-benzo[1,2,4]triazin-3-ylamine-1-oxide (100 mg, 0.42 mmol) dissolved in 6 ml N,N-Dimethylacetamide in a 20 ml vial, 2,6-dimethylphenylboronic acid (240 mg, 1.6 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 mmol) were added to the mixture. The mixture was reflux overnight. The crude product was poured into 50 ml saturated $NaHCO_3$ solution, and $CH_2Cl_2$ was used to extract the product. Solvent in the organic phase was removed under vacuum. The residue was dissolved in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 60 mg 7-(2,6-Dimethyl-phenyl)-benzo[1,2,4]triazin-3-ylamine was obtained. Yield: 60%; ESI-MS: [M+H]$^+$, 251; $^1$H NMR (DMSO-d$_6$): δ 2.03 (s, 6 H), 7.23–7.16 (m, 3 H), 7.62–7.58 (m, 2 H), 7.95 (m, 1 H).

7-(4-Phenoxy-phenyl)-benzo[1,2,4]triazin-3-ylamine

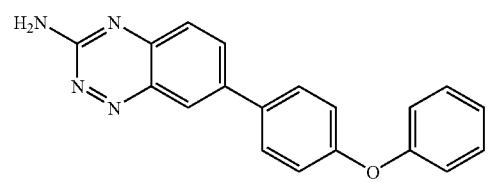

To a solution of 7-Bromo-benzo[1,2,4]triazin-3-ylamine-1-oxide (100 mg, 0.42 mmol) dissolved in 6 ml N,N-Dimethylacetamide in a 20 ml vial, 4-Phenoxyphenylboronic acid (177 mg, 0.83 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 mmol) were added to the mixture. The mixture was reflux overnight. The crude product was poured into 50 ml saturated $NaHCO_3$ solution, and $CH_2Cl_2$ was used to extract the product. Solvent in the organic phase was removed under vacuum. The residue was dissolved in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 20 mg 3-(3-Amino-benzo[1,2,4]triazin-7-yl)-benzonitrile was obtained. Yield: 15.4%; ESI-MS: [M+H]$^+$, 315; $^1$H NMR (DMSO-d$_6$): δ 7.09–7.13 (m, 5 H), 7.44 (m, 2 H), 7.62 (d, J=8.89 Hz, 2 H), 7.87(m, 2 H), 8.15 (dd, J$_1$=8.89 Hz, J$_2$=2.34 Hz, 1 H), 8.43 (d, J=2.34 Hz, 1 H).

7-(2,6-Dimethoxy-phenyl)-benzo[1,2,4]triazin-3-ylamine

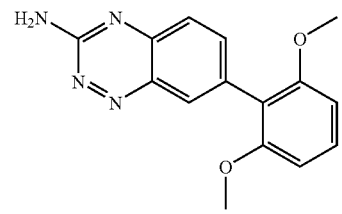

To a solution of 7-Bromo-benzo[1,2,4]triazin-3-ylamine-1-oxide (100 mg, 0.42 mmol) dissolved in 6 ml N,N-Dimethylacetamide in a 20 ml vial, 2,6-dimethoxy-phenylboronic acid (302 mg, 1.66 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 mmol) were added to the mixture. The mixture was reflux overnight. The crude product was poured into 50 ml saturated NaHCO$_3$ solution, and CH$_2$Cl$_2$ was used to extract the product. Solvent in the organic phase was removed under vacuum. The residue was dissolved in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 40 mg 7-(2,6-Dimethoxyphenyl)-benzo[1,2,4]triazin-3-ylamine was obtained. Yield: 34.2%, ESI-MS: [M+H]$^+$, 283; $^1$H NMR (DMSO-d$_6$): δ 3.71 (s, 6 H), 6.80 (d, J=8.47 Hz, 2 H), 7.36 (t, J=8.39 Hz, 1 H), 7.52 (d, J=8.85 Hz, 1 H), 7.66(dd, J$_1$=8.85 Hz, J$_2$=1.91 Hz, 1 H), 8.00 (d, J=1.91 Hz, 1 H).

7-(4-t-Butyl-phenyl)-benzo[1,2,4]triazin-3-ylamine

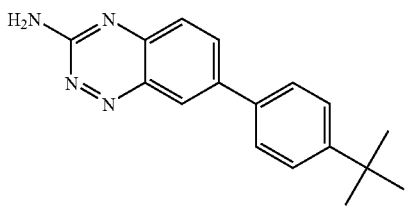

To a solution of 7-Bromo-benzo[1,2,4]triazin-3-ylamine-1-oxide (100 mg, 0.42 mmol) dissolved in 6 ml N,N-Dimethylacetamide in a 20 ml vial, 4-t-butyl-phenylboronic acid (148 mg, 0.83 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 mmol) were added to the mixture. The mixture was reflux overnight. The crude product was poured into 50 ml saturated NaHCO$_3$ solution, and CH$_2$Cl$_2$ was used to extract the product. Solvent in the organic phase was removed under vacuum. The residue was dissolved in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 20 mg 7-(4-t-Butyl-phenyl)-benzo[1,2,4]triazin-3-ylamine was obtained. Yield: 18%, ESI-MS: [M+H]$^+$, 279; $^1$H NMR (DMSO-d$_6$): δ 1.34 (s, 9 H), 7.53 (d, J=8.66 Hz, 2 H), 7.61 (d, J=8.85 Hz, 1 H), 7.77 (d, J=8.66 Hz, 2 H), 8.16 (dd, J$_1$=8.84 Hz, J$_2$=1.89 Hz, 1 H), 8.43 (d, J=1.89 Hz, 1 H).

7-(2-Trifluoromethyl-phenyl)-benzo[1,2,4]triazin-3-ylamine

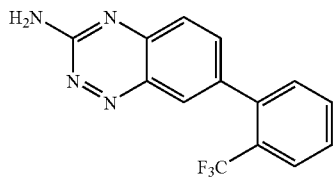

To a solution of 7-Bromo-benzo[1,2,4]triazin-3-ylamine-1-oxide (100 mg, 0.42 mmol) dissolved in 6 ml N,N-Dimethylacetamide in a 20 ml vial, 2-trifluoromethyl phenylboronic acid (157 mg, 0.83 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 mmol) were added to the mixture. The mixture was reflux overnight. The crude product was poured into 50 ml saturated NaHCO$_3$ solution, and CH$_2$Cl$_2$ was used to extract the product. Solvent in the organic phase was removed under vacuum. The residue was dissolved in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 20 mg 7-(2-Trifluoromethyl-phenyl)-benzo[1,2,4]triazin-3-ylamine was obtained. Yield: 16.5%, ESI-MS: [M+H]$^+$, 291; $^1$H NMR (DMSO-d$_6$): δ 7.56 (d, J=7.56 Hz, 1 H), 7.60 (d, J=8.66 Hz, 1 H), 7.68–7.80 (m, 3 H), 7.89 (d, J=7.56 Hz, 1 H), 8.11 (d, J=1.46 Hz, 1 H).

7-Biphenyl-4-yl-benzo[1,2,4]triazin-3-ylamine

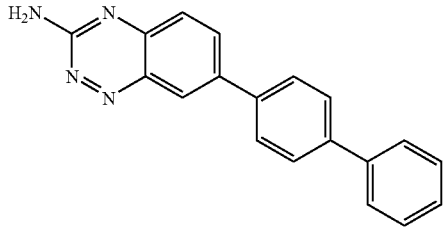

To a solution of 7-Bromo-benzo[1,2,4]triazin-3-ylamine-1-oxide (100 mg, 0.42 mmol) dissolved in 6 ml N,N-Dimethylacetamide in a 20 ml vial, 4-biphenylboronic acid (164 mg, 0.83 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 mmol) were added to the mixture. The mixture was reflux overnight. The crude product was poured into 50 ml saturated NaHCO$_3$ solution, and CH$_2$Cl$_2$ was used to extract the product. Solvent in the organic phase was removed under vacuum. The residue was dissolved in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 15 mg 7-Biphenyl-4-yl-benzo[1,2,4]triazin-3-ylamine was obtained. Yield: 12.1%, ESI-MS: [M+H]$^+$, 299; $^1$H NMR (DMSO-d$_6$): δ 7.41 (m, 1 H), 7.50 (m, 2 H), 7.55 (m, 2 H), 7.64 (d, J=8.84 Hz, 1 H), 7.83 (m, 2 H), 7.96 (m, 2 H), 8.24 (dd, J$_1$=8.84 Hz, J$_2$=1.93 Hz, 1H), 8.53 (d, J=1.93 Hz, 1 H).

7-Benzofuran-2-yl-benzo[1,2,4]triazin-3-ylamine

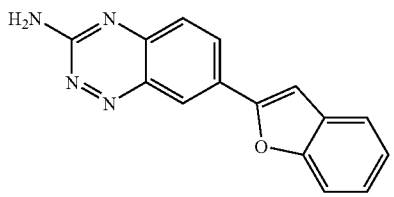

To a solution of 7-Bromo-benzo[1,2,4]triazin-3-ylamine-1-oxide (100 mg, 0.42 mmol) dissolved in 6 ml N,N-Dimethylacetamide in a 20 ml vial, 2-Benzofuranboronic acid (134 mg, 0.83 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 umol) were added to the mixture. The mixture was reflux overnight. The crude product was poured into 50 ml saturated NaHCO$_3$ solution, and CH$_2$Cl$_2$ was used to extract the product. Solvent in the organic phase was removed under vacuum. The residue was dissolved in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 10 mg 7-Benzofuran-2-yl-benzo[1,2,4]triazin-3-ylamine was obtained. Yield: 9.3%, ESI-MS: [M+H]$^+$, 263; $^1$H NMR (DMSO-d$_6$): δ 6.54 (s, 1 H), 7.29 (t, J=7.22 Hz, 1 H), 7.36 (t, J=7.23 Hz, 1 H), 7.64–7.71 (m, 3 H), 7.34 (dd, J$_1$=8.86 Hz, J$_2$=1.86 Hz, 1 H), 8.63 (d, J=1.86 Hz, 1 H).

7-Dibenzofuran-4-yl-benzo[1,2,4]triazin-3-ylamine

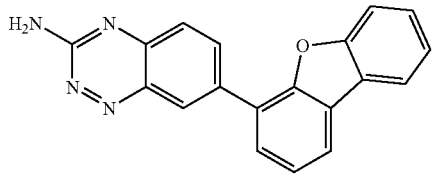

To a solution of 7-Bromo-benzo[1,2,4]triazin-3-ylamine-1-oxide (100 mg, 0.42 mmol) dissolved in 6 ml N,N-Dimethylacetamide in a 20 ml vial, 4-Dibenzofuranboronic acid (176 mg, 0.83 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 umol) were added to the mixture. The mixture was reflux overnight. The crude product was poured into 50 ml saturated NaHCO$_3$ solution, and CH$_2$Cl$_2$ was used to extract the product. Solvent in the organic phase was removed under vacuum. The residue was dissolved in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 5 mg 7-Dibenzofuran-4-yl-benzo[1,2,4]triazin-3-ylamine was obtained. Yield: 3.9%, ESI-MS: [M+H]$^+$, 263; $^1$H NMR (DMSO-d$_6$): δ 7.46 (t, J=7.62 Hz, 1 H), 7.57 (t, J=7.92 Hz, 2 H), 7.72 (t, J=8.85 Hz, 1 H), 7.80 (d, J=8.20 Hz, 1 H), 7.90 (d, J=8.07 Hz, 1 H), 8.23 (m, 2 H), 8.38 (dd, J$_1$=8.84 Hz, J$_2$=2.06 Hz, 1 H), 8.63 (d, J=2.06 Hz, 1 H).

7-Naphthalen-1-yl-benzo[1,2,4]triazin-3-ylamine

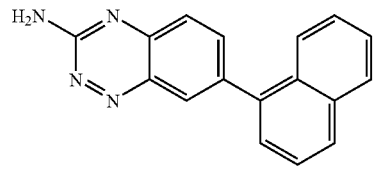

To a solution of 7-Bromo-benzo[1,2,4]triazin-3-ylamine-1-oxide (100 mg, 0.42 mmol) dissolved in 6 ml N,N-Dimethylacetamide in a 20 ml vial, 1-Naphthylboronic acid (143 mg, 0.83 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 umol) were added to the mixture. The mixture was reflux overnight. The crude product was poured into 50 ml saturated NaHCO$_3$ solution, and CH$_2$Cl$_2$ was used to extract the product. Solvent in the organic phase was removed under vacuum. The residue was dissolved in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 10 mg 7-Naphthalen-1-yl-benzo[1,2,4]triazin-3-ylamine was obtained. Yield: 8.8%, ESI-MS: [M+H]$^+$, 273; $^1$H NMR (DMSO-d$_6$): δ 7.54–7.69 (m, 5 H), 7.84 (d, J=8.31 Hz, 1 H), 7.94 (dd, J$_1$=8.60 Hz, J$_2$=1.68 Hz, 1 H), 8.05 (m, 2 H), 8.26 (d, J=1.68 Hz, 1 H).

3-(3-Amino-benzo[1,2,4]triazin-7-yl)-phenol

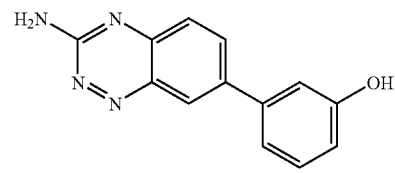

To a solution of 7-Bromo-benzo[1,2,4]triazin-3-ylamine-1-oxide (100 mg, 0.42 mmol) dissolved in 6 ml N,N-Dimethylacetamide in a 20 ml vial, 3-hydroxyphenylboronic acid (114.5 mg, 0.83 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 umol) were added to the mixture. The mixture was reflux overnight. The crude product was poured into 50 ml saturated NaHCO$_3$ solution, and CH$_2$Cl$_2$ was used to extract the product. Solvent in the organic phase was removed under vacuum. The residue was dissolved in a mixture of 2 ml N,N-Dimethylacetamide and 1 ml ethyl alcohol in a 20 ml vial with a septum. Catalytic amount of 10% Palladium on carbon was added to the mixture. A balloon filled with hydrogen was placed on the top of the vial. The mixture was stirred at room temperature for 2 hours. Celite was used to remove the palladium and carbon. Preparative HPLC was used to isolate the final product. 15 mg 3-(3-Amino-benzo[1,2,4]triazin-7-yl)-phenol was obtained. Yield: 15%, ESI-MS: [M+H]$^+$, 239; $^1$H NMR (DMSO-d$_6$): δ 6.82 (dd, J$_1$=7.94 Hz, J$_2$=1.98 Hz, 1 H), 7.17 (m, 1 H), 7.23 (d, J=7.80 Hz, 1 H), 7.31 (t, J=7.73 Hz, 1 H), 7.60 (d, J=8.83 Hz, 1 H), 8.08 (dd, J$_1$=8.83 Hz, J$_2$=1.94 Hz, 1 H), 8.36 (d, J=1.94 Hz, 1 H).

[7-(2,6-Dimethyl-phenyl)-benzo[1,2,4]triazin-3-yl]-phenyl-amine

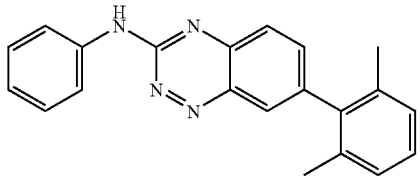

7-(2,6-Dimethyl-phenyl)-benzo[1,2,4]triazin-3-ylamine (24 mg, 0.096 mmol) was dissolved in aniline, sulfamic acid (18 mg, 0.19 mmol) was added. The mixture was reflux overnight. The final product was isolated by preparative HPLC. Yield: 32%. ESI-MS: [M+H]$^+$, 327; $^1$H NMR (DMSO-d$_6$): δ 2.05(s, 6 H), 7.09(t, J=7.35 Hz, 1 H), 7.18–7.25 (m, 3 H), 7.40(m, 2 H), 7.71(dd, J$_1$=8.5 Hz, J$_2$=1.9 Hz, 1 H), 7.84(d, J=8.5 Hz, 1 H), 8.00(d, J=7.6 Hz, 2 H), 8.11(d, J=1.9 Hz, 1 H).

(7-Bromo-5-methyl-benzo[1,2,4]triazin-3-yl)-phenyl-amine

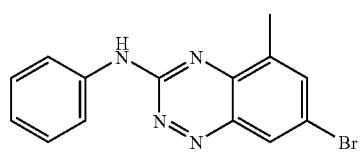

7-Bromo-5-methyl-benzo[1,2,4]triazin-3-ylamine-1-oxide (266 mg, 1.04 mmol) was dissolved in 5 ml acetic acid in a 20 ml vial, a few drops of water was added followed by adding of 100 mg Fe powder. The mixture was kept at 100° C. for 30 minutes. The solvent was removed under vacuum. The residue was dissolved in 5 ml aniline, sulfamic acid (202 mg, 2.08 mmol) was added to the mixture. The mixture was heat at 140° C. for overnight. The final product was isolated by preparative HPLC. Yield: 18.3%, ESI-MS: [M+H]$^+$, 315, 317.

(7-Bromo-5-methyl-benzo[1,2,4]triazin-3-yl)-[3-(4-methyl-piperazin-1-yl)-propyl]-amine

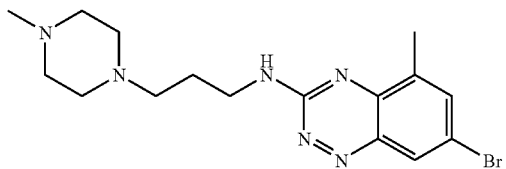

7-Bromo-5-methyl-benzo[1,2,4]triazin-3-ylamine-1-oxide (200 mg, 0.78 mmol) was dissolved in 5 ml acetic acid in a 20 ml vial, a few drops of water was added followed by adding of 100 mg Fe powder. The mixture was kept at 100° C. for 30 minutes. The solvent was removed under vacuum. The residue was dissolved in 5 ml 3-(4-Methyl-piperazin-1-yl)-propylamine, sulfamic acid (152 mg, 1.57 mmol) was added to the mixture. The mixture was heat at 140° C. for overnight. The final product was isolated by preparative HPLC. Yield: 67.3%, ESI-MS: [M+H]$^+$, 379, 381. $^1$H NMR (DMSO-d$_6$): δ 1.05(m, 2H), 1.97 (s, 2 H), 2.77–3.20 (b, 8 H), 3.5 (b, 8 H), 7.84 (d, J=1.96 Hz, 1 H), 8.29 (d, J=1.96 Hz, 1 H).

[5-Methyl-7-(2,4,6-trimethyl-phenyl)-benzo[1,2,4]triazin-3-yl]-phenyl-amine

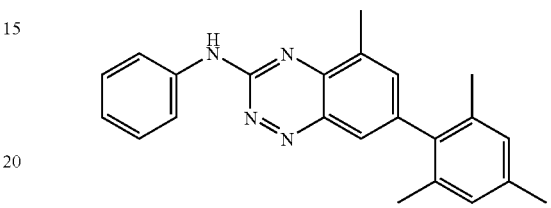

To a solution of (7-Bromo-5-methyl-benzo[1,2,4]triazin-3-yl)-phenyl-amine (10 mg, 0.032 mmol) dissolved in 2 ml N,N-Dimethylacetamide in a 20 ml vial, 2,4,6-trimethylphenylboronic acid (21 mg, 0.128 mmol) dissolved in 1 ml ethanol and potassium carbonate (6.4 mg, 0.06 mmol) dissolved in 1 ml water were added. Triphenylphosphine (1 mg, 0.0038 mmol) and tris(dibenzylideneacetone) dipalladium (0) (1 mg, 1.09 umol) were added to the mixture. The mixture was reflux overnight. The crude product was filtered and purified by preparative HPLC. 3 mg [5-Methyl-7-(2,4,6-trimethyl-phenyl)-benzo[1,2,4]triazin-3-yl]-phenyl-amine was isolated. Yield: 26.8%; ESI-MS: [M+H]$^+$, 355; $^1$H NMR (CDCl$_3$): δ 2.06 (s, 6 H), 2.36 (s, 3 H), 2.72 (s, 3 H), 6.99 (s, 2 H), 7.17 (m, 1 H), 7.45 (m, 2 H), 7.57 (m, 1 H), 7.89 (d, J=1.36 Hz, 1 H), 7.94(d, J=8.76 Hz, 2 H).

[7-(2-Fluoro-6-methoxy-phenyl)-5-methyl-benzo[1,2,4]triazin-3-yl]-phenyl-amine

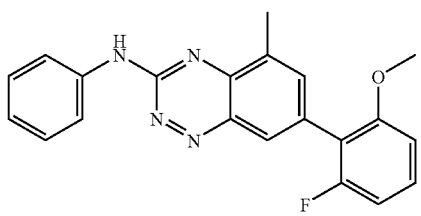

To a solution of (7-Bromo-5-methyl-benzo[1,2,4]triazin-3-yl)-phenyl-amine (10 mg, 0.032 mmol) dissolved in 2 ml N,N-Dimethylacetamide in a 20 ml vial, 2-Fluoro-6-methoxy-phenylboronic acid (22 mg, 0.128 mmol) dissolved in 1 ml ethanol and potassium carbonate (6.4 mg, 0.06 mmol) dissolved in 1 ml water were added. Triphenylphosphine (1 mg, 0.0038 mmol) and tris(dibenzylideneacetone) dipalladium (0) (1 mg, 1.09 umol) were added to the mixture. The mixture was reflux overnight. The crude product was filtered and purified by preparative HPLC. 2 mg [7-(2-Fluoro-6-methoxy-phenyl)-5-methyl-benzo[1,2,4]triazin-3-yl]-phenyl-amine was isolated. Yield: 17.5%; ESI-MS: [M+H]$^+$, 361; $^1$H NMR (CDCl$_3$): δ 2.73 (s, 3 H), 3.83 (s, 3 H), 6.83–6.86 (m, 2H), 7.14 (m, 1 H), 7.34 (m, 1 H), 7.45 (m, 2 H), 7.75(s, 1 H), 7.92(m, 2 H), 8.24(s, 1 H).

[7-(2,6-Dimethoxy-phenyl)-5-methyl-benzo[1,2,4]triazin-3-yl]-phenyl-amine

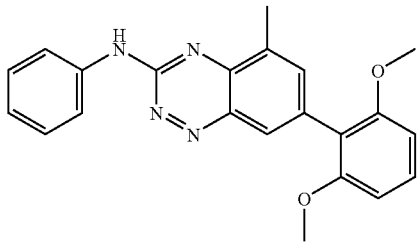

To a solution of (7-Bromo-5-methyl-benzo[1,2,4]triazin-3-yl)-phenyl-amine (10 mg, 0.032 mmol) dissolved in 2 ml N,N-Dimethylacetamide in a 20 ml vial, 2,6-dimethoxyphenylboronic acid (23 mg, 0.126 mmol) dissolved in 1 ml ethanol and potassium carbonate (6.4 mg, 0.06 mmol) dissolved in 1 ml water were added. Triphenylphosphine (1 mg, 0.0038 mmol) and tris(dibenzylideneacetone) dipalladium (0) (1 mg, 1.09 umol) were added to the mixture. The mixture was reflux overnight. The crude product was filtered and purified by preparative HPLC. 5 mg [7-(2,6-Dimethoxy-phenyl)-5-methyl-benzo[1,2,4]triazin-3-yl]-phenyl-amine was isolated. Yield: 42.4%; ESI-MS: [M+H]$^+$, 373; $^1$H NMR (CDCl$_3$): δ 2.72 (s, 3 H), 3.78 (s, 6 H), 6.70 (d, J=8.4 Hz, 2 H), 7.13 (m, 1 H), 7.35 (t, J=8.38 Hz, 1 H), 7.44 (m, 2 H), 7.89 (m, 1 H), 7.92 (dd, J$_1$=8.78 Hz, J$_2$=2.02 Hz, 2 H), 8.18 (d, J=2.02 Hz, 1 H).

[7-(2,6-Dimethyl-phenyl)-5-methyl-benzo[1,2,4]triazin-3-yl]-phenyl-amine

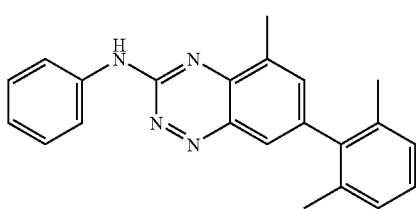

To a solution of (7-Bromo-5-methyl-benzo[1,2,4]triazin-3-yl)-phenyl-amine (60 mg, 0.19 mmol) dissolved in 3 ml N,N-Dimethylacetamide in a 20 ml vial, 2,6-dimethyl-phenylboronic acid (114 mg, 0.76 mmol) dissolved in 2 ml ethanol and potassium carbonate (31 mg, 0.3 mmol) dissolved in 1 ml water were added. Triphenylphosphine (4.5 mg, 0.0171 mmol) and tris(dibenzylideneacetone) dipalladium (0) (4.5 mg, 4.9 umol) were added to the mixture. The mixture was reflux overnight. The crude product was filtered and purified by preparative HPLC. 30 mg [7-(2,6-Dimethyl-phenyl)-5-methyl-benzo[1,2,4]triazin-3-yl]-phenyl-amine was isolated. Yield: 46%; ESI-MS: [M+H]$^+$, 341; $^1$H NMR (DMSO-d$_6$): δ 2.05 (s, 6 H), 2.67(s, 3H), 7.07(t, J=7.33 Hz, 1 H), 7.17–7.24 (m, 3 H), 7.41 (t, J=7.56 Hz, 2 H), 7.62 (d, J=1.49 Hz, 1 H), 7.93 (d, J=1.49 Hz, 1 H), 8.05 (d, J=7.72 Hz, 1H).

7-Naphthalen-2-yl-benzo[1,2,4]triazin-3-ylamine-1-oxide

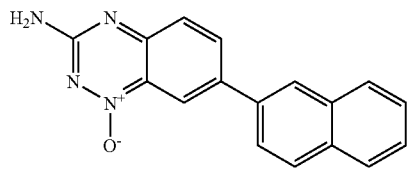

To a solution of 7-Bromo-benzo[1,2,4]triazin-3-ylamine-1-oxide (100 mg, 0.42 mmol) dissolved in 6 ml N,N-Dimethylacetamide in a 20 ml vial, 2-Naphthylboronic acid (143 mg, 0.83 mmol) dissolved in 1 ml ethanol and potassium carbonate (64 mg, 0.6 mmol) dissolved in 1 ml water were added. Triphenylphosphine (9 mg, 0.034 mmol) and tris(dibenzylideneacetone) dipalladium (0) (9 mg, 9.83 umol) were added to the mixture. The mixture was reflux overnight. The crude product was poured into 50 ml saturated NaHCO$_3$ solution, and CH$_2$Cl$_2$ was used to extract the product. Solvent in the organic phase was removed under vacuum. Preparative HPLC was used to isolate the final product. 20 mg 7-Naphthalen-2-yl-benzo[1,2,4]triazin-3-ylamine-1-oxide was obtained. Yield: 16.7%, ESI-MS: [M+H]$^+$, 289; $^1$H NMR (DMSO-d$_6$): δ 7.56 (m, 2 H), 7.68 (d, J=8.84 Hz, 1 H), 7.95 (m, 2 H), 8.05 (d, J=8.64 Hz, 2 H), 8.33 (dd, J$_1$=8.84 Hz, J$_2$=1.87 Hz, 1 H), 8.38 (s, 1 H), 8.51 (d, J=1.87 Hz, 1 H).

General Procedure for the 6-alkyl Substituted Pteridine Synthesis

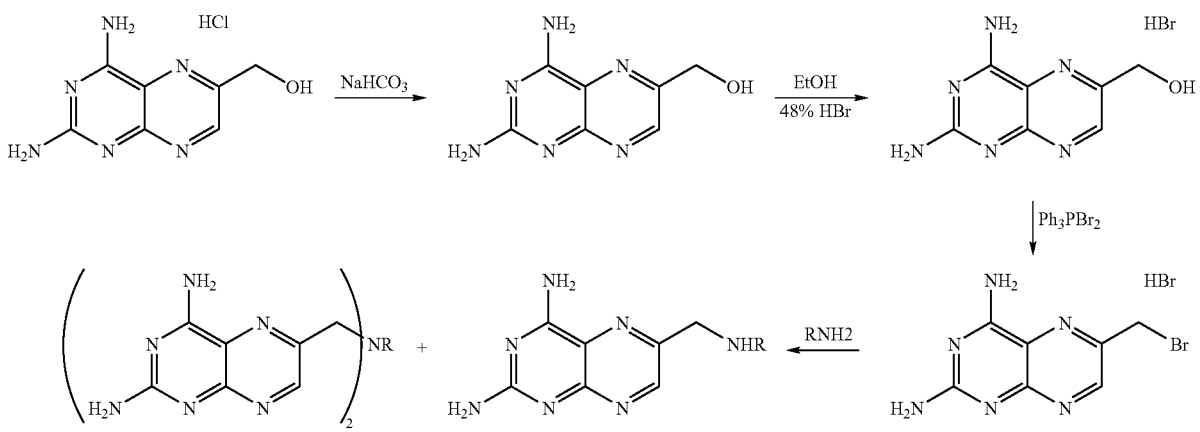

6-Bromomethyl-2,4-pteridinediamine

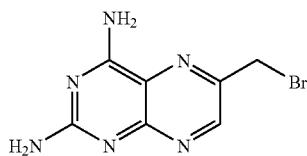

To the solution of dibromotriphenylphosphine (2.4337 g, 5.76 mmol) of 2 ml anhydrous N,N-dimethylacetamide was added (2,4-Diamino-Pteridin-6-yl)-methanol hydrobromide (335.8 mg, 1.747 mmol). The mixture is the stirred at RT for overnight. The solution was treated with benzene. The filtered solid was then successively treated with benzene and ether and evaporate the remaining solid. The residue was dissolved in minimum 48% HBr at RT which then was added MeCN to give a tan solid precipitate. Collect the solid in ice water bath and wash it with MeCN and ether. 352 mg product was obtained. Yield 60%; $^1$H NMR (500 MHz, DMSO-d6): δ 4.86021(s, 2H), 9.01 (s, 1H), 9.15 (s, 2H), 9.22 (s, 2H); ESI-MS: 255, 257(M$^+$+1)

2-[(2,4-Diamino-pteridin-6-ylmethyl)-amino]-3-(4-hydroxy-phenyl)-propionic acid tert-butyl ester

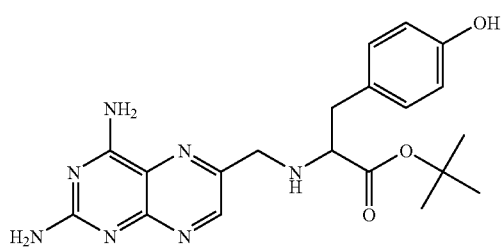

To a solution of 6-bromomethyl-2,4-pteridinediamine hydrobromide (31.2 mg, 0.116 mmol) in anhydrous N,N dimethylacetamide was added 2-amino-3-(4-hydroxy-phenyl)-propionic acid tert-butyl ester (30.22 mg, 0.127 mmol). The reaction mixture was stirred at 50° C. overnight. The crude product was poured into saturated bicarbonate solution. The resulted precipitate was collected and purified by preparative HPLC. 17.2 mg product was obtained. Yield: 71%; $^1$H NMR (500 MHz, DMSO-d6): δ 1.33577 (s, 9H), 2.94185–3.02295 (m, 2H), 3.6550(b, 1H), 4.0878 (s, 2H), 6.70174–6.72384 (dd, J$_1$=8.545 Hz, J$_2$=2.59 Hz, 2H), 7.02394–7.04103 (d, J=8.545 Hz, 2H); 9.38501 (s, 1H); ESI-MS: 412 (M$^+$+1)

6-[{(Pyridin-2-ylmethyl)-amino]-methyl}-2,4-pteridinediamine

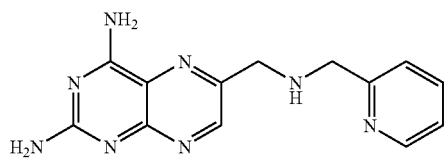

To a solution of 6-bromomethyl-2,4-pteridinediamine hydrobromide (51 mg, 0.2 mmol) in anhydrous N,N dimethylacetamide was added 2-(aminomethyl) pyridine (22.48 ul, 0.22 mmol). The reaction mixture was stirred at 50° C. overnight. The crude product was poured into saturated bicarbonate solution. The resulted precipitate was collected and purified by preparative HPLC. 32.3 mg product was obtained. Yield: 57%; $^1$H NMR (500 MHz, DMSO-d6): δ 3.93801 (s, 2H), 4.05772(s, 2H), 7.5758–7.6003 (m, 1H), 7.97993–8.00181 (m, 1H), 8.49332–8.50942 (d, J=8.05 Hz, 1H), 8.62592–8.64301 (d, J=8.545 Hz, 1H), 8.9938(s, 1H); ESI-MS: 283 (M$^+$+1)

6-{[(Naphthalen-1-yl-methyl)-amino]-methyl}-2,4-pteridinediamine

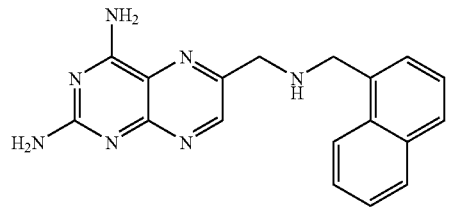

To a solution of 6-bromomethyl-2,4-pteridinediamine hydrobromide (51 mg, 0.2 mmol) in anhydrous N,N dimethylacetamide was added 1-aminomethyl-naphthalene (31.67 ul, 0.22 mmol). The reaction mixture was stirred at 50° C. overnight. The crude product was poured into saturated bicarbonate solution. The resulted precipitate was collected and purified by preparative HPLC. 9 mg product was obtained. Yield: 15%; $^1$H NMR(500 MHz, DMSO-d6): δ 4.6479(s, 2H ), 4.7893(s, 2H), 7.575–7.6244(m, 3H), 7.74232–7.7570(d, J=6.91 Hz, 1H), 7.9935–8.0276(dd, J$_1$=8.06 Hz, J$_2$ =8.995 Hz, 2H), 8.1670–8.1831(d, J=8.04 Hz, 1H), 8.8430(s, 1H); ESI-MS: m/z 332 (M$^+$+1)

6-(Benzylamino-methyl)-2,4-pteridinediamine

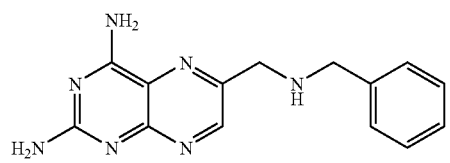

To a solution of 6-bromomethyl-2,4-pteridinediamine hydrobromide (35.7 mg, 0.106 mmol) in anhydrous N,N dimethylacetamide was added benzylamine (28.6 ul, 0.212 mmol). The reaction mixture was stirred at 50° C. overnight. The crude product was poured into saturated bicarbonate solution. The resulted precipitate was collected and purified by preparative HPLC. 17.7 mg product was obtained. Yield: 62%; $^1$H NMR (500 MHz, DMSO-d6): δ 4.30499(s, 2H), 4.51599(s, 2H), 7.42787–7.47298(m, 3H), 7.50007–7.51927 (m, 2H), 8.87751(s, 1H); ESI-MS: m/z 282 (M$^+$+1)

6-{[(Adamantan-1-yl-methyl)-amino]-methyl}-2,4-pteridinediamine

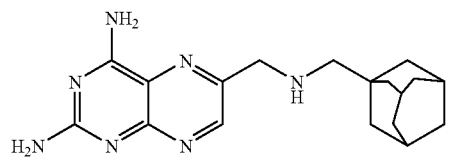

To a solution of 6-bromomethyl-2,4-pteridinediamine hydrobromide (41.6 mg, 0.124 mmol) in anhydrous N,N dimethylacetamide was added 1-aminomethyl adamantane (35.43 ul, 0.2 mmol). The reaction mixture was stirred at 50° C. overnight. The crude product was poured into saturated bicarbonate solution. The resulted precipitate was collected and purified by preparative HPLC. 12.7 mg product was obtained. Yield: 40%; $^1$H NMR (500 MHz, DMSO-d6): δ 1.56754–1.67101(m, 13H), 1.96741(s, 2H), 2.71139(s, 2H), 4.49166(s, 2H), 8.89918(s, 1H); ESI-MS: m/z 340 (M$^+$+1)

6-(3,4-Dimethoxy-benzylamino)-2,4-pteridinediamine

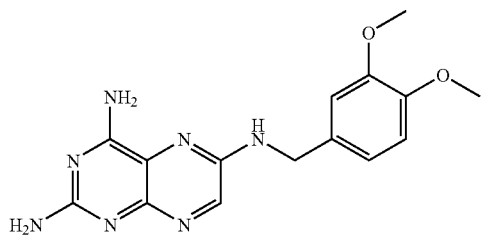

To a solution of 6-bromomethyl-2,4-pteridinediamine hydrobromide (59 mg, 0.176 mmol) in anhydrous N,N dimethylacetamide was added 3,4-dimethoxy-benzylamine (51.15 ul, 0.3512 mmol). The reaction mixture was stirred at 50° C. overnight. The crude product was poured into saturated bicarbonate solution. The resulted precipitate was collected and purified by preparative HPLC. 20.3 mg product was obtained. Yield: 34%; $^1$H NMR (500 MHz, DMSO-d6): δ 3.67534(s, 3H), 3.70494(s, 3H), 4.05412 (b, 4H), 6.78852–6.80460 (d, J=8.04 Hz, 1H), 6.83624 (s, 1H), 6.83624–6.85393 (d, J=8.195 Hz, 1H); 8.96623(s, 1H), 9.00584(s, 2H), 9.5577(s, 2H); ESI-MS: 342 (M$^+$+1)

6-[2,2-Dimethyl-propylamino)-methyl]-2,4-pteridinediamine

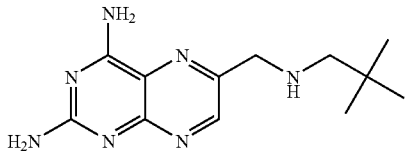

To a solution of 6-bromomethyl-2,4-pteridinediamine hydrobromide (75.2 mg, 0.2237 mmol) in anhydrous N,N dimethylacetamide was added 2,2-dimethyl-propylamine (136.48 ul, 1.16 mmol). The reaction mixture was stirred at room temperature overnight. The resulted precipitate was collected and purified by preparative HPLC. 8.3 mg product was obtained. Yield: 14.2%; $^1$H NMR (500 MHz, DMSO-d6): δ 0.98591 (s, 9H ), 2.82895(s, 2H), 4.38765(s, 2H), 8.77458(s, 1H); ESI-MS: m/z 262 (M$^+$+1)

6-{[2-(3,4-Dimethoxy-phenyl)ethylamino]-methyl}-2,4-pteridinediamine

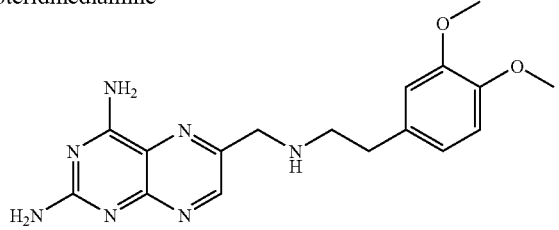

To a solution of 6-bromomethyl-2,4-pteridinediamine hydrobromide (55 mg, 0.1638 mmol) in anhydrous N,N dimethylacetamide was added 2-(3,4-dimethoxyphenyl) ethylamine hydrochloride (55 ul, 0.32 mmol). The reaction mixture was stirred at 50° C. overnight. The crude product was poured into saturated bicarbonate solution. The resulted precipitate was collected and purified by preparative HPLC. 3.8 mg product was obtained. Yield: 19.6%; $^1$H NMR (500 MHz, DMSO-d6): δ 2.75943–2.79062 (t, J=7.37 Hz, 2H), 2.92110–2.95356 (t, J=7.365 Hz, 2H), 3.72197(s, 3H), 3.75135(s, 3H), 4.54559(s, 2H), 6.74441–6.77765 (dd, J$_1$=8.26 Hz, J$_2$=1.955 Hz, 1H), 6.84994 (s, 1H), 6.88406–6.90401 (dd, J$_1$=8.195 Hz, J$_2$=1.735 Hz, 1H); 8.87126(s, 1H); ESI-MS: m/z 356 (M$^+$+1)

6-{[2-(3,4-Dihydroxy-phenyl)ethylamino]-methyl}-2,4-pteridinediamine

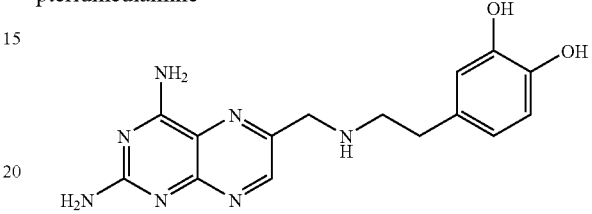

To a solution of 6-bromomethyl-2,4-pteridinediamine hydrobromide (67.3 mg, 0.2003 mmol) in anhydrous N,N dimethylacetamide was added 2-(3,4-dihydroxyphenyl) ethylamine (43.6 mg, 0.23 mmol). Under positive pressure of Argon, iPr$_2$EtN (32.63 ul) was added. The reaction mixture was stirred at 50° C. for 4 hrs and then at Room temperature overnight. The crude product was poured into saturated bicarbonate solution. The resulted precipitate was collected and purified by preparative HPLC. 14.8 mg product was obtained. Yield: 22.6%; $^1$H NMR (500 MHz, DMSO-d6): δ 2.69242 (b, 4H), 4.03353 (s, 2H), 6.37542–6.39065 (d, J=7.615 Hz, 1H), 6.4851(s, 1H), 6.56632–6.58226 (d, J=7.97 Hz, 1H), 8.80972 (s, 1H); ESI-MS: m/z 328 (M$^+$+1)

4-{2-[Di(2,4-diaminopteridin-6-yl-methyl)-amino]-ethyl}-benzene-1,2-diol

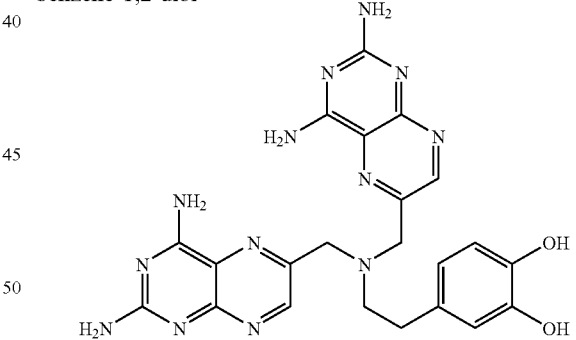

To a solution of 6-bromomethyl-2,4-pteridinediamine hydrobromide (67.3 mg, 0.2003 mmol) in anhydrous N,N dimethylacetamide was added 2-(3,4-dihydroxyphenyl) ethylamine hydrochloride (43.6 mg, 0.23 mmol). Under positive pressure of Argon, iPr$_2$EtN (32.63 ul) was added. The reaction mixture was stirred at 50° C. for 4 hrs and then at Room temperature overnight. The crude product was poured into saturated bicarbonate solution. The resulted precipitate was collected and purified by preparative HPLC. 3.2 mg product was obtained. Yield: 6.4%; $^1$H NMR (500 MHz, DMSO-d6): δ 2.63154–2.63891 (m, 2H), 2.72839(m, 2H), 4.03844 (s, 4H ), 6.32227–6.33832 (d, J=8.025 Hz, 1H), 6.38857 (s, 1H), 6.51654–6.53241 (d, J=8.835 Hz, 1H), 8.67743 (s, 2H); ESI-MS: m/z 502 (M$^+$+1)

6-{[2-(3,4-Dihydroxy)-benzylamino]-methyl}-2,4-pteridinediamine

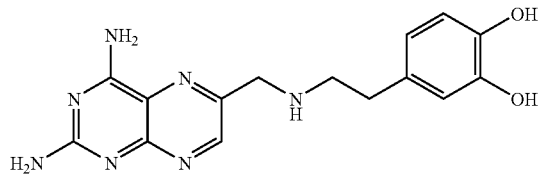

To a solution of 6-bromomethyl-2,4-pteridinediamine hydrobromide (64 mg, 0.1905 mmol) in anhydrous N,N dimethylacetamide was added 2-(3,4-dihydroxybenzyl) amine hydrochloride (36.795 mg, 0.23 mmol). Under positive pressure of Argon, iPr$_2$EtN(40.15 ul) was added. The reaction mixture was stirred at 50° C. for 4 hrs and then at Room temperature overnight. The crude product was poured into saturated bicarbonate solution. The resulted precipitate was collected and purified by preparative HPLC. 7.8 mg product was obtained. Yield: 13.1%; $^1$H NMR (500 MHz, DMSO-d6): δ 3.91255 (s, 2H), 4.61898(s, 2H), 6.6094–6.62572(d, J=8.16 Hz, 1H), 6.64921–6.66517(d, J=7.98 Hz, 1H), 6.79669–6.79963 (d, J=1.47 Hz, 1H), 8.88104 (s, 1H); ESI-MS: 314 (M$^+$+1)

3-(4-tert-Butoxy-phenyl)-2-[(2,4-diamino-pteridin-6-ylmethyl)-amino]-propionic acid tert-butyl ester

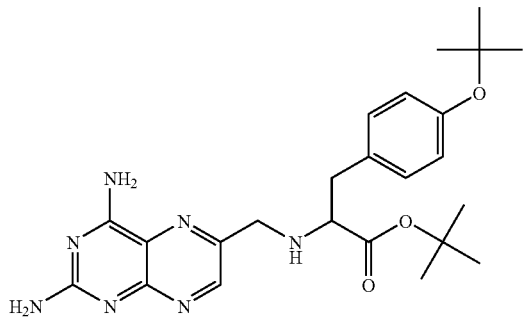

To a solution of 6-bromomethyl-2,4-pteridinediamine hydrobromide (53.7 mg, 0.1598 mmol) in anhydrous N,N dimethylacetamide was added 2-amino-3-(4-tert-butoxy-phenyl)-propionic acid tert-butyl ester hydrochloride (51.58 mg, 0.1758 m mol). Under positive pressure of Argon, iPr$_2$EtN (33.69 ul) was added. The reaction mixture was stirred at 50° C. for 4 hrs and then at room temperature overnight. The crude product was poured into saturated bicarbonate solution. The resulted precipitate was collected and purified by preparative HPLC. 27.6 mg product was obtained. Yield: 41%; $^1$H NMR (500 MHz, DMSO-d6): δ 1.22491(s, 9H), 1.26835 (s, 9H), 2.921–2.971 (m, 2H), 4.130 (b, 1H), 4.427(s, 2H), 6.91485–6.93165(d, J=8.4 Hz, 2H), 7.16037–7.17723(d, J=8.43 Hz, 1H), 8.89353 (s, 1H); 9.13119 (s, 2H), 9.30829 (s, 2H); ESI-MS: m/z 468 (M$^+$+1)

1-{[di-(2,4-Diaminopteridin-6-yl-methyl)]-amino-methyl}-naphthalene

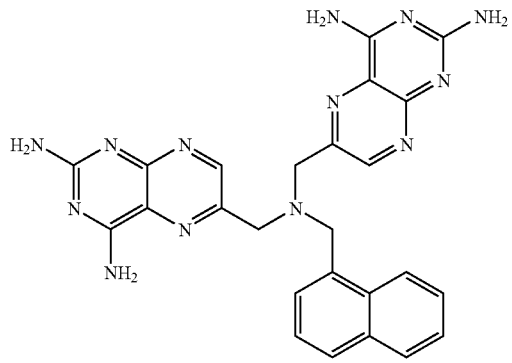

To a solution of 6-bromomethyl-2,4-pteridinediamine hydrobromide (51 mg, 0.2 mmol) in anhydrous N,N dimethylacetamide was added 1-aminomethyl-naphthalene (31.67 ul, 0.22 mmol). The reaction mixture was stirred at 50° C. overnight. The crude product was poured into saturated bicarbonate solution. The resulted precipitate was collected and purified by preparative HPLC. 9 mg product was obtained. Yield: 15%; $^1$H NMR(500 MHz, DMSO-d6): δ 4.0970 (s, 4H), 4.2526 (s, 2H), 7.3530–7.3692 (dd, J$_1$=7.25 Hz, J$_2$=7.25 Hz, 2H), 7.439–7.5202 (m, 2H), 7.5414–7.5553 (d, J=6.94 Hz, 1H), 7.67408–7.69065 (d, J=8.285 Hz, 1H), 7.78789–7.7713 (d, J=8.285 Hz, 1H), 8.14819–8.1313 (d, J=8.44 Hz, 1H), 8.7144 (s, 2H), 8.93305 (s, 2H), 9.23424(s, 2H); ESI-MS: m/z 506 (M$^+$+1)

Quinazolines

General Procedure for the 3H-quinazolin-4-one Synthesis

Method 1:

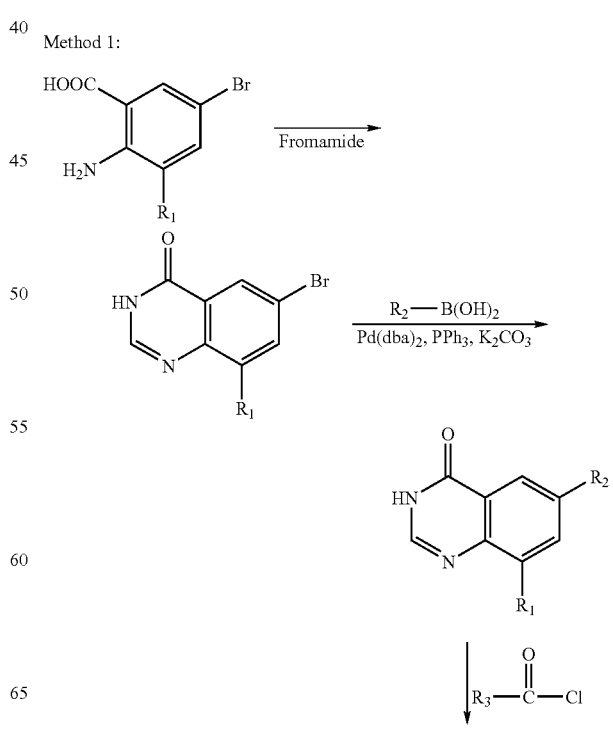

-continued

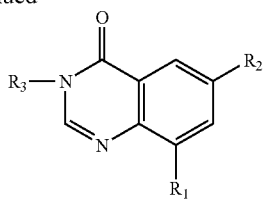

Method 2:

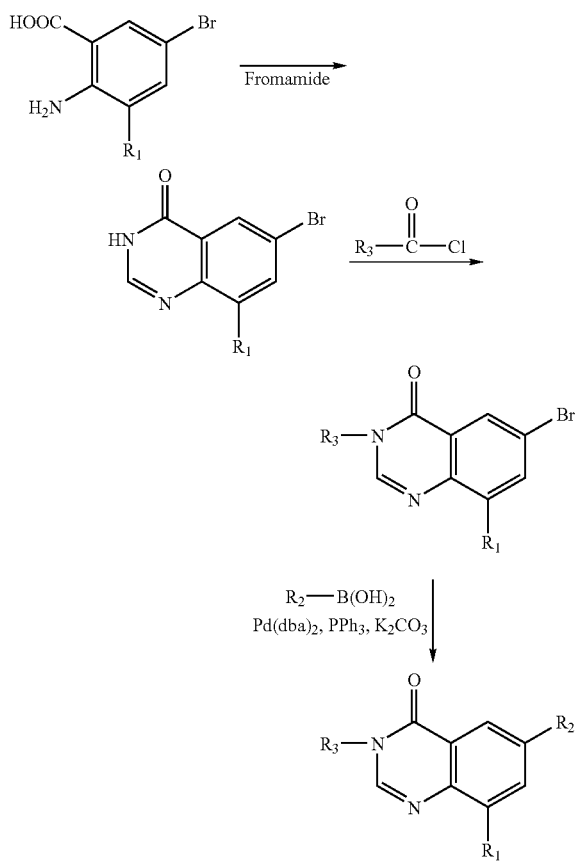

6-bromo-3H-quinazolin-4-one

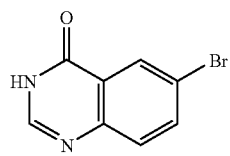

2-Amino-5-Bromo-benzoic acid (10.817 g, 50 mmol) was suspended in 70 ml formamide. The mixture was heated at 180° C. for 7 hrs. The cooled solution was diluted with 100 ml cold water and filtered. The tan solid was washed with di water and used for the next step reaction without further purification. 10.2 g product was obtained. Yield: 90%. $^1$H NMR (500 MHz, DMSO-d6): δ 7.61430–7.63179(d, J=8.745 Hz, 1H), 7.94922–7.97149 (dd, $J_1$=8.75 Hz, $J_2$=2.385 Hz, 1H), 8.142421(s, 1H), 8.19136–8.19609(d, J=2.365 Hz, 1H); ESI-MS: m/z 225, 227(M$^+$+1)

6-(2,6-Dimethylphenyl)-3H-quinazolin-4-one

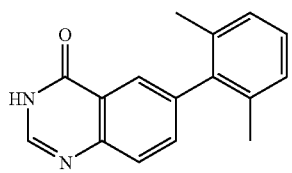

To a solution of 6-bromo-3H-quinazolin-4-one (43.1 mg, 0.1915 mmol) dissolved in 2 ml N,N-dimethylacetamide in a 20 ml vial, 2,6-dimethylphenylboronic acid (114.9 mg, 0.76 mmol) dissolved in 1 ml ethanol and potassium carbonate (26.7 mg, 0.193 mmol) dissolved in 1 ml water were added. Triphenylphosphine (5 mg, 0.019 mmol) and tris (dibenzylideneacetone)dipalladium(0) (3.5 mg, 3.8 umol) were added to the mixture which refluxed overnight. The crude product was poured into 50 ml saturated bicarbonate solution and methylene chloride was used to extract the product. Solvent in the organic phase was removed under vacuum. The resulted residue was purified by preparative HPLC. 19.2 mg product was obtained. Yield: 40%; $^1$H NMR (500 MHz, DMSO-d6): δ 1.96741(s, 6H), 7.114769–7.16307(d, J=7.69 Hz, 2H), 7.19260–7.22248(dd, $J_1$=8.62 Hz, $J_2$=6.31 Hz 1H), 7.60434–7.62503(dd, $J_1$=8.335 Hz, $J_2$=1.97 Hz, 1H), 7.75179–7.76829(d, J=8.25 Hz, 1H), 7.81882–7.82258(d, J=1.88 Hz, 1H), 8.17882 (s, 1H); ESI-MS: m/z 251 (M$^+$+1)

6-(2,6-Dimethoxlphenyl)-3H-quinazolin-4-one

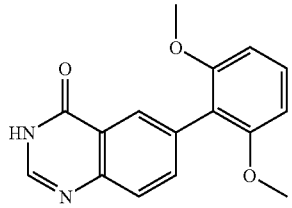

To a solution of 6-bromo-3H-quinazolin-4-one (43.1 mg, 0.1915 mmol) dissolved in 2 ml N,N-dimethylacetamide in a 20 ml vial, 2,6-dimethylphenylboronic acid (139.4 mg, 0.76 mmol) dissolved in 1 ml ethanol and potassium carbonate (26.7 mg, 0.193 mmol) dissolved in 1 ml water were added. Triphenylphosphine (5 mg, 0.019 mmol) and tris (dibenzylideneacetone)dipalladium (0) (3.5 mg, 3.8 umol) were added to the mixture which refluxed overnight. The crude product was poured into 50 ml saturated bicarbonate solution and methylene chloride was used to extract the product. Solvent in the organic phase was removed under vacuum. The resulted residue was purified by preparative HPLC. 38.2 mg product was obtained. Yield: 71%; $^1$H NMR (500 MHz, DMSO-d6): δ 3.67800(s, 6H), 6.77555–6.79250 (d, J=8.475 Hz, 1H), 7.33529–7.36895(dd, $J_1$=8.415 Hz, $J_2$=8.415 Hz 1H), 7.65311(s, 2H), 7.93672 (s, 1H), 8.13028 (s, 1H); ESI-MS: m/z 283 (M$^+$+1)

6-(2-chloro-6-methoxyphenyl)-3H-quinazolin-4-one

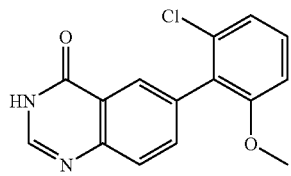

To a solution of 6-bromo-3H-quinazolin-4-one (38.9 mg, 0.1728 mmol) dissolved in 2 ml N,N-dimethylacetamide in a 20 ml vial, 2-chloro-6-methoxy-phenylboronic acid (128.88 mg, 0.6914 mmol) dissolved in 1 ml ethanol and potassium carbonate (26.28 mg, 0.19 mmol) dissolved in 1 ml water were added. Triphenylphosphine (4.5 mg, 0.017 mmol) and tris(dibenzylideneacetone)dipalladium(0) (3.2 mg, 3.5 umol) were added to the mixture which refluxed overnight. The crude product was poured into 5 ml saturated bicarbonate solution and methylene chloride was used to extract the product. Solvent in the organic phase was removed under vacuum. The resulted residue was purified by preparative HPLC. 3.4 mg product was obtained. Yield: 24.3%; $^1$H NMR (500 MHz, DMSO-d6): δ 3.70812(s, 3H), 7.13816–7.15637 (dd, $J_1$=7.945 Hz, $J_2$=0.32 Hz, 1H), 7.18430–7.20184 (dd, $J_1$=7.85 Hz, $J_2$=0.92 Hz 1H), 7.40806–7.44074 (dd, $J_1$=8.205 Hz, $J_2$=8.135 Hz, 1H), 7.66531–7.68611 (dd, $J_1$=8.305 Hz, $J_2$=2.04 Hz, 1H), 7.71531–7.73209 (d, J=8.39 Hz, 1H), 7.92946–7.93334 (d, J=1.94 Hz, 1H), 8.16800 (s, 1H); ESI-MS: m/z 287 ($M^+$+1)

6-(2,4,6-trimethylphenyl)-3H-quinazolin-4-one

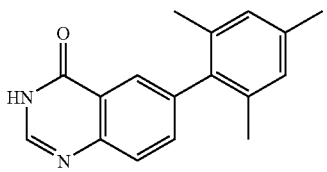

To a solution of 6-bromo-3H-quinazolin-4-one (43.1 mg, 0.1915 mmol) dissolved in 2 ml N,N-dimethylacetamide in a 20 ml vial, 2,4,6-trimethylphenylboronic acid (114.9 mg, 0.76 mmol) dissolved in 1 ml ethanol and potassium carbonate (26.7 mg, 0.193 mmol) dissolved in 1 ml water were added. Triphenylphosphine (5 mg, 0.019 mmol) and tris (dibenzylideneacetone)dipalladium (0) (3.5 mg, 3.8 umol) were added to the mixture which refluxed overnight. The crude product was poured into 50 ml saturated bicarbonate solution and methylene chloride was used to extract the product. Solvent in the organic phase was removed under vacuum. The resulted residue was purified by preparative HPLC. 19.2 mg product was obtained. Yield: 40%; $^1$H NMR (500 MHz, DMSO-d6): δ 1.96741(s, 6H), 7.114769–7.16307(d, J=7.69 Hz, 2H), 7.19260–7.22248(dd, $J_1$=8.62 Hz, $J_2$=6.31 Hz 1H), 7.60434–7.62503(dd, $J_1$=8.335 Hz, $J_2$=1.97 Hz, 1H), 7.75179–7.76829(d, J=8.25 Hz, 1H), 7.81882–7.82258(d, J=1.88 Hz, 1H), 8.17882 (s, 1H); ESI-MS: m/z 265 ($M^+$+1)

6-(Naphthalene-1-yl)-3H-quinazolin-4-one

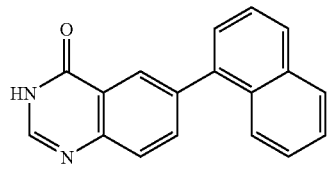

To a solution of 6-bromo-3H-quinazolin-4-one (45.2 mg, 0.2 mmol) dissolved in 2 ml N,N-dimethylacetamide in a 20 ml vial, naphthalene-1-boronic acid (69.4 mg, 0.4 mmol) dissolved in 1 ml ethanol and potassium carbonate (30.5 mg, 0.22 mmol) dissolved in 1 ml water were added. Tripenylphosphine (5.27 mg, 0.02 mmol) and tris(dibenzylideneacetone)dipalladium (0) (3.6 mg, 4 umol) was added to the mixture which refluxed overnight. The crude product was poured into 50 ml saturated bicarbonate solution and methylene chloride was used to extract the product. Solvent in the organic phase was removed under vacuum. The resulted residue was purified by preparative HPLC. 32.9 mg product was obtained. Yield: 62%; $^1$H NMR (500 MHz, DMSO-d6): δ 7.52083–7.54615(m, 2H), 7.56877–7.58461 (dd, J=6.88 Hz, 1H), 7.61224–7.64281(dd, $J_1$=8.255 Hz, $J_2$=8.285 Hz, 1H), 7.78775–7.804 (d, J=8.125 Hz, 1H), 7.82384–7.84054(d, J=8.35 Hz, 1H), 7.93472–7.95545(dd, $J_1$=8.365 Hz, $J_2$=2 Hz, 1H), 8.00847–8.02533(d, J=8.43 Hz, 1H), 8.03829–8.05347(d, J=7.59 Hz, 1H), 8.15915–8.16300 (d, J=1.925 Hz, 1H), 8.19218 (s, 1H); ESI-MS: m/z 273 ($M^+$+1)

6-(Naphthalene-2-yl)-3H-quinazolin-4-one

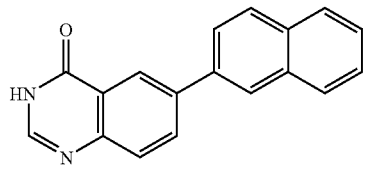

To a solution of 6-bromo-3H-quinazolin-4-one (47.1 mg, 0.2093 mmol) dissolved in 2 ml N,N-dimethylacetamide in a 20 ml vial, naphthalene-1-boronic acid (73 mg, 0.4244 mmol) dissolved in 1 ml ethanol and potassium carbonate (32.7 mg, 0.2366 mmol) dissolved in 1 ml water were added. Triphenylphosphine (5.5 mg, 0.021 mmol) and tris(dibenzylideneacetone)dipalladium (0) (3.8 mg, 4.1 umol) were added to the mixture which refluxed overnight. The crude product was poured into 50 ml saturated bicarbonate solution and methylene chloride was used to extract the product. Solvent in the organic phase was removed under vacuum. The resulted residue was purified by preparative HPLC. 26.3 mg product was obtained. Yield: 46%; $^1$H NMR (500 MHz, DMSO-d6): δ 7.54020–7.58965 (m, 2H), 7.80614–7.82312 (d, J=8.49 Hz, 1H), 7.94743–7.96828 (dd, $J_1$=8.505 Hz, $J_2$=1.91 Hz, 1H), 7.96828–7.98243 (d, J=8.035 Hz, 1H), 8.05455–8.07187 (d, J=8.63 Hz, 1H), 8.16005(s, 1H), 8.30107–8.3226(dd, $J_1$=8.58 Hz, $J_2$=2.25 Hz, 1H), 8.37163–8.37447(d, J=1.42 Hz, 1H), 8.50638–8.51090(d, J=2.26 Hz, 1H); ESI-MS: m/z 273 ($M^+$+1)

6-(4-phenoxy-phenyl)-3H-quinazolin-4-one

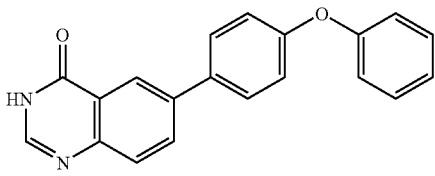

To a solution of 6-bromo-3H-quinazolin-4-one (44.8 mg, 0.199 mmol) dissolved in 2 ml N,N-dimethylacetamide in a 20 ml vial, naphthalene-1-boronic acid (85.22 mg, 0.3981 mmol) dissolved in 1 ml ethanol and potassium carbonate (30.26 mg, 0.2198 mmol) dissolved in 1 ml water were added. Triphenylphosphine (5.2 mg, 0.020 mmol) and tris(dibenzylideneacetone)dipalladium (0) (3.64 mg, 4.0 umol) were added to the mixture which refluxed overnight. The crude product was poured into 50 ml saturated bicarbonate solution and methylene chloride was used to extract the product. Solvent in the organic phase was removed under vacuum. The resulted residue was purified by preparative HPLC. 25.3 mg product was obtained. Yield: 41%; $^1$H NMR(500 MHz, DMSO-d6): δ 7.09215–7.12687(dd, $J_1$=8.58 Hz, $J_2$=8.78 Hz, 4H), 7.17733–7.20876 (dd, $J_1$=6.48 Hz, $J_2$=7.375 Hz, 1H), 7.42050–7.45247($J_1$=7.56 Hz, $J_2$=6.45 Hz, 2H), 7.74247–7.75949(d, J=8.51 Hz, 1H), 7.79084–7.80838(dd, $J_1$=6.73 Hz, $J_2$=2.08 Hz, 2H), 8.1191–8.1408(dd, $J_1$=8.395 Hz, $J_2$=2.355 Hz, 1H), 8.14531 (s, 1H), 8.31298–8.31761(d, J=2.315 Hz, 1H); ESI-MS: m/z 315 (M$^+$+1)

6-Bromo-3-(3-hydroxy-propionyl)-3H-quinazolin-4-one

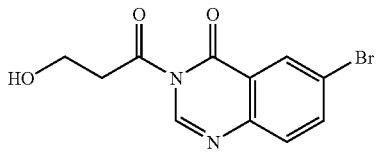

To a suspension of NaH (60% in mineral oil, 199 mg) in 20 ml of N,N-dimethylacetamide was added 6-bromo-3H-quinazolin-4-one(0.9335 mg, 4.148 mmol). The mixture was stirred at room temperature for 40 mins resulting clear red solution. Acroyl chloride (471.8 ul, 5.8072 mmol) was added. The solution was heated at 70° C. for 8 hrs, cooled to room temperature, and poured into 30 ml of ice water. Methylene chloride added and product was in the water phase. The water solvent was evaporated under vacuum. The resulted residue was purified by preparative HPLC. 1.1 g product was obtained. Yield: 74.7%; $^1$H NMR (500 MHz, DMSO-d6): δ 2.73412–2.76135(t, J=6.805 Hz, 2H), 4.14197–4.16922(t, J=6.815 Hz, 2H), 7.62305–7.64046(d, J=8.705 Hz, 1H), 7.96596–7.98797(dd, $J_1$=8.635 Hz, $J_2$=2.38 Hz, 1H), 8.2287–8.2335(d, J=2.4 Hz, 1H), 8.41991 (s, 1H); ESI-MS: m/z 297, 299 (M$^+$+1)

6-(2,6-Dimethylphenyl)-3-(3-hydroxy-propionyl)-3H-quinazolin-4-one

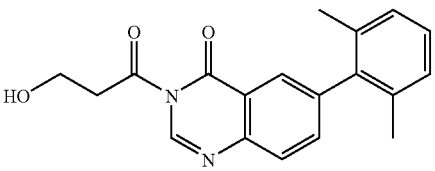

To a solution of 6-Bromo-3-(3-hydroxy-propionyl)-3H-quinazolin-4-one (9.8 mg, 0.033 mmol) dissolved in 1 ml N,N-dimethylacetamide in a 20 ml vial, 2,6-dimethylphenyl boronic acid (9.89 mg, 0.066 mmol) dissolved in 0.5 ml ethanol and potassium carbonate (5 mg, 0.036 mmol) dissolved in 0.5 ml water were added. Triphenylphosphine (0.87 mg, 3.3 umol) and tris(dibenzylideneacetone)dipalladium(0) (0.6 mg, 0.6 umol) were added to the mixture which refluxed overnight. The crude product was poured into 5 ml saturated bicarbonate solution and methylene chloride was used to extract the product. Solvent in the organic phase was removed under vacuum. The resulted residue was purified by preparative HPLC. 5.2 mg product was obtained. Yield: 49%; $^1$H NMR (500 MHz, DMSO-d6): δ 1.96247(s, 6H), 2.76290–2.79002(t, J=6.805 Hz, 2H), ), 4.15954–4.18664 (t, J=6.785 Hz, 2H), 7.14682–7.7.1621(d, J=7.64 Hz, 1H), 7.19338–7.21062(dd, $J_1$=8.62 Hz, $J_2$=6.41 Hz, 1H), 7.60532–7.62604(dd, $J_1$=8.365 Hz, $J_2$=2.03 Hz, 1H), 7.75204–7.76861 (d, J=8.285 Hz, 1H), 7.84928–7.85312(d, J=1.92 Hz, 1H), 8.41195(s, 1H); ESI-MS: m/z 323 (M$^+$+1)

6-(2-chloro-6-methoxyphenyl)-3-(3-hydroxy-propionyl)-3H-quinazolin-4-one

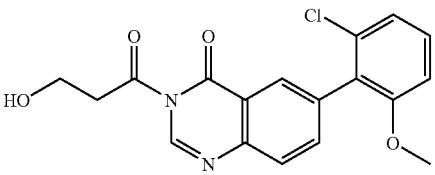

To a solution of 6-Bromo-3-(3-hydroxy-propionyl)-3H-quinazolin-4-one (11.6 mg, 0.039 mmol) dissolved in 1 ml N,N-dimethylacetamide in a 20 ml vial, 2-chloro-6-methoxy-phenylboronic acid (14.55 mg, 0.078 mmol) dissolved in 0.5 ml ethanol and potassium carbonate (5.92 mg, 0.043 mmol) dissolved in 0.5 ml water were added. Triphenylphosphine (1 mg, 3.8 umol) and tris(dibenzylideneacetone)dipalladium (0) (0.7 mg, 0.78 umol) were added to the mixture which refluxed overnight. The crude product was poured into 5 ml saturated bicarbonate solution and methylene chloride was used to extract the product. Solvent in the organic phase was removed under vacuum. The resulted residue was purified by preparative HPLC. 3.4 mg product was obtained. Yield: 24.3%; $^1$H NMR (500 MHz, DMSO-d6): δ 2.75538–2.78226(t, J=6.835 Hz, 2H), 3.70334(s, 3H), 4.15877–4.18594 (t, J=6.785 Hz, 2H), 7.13724–7.15535 (dd, $J_1$=8.68 Hz, $J_2$=0.75 Hz, 1H), 7.18337–7.20169 (dd, $J_1$=8.375 Hz, $J_2$=0.885 Hz, 1H), 7.41001–7.44275 (dd, $J_1$=8.215 Hz, $J_2$=8.185 Hz, 1H), 7.66453–7.68523 (dd, $J_1$=8.38 Hz, $J_2$=2.0 Hz, 1H), 7.72 (d, J=8.4 Hz, 1H), 7.96 (d, J=1.9 Hz, 1H), 8.41 (s, 1H); ESI-MS: m/z 359 (M$^+$+1)

2-hydroxy-4-aminoquinazolines

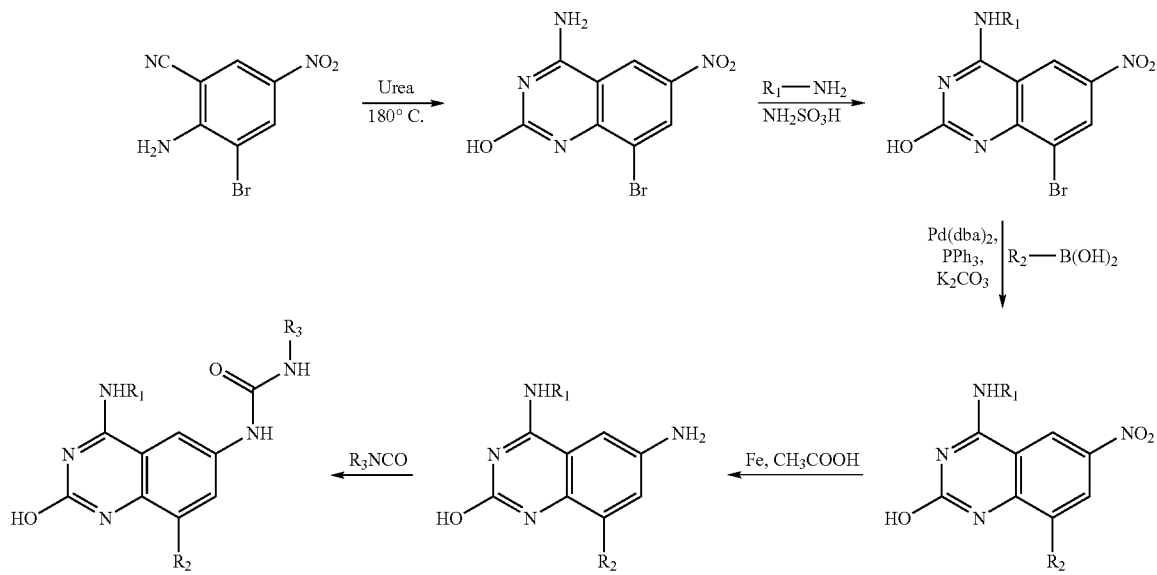

4-Amino-8-bromo-6-nitro-quinazolin-2-ol

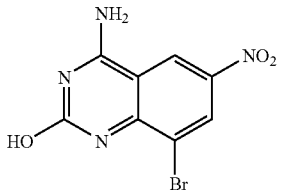

2-Amino-3-bromo-5-nitro-benzonitrile (1.9003 g, 7.85 mmol) was heated with urea (1.8862 g, 31.4 mmol) at 180–185° C. for 3 hrs. The cooled mixture was powered and treated with bicarbonate solution, filtered and washed with water. The solid was the collected and washed with ethanol, ether, and used for the next step reaction without further purification. 2.0 g product was obtained. Yield 89%; $^1$H NMR (500 MHz, DMSO-d6): δ 8.44455–8.45011(d, J=2.78 Hz, 1H), 8.87071–8.87544(d, J=2.365 Hz, 1H), 9.39866–9.40333(d, J=2.335 Hz, 1H), 9.50740–9.51282(d, J=2.71 Hz, 1H); ESI-MS: 285, 287 (M$^+$+1)

8-Bromo-4-[3-(4-methyl-piperazin-1yl)-propylamino]-6-nitro-quinazolin-2-ol

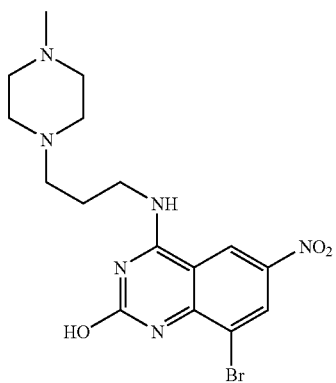

A mixture of 4-amino-8-bromo-6-nitro-quinazolin-2-ol (24.1 mg, 0.0845 mmol), sulfamic acid (16.4 mg, 0.169 mmol) and 1-(3-aminopropyl)-4-methylpiperazine (1 ml) was heated at reflux for 7 h. The cooled reaction mixture was poured into 10 ml ice water. The resulting precipitate was collected and purified by preparative HPLC. 19.2 mg product was obtained. Yield: 40%; $^1$H NMR (500 MHz, DMSO-d6): δ 1.91521–1.95482 (m, 2H), 2.78103(s, 8H), 3.16555 (b, 4H), 8.68221–8.68666(d, J=2.225 Hz, 1H), 9.10824–9.11291(d, J=2.335 Hz, 1H); ESI-MS: 425, 427 (M$^+$+1)

Preparation of (6,7-Diphenyl-pteridin-4-yl)-(3-(4-methyl-piperazin-1-yl)-propyl)-amine

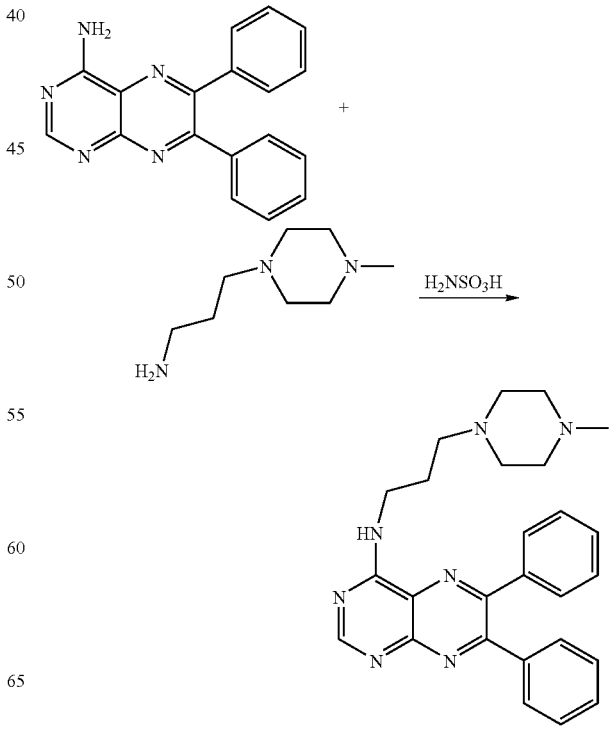

6,7-Diphenyl-pteridin-4-ylamine (200 mg, 0.669 mmol) and sulfamic acid (300 mg, 1.91 mmol) were dissolved in 4 ml 1-(3-aminopropyl)-4-methylpiperazine. The mixture was reflux for overnight. Preparative HPLC was used to isolated the product. 50 mg (6,7-Diphenyl-pteridin-4-yl)-(3-(4-methyl-piperazin-1-yl)-propyl)-amine was obtained. Yield: 17%, ESI-MS: [M+H]+, 441

Representative Synthesis of Compounds of Structure IV

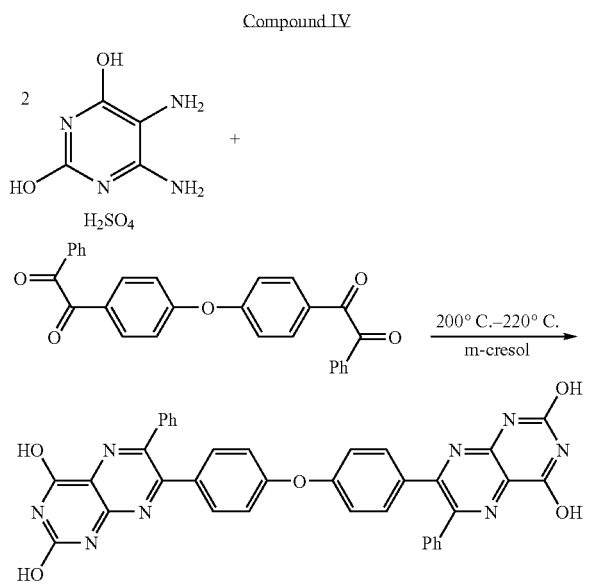

A 3-mL reaction flask equipped with a stirring vane and a teflon cap was charged with the bis(benzil) species (122 mg; 0.324 mmol) and 5,6-diamino-2,4-dihydroxy pyrimidine sulfate (156 mg; 0.649 mmol; 2.00 equiv). The vial was heated to ca. 210° C. for 2 h and then the contents were poured into 30 mL of ether, the resulting solid was sonicated vortexed and centrifuged. The resulting solid was washed 2×20 mL of ethyl acetate-ether (1:1), and dried in a vacuum dessicator resulting in 120 mg (96%) of an orange solid bis(pteridine). MS (M+H+: calcd 647; found 647).

Representative Synthesis of Compounds of Structure V

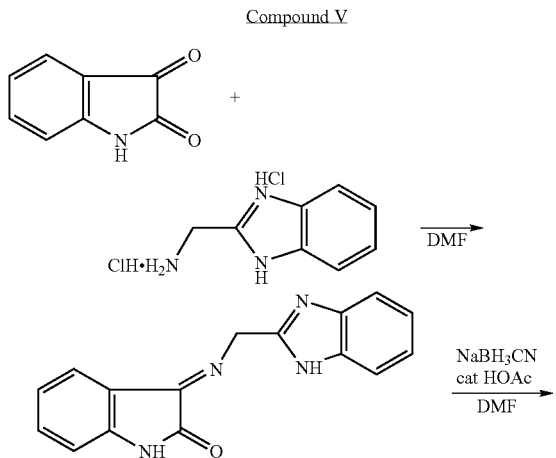

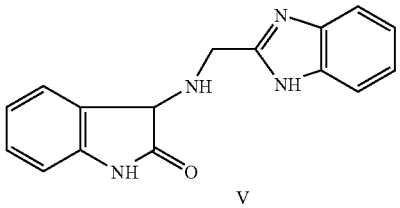

A 5-mL, single-necked, round-bottomed flask with a stirring bar and a septum was charged with 2-aminomethylbenzimidazole (119 mg; 0.500 mmol; 1.00 equiv). It does not dissolve in 3 mL of DMF even with heating. To this slurry was added isatin (73.8 mg; 0.502 mmol; 1.00 equiv). The solution is a bright orange-yellow. A few drops of glacial HOAc were added, the reaction was stirred for 15 min, and then sodium cyanoborohydride (62.0 mg; 0.980 mmol; 1.97 equiv). The solution turned a light straw-yellow in 30 min. After stirring for 2 d at room temperature, the reaction was worked up by pouring the mixture into 50:50 saturated aqueous sodium bicarbonate-ice. The white precipitate formed was extracted with ethylacetate (2×20 mL). The combined organic layer was extracted again with 10 mL satd sodium bicarbonate, dried (anhydrous $Na_2SO_4$), filtered, and concentrated by rotary evaporation to yield an orange-yellow oil that solidified on standing. The crude was recrystallized from ethylacetate-hexanes to yield 98.9 mg of an orange foam. MS (M+H+: calcd 279; found 279)

EXAMPLE 2

Anti-Cancer Therapy with Vasculostatic Agents

Figure 2:
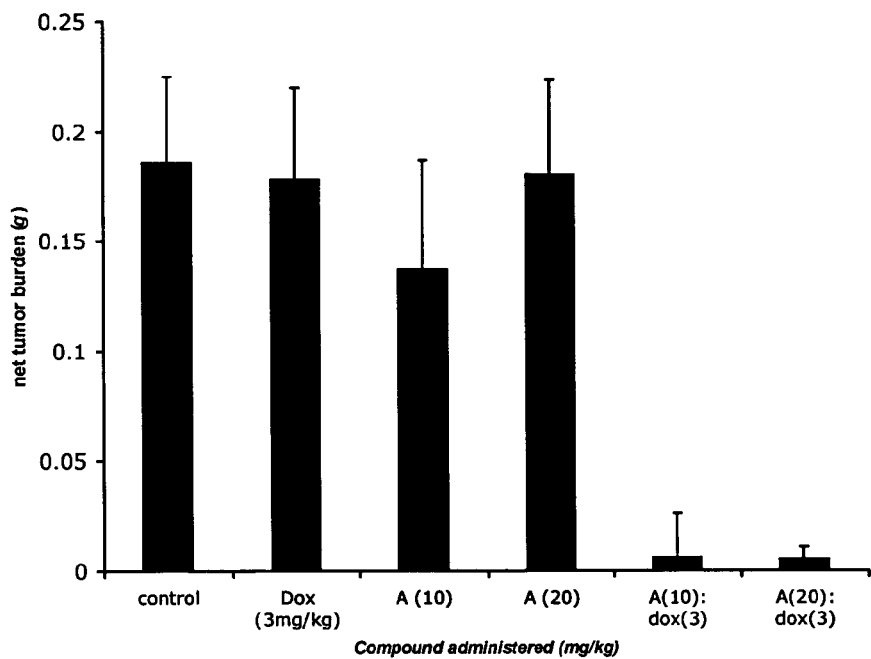
FIG. 2 shows the results of 6,7-bis(4-hydroxyphenyl)-pteridin-4-ylamine, sulfate salt and doxorubicin for treatment of lung metastases. Syngeneic Lewis lung carcinoma cells were injected I.V. in order to establish lung metastases in Balb/C mice. Beginning 10 days after cells were injected, doxorubicin (3 mg/kg) and/or 6,7-bis(4-hydroxyphenyl)-pteridin-4-ylamine, sulfate salt (various doses as shown) was given I.P. every 3 days for 3 cycles. Animals were sacrificed at day 20, lungs were collected, and weighed. Net tumor burden is the weight of tumor-bearing lungs minus the average weight of normal control lungs. N=5/group, p<0.02.
Figure 6:
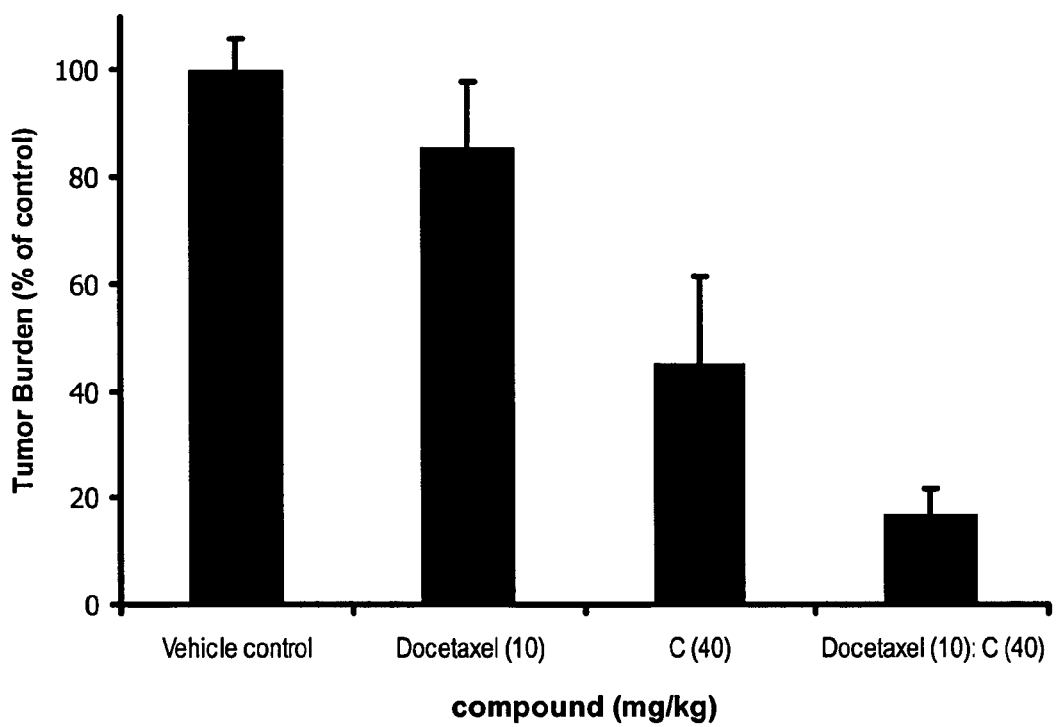
FIG. 6 illustrates the effect of compounds administered in conjunction with docetaxel in the in vivo model of metastatic colon cancer (CT-26 adenocarcinoma) described for FIG. 4. 2,3-Bis(3,4-dihydroxyphenyl)-pyrido[2,3-b]pyrazin-6-ylamine dihydrochloride salt (compound C) from FIG. 1 is shown in FIG. 6 as compound C. N=5/group, p<0.02.

The following experiments show the use of vasculostatic agents of the invention alone and in combination with chemotherapeutic agents for treatment of cancer. FIG. 2 shows the synergistic results of co-drug therapy utilizing 6,7-bis(4-hydroxyphenyl)-pteridin-4-ylamine, sulfate salt, (compound A—in this example formulated in 50% PEG400: 50% water) illustrated in FIG. 1, with doxorubicin (in this example formulated in 50% PEG400:50% water). In the experiment shown in FIG. 2, syngeneic Lewis lung carcinoma cells were injected I.V. in order to establish lung metastases in Balb/C mice. Beginning 10 days after cells were injected, doxorubicin (3 mg/kg) and/or 6,7-bis(4-hydroxyphenyl)-pteridin-4-ylamine, sulfate salt, (compound A—various doses as shown) was given I.P. every 3 days for 3 cycles. Animals were sacrificed at day 20, lungs were collected, and weighed. Net tumor burden is the weight of tumor-bearing lungs minus the average weight of normal control lungs. N=5/group, p<0.02. As shown in FIG. 2 6,7-Bis(4-hydroxyphenyl)-pteridin-4-ylamine, sulfate salt (compound A) had a profound effect on tumor burden in animals, typically reducing tumor burden by 25% as a stand alone agent or by greater than 90% in combination with doxorubicin.

Figure 3:
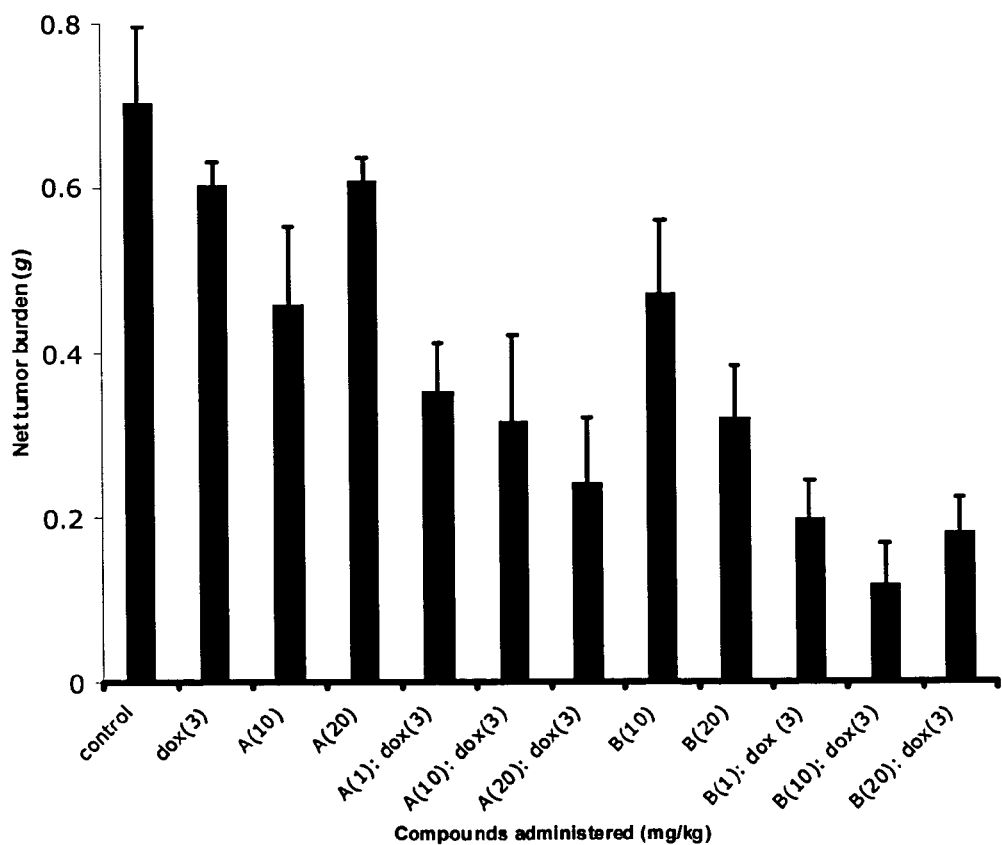
FIG. 3 illustrates the effect of compounds administered in conjunction with doxorubicin in an in vivo model of metastatic colon cancer (CT-26 adenocarcinoma). Syngeneic CT-26 Colon carcinoma cells were injected I.V. in order to establish lung metastases in Balb/C mice. Beginning 10 days after cells were injected, indicated test agents were given I.P. every 3 days for 3 cycles. Animals were sacrificed at day 20, lungs were collected, and weighed. Net tumor burden is the weight of tumor-bearing lungs minus the average weight of normal control lungs. N=5/group, p<0.02. In these graphs, compound A is 6,7-bis(4-hydroxyphenyl)-pteridin-4-ylamine sulfate salt, and compound B is 6,7-diphenyl-pteridine-2,4-diamine.

FIG. 3 shows the results of using 6,7-bis(4-hydroxyphenyl)-pteridin-4-ylamine sulfate salt (compound A—in this example formulated in 50% PEG400:50% water), and 6,7-diphenyl-pteridine-2,4-diamine (compound B—in this example formulated in 50% PEG400:50% water) with doxorubicin to treat colon carcinoma. Syngeneic CT-26 Colon carcinoma cells were injected I.V. in order to establish lung metastases in Balb/C mice. Beginning 10 days after cells were injected, indicated test agents were given I.P. every 3 days for 3 cycles. Animals were sacrificed at day 20, lungs were collected, and weighed. Net tumor burden is the weight of tumor-bearing lungs minus the average weight of normal control lungs. N=5/group, p<0.02. In this model, as shown in FIG. 3 6,7-Bis(4-hydroxyphenyl)-pteridin-4-ylamine, sulfate salt (compound A) typically reduced tumor burden by 35% as a stand alone agent or by greater than 60% in combination with doxorubicin. Similarly, in this model, 6,7-diphenyl-pteridine-2,4-diamine (compound B) typically reduced tumor burden by 35% as a stand alone agent or by greater than 65% in combination with doxorubicin.

Figure 4:
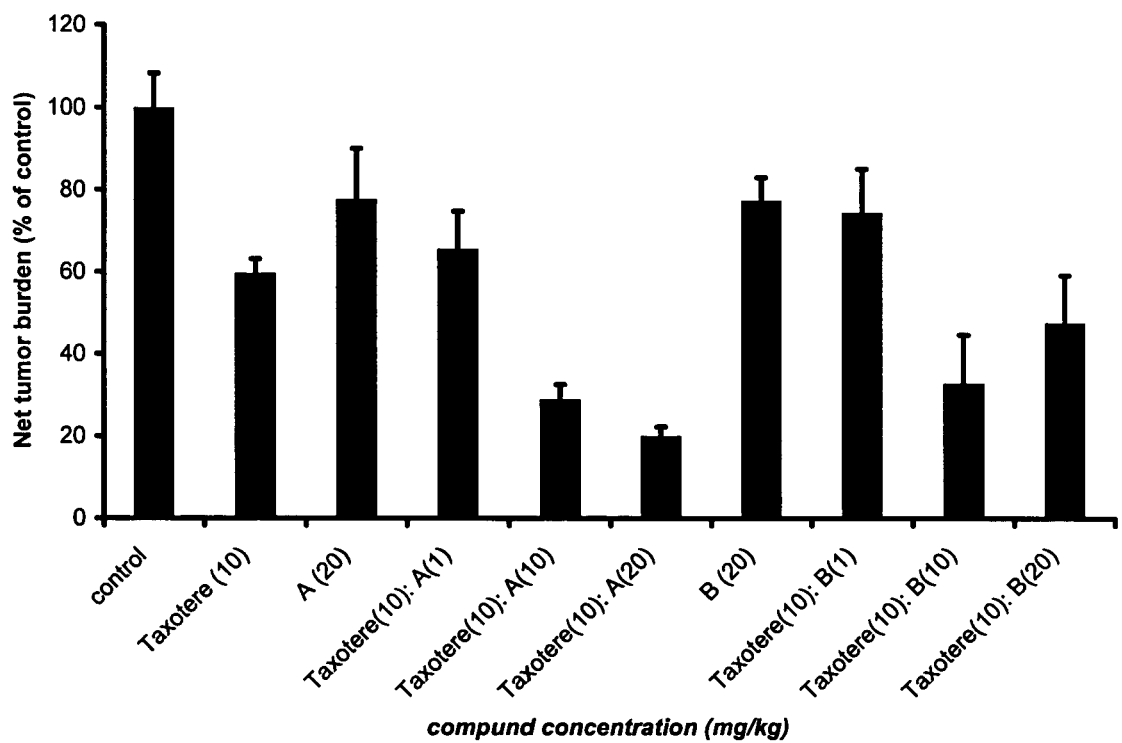
FIG. 4 illustrates the effects of compounds of the present invention for co-drug therapy with Taxotere as described herein. Syngeneic CT-26 Colon carcinoma cells were used in order to establish lung metastases in Balb/C mice as described for FIG. 3. 6,7-bis(4-hydroxyphenyl)-pteridin-4-ylamine, sulfate salt (compound A) and 6,7-diphenyl-pteridine-2,4-diamine (compound B) from FIG. 1 are shown in FIG. 4.

FIG. 4 illustrates the effects of the compounds of the present invention for co-drug therapy with docetaxel (Taxotere®—in this example formulated in 12.5% Cremaphore: 12.5% Ethanol:75% normal saline) as described herein. Syngeneic CT-26 Colon carcinoma cells were injected I.V. in order to establish lung metastases in Balb/C mice. Beginning 10 days after cells were injected, indicated test agents were given I.P. every 3 days for 3 cycles. Animals were sacrificed at day 20, lungs were collected, and weighed. Net tumor burden is the weight of tumor-bearing lungs minus the average weight of normal control lungs. N=5/group, p<0.02. 6,7-bis(4-hydroxyphenyl)-pteridin-4-ylamine, sulfate salt (compound A—in this example formulated in 50% PEG400: 50% water) and 6,7-diphenyl-pteridine-2,4-diamine (compound B—in this example formulated in 50% PEG400:50% water) from FIG. 1 are shown in FIG. 4. In this model, as shown in FIG. 4, 6,7-Bis(4-hydroxyphenyl)-pteridin-4-ylamine, sulfate salt (compound A) typically reduced tumor burden by 25% as a stand alone agent or by greater than 80% in combination with docetaxel. Similarly, in this model 6,7-diphenyl-pteridine-2,4-diamine (compound B) typically reduced tumor burden by 20% as a stand alone agent or by greater than 70% in combination with doxorubicin.

Figure 5:
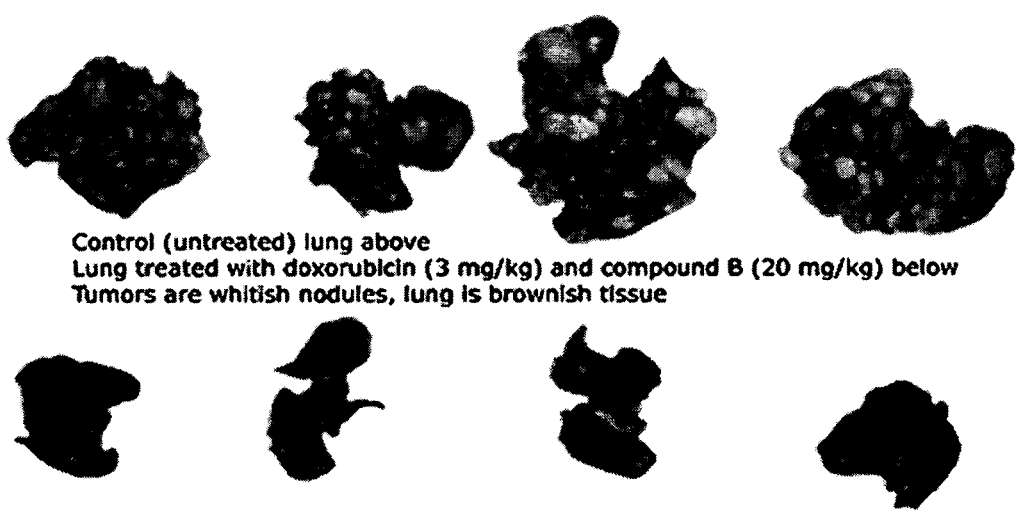
FIG. 5 shows a photo of representative lung samples from the experiment shown in FIG. 4 with 6,7-diphenyl-pteridine-2,4-diamine (compound B) and doxorubicin.

FIG. 5 shows a photo of representative lung samples from the experiment shown in FIG. 3 with 6,7-diphenyl-pteridine-2,4-diamine (compound B—in this example formulated in 50% PEG400:50% water) and doxorubicin (in this example formulated in 50% PEG400:50% water). The tumors in the lungs are apparent in the vehicle (control) lungs, and the vasculostatic agent plus doxorubicin treated lungs show a dramatic reduction in tumor burden.

FIG. 6 illustrates the effect of compounds administered in conjunction with docetaxel (Taxotere®—in this example formulated in 12.5% Cremaphore:12.5% Ethanol:75% normal saline ) in the in vivo model of metastatic colon cancer (CT-26 adenocarcinoma) described for FIG. 4. 2,3-Bis(3,4-dihydroxyphenyl)-pyrido[2,3-b]pyrazin-6-ylamine dihydrochloride salt (compound C—in this example formulated in 50% PEG400:50% water) from FIG. 1 is shown in FIG. 6 as compound C. N=5/group, p<0.02. In this model, as shown in FIG. 6, 2,3-Bis(3,4-dihydroxyphenyl)-pyrido[2,3-b]pyrazin-6-ylamine dihydrochloride salt (compound C) typically reduced tumor burden by 65% as a stand alone agent or by greater than 85% in combination with docetaxel.

Similarly, 2,3-bis(4-hydroxyphenyl)-pyrido[2,3-b]pyrazin-6-ylamine dihydrochloride salt inhibited tumor burden alone or with co-drug therapy using docetaxel (Taxotere®—in this example formulated in 12.5% Cremaphore: 12.5% Ethanol:75% normal saline) as described herein. Syngeneic CT-26 Colon carcinoma cells were injected I.V. in order to establish lung metastases in Balb/C mice. Beginning 10 days after cells were injected, indicated test agents were given I.P. every 3 days for 3 cycles. Animals were sacrificed at day 20, lungs were collected, and weighed. Net tumor burden is the weight of tumor-bearing lungs minus the average weight of normal control lungs. N=5/group, p<0.02. 2,3-Bis(4-hydroxyphenyl)-pyrido[2,3-b]pyrazin-6-ylamine dihydrochloride salt in 50% PEG400:50% water) typically reduced tumor burden by 63% as a stand alone agent or by greater than 78% in combination with docetaxel.

EXAMPLE 3

Inhibition of Vascular Permeability

IL-2 is used clinically to treat metastatic melanoma and renal cell carcinoma and the dose-limiting toxicity for IL-2 is Vascular Leak Syndrome (VLS). Two representative examples from distinct chemotype series were selected for initial study in the reduction of IL-2-induced VLS (see FIG. 1 compounds). The compounds were pre-screened for in vivo reduction of vascular permeability and there was no observable gross toxicity as single agents at 20-fold higher doses.

Figure 7:
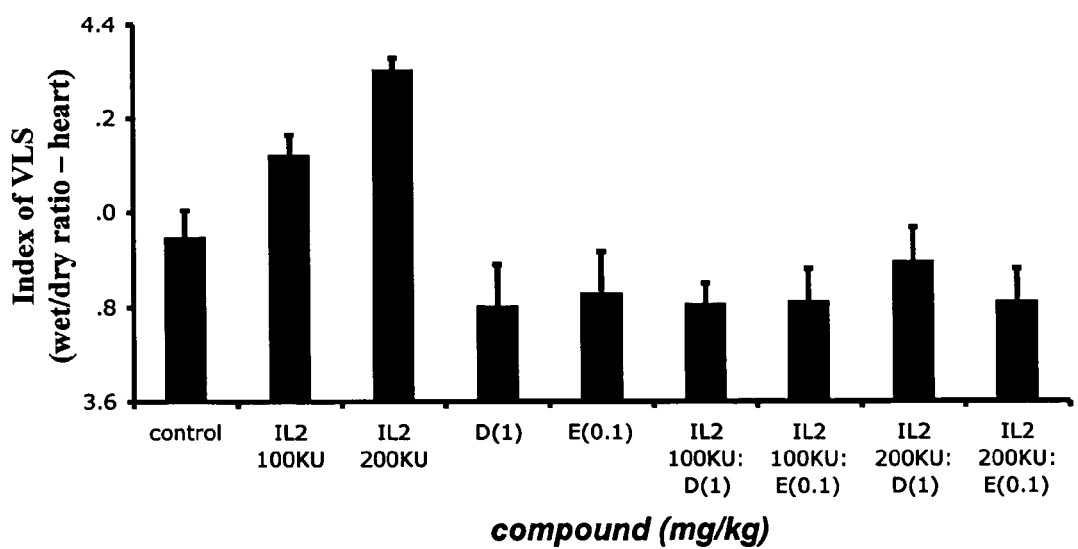
FIGS. 7 and 8 illustrate the effects of compounds of the invention for their capacity to inhibit IL-2 induced VLS. The graphs present representative examples of compounds cited in this application and their effects on VLS. In the graphs, compound D is N-(2-(1H-indol-2-yl)-phenyl)-phthalamic acid and compound E is 6,7-bis(3-hydroxyphenyl)-pteridine-2,4-diamine.
Figure 8:
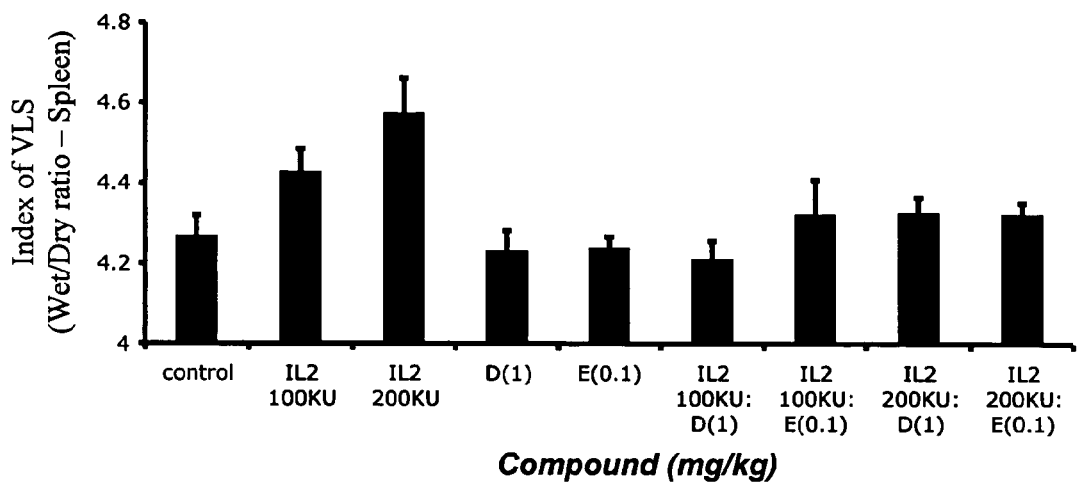

The results of the studies shown in FIGS. 7–8 indicate that representative compounds of the invention show inhibition of vascular leak in vivo. There were no effects on T cell proliferation in prescribed dose range (see FIGS. 10–11) and no effects on anti-tumor activity of IL-2 (melanoma model; see FIG. 9). The following experiments exemplify the results for co-drug therapy.

BalbC mice were given 9 injections of the indicated dose of murine IL-2 (in this example formulated in saline with 5% bovine serum albumin) and/or invention compounds over a period of 4 days. Animals were then sacrificed followed by collection, blotting and weighing (wet weight) of heart, lungs, and spleen. Organs were then dried at 80° C. for 24 hours and weighed (dry weight). N=5/group, p<0.02. N-(2-(1H-indol-2-yl)-phenyl)-phthalamic acid (compound D—in the 1 mg/kg range, in this example formulated in 50% PEG400:50% water) and 6,7-bis(3-hydroxyphenyl)-pteridine-2,4-diamine, sulfate salt (compound E—in the 0.1 mg/kg range, in this example formulated in 50% PEG400: 50% water) typically reduced VLS in the heart by >100%. The results are shown in FIG. 7.

BalbC mice were given 9 injections of the indicated dose of murine IL-2 and/or invention compounds over a period of 4 days. Animals were then sacrificed followed by collection, blotting and weighing (wet weight) of heart, lungs, and spleen. Organs were then dried at 80° C. for 24 hours and weighed (dry weight). N=5/group, p<0.02. N-(2-(1H-indol-2-yl)-phenyl)-phthalamic acid (compound D—in the 1 mg/kg range, in this example formulated in 50% PEG400: 50% water) and 6,7-bis(3-hydroxyphenyl)-pteridine-2,4-diamine, sulfate salt (compound E—in the 0.1 mg/kg range, in this example formulated in 50% PEG400:50% water) typically reduced VLS in the spleen by >100%. The results are shown in FIG. 8.

Figure 9:
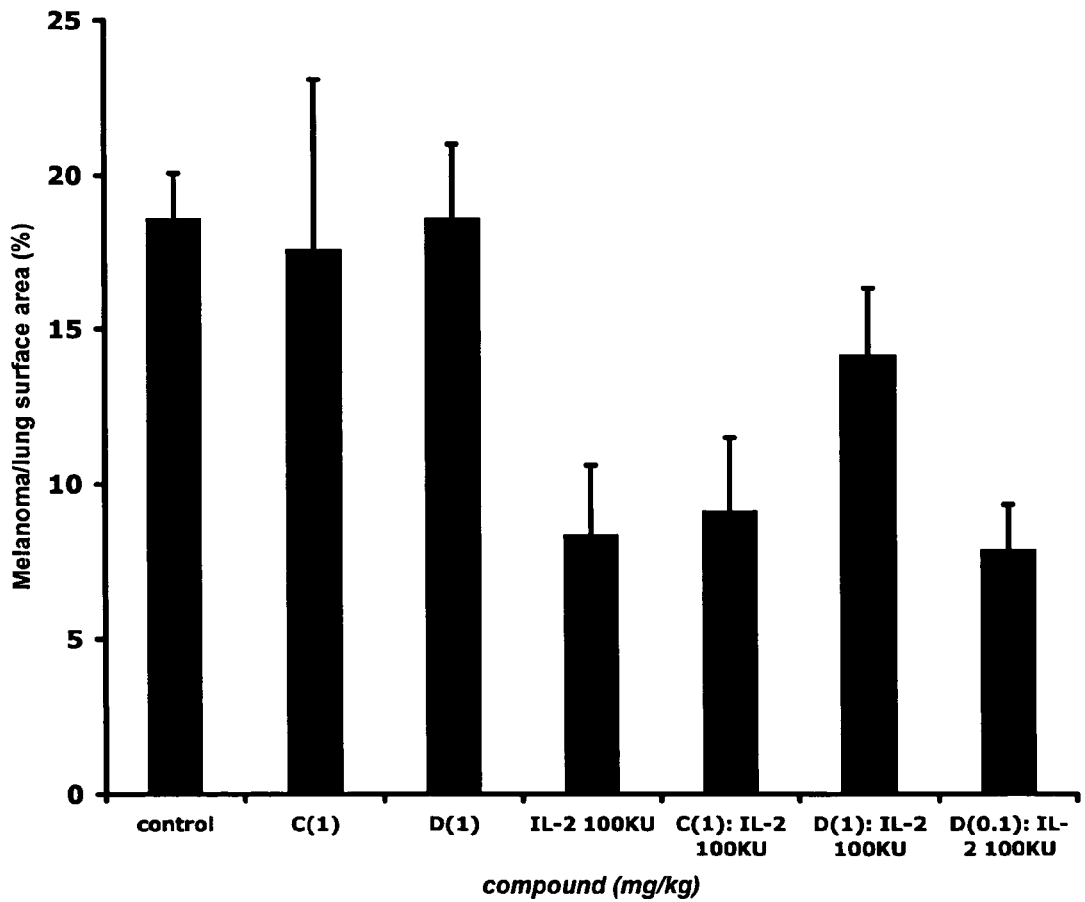
FIG. 9 illustrates the effects of compounds of the invention for their effect on IL-2 induced anti-tumor actions. The graph presents representative examples of compounds cited in this application and their effects on IL-2 mediated reductions in metastatic melanoma tumor burden. In the graphs, compound D is N-(2-(1H-indol-2-yl)-phenyl)-phthalamic acid and compound E is 6,7-bis(3-hydroxyphenyl)-pteridine-2,4-diamine. Invention compound concentrations are listed in parenthesis in mg/kg while IL-2 concentration is given in parenthesis kilounits.

Syngeneic B16 melanoma cells were injected I.V. in order to establish lung metastases in C57 mice. Beginning 10 days after cells were injected, 100,000U of IL-2 and/or indicated invention compounds were given I.P. every 8 hours for 5 days. Animals were sacrificed at day 18, lungs were collected and scored using image analysis software. N=5/group, p<0.02. N-(2-(1H-indol-2-yl)-phenyl)-phthalamic acid (compound D—in the 1 mg/kg range, in this example formulated in 50% PEG400:50% water) and 6,7-bis(3-hydroxyphenyl)-pteridine-2,4-diamine, sulfate salt (compound E—in the 0.1 mg/kg range, in this example formulated in 50% PEG400:50% water) typically had no significant impact on the anti-tumor activity of IL-2. Invention compound concentrations are listed in parenthesis in mg/kg while IL-2 concentration is given in parenthesis kilounits. The results are shown in FIG. 9.

Figure 10:
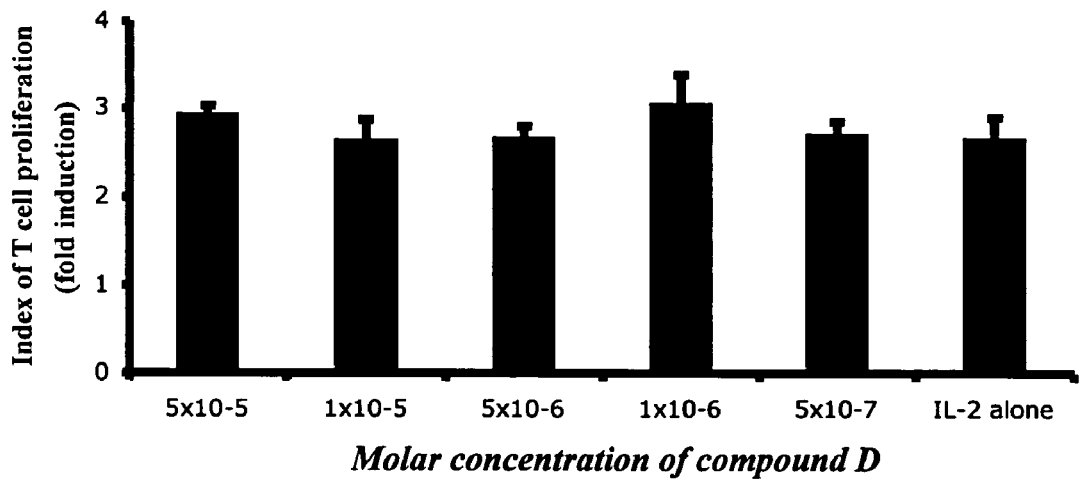
FIGS. 10 and 11 illustrate the effects of compounds of the invention for their capacity to inhibit IL-2 induced T-cell proliferation. The graphs present representative examples of compounds cited in this application and their effects on T-cell proliferation. In the graphs, compound D is N-(2-(1H-indol-2-yl)-phenyl)-phthalamic acid and compound E is 6,7-bis(3-hydroxyphenyl)-pteridine-2,4-diamine.

An IL-2 dependent human T cell line, CTLL2, was used to evaluate IL-2 dependent proliferation over 96 hours in the presence of 50 pg of human recombinant IL-2 (R&D Systems) and the indicated compounds using the XTT assay. N-(2-(1H-indol-2-yl)-phenyl)-phthalamic acid (compound D—in the 1 mg/kg range, in this example formulated in 50% PEG400:50% water) typically had no significant impact on IL-2 induced T-cell proliferation. The results are shown in FIG. 10.

Figure 11:
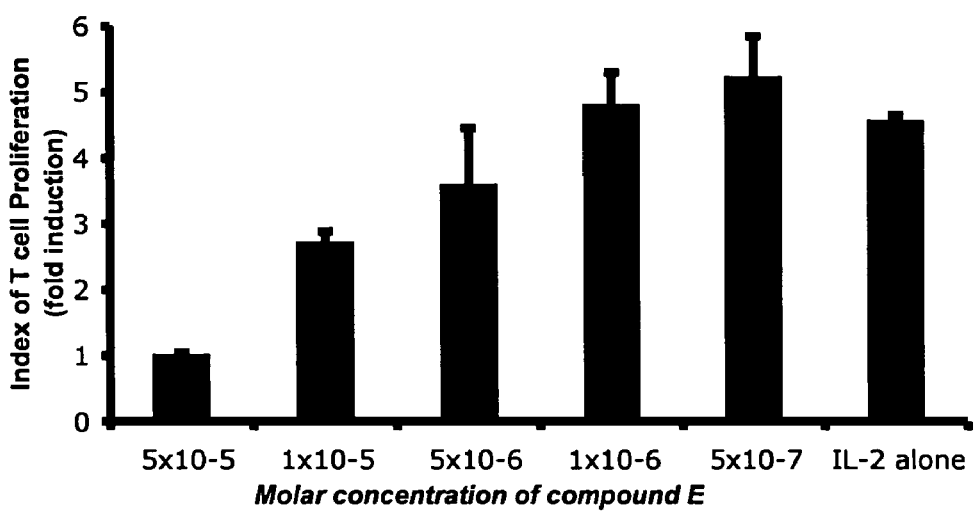

An IL-2 dependent human T cell line, CTLL2, was used to evaluate IL-2 dependent proliferation over 96 hours in the presence of 50 pg of human recombinant IL-2 (R&D Systems) and the indicated compounds using the XTT assay. 6,7-bis(3-hydroxyphenyl)-pteridine-2,4-diamine, sulfate salt (compound E—in the 0.1 mg/kg range, in this example formulated in 50% PEG400:50% water) typically had no significant impact on IL-2 induced T-cell proliferation in the therapeutic range (<1 µM). The results are shown in FIG. 11.

Thus, representative examples from two distinct chemotype series in the present application (shown in FIG. 1) indicate that, for example, N-(2-(1H-indol-2-yl)-phenyl)-phthalamic acid (compound D—in the 1 mg/kg range, in this example formulated in 50% PEG400:50% water) and 6,7-bis(3-hydroxyphenyl)-pteridine-2,4-diamine, sulfate salt (compound E—in the 0.1 mg/kg range, in this example formulated in 50% PEG400:50% water), are effective in reducing VLS by 80–100% in vivo.

Both of the exemplary compounds performed well in important initial tests, including 1) inhibition of VLS at normal and elevated doses of IL-2; 2) no interference with IL-2 mediated anti-tumor activity; 3) no inhibition of IL-2 induced T cell proliferation in the likely therapeutic dose range; and 4) neither compound elicited gross observable toxicity. These results indicate that invention compounds could be used in conjunction with IL-2 to prevent dose-limiting VLS and thereby increase the clinical application and therapeutic dose range of IL-2.

Acute Respiratory Distress Syndrome (ARDS) is an acute, severe injury to most or all of both lungs causing fluid leak into the lungs. Patients with ARDS experience severe shortness of breath and often require mechanical ventilation (life support) because of respiratory failure. ARDS has also been called some of the following terms: Non-cardiogenic pulmonary edema; Increased-permeability pulmonary edema; Stiff lung; Shock lung; Adult respiratory distress syndrome; Acute respiratory distress syndrome. Two representative compounds of the invention were selected for initial study in the reduction of ARDS.

Figure 12:
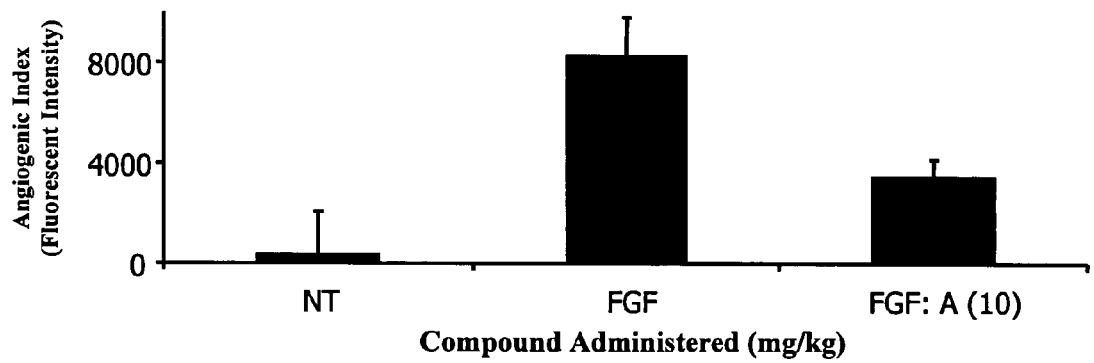
FIG. 12 illustrates the effects of invention compounds for their capacity to inhibit edema associated with Acute Respiratory Distress Syndrome (ARDS). NIH Swiss mice were given an intraperitoneal injection of 1.5 mg/kg Oleic Acid of (in this example formulated in saline) and/or invention compounds. Four hours subsequent to injection animals were sacrificed followed by collection, blotting and weighing (wet weight) of the lungs. Lungs were then dried at 80° C. for 24 hours and weighed (dry weight). N=4/group, 6,7-bis(3-hydroxyphenyl)-pteridine-2,4-diamine, sulfate salt (compound E—in the 0.5 mg/kg range, in this example formulated in 50% PEG400:50% water) typically reduced ARDS-associated edema by >50% while 4-[4-amino-6-(3,4-dihydroxyphenyl)pteridin-7-yl]benzene-1,2-diol (compound F—in the 0.5 mg/kg range, in this example formulated in 50% PEG400:50% water) typically reduced ARDS-induced edema by >100%.

NIH Swiss mice were given an intraperitoneal injection of 1.5 mg/kg Oleic Acid of (in this example formulated in saline) and/or invention compounds. Four hours subsequent to injection animals were sacrificed followed by collection, blotting and weighing (wet weight) of the lungs. Lungs were then dried at 80° C. for 24 hours and weighed (dry weight). N=4/group, 6,7-bis(3-hydroxyphenyl)-pteridine-2,4-diamine, sulfate salt (compound E—in the 0.5 mg/kg range, in this example formulated in 50% PEG400:50% water) typically reduced ARDS-induced edema by >50% while 4-[4-amino-6-(3,4-dihydroxyphenyl)pteridin-7-yl]benzene-1,2-diol (compound F—in the 0.5 mg/kg range, in this example formulated in 50% PEG400:50% water) typically reduced ARDS-induced edema by >100%. The results are shown in FIG. 12.

EXAMPLE 4

Inhibition of VEGF-induced Edema

Miles Assay Data

A rodent model of vascular edema, the Miles assay, was used to screen compounds for their ability to inhibit VEGF-induced edema. The table below presents several examples drawn from these studies, in which compounds cited in this application successfully inhibited edema formation.

| Treatment | Dose (mg/kg BW) | Score (scale of 0–12) |
|---|---|---|
| Vehicle | | 12 |
| 4-{[(2,4-Diamino-pteridin-6-ylmethyl)-amino]-methyl}-benzene-1,2-diol | 5 mg/kg | 4 |
| 4-(2,4-Diamino-pteridin-6-yl)-phenol (sulfate salt) | 5 mg/kg | 2 |
| 2-[2-(1H-Indol-2-yl)-phenyl]-isoindole-1,3-dione | 1.5 mg/kg | 3 |
|  | 1.5 mg/kg | 3 |
| 6,7-Bis-(3-hydroxy-phenyl)-pteridine-2,4-diol | 1.5 mg/kg | 3 |
| 3-(4-Hydroxy-phenyl)-N-[2-(1H-indol-2-yl)-phenyl]-propionamide | 1.5 mg/kg | 2 |
| 2-(4-Hydroxy-phenyl)-N-[2-(1H-indol-2-yl)-phenyl]-acetamide | 1.5 mg/kg | 2 |

-continued

| Treatment | Dose (mg/kg BW) | Score (scale of 0–12) |
|---|---|---|
| 2-(3,4-Dihydroxy-phenyl)-N-[2-(1H-indol-2-yl)-phenyl]-acetamide | 0.5 mg/kg | 7 |
| N-[2-(2,3-Dihydro-1H-indol-2-yl)-phenyl]-2-hydroxy-benzamide | 0.5 mg/kg | 5 |
| 3-[2-(1H-Indol-2-yl)-phenylcarbamoyl]-pyridine-2-carboxylic acid | 0.5 mg/kg | 5 |
| 2-Hydroxy-5-(6-phenyl-pteridin-4-ylamino)-benzenesulfonic acid | 0.5 mg/kg | 6 |
| 5-(6-Phenyl-pteridin-4-ylamino)-quinolin-8-ol hydrochloride salt | 0.5 mg/kg | 5 |
| 3,4-Dihydroxy-N-[2-(1H-indol-2-yl)-phenyl]-benzamide | 0.1 mg/kg | 6 |
| 6-{[(Pyridin-2-ylmethyl)-amino]-methyl}-pteridine-2,4-diamine | 0.1 mg/kg | 4 |
| 6-{[(Naphthalen-2-ylmethyl)-amino]-methyl}-pteridine-2,4-diamine | 0.1 mg/kg | 4 |
| 2,3-(3,4-Dihydroxyphenyl)-pyrido[3,4-b]pyrazin-8-ylamine | 0.01 mg/kg | 6 |
| 3-[2,4-diamino-6-(3-hydroxyphenyl)pteridin-7-yl]phenol dihydrochloride salt | 1 mg/kg | 4 |
| 3-[2,4-diamino-6-(3-hydroxyphenyl)pteridin-7-yl]phenol dihydrochloride salt | 0.1 mg/kg | 4 |
| 3-[2,4-diamino-6-(3-hydroxyphenyl)pteridin-7-yl]phenol dihydrochloride salt | 0.01 mg/kg | 3 |
| 4-[4-amino-6-(3,4-dihydroxyphenyl)pteridin-7-yl]benzene-1,2-diol chloride salt | 1 mg/kg | 5 |
| 4-[4-amino-6-(3,4-dihydroxyphenyl)pteridin-7-yl]benzene-1,2-diol chloride salt | 0.1 mg/kg | 3 |
| 4-[4-amino-6-(3,4-dihydroxyphenyl)pteridin-7-yl]benzene-1,2-diol chloride salt | 0.01 mg/kg | 6 |

Sprague-Dawley rats were first injected IV with vehicle alone or test agent, followed by IV injection of Evans blue dye, followed by intradermal injections of saline and VEGF (200 ng/injection site) along both shaved flanks. After 45 min, intradermal injection sites were photographed and then scored by a blinded observer for extravasation of Evans blue dye into the dermis (dermal bluing) according to a 4 point scoring system (3=maximal bluing, ≧75% of response in vehicle-treated animals; 2=medium bluing, >25% but <75% of vehicle-treated animals; 1=minimal bluing, ≦25% of vehicle-treated animals; 0=bluing equivalent to saline injection sites on same animal). Individual scores for 4 injection sites (from 2 separate animals) were summed and are shown as a scale of 0–12, with a lower score indicating the greater anti-edema activity; note that all vehicle-treated groups score a value of 12, based on the scoring system outlined above.

The ability of test agents to influence edema induced by agonists other than VEGF was also tested. Compounds cited in this application inhibited edema formation induced using histamine as an agonist, for example, as shown below.

| Treatment | Dose (mg/kg BW) | Score with VEGF as agonist (scale of 0–12) | Score with histamine as agonist (scale of 0–12) |
|---|---|---|---|
| Vehicle | | 12 | 12 |
| 6,7-bis(4-hydroxyphenyl)-pteridin-4-ylamine sulfate salt | 1.5 mg/kg | 4 | 3 |
| 6,7-Diphenyl-pteridin-4-ol | 1.5 mg/kg | 3 | 4 |
| 3,4,5-Trihydroxy-N-[2-(1H-indol-2-yl)-phenyl]-benzamide | 1.5 mg/kg | 4 | 7 |
| 3,4,5-Trihydroxy-N-(1H-indol-2-yl)-benzamide | 1.5 mg/kg | 5 | 7 |

The ability of test agent to influence vascular edema was tested as above, except that the ability to block edema was tested using either VEGF or histamine as the agonist (200 ng and 10 μg/injection site, respectively).

EXAMPLE 5

Reduction of Myocardial Infarction

Myocardial Infarct Data

A rodent model of acute myocardial infarct, in which the proximal left anterior descending coronary artery (LAD) is occluded for 60 min followed by reperfusion, was used to determine whether test agents reduced infarct size at 24 hours. Several examples of the compounds cited in this application significantly reduced infarct size as compared to controls.

| Study # | Treatment | Dose (mg/kg BW) | Infarct (% AAR, mean ± SEM) | % Infarct reduction |
|---|---|---|---|---|
| 1 | Vehicle | | 75.9 ± 1.8 | |
| | 6,7-bis(4-hydroxyphenyl)-pteridin-4-ylamine sulfate salt | 1.5 | 60.6 ± 1.8 | 20% |
| 2 | Vehicle | | 54.0 ± 2.9 | |
| | 6,7-bis(3,4-dihydroxyphenyl)-pteridine-2,4,-diamine, hydrochloride salt | 1.5 | 36.3 ± 6.3 | 33% |
| 3 | Vehicle | | 54.0 ± 2.9 | |
| | 3-[2,4-diamino-6-(3-hydroxyphenyl)pteridin-7-yl] phenol dihydrochloride salt | 1.0 | 46.4 ± 2.6 | Not significant |
| | 3-[2,4-diamino-6-(3-hydroxyphenyl)pteridin-7-yl] phenol dihydrochloride salt | 0.1 | 37.7 ± 5.8 | 30% |
| 4 | Vehicle | | 61.9 ± 3.1 | |
| | 4-[4-amino-6-(3,4-dihydroxyphenyl)pteridin-7-yl]benzene-1,2-diol chloride salt | 1.0 mg/kg | 40.1 ± 2.0 | 35% |
| | 4-[4-amino-6-(3,4-dihydroxyphenyl)pteridin-7-yl]benzene-1,2-diol chloride salt | 0.1 mg/kg | 37.1 ± 2.6 | 40% |
| | 6,7-Bis(3-hydroxyphenyl)-pteridine-4-ylamine hydrochloride salt | 1.0 mg/kg | 39.1 ± 7.5 | 37% |
| | 6,7-Bis(3-hydroxyphenyl)-pteridine-4-ylamine hydrochloride salt | 0.1 mg/kg | 39.1 ± 4.2 | 37% |
| 5 | Vehicle | | 54.9 ± 3.1 | |
| | 3-[2,4-Diamino-6-(3-hydroxyphenyl)pteridin-7-yl]phenol dibromide salt | 0.5 mg/kg | 31.6 ± 6.2 | 42% |
| | 6,7-bis(3-hydroxyphenyl)-pteridine-2,4-diamine (PF1) | 0.5 mg/kg | 37.8 ± 4.5 | 31% |
| | 6,7-bis(3-hydroxyphenyl)-pteridine-2,4-diamine (PF2) | 0.5 mg/kg | 35.4 ± 1.8 | 35% |
| | 6,7-bis(3-hydroxyphenyl)-pteridine-2,4-diamine (PF5) | 0.5 mg/kg | 38.7 ± 5.3 | 29% |

Myocardial infarcts were created in Sprague-Dawley rats (200–300 g body weight) by a 60 min occlusion of the LAD followed by LAD reperfusion. At 90 min post-reperfusion, either vehicle alone or test agents were injected IV. At 24 hr post-treatment, the ischemic zone (area at-risk, AAR) was delineated by re-ligation of the LAD followed by IV injection of alkali blue dye, after which hearts were sectioned along the short axis and stained using triphenyltetrazolium chloride to delineate viable from infarcted myocardium. Photographic images were then analyzed using morphometric software to calculate infarct area as a percent of the at-risk area.

Study 1: Group sizes N=5–6; 6,7-bis(4-hydroxyphenyl)-pteridin-4-ylamine sulfate salt differs from vehicle control (P<0.0005).

Study 2: Group sizes N=5; 6,7-bis(3,4-dihydroxyphenyl)-pteridine-2,4-diamine hydrochloride salt differs from vehicle control (P<0.035).

Study 3: Group sizes N=3–5; 3-[2,4-diamino-6-(3-hydroxyphenyl)pteridin-7-yl]phenol dihydrochloride salt at 0.1 mg/kg differs from vehicle control (P<0.03).

Study 4: Group sizes N=4–5; all 4-[4-amino-6-(3,4-dihydroxyphenyl)pteridin-7-yl]benzene-1,2-diol chloride salt and 6,7-Bis(3-hydroxyphenyl)-pteridine-4-ylamine hydrochloride salt treatment groups differ from vehicle control (P<0.02).

Study 5: 3-[2,4-Diamino-6-(3-hydroxyphenyl)pteridin-7-yl]phenol dibromide salt was delivered in 8% PEG400 (Vehicle), while 6,7-Bis(3-hydroxyphenyl)-pteridine-2,4-diamine was delivered as one of three product formulations (PF1=2.8% hydroxypropyl-β-cyclodextrin, 1.84% PEG400, and 0.009% EDTA in 20 mM pH 3 citrate buffer; PF2=1.8% hydroxypropyl-β-cyclodextrin and 0.06% polyvinylpyrrolidone in 20 mM pH 3 citrate buffer; PF3=0.8% sulfonbutyl ether-β-cyclodextrin and 0.03% polyvinylpyrrolidone in 20 mM pH 3 citrate buffer). Group sizes N=5–6; all treatment groups differ from vehicle control (P<0.05).

The following studies were performed as described above, except that the timing of 3-[2,4-diamino-6-(3-hydroxyphenyl)pteridin-7-yl] phenol dihydrochloride salt administration (at 0.1 mg/kg) was varied. In one group, 3-[2,4-diamino-6-(3-hydroxyphenyl)pteridin-7-yl]phenol dihydrochloride salt was administered at both 60 and 240 min post-occlusion.

| Treatment | Administration time (min post-occlusion) | Infarct (% AAR, mean ± SEM) | % Infarct reduction |
|---|---|---|---|
| Vehicle | 60 | 54.0 ± 2.9 | — |
| 3-[2,4-diamino-6-(3-hydroxyphenyl)pteridin-7-yl] phenol dihydrochloride salt | 60 | 21.6 ± 5.7 | 60% |
| 3-[2,4-diamino-6-(3-hydroxyphenyl)pteridin-7-yl] phenol dihydrochloride salt | 120 | 18.8 ± 5.6 | 65% |
| 3-[2,4-diamino-6-(3-hydroxyphenyl)pteridin-7-yl] phenol dihydrochloride salt | 240 | 19.1 ± 4.0 | 65% |
| 3-[2,4-diamino-6-(3-hydroxyphenyl)pteridin-7-yl] phenol dihydrochloride salt | 60 and 240 | 24.2 ± 4.9 | 55% |

Group sizes N=4–5; all 3-[2,4-diamino-6-(3-hydroxyphenyl)pteridin-7-yl] phenol dihydrochloride salt treatment groups differ from vehicle control (P<0.001).

Stroke Data

A rodent model of cerebral stroke, in which the middle cerebral artery is permanently occluded, was used to determine whether test agents reduced infarct size at 24 hours. Several examples of the compounds cited in this application significantly reduced infarct size as compared to controls, and to a greater degree than two commercially available compounds (PP1 and SU6656) described in the literature as Src kinase inhibitors.

| Study # | Treatment | Infarct area in mm$^3$ (mean ± SEM) | % Infarct reduction |
|---|---|---|---|
| 1 | Vehicle | 42.4 ± 6.25 | — |
|   | PP1 | 35.4 ± 6.4 | Not significant |
|   | SU6656 | 24.3 ± 5.3 | Not significant |
|   | 6,7-Di-pyridin-2-yl-pteridin-4-ylamine | 27.2 ± 2.63 | Not significant |
|   | 6,7-Diphenyl-pteridine-2,4-diol | 20.2 ± 4.19 | 52% |
|   | N-(2-(1H-Indol-2-yl)-phenyl)-phthalamic acid | 15.6 ± 5.16 | 63% |
| 2 | Vehicle | 39.0 ± 5.0 | — |
|   | 6,7-bis(4-hydroxyphenyl)-pteridin-4-ylamine, sulfate salt | 18.3 ± 2.6 | 53% |

Cerebral strokes were created in mice by permanent ligation of the middle cerebral artery using a cauterizing tool, followed 60 min later by IV injection of either vehicle alone (50% PEG400 in water) or test agents (at 1 mg/kg BW). Twenty four hours later, brains were sectioned and stained using triphenyltetrazolium chloride to delineate viable from infarcted tissue. Photographic images were then analyzed using morphometric software to calculate infarct area.

Study 1: Group sizes N=5–6; the 6,7-diphenyl-pteridine-2,4-diol and N-(2-(1H-indol-2-yl)-phenyl)-phthalamic acid groups differ from vehicle control (P<0.05 and P<0.01, respectively).

Study 2: Group sizes N=6–7; the 6,7-bis(4-hydroxyphenyl)-pteridin-4-ylamine, sulfate salt group differs from vehicle control (P<0.006).

EXAMPLE 6

Inhibition of Src-family Kinases, c-Src and Yes

The ability of compounds to inhibit the activity of two Src-family kinases (c-Src and Yes) was directly tested. The table below presents data for several compounds, which in most cases inhibited one or both kinases at concentrations of ≦10 μM.

| Compound | Src kinase (IC$_{50}$ value) | Yes kinase (IC$_{50}$ value) |
|---|---|---|
| 6,7-bis(3-hydroxyphenyl)-pteridine-2-amine | 27.6 μM | 3.8 μM |
| 6,7-bis(3,4-dihydroxyphenyl)-pteridine-2,4-diamine, hydrochloride salt | 2.6 μM | 1.1 μM |
| 2,3-(3,4-Dihydroxyphenyl)-pyrido[3,4-b]pyrazin-8-ylamine | 1.6 μM | 1.0 μM |
| 4-[4-amino-6-(3,4-dihydroxyphenyl)pteridin-7-yl]benzene-1,2-diol chloride salt | 1.3 μM | ND |
| 6,7-Bis-(3,4-dihydroxyphenyl)-pteridine-2,4-diol | 1.8 μM | 0.9 μM |
| 3,4-Dihydroxy-N-[2-(1H-indol-2-yl)-phenyl]-benzamide | 337 nM | 303 nM |
| 2,3-Bis(3,4-dihydroxyphenyl)-pyrido[2,3-b]pyrazin-6-ylamine dihydrochloride salt | 1.3 μM | 756 nM |
| 6,7-Bis(3-hydroxyphenyl)-pteridine-4-ylamine hydrochloride salt | 10.0 μM | 6.3 μM |
| 4-[4-amino-6-(3,4-dihydroxyphenyl)pteridin-7-yl]benzene-1,2-diol methanesulfonate | 0.8 μM | ND |
| 3-(3-Amino-benzo[1,2,4]triazin-7-yl)-phenol | 12.0 μM | 6.8 μM |
| 7-Naphthalen-1-yl-benzo[1,2,4]triazin-3-ylamine | 0.9 μM | 9.3 μM |
| 6,7-Bis(3-hydroxyphenyl)-pteridine-4-ylamine hydrobromide salt | 8.8 μM | ND |
| 7-(2-Trifluoromethyl-phenyl)-benzo[1,2,4]triazin-3-ylamine | 9.2 μM | 7.0 μM |
| [7-(2,6-Dimethyl-phenyl)-benzo[1,2,4]triazin-3-yl]-phenyl-amine | 925 nM | 822 nM |

-continued

| Compound | Src kinase (IC$_{50}$ value) | Yes kinase (IC$_{50}$ value) |
|---|---|---|
| [7-(2,6-Dimethyl-phenyl)-5-methyl-benzo[1,2,4]triazin-3-yl]-phenyl-amine | 294 nM | ND |
| 4-[(Phenyl-pteridin-4-ylamino)-methyl]-benzene-1,2-diol | 420 nM | ND |
| 4-[2-(6-Phenyl-pteridin-4-ylamino)-ethyl]benzene-1,2-diol | 317 nM | ND |

Kinase reactions were conducted in 96-well plates by combining recombinant human c-Src or Yes (280 ng/well, Panvera, Madison Wis.), ATP (3 µM), a tyrosine kinase substrate (PTK2, 250 µM, Promega Corp., Madison Wis.), and test agents (at concentrations ranging from 1 nM to 100 µM); the buffer used was Src kinase reaction buffer (Upstate U.S.A., Lake Placid N.Y.). After reacting at 90 minutes at room temperature, residual ATP was determined using a luciferase-based assay (KinaseGlo, Promega Corp.) as a measure of kinase activity. Data from four wells were then averaged and used to determine IC$_{50}$ values for the test compounds (Prism software package, GraphPad Software, San Diego Calif.). ND: not determined.

EXAMPLE 7

Effects of Invention Compounds on Angiogenesis

Figure 13:
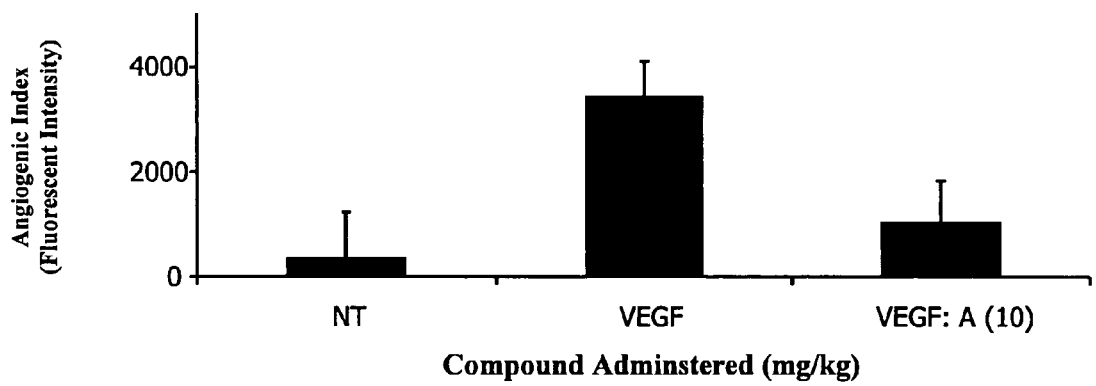
FIGS. 13 and 14 illustrate the effects of invention compounds for their capacity to inhibit angiogenesis in vivo. The graph presents representative examples of compounds cited in this application which successfully inhibited angiogenesis in vivo. Tumor extracellular matrix infused with the 160 ng of the described growth factors were injected subcutaneously in a Balb/C mouse. The described invention compound was injected daily at the described concentration for 5 days. After 5 days the animals were sacrificed and angiogenesis quantified based on the binding of fluorescently labeled, endothelium specific FITC-lectin. In the graph, compound A is 6,7-bis(4-hydroxyphenyl)-pteridin-4-ylamine sulfate salt.
Figure 14:
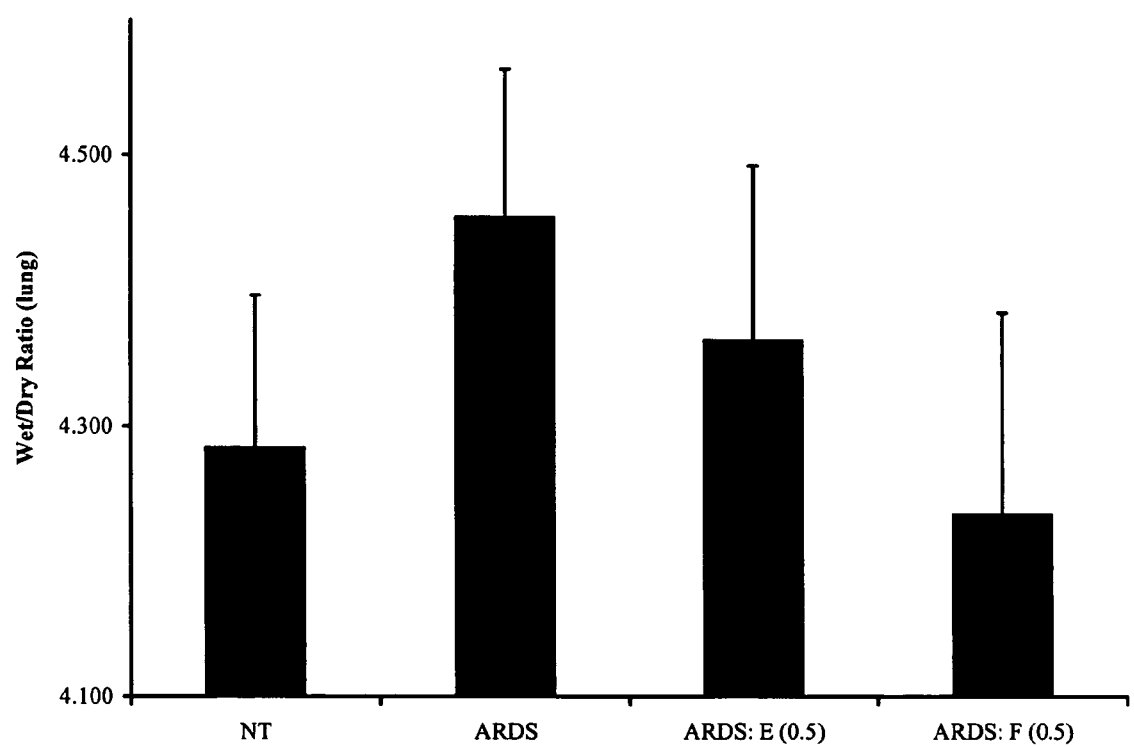

Referring to FIGS. 13 and 14, a murine model of angiogenesis was used to screen compounds for their capacity to inhibit angiogenesis. The graph presents representative examples of compounds cited in this application which successfully inhibited angiogenesis in vivo. In the graph, compound A is 6,7-bis(4-hydroxyphenyl)-pteridin-4-ylamine sulfate salt. Athymic WeHi (nu/nu) mice were first injected with 400 µls of an ice-cold tumor-derived extracellular matrix substrate, matrigel (Becton-Dickinson) infused with 400 ng/ml of bFGF or VEGF (R&D Systems) which rapidly solidifies into a subdermal plug at body temperature. Mice were subsequently injected intaperitoneally with 10 mg/kg of the indicated compounds bid for four days. On the fourth day mice were injected intravenously with 0.5 mgs of a FITC-conjugated endothelial specific lectin (Banderiea Simplifica, Vector Laboratories). Twenty minutes after injection of the lectin, mice were euthanized, matrigel plugs were then extracted, solublized in PBS with mechanical grinding and the fluorescent content of individual plugs was quantified. Values shown are normalized to control values from groups of 5.

Although the invention has been described with reference to the presently preferred embodiment, it should be understood that various modifications can be made without departing from the spirit of the invention. Accordingly, the invention is limited only by the following claims.

What is claimed is:

1. A compound of structure (III):

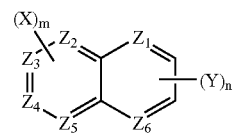

III wherein:
each of $Z_2$ and $Z_4$ is C, each of $Z_1$, $Z_3$, $Z_5$, and $Z_6$ is N;
each X is $NH_2$;
each Y is independently selected from a group consisting of $-OR^d$, $-NR^d{}_2$, $-SR^d$, and $-OPO_3H_2$, wherein $R^d$ is selected from a group consisting of H, lower alkyl, aryl, and $-(CH_2)_2NH(CH_2CH_3)$; or
each Y is independently selected from a group consisting of alkyl, substituted alkyl, aryl, substituted aryl, and halogen, wherein said substituents are selected from a group consisting of halogen, $-OR^e$, $-NR^e{}_2$, $-SR^e$, and $-P(O)(OH)_2$, wherein $R^e$ is selected from a group consisting of $-H$, lower alkyl, and aryl; or
each Y is independently selected from a group consisting of $CH_2$glycinyl, $CH_2NHethoxy$, $CH_2NHCH_2$alkyl, $CH_2NHCH_2$t-Bu, $CH_2NHCH_2$aryl, and $CH_2NHCH_2$substituted aryl; or
when n is 2, each Y is taken together to form a fused aromatic ring system; and
m and n are each independently 1 to 4,
wherein when m=n=2, Y is not phenyl or 4-hydroxyphenyl, or tautomers thereof.

2. A pharmaceutical composition comprising a compound of claim 1 in a pharmaceutically acceptable carrier.

3. A compound of claim 1 having the structure:

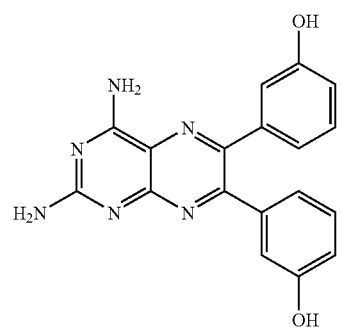

or pharmaceutically acceptable salts thereof.

4. A compound of claim 1 having the structure:

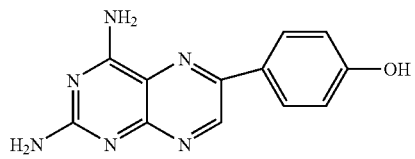

or pharmaceutically acceptable salts thereof.

5. A compound of claim 1 having the structure:

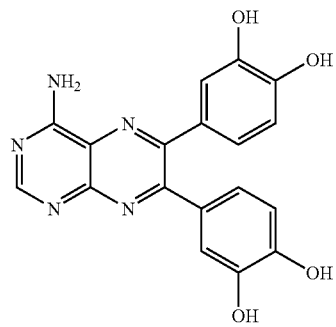

or pharmaceutically acceptable salts thereof.

6. A compound of claim 1 having the structure:

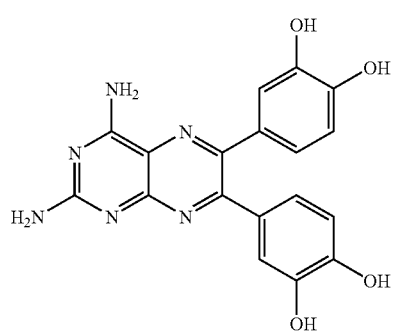

or pharmaceutically acceptable salts thereof.

7. A compound of claim 1 having any one of the structures:

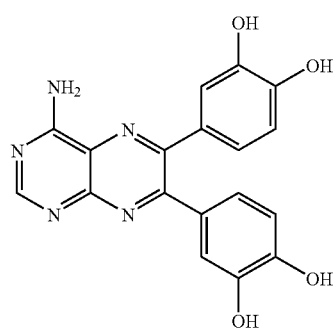

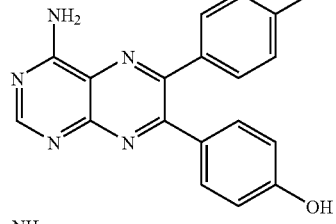

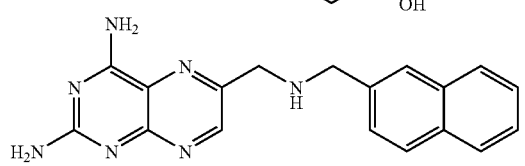

-continued

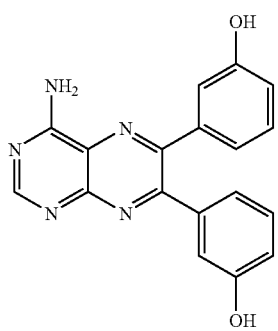

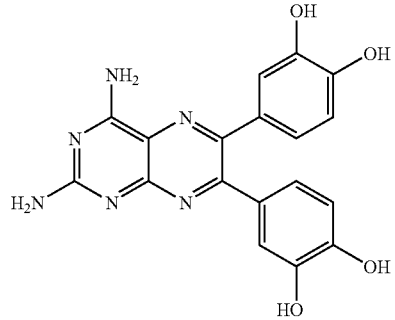

or pharmaceutically acceptable salts thereof.

8. A compound of claim 1 having the structure:

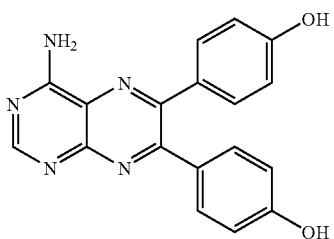

or pharmaceutically acceptable salts thereof.

9. A compound having the structure:

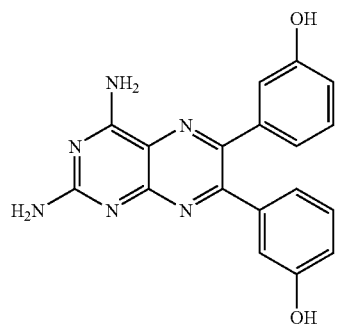

or pharmaceutically acceptable salts thereof.

* * * * *